(12) United States Patent
Steffan et al.

(10) Patent No.: US 7,592,363 B2
(45) Date of Patent: Sep. 22, 2009

(54) INDAZOLES

(75) Inventors: Robert J. Steffan, Langhorne, PA (US); Edward M. Matelan, Royersford, PA (US); Stephen M. Bowen, Mohnton, PA (US); John W. Ullrich, Exton, PA (US); Jay E. Wrobel, Lawrence, NJ (US); Edouard Zamaratski, Uppsala (SE); Lars Kruger, Stockholm (SE); Annabel L. Olsen Hedemyr, Stockholm (SE); Aiping Cheng, Huddinge (SE); Tomas Hansson, Nynashamn (SE); Rayomand J. Unwalla, Eagleville, PA (US); Christopher P. Miller, Wayne, PA (US); Patrik P. Rhönnstad, Kungsör (SE)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 11/194,263

(22) Filed: Aug. 1, 2005

(65) Prior Publication Data

US 2006/0030612 A1 Feb. 9, 2006

Related U.S. Application Data

(60) Provisional application No. 60/598,573, filed on Aug. 3, 2004, provisional application No. 60/669,737, filed on Apr. 8, 2005.

(51) Int. Cl.
*A61K 31/4162* (2006.01)
*C07D 231/56* (2006.01)
(52) U.S. Cl. .................................. 514/406; 548/361.1
(58) Field of Classification Search .............. 548/361.1; 514/406
See application file for complete search history.

(56) References Cited

U.S. PATENT DOCUMENTS

| 3,152,135 | A | 10/1964 | Shavel, Jr. et al. |
| 3,541,110 | A | 11/1970 | Bell et al. |
| 5,173,496 | A | 12/1992 | Bruneau et al. |
| 5,227,486 | A | 7/1993 | Merce-Vidal et al. |
| 5,321,028 | A * | 6/1994 | Vandenberk et al. ..... 514/259.2 |
| 6,005,109 | A | 12/1999 | Faraci et al. |
| 6,350,748 | B1 | 2/2002 | Takeyama et al. |
| 6,608,049 | B2 | 8/2003 | Woltering et al. |
| 2002/0091116 | A1 | 7/2002 | Zhu et al. |
| 2004/0167127 | A1* | 8/2004 | Steffan et al. ............ 514/227.8 |

FOREIGN PATENT DOCUMENTS

| DE | 19612291 | 6/1993 |
| EP | 502786 | 4/1996 |
| EP | 284174 | 9/1998 |
| JP | 04-282372 | 10/1992 |
| JP | 07017950 | 6/1993 |
| WO | WO 2005/016892 | 2/1995 |
| WO | WO 00/27394 | 5/2000 |
| WO | WO 00/63207 | 10/2000 |
| WO | WO 01/19798 | 3/2001 |
| WO | WO 01/58869 | 8/2001 |
| WO | WO 01/64642 | 9/2001 |
| WO | WO 02/00651 | 1/2002 |
| WO | WO 02/16348 | 2/2002 |
| WO | WO 03/035625 | 5/2003 |
| WO | WO 03/078403 | 9/2003 |
| WO | WO 2004/031159 | 4/2004 |
| WO | WO 2004/050634 | 6/2004 |

OTHER PUBLICATIONS

Fernandez et al. "A Convenient Route to the Soluble Guanylate Cyclase Activator YC-1 and Its N2 Regioisomer" Heterocycles, 2001, vol. 55, No. 9, pp. 1813-1816.*
Watanabe et al. "Expression of the LXRa Protein in Human Atherosclerotic Lesions" Arteriosclerosis, Thrombosis, and Vascular Biology, 2005, vol. 25, No. 3, pp. 622-627.*
Alty, Adam Charles, et al., "Thermal conversion of fluorinated azocompounds into indazoles: the case of 2,5,6-trifluoro-4- (2,4,6-trimethylphenylaz o) pyrimidine," *Journal of Fluorine Chemistry* (1998) 41 (3): 439-42.
Bennett et al., "Liver X receptor agonist as a treatment for atherosclerosis," *Expert Opinion on Therapeutic Patents*, Ashley Publications GB 14 (7): 967-982.
Cao, G., et al., "Antidiabetic Action of a Liver X Receptor Agonist Mediated by Inhibition of Hepatic Gluconeogenesis," *J. Biol. Chem.* (Jan. 2003) 278:1131-1136.
Joseph, S.B., et al. "LXRs: New Therapeutic Targets in Atherosclerosis?" *Current Opinion in Pharmacology* (2003) 3:192-97.
Joseph, S.B., et al., "Reciprocal Regulation of Inflammation and Lipid Metabolism by Liver X Receptors," *Nature Medicine* (2003) 9(2):213-19.

(Continued)

*Primary Examiner*—Rei-Tsang Shiao
*Assistant Examiner*—Joseph R Kosack
(74) *Attorney, Agent, or Firm*—Fish & Richardson P.C.

(57) ABSTRACT

This invention provides compounds of Formula (I) or (Ia):

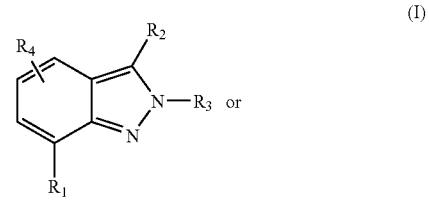

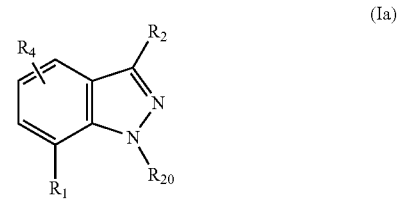

that are useful in the treatment or inhibition of LXR mediated diseases.

43 Claims, No Drawings

OTHER PUBLICATIONS

McKinnon, D.M., et al., "2,1-Benzisoxazole derivatives," *Canadian Journal of Chemistry* (1971) 49 (12) 2018-22.

Palmer, Michael H. et al., "Reactivity of indazoles and benzotriazole towards N-methylation. Analysis of the proton nuclear magnetic resonance spectra of indazoles and benzotriazoles," *Journal of the Chemical Society, Perkin Transactions 2: Physical Organic Chemistry* (1972-1999) 15: 1695-700.

Sajiki, et al., "The Formation of a Novel Pd/C-Ethylenediamine Complex Catalyst: Chemoselective Hydrogenation without Deprotection of the O-Benzyl and N-Cbz Groups," *JOC* (1998) 63:7990-92.

Shutske, G.M. et al., "Heterocyclic oxyacetic acid diuretics: indazole benzisothiazole, and benzisothiazole 1,1-dioxide analogs of [[7-chloro-3-(2-fluorophenyl) 1,2-benzisoxazol-6-yl] oxy]acetic acid," *Journal of Medicinal Chemistry, American Chemical Society* (1983) 26: 1307-1311.

Steffan, R.J., et al., "Synthesis and activity of substituted 4-(indazol-3-yl) phenols as pathway-selective estrogen receptor ligands useful in the treatment of rheumatoid arthritis," *Journal of Medicinal Chemistry, American Chemical Society* (Dec. 16, 2004) 47(26):6435-6438.

Sun, Y., "Expression of LXR target genes decreases cellular amyloid beta peptide secretion," *J. Biol. Chem.* (May 2003) 10:1074.

Urganoker, S. et al., "Ligand-, Copper-, and Amine-Free Sonogashira Reaction of Aryl Iodides and Bromides with Terminal Alkynes," *J. Org. Chem.* (2004) 69:5752-55.

Adger et al., "1,2,3-Benzotriazines," *Journal of the Chemical Society, Perkin Transactions 1*, (1975) (1):31-40.

Frontana-Uribe et al., "2-Substituted indazoles from electrogenerated," *Tetrahedron* (1998) 54(13):3197-3206.

Kametani et al., ",", *Journal of Heterocyclic Chemistry* (1970) 7(4):815-820.

Strandtmann et al., ",", *J Med Chem* (1963) 6(6):719-725.

Takada et al., ",", *J of Organic Chem* (1982) 47(22):4323-4326.

Taylor et al., "Bicyclobenzodiazepinones" from 3-oxo-1,2-diazetidinium hydroxide, inner salts, *Tetrahedron* (1991) 47(46):9599-9620.

Yamazaki et al., "Consecutive [1,5]-sigmatropic and dissociation-recombination processes in rearrangements of 3-substituted 3-acyl-3*H*-indazoles to 1-acylindazoles," *Tetrahedron Letters* (1974) (49/50):4421-4424.

* cited by examiner

INDAZOLES

CROSS-REFERENCE TO RELATED APPLICATION

This application claims priority benefit of U.S. Provisional Application Ser. No. 60/598,573, filed Aug. 3, 2004, and 60/669,737, filed Apr. 8, 2005, each of which is incorporated herein by reference in its entirety.

BACKGROUND OF THE INVENTION

This invention provides indazoles that are useful in the treatment or inhibition of LXR (Liver X receptor) mediated diseases, e.g., cardiovascular diseases, a process for preparing them, and pharmaceutical compositions containing them.

Atherosclerosis, a complex disease of lipid disorder and inflammation, is the leading cause of death in developed countries. A number of independent risk factors have been identified and the most notable are high levels of serum LDL cholesterol and low HDL cholesterol. Although the most effective therapies such as statins have been shown to lower LDL cholesterol significantly (20-60%), still most patients experience adverse coronary events. Also, statins have their own undesirable side effect profile (myotoxicity), which prevents many patients from taking them. Therefore, additional therapeutic strategies to not only decrease LDL cholesterol, but also to increase HDL cholesterol, are critically needed. The important reason to increase HDL cholesterol is to increase cholesterol transport from peripheral tissues to liver for metabolism and excretion. This function of transporting cholesterol from periphery to liver is called reverse cholesterol transport and HDL plays a major role in this pathway. In addition, HDL has been suggested to inhibit the oxidation of LDL cholesterol, reduce the inflammatory response of endothelial cells, inhibit the coagulation pathway and promote the availability of nitric oxide. The key transporter involved in HDL production and reverse cholesterol transport is ABCA1. Therefore, upregulation of ABCA1 results in increased reverse cholesterol transport as well as inhibition of cholesterol absorption in the gut.

LXRs, originally identified from liver as orphan receptors, are members of the nuclear hormone receptor super family and are involved in the regulation of cholesterol and lipid metabolism. They are ligand-activated transcription factors and bind to DNA as obligate heterodimers with retinoid X receptors. While LXRα is restricted to certain tissues such as liver, kidney, adipose, intestine and macrophages, LXRβ displays a ubiquitous tissue distribution pattern. Activation of LXRs by oxysterols (endogenous ligands) in macrophages results in the expression of several genes involved in lipid metabolism and reverse cholesterol transport, including ABCA1, ABCG1 and ApoE. Studies have been conducted in LXRα k/o, LXRβ k/o and double k/o mice to determine the physiological role of LXRs in lipid homeostasis and atherosclerosis. The data indicate that in double k/o mice on normal chow diet, increased cholesterol accumulation was observed in macrophages (foam cells) of the spleen, lung and arterial wall. This was associated with reduced serum HDL cholesterol and increased LDL cholesterol despite normal total cholesterol levels. While LXRα k/o mice did not show significant changes in hepatic gene expression, LXRβ k/o mice showed a 58% decrease in hepatic ABCA1 expression and a 208% increase in SREBP1c expression, suggesting that LXRβ may be involved in the regulation of liver SREBP1c expression. Agonists of LXRα or β are very effective in upregulating ABCA1 expression (desirable effect) in macrophages. The biological activities of several agonists have been shown in two atherosclerotic mouse models (ApoE k/o and LDLR k/o). Treatment of these mice with agonists for 12 weeks resulted in significant inhibition of atherosclerotic lesions. While these two compounds had variable effects on serum cholesterol and lipoprotein levels, both compounds caused a significant increase in serum HDL cholesterol and triglyceride levels. These in vivo data agree well with the in vitro data obtained for the compounds in macrophages.

In addition to the lipid and triglyceride effects described above, a very recent communication in Nature Medicine (9: 213-219, 2003) presents convincing data that activation of LXRs results in the inhibition of inflammation and proinflammatory gene expression in three different models of inflammation (LPS-induced sepsis, acute contact dermatitis of the ear and chronic atherosclerotic inflammation of the artery wall). These data suggest that LXR modulators can mediate a two-pronged effect (removal of cholesterol from the macrophages and inhibition of vascular inflammation) resulting in the inhibition of atherosclerotic lesions.

DESCRIPTION OF THE INVENTION

In some embodiments, the present invention provides compounds having the Formula (I) or (Ia):

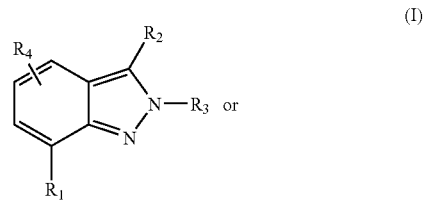

(I)

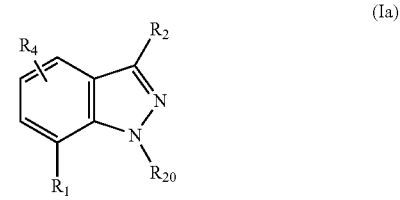

(Ia)

wherein:
$R_1$ is $C_{1-6}$ alkyl, CN, $CO_2R_5$, $C(O)R_5$, $C_{2-6}$ alkenyl, $C_{3-8}$ cycloalkenyl, $C_{2-6}$, alkynyl, $NR_5R_6$, $C(O)NR_5R_6$, phenyl, thiophene, $C_{1-3}$ alkoxy, halogen, or $S(O)_kR_5$; wherein:
  said $C_{1-6}$ alkyl is optionally substituted with from 1 to 7 substituents independently selected from the group consisting of halogen and OH;
  k is 0, 1 or 2;
  each $R_5$ and each $R_6$ is independently H, $C_{1-6}$ alkyl, $C_{3-8}$ cycloalkyl, $S(O)_2$-alkyl or arylalkyl; or
  each $R_5$ and each $R_6$, together with the nitrogen atom to which they are attached, form independently:
    a) a 3 to 7 membered saturated ring that is optionally substituted with $C_{1-3}$ alkyl, $CH_2OH$, or $C(=O-O)NH_2$; or
    b) a 3 to 7 membered ring containing in its backbone one or two additional heteroatoms that is optionally substituted with up to three substituents independently selected from the group consisting of =O, $C_{1-3}$ alkyl, $COC_{1-6}$ alkyl, and $CO_2C_{1-6}$ alkyl;
  provided that when $R_1$ is $S(O)_kR_5$, then said $R_5$ of said $S(O)_kR_5$ is not $S(O)_2$-alkyl;

$R_2$ is $C_{3-8}$ alkyl, $C_{3-8}$ cycloalkyl, $C_{2-8}$ alkenyl, $C_{3-8}$ cycloalkenyl, $C_{2-8}$ alkynyl, $NR_7R_8$, arylalkyl, heteroaryl, heteroarylalkyl or heterocycloalkyl, wherein said $C_{3-8}$ alkyl, said $C_{3-8}$ cycloalkyl and said arylalkyl are each optionally substituted with up to four substituents independently selected from the group consisting of halogen, CN and $OR_7$, and wherein said heteroaryl is optionally substituted with YD; or $R_2$ is phenyl substituted with up to four substituents independently selected from the group consisting of $C_{1-3}$ alkyl, $C_{2-8}$ alkenyl, $C_{2-8}$ alkynyl, $C_{1-3}$ alkoxy, $C_{3-8}$ cycloalkyl, halogen, OH, $CH_2OH$, CN, $NR_7R_8$, $N(R_7)C(O)NR_5R_6$, $S(O)_m R_7$, phenyl, $NO_2$, $C(O)R_7$, $OC(O)R_7$, $C(O)NR_7R_8$, $C(O)NR_7D$ and YD, providing any OH group present is not in the para position; wherein:
said $C_{1-3}$ alkyl and said $C_{1-3}$ alkoxy are each optionally substituted with
from 1 to 7 fluorine atoms;
m is 0 to 2; and
$R_5$ and $R_6$ are as previously defined;
each $R_7$ and each $R_8$ is independently H or $C_{1-3}$ alkyl; or
each $R_7$ and each $R_8$, together with the N atom to which they are attached, form independently:
a) a 3 to 7 membered saturated ring which is optionally substituted with $C_{1-3}$ alkyl, $CO_2R_{14}$, $CH_2CO_2R_{14}$, $OCH_2CO_2R_{14}$, $CH_2OCH_2CO_2R_{14}$, $C(O)NR_{14}R_{15}$, $CH_2OH$, or $CH_2CH_2OH$; or
b) a 3 to 7 membered ring containing in its backbone one or two additional heteroatoms that is optionally substituted with $CH_2CO_2R_{14}$; wherein $R_{14}$ and $R_{15}$ are each independently H or $C_{1-3}$ alkyl;
Y is a bond, $CH_2$, $CH_2CH_2$, $C_{2-4}$ alkynylenyl, —O—, $CH_2OCH_2$, $OCH_2$, $CH_2O$, —$N(R_7)$—, —$N(COR_7)$—, $S(O)_j$, —$N(R_7)CH_2$—, —$N(R_7)CONR_8$—, —$N(COR_7)CH_2$—, $S(O)_jCH_2$, —$CH_2N(R_7)CH_2$—, —$CH_2N(COR_7)CH_2$—, —$OCH_2O$—, —$OC(R_7)(CO_2R_8)$— or —$CH_2S(O)_jCH_2$—; wherein $R_7$ and $R_8$ are as previously defined; and j is 0, 1 or 2;
D is tetrahydronaphthalene, tetrahydronaphthalol, tetralone, naphthalene, anthracene, benzyl or phenyl, each of which is optionally substituted with up to five independently selected R groups;
each R is independently selected from the group consisting of $C_{1-6}$ alkyl, $C_{1-3}$ alkoxy, halogen, —C(=O)H, —C(O)—$C_{1-3}$ alkyl, $CH_2OH$, CN, $NH_2$, $NO_2$, $C_{2-4}$ alkenyl, $C_{2-4}$ alkynyl, $S(O)_jR_9$, and WX; wherein said $C_{1-6}$ alkyl and said $C_{1-3}$ alkoxy are each optionally substituted with from 1 to 7 fluorine atoms; and j is 0, 1 or 2; or
D is a heterocycloalkyl, heterocycloalkylalkyl, heteroarylalkyl, heteroaryl or arylalkyl group, each of which is optionally substituted with up to four independently selected $R_a$ groups;
each $R_a$ is independently selected from the group consisting of $C_{1-8}$ alkyl, phenyl, benzyl, $C_{3-8}$cycloalkyl $C_{7-11}$ arylalkyl, $C_{1-3}$ alkoxy, halogen, —C(=O)H, —C(O)—$C_{1-3}$ alkyl, $CH_2OH$, CN, $NO_2$, $NH_2$, OH, =O, $C_{2-6}$ alkenyl, $C_{2-4}$ alkynyl, $S(O)_jR_9$ and WX; wherein said $C_{1-8}$ alkyl, said $C_{2-6}$ alkenyl, said $C_{2-4}$ alkynyl and said $C_{1-3}$ alkoxy are each optionally substituted with from 1 to 7 fluorine atoms; and
j is 0, 1 or 2;
W is a bond, —$CH_2$—, —$CH_2CH_2$—, —$NR_7$—, -Q-N$(R_7)$—, —$CHR_8$—, —$(CHR_8)_2$—, —$CHR_9$—, —$CR_9R_{10}$—, —CO—, —O—, —$OCH_2$—, —$OCHR_9$—, or —$OCR_9R_{10}$—; wherein $R_7$ and $R_8$ are as previously defined; and Q is $C_{1-6}$ alkylenyl;

each $R_9$ and each $R_{10}$ is independently $C_{1-3}$ alkyl or OH; or
any $R_9$ and $R_{10}$, together with the atom to which they are attached, can form a 3 to 7 membered saturated ring that optionally contains one O, N or S atom;
X is $CO_2R_{11}$, $COR_{11}$, $C(R_{11})_2OH$, $CO_2R_5$, $C(O)NR_5R_6$, $NR_5R_6$, $QNR_5CO_2R_6$, OH, $CH_2OH$, CN, $SO_2NR_5R_6$, $P(O)(OR_5)(OR_6)$, cycloalkylalkyl, aryl, arylalkyl, heterocycloalkyl or heteroaryl, wherein:
said aryl, said arylalkyl, said heterocycloalkyl and said heteroaryl are independently each optionally substituted with up to three substituents selected from the group consisting of $C_{1-3}$ alkyl, $C_{1-3}$ alkoxy, halogen, H, OH, $NO_2$ and benzyl that is optionally substituted with up to five halogen atoms; wherein said $C_{1-3}$ alkyl and said $C_{1-3}$ alkoxy are each optionally substituted with from 1 to 7 fluorine atoms;
Q is $C_{1-6}$ alkylenyl;
$R_{11}$ is H or $C_{1-6}$ alkyl; and
$R_5$ and $R_6$ are as previously defined;
$R_3$ is $C_{1-8}$ alkyl, $C_{2-8}$ alkenyl, $C_{2-8}$ alkynyl, $C_{3-8}$ cycloalkyl, $C_{3-8}$ cycloalkenyl, phenyl, or ZA; wherein:
said phenyl is optionally substituted with $C_{1-3}$ alkyl;
Z is $CH_2$, $CH_2CH_2$, or $CH_2O$;
A is biphenyl, benzyl, naphthyl, pyridyl, 8-quinolyl, $C_{3-8}$ cycloalkyl or phenyl; wherein said phenyl is optionally substituted with up to five independently selected $R_{18}$ groups; wherein
each said $R_{18}$ is independently selected from the group consisting of $C_{1-6}$ alkyl, $C_{1-3}$ alkoxy, halogen, OH, $NO_2$, CN, phenyl, pyrrol-1-yl, $C(O)R_{12}$, $CO_2R_{12}$, $NR_{12}R_{13}$, $C(O)NR_{12}R_{13}$ and $S(O)_nR_{12}$; wherein said $C_{1-6}$ alkyl and said $C_{1-3}$ alkoxy are each optionally substituted with from 1 to 7 fluorine atoms; n is 0, 1 or 2; and $R_{12}$ and $R_{13}$ are each independently H or $C_{1-3}$ alkyl;
$R_{20}$ is H or $C_{1-3}$ alkyl; and
$R_4$ is H, halogen, methyl or methoxy;
provided that when the compound has the structure (Ia), then $R_2$ is phenyl or heteroaryl, each of which is substituted by YD, wherein YD is as previously defined;
or a pharmaceutically acceptable salt thereof, which are useful in the treatment of LXRmediated diseases.

In particular, the compounds of this invention are useful in the treatment and inhibition of atherosclerosis and atherosclerotic lesions, lowering LDL cholesterol levels, increasing HDL cholesterol levels, increasing reverse cholesterol transport, inhibiting cholesterol absorption, treatment or inhibition of Alzheimer's disease, type I diabetes, type II diabetes, multiple sclerosis, rheumatoid arthritis, acute coronary syndrome, restenosis, inflammatory bowel disease (IBD), Crohn's disease, endometriosis, celiac, and thyroiditis.

The present compounds also are useful for the treatment of TH-1 mediated diseases, particularly in mammals. Accordingly, in some embodiments, the present invention provides methods of treating a Th1-mediated disease in a mammal in need thereof, which comprises providing to said mammal an effective amount of a compound as described herein. Non-limiting examples of Th1-mediated diseases to which the methods of the invention are amenable include multiple sclerosis, rheumatoid arthritis, autoimmune thyroid disease, inflammatory bowel disease, Crohn's disease and atherosclerosis.

The present compounds are further useful for suppression of lymphocyte function or activation in a mammal. Thus, in a further aspect, the invention provides methods for suppressing lymphocyte function or activation in a mammal in need thereof, which comprises providing to said mammal an effective amount of a compound as described herein. In some embodiments, the lymphocyte function that is suppressed is lymphokine production.

The present compounds find further use in the suppression of macrophage function or activation in a mammal. Thus, in a further aspect, the invention provides methods for suppressing macrophage function or activation in a mammal in need thereof, which comprises providing to said mammal an effective amount of a compound as described herein.

In a further aspect, the present compounds find further use in suppressing cytokine production in a mammal. Accordingly, the present invention further provides methods of suppressing cytokine production in a mammal in need thereof, which comprises providing to said mammal an effective amount of a compound as described herein.

Pharmaceutically acceptable salts of the compounds of Formula (I) or (Ia) with an acidic moiety can be formed from organic and inorganic bases. Suitable salts from bases are, for example, metal salts, such as alkali metal or alkaline earth metal salts, for example, sodium, potassium, or magnesium salts; or salts with ammonia or an organic amine, such as morpholine, thiomorpholine, piperidine, pyrrolidine, a mono-, di- or tri-lower alkylamine, for example, ethyl-tert-butyl-, diethyl-, diisopropyl-, triethyl-, tributyl- or dimethyl-propylamine, or a mono-, di-, or trihydroxy lower alkylamine, for example, mono-, di- or triethanolamine. Furthermore, internal salts may be formed. Similarly, when a compound of the present invention contains a basic moiety, salts can be formed from organic and inorganic acids. For example, salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

Preferred compounds of the invention include compounds of Formula (I) or (Ia) described hereinbefore, wherein:

$R_1$ is $C_{1-6}$ alkyl, CN, $CO_2R_5$, $NR_5R_6$, halogen; wherein said $C_{1-6}$ alkyl is optionally substituted with from 1 to 7 substituents independently selected from the group consisting of halogen and OH;

$R_5$ and $R_{1-6}$ are as previously defined;

$R_2$ is as defined above;

$R_3$ is phenyl optionally substituted with $C_{1-3}$ alkyl; or ZA; wherein:
    Z is $CH_2$;
    A is pyridyl or phenyl, wherein said phenyl is optionally substituted with up to five independently selected $R_{18}$ groups, wherein:
        each said $R_{18}$ is independently selected from the group consisting of $C_{1-6}$ alkyl, $C_{1-3}$ alkoxy, halogen, OH, $NO_2$, and CN, wherein said $C_{1-6}$ alkyl and said $C_{1-3}$ alkoxy are each optionally substituted with from 1 to 7 fluorine atoms;

$R_{20}$ is as defined above; and
$R_4$ is H or halogen; or a pharmaceutically acceptable salt thereof.

Further preferred compounds of the invention include compounds of Formula (I) or (Ia) described hereinbefore, wherein:

$R_1$ is $C_{1-6}$ alkyl, CN, or halogen; wherein said $C_{1-6}$ alkyl is substituted with from 1 to 7 fluorine atoms;

$R_2$ is arylalkyl, heteroaryl or heteroarylalkyl, wherein said arylalkyl is optionally substituted with up to four substituents independently selected from the group consisting of halogen, CN and $OR_7$, and said heteroaryl is optionally substituted with YD; or $R_2$ is phenyl substituted with up to four substituents independently selected from the group consisting of $C_{1-3}$ alkyl, $C_{1-3}$ alkoxy, halogen, $CH_2OH$, CN, $NR_7R_8$, $N(R_7)C(O)NR_5R_6$, $S(O)_mR_7$, $NO_2$, $OC(O)R_7$ and YD, providing any OH group present is not in the para position; wherein said $C_{1-3}$ alkyl and said $C_{1-3}$ alkoxy are each optionally substituted with from 1 to 7 fluorine atoms, and m, $R_5$, $R_6$, $R_7$, and $R_8$ are as previously defined;

Y is a bond, $CH_2$, $CH_2CH_2$, $C_{2-4}$ alkynylenyl, —O—, $OCH_2$, $CH_2O$, —$NR_7$—, —$N(R_7)CH_2$—, —$N(R_7)CONR_8$—, —$OCH_2O$— or —$OC(R_7)CO_2R_8$—;

D is benzyl or phenyl each of which is optionally substituted with up to five independently selected R groups;
    each R is independently selected from the group consisting of $C_{1-6}$ alkyl, $C_{1-3}$ alkoxy, halogen, —C(=O)H, —C(O)—$C_{1-3}$ alkyl, $CH_2OH$, CN, $NO_2$, $C_{2-4}$ alkenyl, $C_{2-4}$ alkynyl, $S(O)_jR_9$, and WX; wherein said $C_{1-6}$ alkyl and said $C_{1-3}$ alkoxy are each optionally substituted with from 1 to 7 fluorine atoms; and j, $R_9$, and WX are as previously defined; or D is a heterocycloalkyl, heterocycloalkylalkyl, heteroarylalkyl, heteroaryl, or arylalkyl group, each of which is optionally substituted with up to four independently selected $R_a$ groups;
    each $R_a$ is independently selected from the group consisting of $C_{1-8}$ alkyl, phenyl, benzyl, $C_{3-8}$ cycloalkyl, $C_{7-11}$ arylalkyl, $C_{1-3}$ alkoxy, halogen, —C(=O)H, —C(O)—$C_{1-3}$ alkyl, $CH_2OH$, CN, $NO_2$, $NH_2$, OH, =O, $C_{2-6}$ alkenyl, $C_{2-4}$ alkynyl, $S(O)_jR_9$, and WX; wherein said $C_{1-8}$ alkyl and said $C_{1-3}$ alkoxy are each optionally substituted with from 1 to 7 fluorine atoms, and j, $R_9$, and WX are as previously defined;

$R_3$ is ZA; wherein:
    Z is $CH_2$;
    A is phenyl, wherein said phenyl is optionally substituted with up to five independently selected $R_{18}$ groups:
        each $R_{18}$ is independently selected from the group consisting of $C_{1-6}$ alkyl, $C_{1-3}$ alkoxy, halogen, OH, $NO_2$, and CN, wherein said $C_{1-6}$ alkyl and said $C_{1-3}$ alkoxy are optionally substituted with from 1 to 7 fluorine atoms;

$R_{20}$ is as previously defined; and
$R_4$ is H; or a pharmaceutically acceptable salt thereof.

In some embodiments, the ring system formed by $R_5$, $R_6$ and the nitrogen atom to which they are attach that includes one or two additional heteroatoms, which optionally can be substituted as previously described herein, is, for example and without limitation, morpholine, pyridine, piperidine, piperidinone, piperazine, imidazolone, imidazole, and other such systems as provided as non-limiting examples in the definitions of heterocycloalkyl and heteroaryl hereinbelow.

In some embodiments, the ring system formed by $R_7$, $R_8$ and the nitrogen atom to which they are attach that includes one or two additional heteroatoms is, for example and without limitation, morpholine, pyridine, piperidine, piperidinone, piperazine, and other such systems as provided as non-limiting examples in the definitions of heterocycloalkyl and heteroaryl hereinbelow.

Examples of $R_1$ are $C_{1-6}$ alkyl, CN, $CO_2R_5$, $NR_5R_6$, or halogen; wherein said $C_{1-6}$ alkyl is optionally substituted with from 1 to 7 substituents independently selected from the group consisting of halogen and OH; wherein $R_5$ and $R_6$ are as previously defined. Other examples of $R_1$ include CN, halogen, or $C_{1-6}$ alkyl substituted with from 1 to 7 fluorine atoms, e.g., $R_1$ is $CF_3$, F or Cl. Other examples of $R_1$ are $C_{1-3}$ perhaloalkyl or $C_{1-3}$ perhaloalkoxy. In some embodiments, $R_1$ is $C_{1-3}$ perfluoroalkyl; $C_{1-3}$ perfluoroalkoxy. In one embodiment, $R_1$ is $CF_3$.

Examples of $R_2$ are $C_{3-8}$ alkyl, $C_{3-8}$ cycloalkyl, aryl, arylalkyl, heteroaryl or heterocycloalkyl, wherein:

said $C_{3-8}$ alkyl, said $C_{3-8}$ cycloalkyl and said arylalkyl are each optionally substituted with up to four substituents independently selected from the group consisting of halogen, CN and $OR_7$, wherein $R_7$ is as previously defined; and said heteroaryl is optionally substituted with YD, wherein Y and D are as previously defined; or $R_2$ is phenyl substituted with up to four substituents independently selected from the group consisting of $C_{1-3}$ alkyl, $C_{2-8}$ alkenyl, $C_{2-8}$ alkynyl, $C_{1-3}$ alkoxy, $C_{3-8}$ cycloalkyl, halogen, OH, $CH_2OH$, CN, $NR_7R_8$, $N(R_7)C(O)NR_5R_6$, $S(O)_mR_7$, phenyl, $NO_2$, $C(O)R_7$, $OC(O)R_7$, $C(O)NR_7R_8$, $C(O)NR_7D$ and YD, providing any OH group present is not in the para position; wherein said $C_{1-3}$ alkyl and said $C_{1-3}$ alkoxy are each optionally substituted with from 1 to 7 fluorine atoms; and m, $R_5$, $R_6$, $R_7$, and $R_8$, Y and D are as previously defined.

In some embodiments $R_2$ is arylalkyl, heteroaryl or heteroarylalkyl, wherein said arylalkyl is optionally substituted with up to four substituents independently selected from the group consisting of halogen, CN and $OR_7$; and said heteroaryl is optionally substituted with YD, wherein Y and D are as previously defined; or $R_2$ is phenyl substituted with up to four substituents independently selected from the group consisting of $C_{1-3}$ alkyl, $C_{1-3}$ alkoxy, halogen, $CH_2OH$, CN, $NR_7R_8$, $N(R_7)C(O)NR_5R_6$, $S(O)_mR_7$, $NO_2$, and YD, wherein said $C_{1-3}$ alkyl and said $C_{1-3}$ alkoxy are each optionally substituted with from 1 to 7 fluorine atoms; m, $R_5$, $R_6$, $R_7$, and $R_8$ are as previously defined;

Y is a bond, $CH_2$, $CH_2CH_2$, $C_{2-4}$ alkynylenyl, —O—, $OCH_2$, $CH_2O$, —$N(R_7)$—, —$N(R_7)CH_2$—, —$N(R_7)CONR_8$—, —$OCH_2O$— or —$OC(R_7)(CO_2R_8)$—;

D is benzyl or phenyl, each of which is optionally substituted with up to five independently selected R groups;
each R is independently selected from the group consisting of $C_{1-8}$ alkyl, $C_{1-3}$ alkoxy, halogen, —C(=O)H, —C(O)—$C_{1-3}$ alkyl, $CH_2OH$, CN, $NO_2$, $C_{2-4}$ alkenyl, $C_{2-4}$ alkynyl, $S(O)_jR_9$, and WX; wherein said $C_{1-6}$ alkyl and said $C_{1-3}$ alkoxy are each optionally substituted with from 1 to 7 fluorine atoms; and j, $R_9$, and WX are as previously defined; or D is a heterocycloalkyl, heteroarylalkyl, heteroaryl, or arylalkyl group, each of which is optionally substituted with up to four independently selected $R_a$ groups;
each $R_a$ is independently selected from the group consisting of $C_{1-8}$ alkyl, phenyl, benzyl, $C_{7-11}$ arylalkyl, $C_{1-3}$ alkoxy, halogen, —C(=O)H, —C(O)—$C_{1-3}$ alkyl, $CH_2OH$, CN, $NO_2$, $NH_2$, OH, =O, $C_{2-6}$ alkenyl, $C_{2-4}$ alkynyl, $S(O)_jR_9$, and WX; wherein said $C_{1-8}$ alkyl, said $C_{2-6}$ alkenyl, $C_{2-4}$ alkynyl and said $C_{1-3}$ alkoxy are each optionally substituted with from 1 to 7 fluorine atoms; and j, $R_9$, and WX are as previously defined.

In other embodiments, $R_2$ is phenyl substituted with up to four substituents independently selected from R, wherein R is $C_{1-3}$ alkyl, $C_{2-8}$ alkenyl, $C_{2-8}$ alkynyl, $C_{1-3}$ alkoxy, $C_{3-8}$ cycloalkyl, halogen, OH, $CH_2OH$, CN, $NR_7R_8$—, $N(R_7)C(O)NR_5R_6$, $S(O)_mR_7$, phenyl, $NO_2$, $C_{1-3}$ perfluoroalkyl, $C(O)R_7$, $OC(O)R_7$, $C(O)NR_7R_8$, $C(O)NR_7D$ and YD, providing any OH group present is not in the para position; wherein said $C_{1-3}$ alkyl and said $C_{1-3}$ alkoxy are each optionally substituted with from 1 to 5 fluorine atoms; and m, $R_5$, $R_6$, $R_7$, $R_8$, Y and D are as previously defined; or $R_2$ is phenyl substituted with an ortho or meta OH; or $R_2$ is phenyl substituted with a meta OH.

In yet further embodiments, $R_2$ is phenyl substituted with YD; e.g., where Y is a bond, $CH_2$, $CH_2CH_2$, $C_{2-4}$ alkynylenyl, —O—, $OCH_2$, $CH_2O$, —$N(R_7)$—, —$N(R_7)CH_2$—, —$N(R_7)CONR_8$—, —$OCH_2O$— or —$OC(R_7)(CO_2R_8)$. In some embodiments, $R_2$ is phenyl substituted with $C_{1-3}$ perfluoroalkyl.

D can be, for example, benzyl or phenyl, each of which is optionally substituted with up to five substituents independently selected from R, wherein R is $C_{1-6}$ alkyl, $C_{1-3}$ alkoxy, halogen, —C(=O)H, —C(O)—$C_{1-3}$ alkyl, $CH_2OH$, CN, $NO_2$, $C_{2-4}$ alkenyl, $C_{2-4}$ alkynyl, $S(O)_jR_9$, or WX; wherein said $C_{1-6}$ alkyl and said $C_{1-3}$ alkoxy are each optionally substituted with from 1 to 7 fluorine atoms; and j, $R_9$ and WX are as previously defined.

In some embodiments D is phenyl that is optionally substituted with up to four independently selected R groups; each R is independently selected from the group consisting of $C_{1-6}$ alkyl, —C(=O)H, $C_{1-3}$ acyl, $C_{1-3}$ alkoxy, halogen, $CH_2OH$, CN, $NO_2$, $C_{2-4}$ alkenyl, $C_{2-4}$ alkynyl, and WX; wherein said $C_{1-6}$ alkyl and said $C_{1-3}$ alkoxy are each optionally substituted with from 1 to 7 fluorine atoms; and WX is as previously defined.

In some embodiments D is a heterocycloalkyl or heteroaryl, each of which is optionally substituted with up to four independently selected $R_a$ groups; each $R_a$ group as defined previously.

In yet further embodiments, R or $R_a$ is $C_{1-3}$ perfluoroalkyl or $C_{1-3}$ perfluoroalkoxy.

Examples of $R_2$ are 2,4-dimethoxyphenyl, phenyl, 4-methoxy-2-methylphenyl, 2-methoxyphenyl, 4-methoxyphenyl, 2-methylphenyl, 2,4-dimethylphenyl, 1,1'-biphenyl-4-yl, 4-methoxy-3,5-dimethylphenyl, 2-naphthyl, 2-vinylphenyl, 4-methoxy-3-methylphenyl, 3-methylphenyl, 2,3-dimethylphenyl, 3-(trifluoromethyl)phenyl, 4-fluorophenyl, 3-chlorophenyl, 3-methoxyphenyl, benzaldehyde-2-yl, 2-isopropylphenyl, 2-cyclohexylphenyl, 2-benzylphenyl, 2-(1,1,2,2-tetrafluoroethoxy)phenyl, 2-chloro-5-fluorophenyl, 9H-fluoren-2-yl, 4-benzylphenyl, benzaldehyde-3-yl, 3-hydroxyphenyl, butyl, isobutyl, pentyl, cyclopentyl, 2-hydroxyphenyl, 1,3-dioxolan-2-yl, 4'-methoxy-1,1'-biphenyl-4-yl, 1,1'-biphenyl-4-ol, cyclohexanyl, 4-methoxy-2-methylphenyl, 4-methoxy-2-methylphenyl, 4-bromophenyl, 3-bromophenyl, 3-(benzyloxy)phenyl, 2-hydroxyphenyl, N-cyclohexamino, and 4-phenoxy-phenyl.

Examples of $R_3$ are phenyl optionally substituted with $C_{1-3}$ alkyl, or ZA, e.g., where Z is $CH_2$; and where A is pyridyl or phenyl, wherein said phenyl is optionally substituted with up to five independently selected $R_{18}$ groups, wherein each $R_{18}$ is independently selected from the group consisting of $C_{1-6}$ alkyl, $C_{1-3}$ alkoxy, $C_{1-3}$ perfluoroalkyl, halogen, OH, $NO_2$, and CN; wherein said $C_{1-6}$ alkyl and said $C_{1-3}$ alkoxy are each optionally substituted with from 1 to 7 fluorine atoms. In one embodiment, $R_{18}$ is $C_{1-3}$ perfluoroalkyl.

In some embodiments, A is phenyl that is optionally substituted with up to five independently selected $R_{18}$ groups, wherein each $R_{18}$ is independently selected from the group consisting of $C_{1-6}$ alkyl, $C_{1-3}$ alkoxy, halogen, OH, $NO_2$, CN, phenyl, pyrrol-1-yl, $C(O)R_{12}$, $CO_2R_{12}$, $NR_{12}R_{13}$, $C(O)NR_{12}R_{13}$, and $S(O)_nR_{12}$; wherein said $C_{1-6}$ alkyl and said $C_{1-3}$ alkoxy are each optionally substituted with from 1 to 7 fluorine atoms; and n, $R_{12}$ and $R_{13}$ are as previously defined. In other such embodiments, $R_{18}$ is $C_{1-3}$ perfluoroalkyl.

In some embodiments, $R_3$ is ZA; wherein Z is $CH_2$; and A is phenyl, wherein said phenyl is optionally substituted with up to five independently selected $R_{18}$ groups, wherein each $R_{18}$ is independently selected from the group consisting of $C_{1-6}$ alkyl, $C_{1-3}$ alkoxy, halogen, OH, $NO_2$, and CN; wherein said $C_{1-6}$ alkyl and said $C_{1-3}$ alkoxy are each optionally substituted with from 1 to 7 fluorine atoms. In other such embodiments, $R_{18}$ is $C_{1-3}$ perfluoroalkyl.

Examples of $R_3$ are 2-allyl, propyl, cyclopentyl, isobutyl, cyclohexylmethyl, 2-ethylbutyl, cyclobutyl, benzyl, 3-methoxybenzyl, 2-naphthylmethyl, 4-methylbenzyl, 2-nitrobenzyl, 2-(trifluoromethyl)benzyl, 4-bromobenzyl, 3-(difluoromethoxy)benzyl, 3-(trifluoromethoxy)benzyl, 3,5-difluorobenzyl, 3,5-dimethylbenzyl, quinolinylmethyl, 2-chloro-4-fluorobenzyl, 3-(1H-pyrrol-1-yl)benzyl, 2-bromobenzyl, 2-methylbenzyl, 5-fluoro-2-methylbenzyl, 6-chloro-2-fluoro-3-methylbenzyl, 1,1'-biphenyl-3-ylmethyl, 2-chlorobenzyl, 1-naphthylmethyl, 2,5-dichlorobenzyl, (difluoromethoxy)benzyl, 3-fluorobenzyl, 4-methylbenzyl, 2,4-dimethylbenzyl, mesitylmethyl, 2,4-dimethylbenzyl, 2-phenylethyl, 2-chloro-6-fluorobenzyl, 4-chloro-2-fluorobenzyl, 4-fluorobenzyl, 4-(methylsulfonyl)benzyl, and phenyl.

Examples of $R_4$ are H or halogen, e.g., F.

In some embodiments, the compounds of Formula (I) or (Ia) can be used in the manufacture of a medicament for treating or inhibiting atherosclerosis or atherosclerotic lesions, lowering LDL cholesterol levels, increasing HDL cholesterol levels, increasing reverse cholesterol transport, inhibiting cholesterol absorption, treating or inhibiting Alzheimer's disease or dementia, treating or inhibiting type I or type II diabetes, treating or inhibiting acute coronary syndrome or restenosis, treating multiple sclerosis, rheumatoid arthritis, inflammatory bowel disease, Crone's disease, or endometriosis, treating or inhibiting celiac or thyroiditis, treating a Th1-mediated disease, suppressing lymphocyte function or activation, suppressing macrophage function or activation, suppressing cytokine production, or increasing ABCA1 activity by 20% or more while increasing SREBP-1c activity by 25% or less, in a mammal in need thereof.

In some such embodiments, the compounds of Formula (I) or (Ia) can be used in the manufacture of a medicament for treating or inhibiting a Th1-mediated disease, for example, multiple sclerosis, rheumatoid arthritis, autoimmune thyroid disease, inflammatory bowel disease, Crohn's disease or atherosclerosis; or lymphocyte function, e.g., lymphokine production.

As used herein, the term "alkyl" includes both branched and straight-chain saturated aliphatic hydrocarbon groups (e.g., $C_1$-$C_8$; $C_1$-$C_6$) having the specified number of carbon atoms, e.g., methyl (Me), ethyl (Et), propyl (Pr), isopropyl (i-Pr), isobutyl (i-Bu), secbutyl (s-Bu), tertbutyl (t-Bu), isopentyl, isohexyl and the like. The term "alkyl" further includes both unsubstituted and mono-, di- and tri-substituted hydrocarbon groups, with halogen substitution particularly preferred. The term, "alkylenyl" refers to a divalent linking alkyl group.

The term "cycloalkyl" is intended to have its normal meaning of a cyclic alkyl group, e.g., a mono, bi-, tri-cyclic, fused, bridged or spiro saturated hydrocarbon moiety, e.g., 3-10 carbon atoms. The term "cycloalkyalkyl" is intended to denote a group of formula -alkyl-cycloalkyl, for example, a cyclopentylmethyl or cyclohexylmethyl group, where alkyl and cycloalkyl are as defined herein.

As used herein the term "alkoxy" has its normal meaning of a group of formula —O-alkyl, e.g., where alkyl is as defined herein.

As used herein, the term "alkenyl" is intended to denote alkyl groups that contain at least one double bond, e.g., 2-8 carbon atoms such as 2-7, including for example but not limited to vinyl, allyl, 2-methyl-allyl, 4-but-3-enyl, 4-hex-5-enyl, 3-methyl-but-2-enyl and the like. The term "cycloalkenyl" is intended to denote a cyclic alkyenyl such as cyclohex-2-enyl.

As used herein, the term "alkynyl" is intended to denote alkyl groups that have at least one triple carbon-carbon bond, e.g., 2-8 carbon atoms such as 2-7. Example alkynyl groups include ethynyl, propynyl, and the like. The term "alkynylenyl" refers to a divalent linking alkynyl group.

As used herein, the term "halogen" has its normal meaning of group seven elements, e.g., F, Cl, Br and I.

As used herein the term "aryl" is intended to mean an aromatic hydrocarbon system, e.g., of 6 to 20 ring carbon atoms, e.g., of 1, 2 or 3 rings, for example, phenyl, naphthyl, naphthalene, anthracene, phenanthrenyl, anthracenyl, pyrenyl and the like. Also included within the definition of aryl are aromatic systems containing one or more fused aromatic rings, for example, fluorenyl groups. Included in the definition of aryl are aromatic systems containing one or more fused saturated or partially saturated hydrocarbon rings, for example, 1,2,3,4-tetrahydronaphthalene and indan.

As used herein, the term "arylalkyl" is intended to mean a group of formula -alkyl-aryl, wherein aryl and alkyl have the definitions herein.

As used herein, the term "acyl" has its accustomed meaning as an alkanoyl group, for example a group of formula —C(O)-alkyl, e.g., —C(O)—$C_{1-3}$ alkyl.

As used herein, the term "heterocycloalkyl" is intended to mean a 5, 6, 7, 8, 9 or 10-membered non-aromatic, preferably but not necessarily, saturated, monocyclic, bicyclic or spirocyclic ring system containing up to three ring hetero atoms selected from O, N and S. Nonlimiting examples of heterocycloalkyl groups include pyrrolidine, piperidine, morpholino, imidaolidine, pyrazolidine, piperazine, pyrazoline, pyrroline, pyran, thiazoline, thiazine, and such moieties that contain spirocyclic ring sytems, for example, 1,2-dioxane groups. Heterocycloalkyl groups also can contain one or more appended alkyl groups. Also included in the definition of heterocycloalkyl are moieties that contain exocyclic heteroatoms, for example, a cycloalkyl ring having a ring carbon attached to an exocyclic O or S atom through a double bond. Further included in the definition of heterocycloalkyl are moieties having one or more aromatic rings fused (i.e., having a bond in common with) to the nonaromatic heterocyclic ring, for example, phthalimidyl, naphthalimidyl pyromellitic diimidyl, phthalanyl, 2,3-dihydrobenzofuran, and benzo derivatives of saturated heterocycles such as indoline and isoindoline groups.

The term "heteroarylalkyl" is intended to denote a group of formula -alkyl-heteroaryl.

The term "heteroaryl" is intended to denote an aryl (e.g., aromatic) group that has at least one non-carbon (i.e., "hetero") ring atom, for example, one or more ring O, N or S atoms. Nonlimiting examples of heteroaryl groups include radicals derived from furan, imidazole, tetrazole, isothiazole, isoxazole, oxathiazole, oxazole, oxazoline, pyrazole, pyrrole, thiophene, oxazine, pyrazine, pyridazine, pyridine, pyrimidine, thiadizine, thiazine, benzodioxine, benzodioxole, benzofuran, benzothiophene, dibenzothiophene, chromene, cinnoline, indazole, indole, indolene, isoindolene, indolizine, isoindole, isoindoline, isoquinoline, naphthyridine, phthalazine, purine, quinazoline, quinoline, and quinolizine.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, isopropyl, n-butyl, sec-butyl, isobutyl, etc.

As used in accordance with this invention, the term "providing," with respect to providing a compound or substance covered by this invention, means either directly administering such a compound or substance, or administering a prodrug, derivative, or analog that will form the effective amount of the compound or substance within the body. This invention also covers providing the compounds of this invention to treat the disease states disclosed herein that the compounds are useful for treating.

The compounds of the present invention can contain an asymmetric atom, and some of the compounds can contain one or more asymmetric atoms or centers, which thus, can give rise to optical isomers (enantiomers) and diastereomers. The present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of Formula (I) or (Ia) can be conveniently prepared by the procedures outlined in the schemes below from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. Although not limited to any one or several sources, classic texts such as Smith, M. B. and March, J., *March's Advanced Organic Chemistry: Reactions, Mechanisms, and Structure*, 5th ed., John Wiley & Sons: New York, 2001; and Greene, T. W. and Wuts, P. G. M. *Protective Groups in Organic Synthesis*, 3rd ed., John Wiley & Sons: New York, 1999, are useful and recognized reference textbooks of organic synthesis known to those in the art.

General Schemes for the Preparation of Compounds of Formula (I) or (Ia)

A convenient synthetic route for preparation of the compounds of formula (I) or (Ia) is presented in Scheme 1. According to Scheme 1, a benzoic acid derivative (III) is transformed into a Weinreb-amide (IV) through the corresponding acid chloride. This compound is reacted with substituted aryl magnesium bromides or aryl lithium compounds to afford ketones (V). Condensation of ketones (V) with hydrazine hydrate in pyridine provides substituted 1H-indazoles (VI), which are subsequently alkylated giving the target 2H-indazoles (I) and 1H-indazole derivatives (Ia). Both derivatives (I) and (Ia) can be further functionalized by the following schemes.

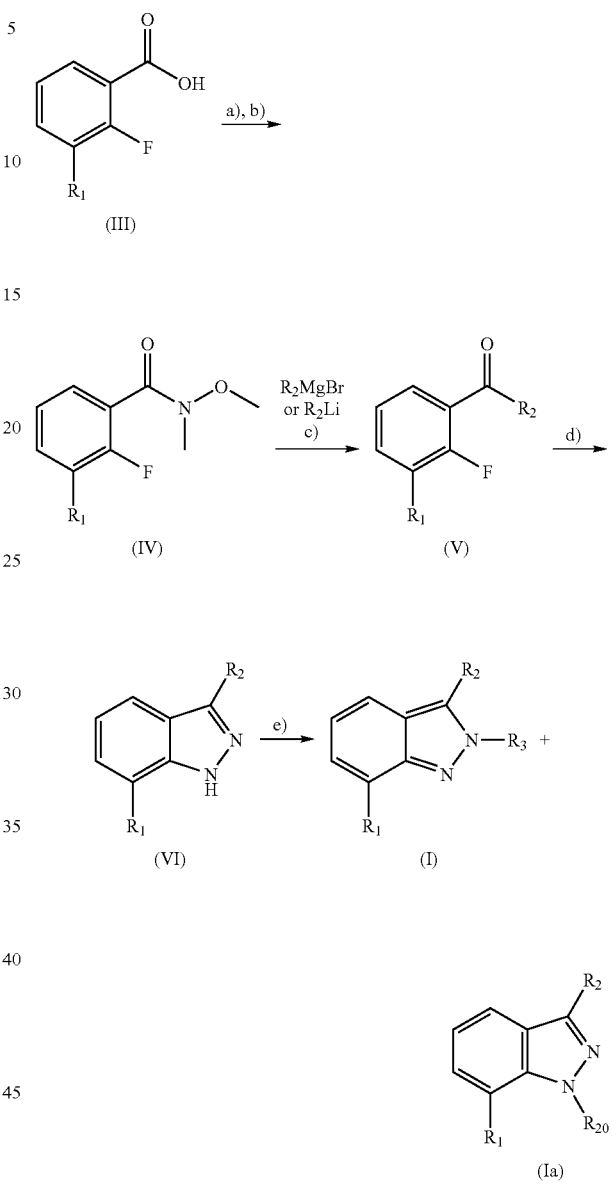

Scheme 1. Reaction conditions: a) $SOCl_2$ (solv.), reflux; b) HN(OMe)Me.HCl, pyridine, DCM, rt; c) THF, 0°-rt; d) $H_2NNH_2$ $H_2O$, DMAP, pyridine, 100° C.; e) benzyl or alkyl halide derivative, with or without base such as NaH, DMF, 120° C.

According to Scheme 2, certain compounds of Formula (I) prepared a shown in Scheme 1, containing OH moiety on the phenyl ring attached to the 3-position of the indazole system, are transformed into corresponding biaryl ethers of Formula (I) upon treatment with substituted aryl halides XPhR in the presence of cesium carbonate and CuI at 200° C. in microwave. 3-(Hydroxyphenyl) derivatives of Formula (I) also can be benzylated under similar conditions to provide phenol-benzylated compounds of Formula (I).

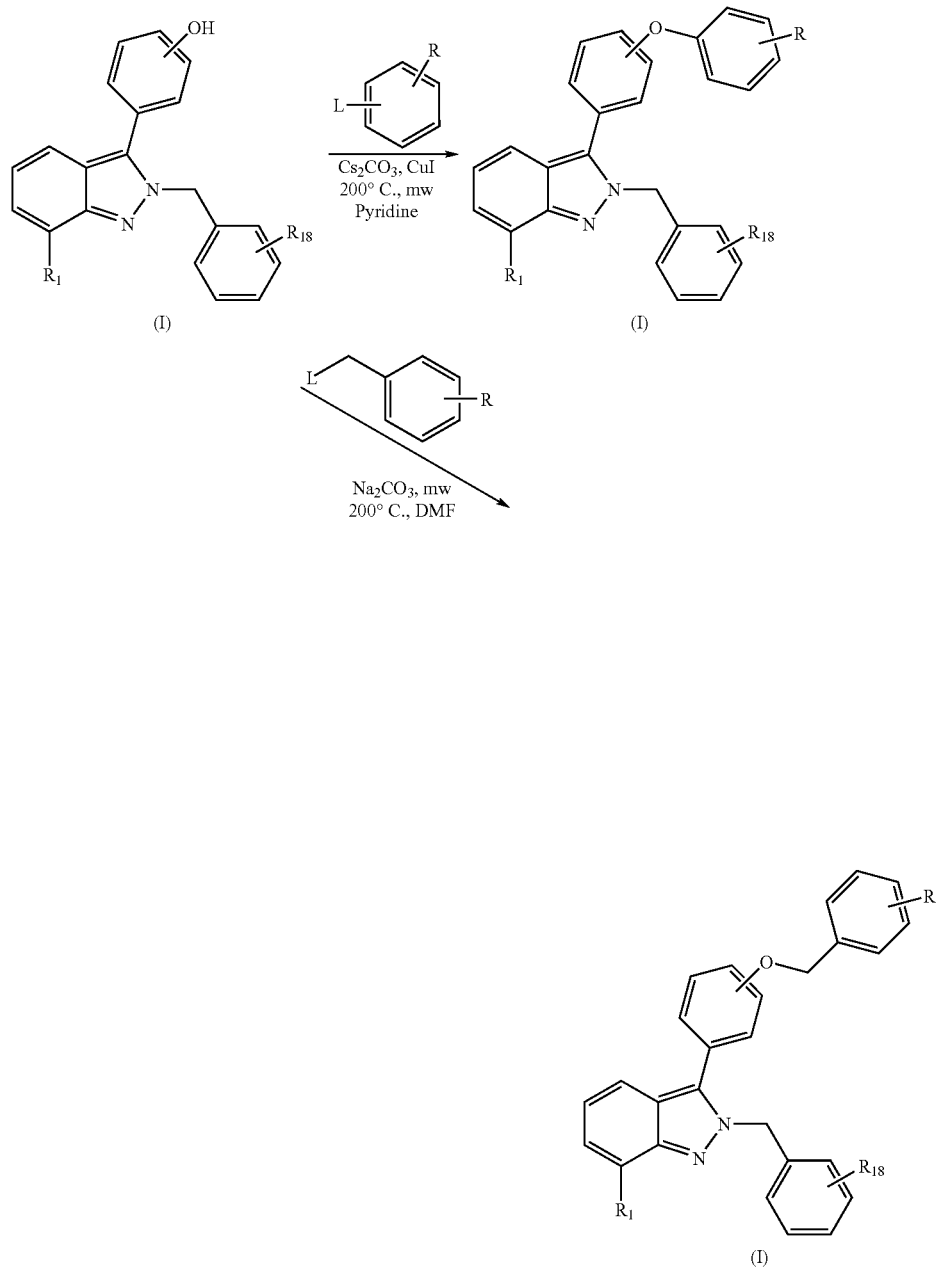

According to Scheme 1, certain compounds of Formula (I), prepared as shown in Scheme 1, may contain halogens on the phenyl ring attached to the 3-postion of the indazole. According to Scheme 3, treatment of such compounds with corresponding organozinc reagents in THF in the presence of a palladium catalyst provides benzyl derivatives of Formula (I).

Palladium catalyzed coupling of the halo-compounds of Formula (I) with substituted arylboronic acids at standard conditions provides biaryl derivatives of Formula (I). These halo-compounds also can be reacted with amines in the presence of base and palladium catalyst in toluene to afford aniline derivatives of Formula (I).

Scheme 3
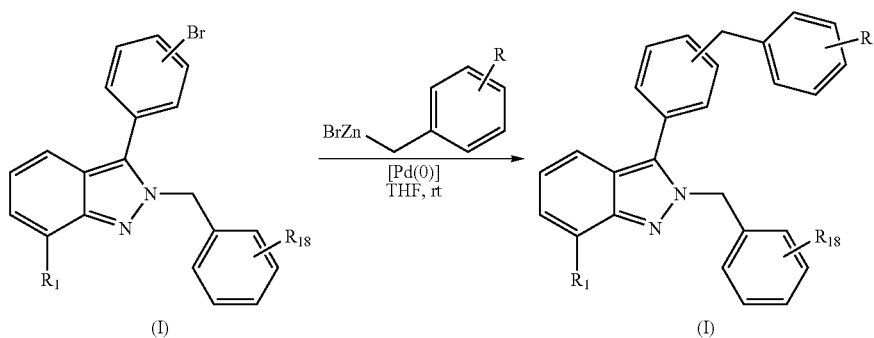
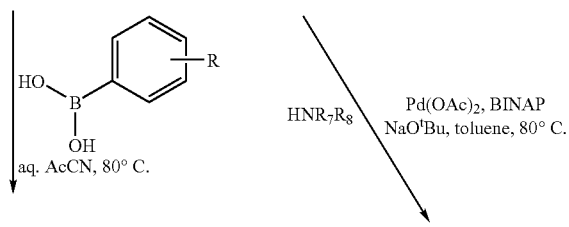
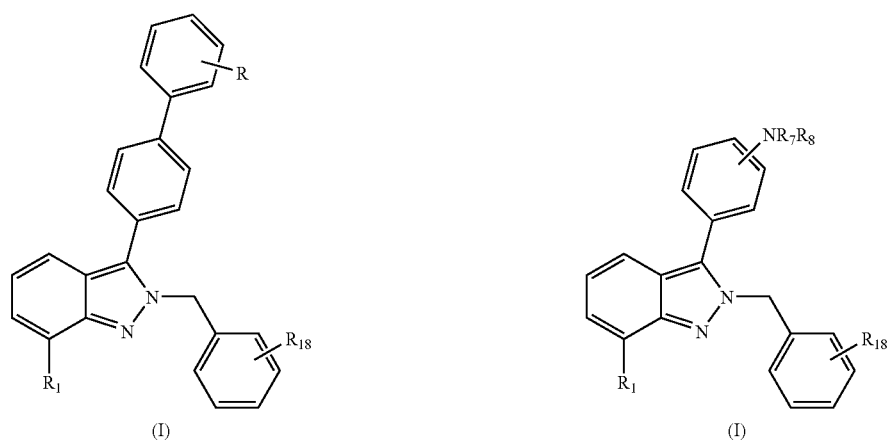

According to Scheme 4 certain compounds of Formula (I) prepared as shown in Scheme 1, containing a formyl moiety on the phenyl ring attached to the 3-postion of the indazole, can be converted to the corresponding benzyl alcohols by a standard NaBH$_4$ reduction procedure and subsequently reacted with substituted benzyl halides in the presence of NaOH to provide dibenzyl ethers of Formula (I).

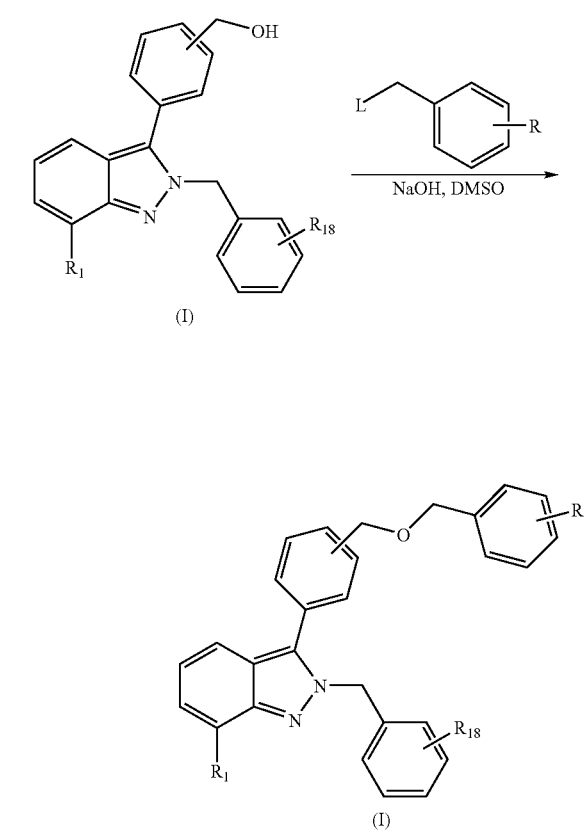

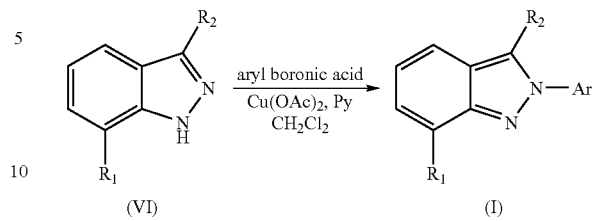

According to Scheme 5, compounds of formula (VI) can be reacted with an aryl boronic acid in the presence of a copper catalyst and suitable solvent to give compounds of Formula (I) in which the R$_3$ group is aryl.

Certain 3-amino-compounds of Formula (I) could be prepared as shown in Scheme 6. According to Scheme 6, substituted o-amino-benzoic acids (VIII) are converted to the corresponding o-azido-derivatives (IX) via standard diazotization procedure. Treatment of these compounds with thionyl chloride provides corresponding acyl chlorides, which are reacted directly with amines to afford amides of formula (X). Amides (X) undergo intramolecular cyclization when heated with thionyl chloride at 100° C. providing 3-chloroindazole derivatives of formula (XI). 3-Chloroindazoles (XI) can be reacted with amines when heated in DMSO to provide the desired 3-amino-indazoles of Formula (I).

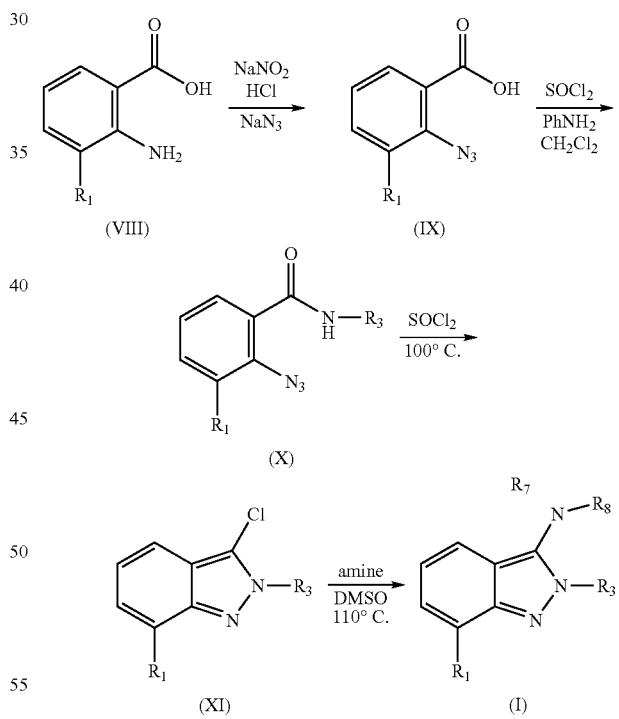

According to Scheme 7, certain compounds of Formula (I) prepared as shown in Scheme 1, containing a bromo moiety on the phenyl ring attached to the 3 position of the indazole, can be converted to the corresponding alkynes by standard Heck coupling with 1-trimethylsilyl-2-tributyltinacetylene in the presence of a palladium(0) catalyst such as palladium-(0)-tetrakis-triphenylphosphine. Subsequent functionalization with aryl iodo compounds via a Sonogashira type coupling, as described by Urganoker, S. and Verkade, J. G., *J Org Chem*

2004, 69, 5752-5755, or similar procedures as known to those skilled in the art, provide aryl alkynyl analogs of Formula (I).

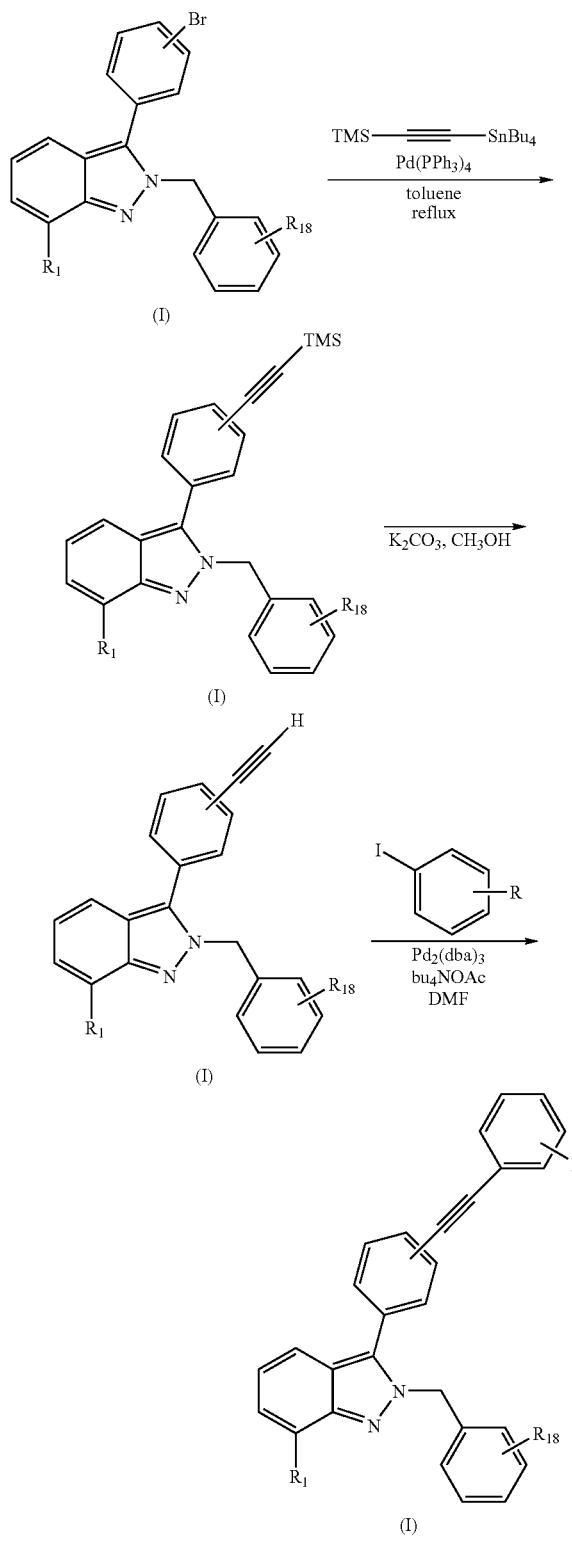

According to Scheme 8, certain compounds of Formula (I) prepared as shown in Scheme 7, containing an alkynylaryl moiety on the phenyl ring attached to the 3 position of the indazole, can be converted to the corresponding saturated analogs by atmoshpheric hydrogenation over ethylenediamine-palladium complex as described by Sajiki et al., *JOC*, 1998, 63, 7990, or by other reductions known to those skilled in the art.

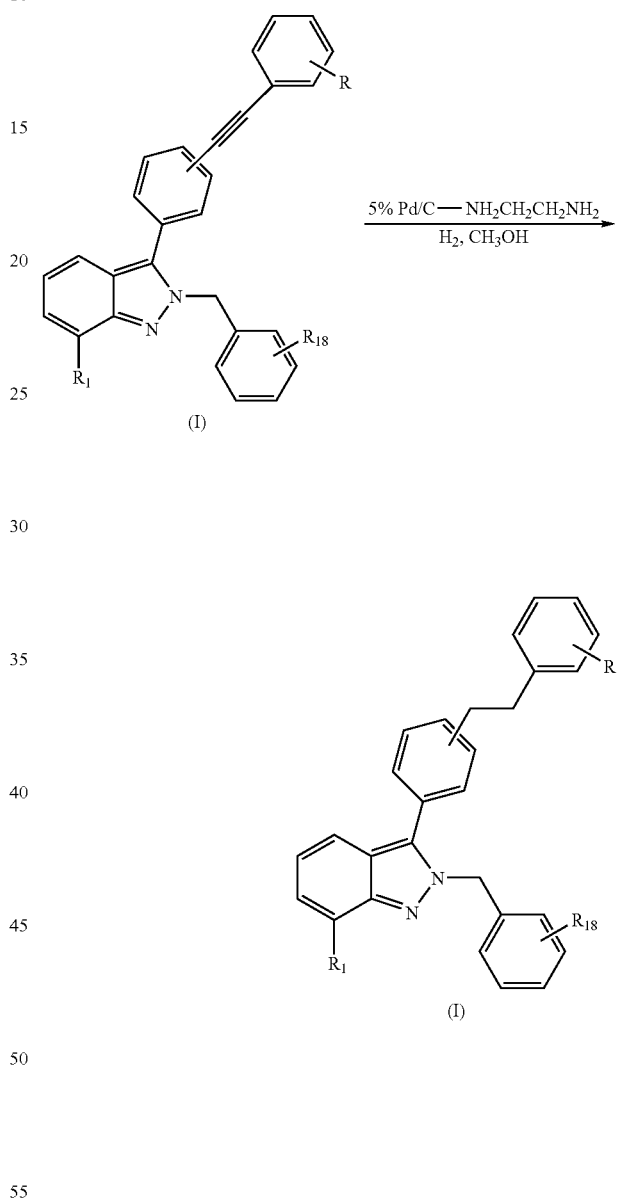

According to Scheme 9, certain compounds of formula (I) prepared as shown in Scheme 7, containing alkynylaryl moiety on the phenyl ring attached to the 3 position of the indazole, can be converted to the corresponding 2-indolyl analogs when the distal ring contains a carbamoyl moiety such as NHCOOCH$_3$. Treatment of the carbamate with tetrabutylammonium fluoride or other suitable base known to those skilled in the art provides the corresponding 2-indolyl compounds of Formula (I), which can be further alkylated at the indole nitrogen by reaction with an alkyl or arylhalide in the presence of a suitable base such as sodium hydride.

Scheme 9

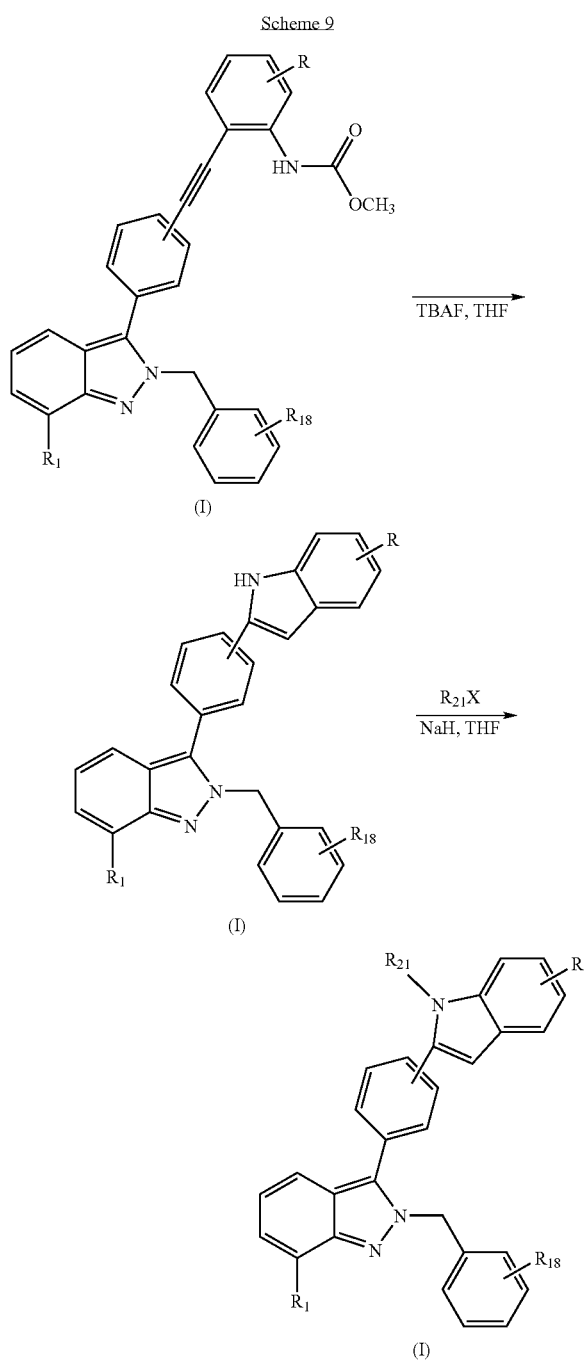

Pharmacological Test Prodcedures

Ligand-Binding Assay for Human LXRβ.

Ligand-binding to the human LXRβ can be demonstrated for the compounds of Formula (I) or (Ia) by the following procedure.

Materials and Methods:

Assay Buffer: 100 mM KCl, 100 mM TRIS (pH 7.4 at +4° C.), 8.6% glycerol, 0.1 mM PMSF*, 2 mM MTG*, 0.2% CHAPS Tracer: $^3$H T0901317

(* not used in wash buffer)

Receptor source: E. coli extract from cells expressing biotinylated hLXRβ (Extract is made in a similar buffer as above, but with 50 mM TRIS.)

Day 1

Washed streptavidin coated flash plates with wash buffer.
Diluted receptor extract to give Bmax ~4000 cpm and added to the wells.
Wrapped the plates in aluminum foil and stored them at +4° C. overnight.

Day 2

Made a dilution series in DMSO of the test ligands.
Made a 5 nM solution of the radioactive tracer in buffer.
Mixed 250 µl diluted tracer with 5 µl of the test ligand from each concentration of the dilution series.
Washed the receptor-coated flash plates.
Added 200 µl per well of the ligand/radiolabel mixture to the receptor-coated flash plates.
Wrapped the plates in aluminum foil and incubated at +4° C. overnight.

Day 3

Aspirated wells, and washed the flash plates. Sealed the plate.
Measured the remaining radioactivity in the plate.

The compounds of Formula (I) or (Ia) described herein have activity (IC50 values) in the LXRβ ligand binding assay in the range between 0.001 to 20 uM.

Quantitative Analysis of ABCA1 Gene Regulation in THP-1 Cells.

The effect of compounds of Formula (I) or (Ia) on the regulation of the ABCA1 gene can be assessed using the following procedure.

Materials and Methods:

Cell Culture.

The THP-1 monocytic cell line (ATCC # TIB-202) was obtained from American Type Culture Collection (Manassas, Va.) and cultured in RPMI 1640 medium (Gibco, Carlsbad, Calif.) containing 10% FBS, 2 mM L-glutamine, and 55 uM beta-Mercaptoethanol (BME). Cells were plated in 96-well format at a density of $7.5 \times 10^4$ in complete medium containing 50-100 ng/ml phorbal 12,13-dibutyrate (Sigma, St. Louis, Mo.) for three days to induce differentiation into adherent macrophages. Differentiated THP-1 cells were treated with test compounds or ligands dissolved in DMSO (Sigma, D-8779) in culture medium lacking phorbal ester. Final concentrations of DMSO did not exceed 0.3% of the media volume. Dose response effects were measured in duplicate, in the range of 0.001 to 30 micromolar concentrations and treated cells were incubated for an additional 24 hrs prior to RNA isolation. Unstimulated cells treated with vehicle were included as negative controls on each plate. An LXR agonist reference, TO901317, was dosed at 0.3 uM and served as a positive control.

RNA Isolation and Quantitation.

Total cellular RNA was isolated from treated cells cultured in 96-well plates using PrepStation 6100 (Applied Biosystems, Foster City, Calif.), according to the manufacturer's recommendations. RNA was resuspended in ribonuclease-free water and stored at −70° C. prior to analysis. RNA concentrations were quantitated with RiboGreen assay, #R-11490 (Molecular Probes, Eugene, Oreg.).

Gene Expression Analysis.

Gene-specific mRNA quantitation was performed by real-time PCR (RT-PCR) with the Perkin Elmer Corp. chemistry on an ABI Prism 7700 Sequence detection system (Applied Biosystems, Foster City, Calif.) according to the manufacturer's instructions. Samples (50-100 ng) of total RNA were assayed in duplicate or triplicate in 50 ul reactions using one-step RT-PCR and the standard curve method to estimate specific mRNA concentrations. Sequences of gene-specific primer and probe sets were designed with Primer Express Software (Applied Biosystems, Foster City, Calif.). The human ABCA1 primer and probe sequences are: forward, CAACATGAATGCCATTTTCCM, reverse, ATAATC-CCCTGAACCCAAGGA, and probe, 6FAM-TAAAGC-CATGCCCTCTGCAGGAACA-TAMRA. RT and PCR reactions were performed according to PE Applied Biosystem's protocol for Taqman Gold RT-PCR. Relative levels of ABCA1 mRNA are normalized using GAPDH mRNA or 18S rRNA probe/primer sets purchased commercially (Applied Biosystems, Foster City, Calif.).

Statistics:

Mean, standard deviation and statistical significance of duplicate evaluations of RNA samples were assessed using ANOVA, one-way analysis of variance, using SAS analysis.

Reagents:
GAPDH Probe and Primers—Taqman GAPDH Control Reagents 402869 or 4310884E
18S Ribosomal RNA—Taqman 18S Control Reagents 4308329
10 Pack Taqman PCR Core Reagent Kit 402930

The compounds of Formula (I) or (Ia) described herein upregulate the transcription of the ABCA1 gene in THP-1 cells (EC50 value) in a range between 0.001 to 15 uM with efficacy values in the range of 20 to 250% when compared to the efficacy shown by 0.3 uM of reference standard T0901317.

Based on the results obtained in the standard pharmacological test procedures, the compounds of this invention are useful in treating or inhibiting LXR mediated diseases. In particular, the compounds of this invention are useful in the treatment and inhibition of atherosclerosis and atherosclerotic lesions, lowering LDL cholesterol levels, increasing HDL cholesterol levels, increasing reverse cholesterol transport, inhibiting cholesterol absorption, treatment or inhibition of Alzheimer's disease, type I diabetes, type II diabetes, multiple sclerosis, rheumatoid arthritis, acute coronary syndrome, restenosis, inflammatory bowel disease (IBD), Crohn's disease, endometriosis, celiac, and thyroiditis.

It is understood that the effective dosage of the active compounds of this invention may vary depending upon the particular compound utilized, the mode of administration, the condition being treated and severity thereof, as well as the various physical factors related to the individual being treated. It is projected that compounds of this invention will be administered at an oral daily dosage of from about 0.05 mg to about 30 mg per kilogram of body weight, preferably administered in divided doses two to six times per day, or in a sustained release form, and may be adjusted to provide the optimal therapeutic result.

The compounds of this invention, as a pharmaceutical composition, can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which also may act as a flavoring agent, sweetening agent, lubricant, solubilizer, suspending agent, filler, glidant, compression aid, binder, or tablet-disintegrating agent; it also can be an encapsulating material. In powders, the carrier is a finely divided solid that is in admixture with the finely divided active ingredient.

Solid dosage unit forms or compositions such as tablets, troches, pills, capsules, powders, and the like, may contain a solid carrier binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose, or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both.

Liquid carriers are used in preparing liquid dosage forms such as solutions, suspensions, dispersions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid carriers for oral and parenteral administration include water (partially containing additives as above, e.g., cellulose derivatives, preferably, sodium carboxymethyl cellulose solution); alcohols, including monohydric alcohols such as ethanol and polyhydric alcohols such as glycols and their derivatives; lethicins; and oils such as fractionated coconut oil and arachis oil. For parenteral administration, the liquid carrier also can be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant.

A liquid pharmaceutical composition such as a syrup or elixir may contain, in addition to one or more liquid carriers and the active ingredients, a sweetening agent such as sucrose, preservatives such as methyl and propyl parabens, a pharmaceutically acceptable dye or coloring agent, or a flavoring agent such as cherry or orange flavoring.

Liquid pharmaceutical compositions that are sterile solutions or suspensions can be administered intraocularly or parenterally, for example, by intramuscular, intraperitoneal or subcutaneous injection. Sterile solutions also can be administered intravenously. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under the conditions of manufacture and storage and must be preserved against the contaminating action of microorganisms such as bacteria and fungi. The carrier can be a solvent or dispersion medium containing a liquid carrier, for example, water, ethanol, polyol (e.g., glycerol, propylene glycol and liquid polyethylene glycol), suitable mixtures thereof, and vegetable oils. The liquid carrier may be suitably mixed with a surfactant such as hydroxypropylcellulose.

The compounds of the present invention also may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may be administered topically, or also transdermally through the use of a transdermal patch containing the active compound and a carrier that is inert to the active compound, which is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient also may be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

EXAMPLES

The following describes the preparation of representative compounds of this invention. Compounds described as homogeneous were determined to be 98% or greater a single peak (exclusive of enantiomers) by analytical reverse phase chromatographic analysis with 254 nM UV detection. Melting points are reported as uncorrected in degrees centigrade. The infrared data is reported as wave numbers at maximum absorption, $v_{max}$, in reciprocal centimeters, $cm^{-1}$. Mass spectral data is reported as the mass-to-charge ratio, m/z; and for high resolution mass spectral data, the calculated and experimentally found masses, $[M+H]^+$, for the neutral formulae M are reported. Nuclear magnetic resonance data is reported as δ in parts per million (ppm) downfield from the standard, tetramethylsilane, along with the solvent, nucleus, and field strength parameters. The spin-spin homonuclear coupling constants are reported as J values in hertz; and the multiplicities are reported as: s, singlet; d, doublet; t, triplet; q, quartet; quintet; or br, broadened.

Preparation of Compounds of Formula (I) or (Ia)

All compound numbers in this section refer to the Schemes above.

Example 1

2-BENZYL-3-(4-METHOXYPHENYL)-7-TRIFLUOROMETHYL-2H-INDAZOLE

Preparation of 2-fluoro-N-methoxy-N-methyl-3-trifluoromethyl-benzamide (compound of formula (IV))

1.04 g (5 mmol) of 2-fluoro-3-(trifluoromethyl)benzoic acid (compound of formula (III)) 3 ml of $SOCl_2$ were dissolved and the mixture was refluxed for 2 hrs. Remaining $SOCl_2$ was removed in vacuo and the residue (crude acid chloride derivative) was dissolved in 5 ml of $CH_2Cl_2$. N,O-Dimethyhydroxylamine hydrochloride (585 mg, 6 mmol) in 8 ml of $CH_2Cl_2$ was added followed by 0.5 ml of pyridine. The reaction mixture was stirred for 1.5 hrs., quenched with aq. $NH_4Cl$ solution and the product was extracted twice with $CH_2Cl_2$, and the combined organic phases were washed with brine and dried over sodium sulfate. Evaporation of solvents in vacuo gave 1.02 g of product as an oil which was pure enough to be used in the next step without further purification.

($CDCl_3$) δ=7.68 (t, 1H), 7.62 (t, 1H), 7.30 (t, 1H), 3.52 (s, br, 3H), 3.35 (s, br, 3H).

LCMS: M+H: 252.3.

Preparation of (2-fluoro-3-trifluoromethyl-phenyl)-(4-methoxy-phenyl)-methanone (compound of formula (V))

1 milliliter of a 1M THF solution of 4-methoxyphenylmagnesium bromide (1 mmol) was added to a solution of 126 mg (0.5 mmol) of 2-fluoro-N-methoxy-N-methyl-3-trifluoromethyl-benzamide in 2 ml of THF at 0° C. The reaction mixture was stirred for 2 hrs. at this temperature and then quenched with saturated $NH_4Cl$ solution and the phases were separated. The aqueous phase was extracted twice with $CH_2Cl_2$ and the combined organic phases were washed with brine and dried over $Na_2SO_4$. The resulting ketone (135 mg) was obtained after flash chromatographic purification using 5% EtOAc in heptane as an eluent.

($CDCl_3$) δ=7.80 (d, 2H), 7.77 (t, 1H), 7.67 (t, 1H), 7.36 (t, 1H), 6.95 (d, 2H), 3.86 (s, 3H).

GC, M/Z: 298.0.

Preparation of 3-(4-methoxy-phenyl)-7-trifluoromethyl-1H-indazole (compound of formula (VI))

(2-Fluoro-3-trifluoromethyl-phenyl)-(4-methoxy-phenyl)-methanone (59.6 mg, 0.2 mmol) was dissolved in 1 ml of pyridine. Hydrazine hydrate (97 μl, 2 mmol) and 4-(dimethylamino)-pyridine (24.4 mg, 0.2 mmol) were added. The reaction mixture was stirred overnight at 100° C. After cooling to room temperature, EtOAc and 1M HCl were added. The organic phase was washed three times with brine, dried over MgSO4 and concentrated under vacuum. Purification of the crude product by flash column chromatography on silica gel (n-heptane/ethyl acetate, 85:15) afforded 56 mg of the analytically pure product.

($CDCl_3$), δ=9.65 (s, br, 1H), 8.18 (d, 1H), 7.89 (d, 2H), 7.68 (d, 1H), 7.21 (t, 1H), 7.07 (d, 2H), 3.89 (s, 3H).

LCMS: M+H: 293.2.

Preparation of 2-benzyl-3-(4-methoxy-phenyl)-7-trifluoromethyl-2H-indazole (compound of Formula (I))

To a solution of 3-(4-methoxy-phenyl)-7-trifluoromethyl-1H-indazole (59 mg, 0.2 mmol) in 0.5 ml DMF were added 72 μl of benzyl bromide (0.6 mmol). The reaction mixture was heated overnight at 120° C. After cooling to room temperature, ethyl acetate was added and the solution was washed three times with brine. The organic layer was dried over $MgSO_4$ and concentrated. Column chromatography (n-heptane/ethyl acetate, 70:30 as eluent) afforded 61 mg of pure product.

($CDCl_3$) δ=7.61 (s, 1H), 7.54 (d, 1H), 7.10-7.20 (m, 5H), 7.02-6.95 (m, 3H), 6.93-6.87 (m, 2H), 5.56 (s, 2H), 3.76 (s, 3H).

LCMS: M+H: 383.2.

Example 2

4-[4-2-BENZYL-7-TRIFLUOROMETHYL-2H-INDAZOL-3-YL)-PHENOXYMETHYL]-BENZOIC ACID

Preparation of 4-(2-benzyl-7-trifluoromethyl-2H-indazol-3-yl)-phenol

2-Benzyl-3-(4-methoxy-phenyl)-7-trifluoromethyl-2H-indazole (38 mg, 0.1 mmol) was dissolved in 2 ml of dry dichloromethane and cooled to −78° C. $BF_3.SMe_2$ was added (1 ml of 1M solution in $CH_2Cl_2$, 1 mmol) and the reaction mixture was allowed to reach room temperature overnight. The reaction mixture was quenched with MeOH followed by the addition of 2M HCl. The product was extracted with $CH_2Cl_2$ and purified by column chromatography on silica (n-heptane/ethyl acetate, 50:50, as eluent). Yield: 32 mg.

(acetone) δ=8.84 (s, br, 1H), 7.80 (d, 1H), 7.67 (d, 1H), 7.40-7.35 (m, 2H), 7.31-7.21 (m, 3H), 7.17 (t, 1H), 7.12 (d, 2H), 7.06-7.01 (m, 2H), 5.71 (s, 2H).

LCMS: M+H: 369.2; M−H: 367.0.

Preparation of 4-[4-(2-benzyl-7-trifluoromethyl-2H-indazol-3-yl)-phenoxymethyl]-benzoic acid methyl ester 4-(2-Benzyl-7-trifluoromethyl-2H-indazol-3-yl)-phenol (180 mg, 0.5 mmol) and potassium carbonate (138 mg, 1.0 mmol) were dissolved in 3 ml of dry DMF and 4-bromomethyl-benzoic acid methyl ester (230 mg, 1.0 mmol) was added. The reaction mixture was run in microwave (Emory's Optimizer, Personal Chemistry) at 200° C. for 30 min. After cooling to room temperature, the reaction mixture was diluted with 1 M HCl (aq.) and the product was extracted three times with $CH_2Cl_2$; and after evaporation of the solvent, it was purified with preparative HPLC using a gradient with acidic mobile phase on an ACE-C8 column to afford 140 mg of analytically pure product.

LCMS: M+H: 517.4.

Rf: 6.68 min (20-100% $CH_3CN$ in 10 min in 0.05% HCOOH in water on an ACE 5 C8 column).

Preparation of 4-[4-(2-benzyl-7-trifluoromethyl-2H-indazol-3-yl)-phenoxymethyl]-benzoic acid 4-[4-(2-Benzyl-7-trifluoromethyl-2H-indazol-3-yl)-phenoxymethyl]-benzoic acid methyl ester (50 mg, 0.1 mmol) was dissolved in 1 ml of methanol, and 24 mg of LiOH (10 eq) were added. The reaction mixture was stirred at 70° C. overnight. After cooling to room temperature, 1M HCl-solution and dichloromethane were added, and the phases were separated. The resulting acid was obtained by standard flash chromatographic purification (43 mg).

(DMSO) δ=7.98 (d, 2H), 7.81 (d, 1H), 7.73 (d, 1H), 7.60 (d, 2H), 7.50 (d, 2H), 7.30-7.18 (m, 6H), 7.00 (d, 2H), 5.72 (s, 2H), 5.29 (s, 2H).

LCMS: M+H: 503.3; M−H: 501.2.

Example 3

4-[4-(2-BENZYL-7-TRIFLUOROMETHYL-2H-INDAZOL-3-YL)-PHENOXY]-BENZOIC ACID

Preparation of 4-[4-(2-benzyl-7-trifluoromethyl-2H-indazol-3-yl)-phenoxy]-benzoic acid methyl ester 4-(2-Benzyl-7-trifluoromethyl-2H-indazol-3-yl)-phenol (180 mg, 0.5 mmol), cesium carbonate (490 mg, 1.5 mmol), CuI (20 mg, 0.1 mmol) and 4-bromo-benzoic acid methyl ester (215 mg, 1.0 mmol) were dissolved in 3 ml of dry pyridine. The reaction mixture was run in microwave (Emory's Optimizer, Personal Chemistry) at 200° C. for 30 min. After cooling to room temperature, the reaction mixture was diluted with 1 M HCl (aq.) and the product extracted three times with $CH_2Cl_2$. Combined organic phases were dried and evaporated, and the crude material was purified with preparative HPLC using a gradient with an acidic mobile phase on an ACE-C8 column to afford 151 mg of analytically pure product.

($CDCl_3$) δ=8.07 (d, 2H), 7.82 (d, 1H), 7.71 (d, 1H), 7.49 (d, 2H), 7.24 (m, 6H), 7.11 (d, 2H), 7.02 (d, 2H), 5.77 (s, 2H).

LCMS: M+H: 489.5, 2M+H: 977.9, M−H: 487.4, 2M−H: 975.5.

Preparation of 4-[4-(2-benzyl-7-trifluoromethyl-2H-indazol-3-yl)-phenoxy]-benzoic acid This compound was prepared from 4-[4-(2-benzyl-7-trifluoromethyl-2H-indazol-3-yl)-phenoxy]-benzoic acid methyl ester in a way described for the preparation of 4-[4-(2-benzyl-7-trifluoromethyl-2H-indazol-3-yl)-phenoxymethyl]-benzoic acid (Example 2).

($CDCl_3$) δ=8.07 (d, 2H), 7.82 (d, 1H), 7.71 (d, 1H), 7.49 (d, 2H), 7.29-7.19 (m, 6H), 7.11 (d, 2H), 7.02 (d, 2H), 5.77 (s, 2H).

LCMS: M+H: 489.5, 2M+H: 977.9; M−H: 487.4, 2M−H: 975.5.

Example 4

[4-(2-BENZYL-7-TRIFLUOROMETHYL-2H-INDAZOL-3-YL)-PHENYL]-PHENYL-AMINE

2-Benzyl-3-(4-bromo-phenyl)-7-trifluoromethyl-2H-indazole (compound of Formula (I) was prepared similar to Example 1 using 4-bromophenyl lithium instead of a Grignard reagent. This compound (43 mg, 0.1 mmol) along with aniline (11 μl, 0.12 mmol), palladium(II) acetate (0.3 mg, 0.001 mmol) and BINAP (1 mg, 0.0015 mmol) was dissolved in 0.5 ml of toluene and the reaction mixture was stirred at room temperature for 10 min. A solution of 13.5 mg of NaO$^t$Bu (0.14 mmol) in 0.5 ml of toluene was added and the reaction mixture was stirred overnight at 80° C. Saturated $NH_4Cl$-solution and dichloromethane were added, and the phases were separated. The resulting product was obtained after flash chromatographic purification using n-heptane/ethyl acetate, 80:20, as eluent. Yield: 27 mg.

($CDCl_3$) δ=7.67 (d, 1H), 7.55 (d, 1H), 7.24 (t, 2H), 7.20-6.99 (m, 12H), 6.98-6.91 (m, 1H), 5.61 (s, 2H).

LCMS: M+H: 444.8; M−H: 442.7.

Example 5

3-[4-(2-BENZYL-7-TRIFLUOROMETHYL-2H-INDAZOL-3-YL)-BENZYL]-BENZOIC ACID METHYL ESTER

2-Benzyl-3-(4-bromo-phenyl)-7-trifluoromethyl-2H-indazole (43 mg, 0.1 mmol) and 4 mg of bis[triphenylphosphine]palladium(II) chloride were dissolved in THF. After 5 minutes, 0.4 ml of a 0.5M solution of 3-(methoxycarbonyl)-benzylzinc bromide in THF (0.2 mmol) were added and the reaction mixture was stirred at room temperature overnight. 1M HCl-solution and dichloromethane were added, and the phases were separated. The resulting product was obtained after flash chromatographic purification using n-heptane/ethyl acetate, 90:10, as eluent. Yield: 47 mg.

(CDCl$_3$) δ=7.88 (s, 1H), 7.85 (d, 1H), 7.61 (d, 1H), 7.52 (d, 1H), 7.28-7.37 (m, 2H), 7.25-7.18 (m, 4H), 7.16-7.11 (m, 3H), 7.02-6.95 (m, 3H), 5.58 (s, 2H), 4.02 (s, 2H), 3.83 (s, 3H).

LCMS: M+H: 501.5.

Example 6

4'-(2-BENZYL-7-TRIFLUOROMETHYL-2H-INDAZOL-3-YL)-BI PHENYL-4-CARBOXYLIC ACID

To a degassed solution of 2-benzyl-3-(4-bromo-phenyl)-7-trifluoromethyl-2H-indazole (22 mg, 0.05 mmol), 8 mg of boronic acid (0.05 mmol) and 21 mg of Na$_2$CO$_3$ (0.2 mmol) in 1 ml of MeCN/water (1:1) mixture, bis-(tri-phenylphosphine)-palladium(II)-chloride was added. The mixture was stirred for 18 hrs. at 80° C. Saturated NH$_4$Cl-solution and dichloromethane were added, and the phases were separated. The resulting product was obtained after flash chromatographic purification using n-heptane/ethyl acetate, 50:50, as eluant. Yield: 18 mg.

(acetone) δ=8.22 (d, 2H), 8.01 (d, 2H), 7.98-7.92 (m, 3H), 7.80-7.73 (m, 3H), 7.36-7.26 (m, 4H), 7.23-7.18 (m, 2H), 5.86 (s, 2H).

LCMS: M+H: 473.3; M−H: 471.5.

Example 7

4-[3-(2-BENZYL-7-TRIFLUOROMETHYL-2H-INDAZOL-3-YL)-BENZYLOXYMETHYL]-BENZOIC ACID

Preparation of [3-(2-benzyl-7-trifluoromethyl-2H-indazol-3-yl)-phenyl]-methanol

To a solution of 116 mg (0.305 mmol) of 3-[2-benzyl-7-(trifluoromethyl)-2H-indazol-3-yl]benzaldehyde (compound of Formula (I)), prepared in a same way as Example 1, in 2 ml of methanol, 23 mg (0.71 mmol) of NaBH$_4$ was added at 0° C. The reaction mixture was stirred at this temperature for 1 hr. Saturated NH$_4$Cl-solution and dichloromethane were added, and the phases were separated. The product was obtained after flash chromatographic purification using dichloromethane as eluant. Yield: 111 mg.

(CDCl$_3$) δ=7.61 (m, 2H), 7.39 (m, 2H), 7.23 (m, 6H), 7.02 (m, 3H), 5.59 (s, 2H), 4.64 (s, 2H), 2.05 (s, br, 1H).

LCMS: M+H: 383.3.

Preparation of 4-[3-(2-benzyl-7-trifluoromethyl-2H-indazol-3-yl)-benzyloxymethyl]-benzoic acid methyl ester

[3-(2-Benzyl-7-trifluoromethyl-2H-indazol-3-yl)-phenyl]-methanol (40 mg, 0.105 mmol) was dissolved in 1 ml of DMSO, and 30 mg of KOH were added. The reaction mixture was stirred at room temperature for 30 min. 4-Bromomethyl-benzoic acid methyl ester (96 mg, 0.42 mmol) was added and the reaction mixture stirred overnight at room temperature. Fifteen (15) volumes of water were added and the precipitate was collected. The product was obtained after flash chromatographic purification using dichloromethane as eluent. Yield: 33 mg.

LCMS: M+H: 531.5

Rf: 6.33 min (20-100% CH$_3$CN in 10 min in 0.05% HCOOH in water on an ACE 5 C8 column).

Preparation of 4-[3-(2-benzyl-7-trifluoromethyl-2H-indazol-3-yl)-benzyloxymethyl]-benzoic acid This compound was prepared from 4-[3-(2-benzyl-7-trifluoromethyl-2H-indazol-3-yl)-benzyloxymethyl]-benzoic acid methyl ester in the same manner described for the preparation of 4-[4-(2-benzyl-7-trifluoromethyl-2H-indazol-3-yl)-phenoxymethyl]-benzoic acid (Example 2).

(MeOD) δ=8.00 (d, 2H), 7.76 (d, 1H), 7.70 (d, 1H), 7.58-7.53 (m, 2H), 7.47-7.38 (m, 4H), 7.25-7.16 (m, 4H), 7.05-6.99 (m, 2H), 5.71 (s, 2H), 4.62 (s, 4H).

LCMS: M+H: 517.4; M−H: 515.3.

Example 8

2-BENZYL-3-PHENYL-7-METHYL-2H-INDAZOLE

This compound was prepared similarly to that of Example 1.

(CDCl$_3$) δ=7.49-7.42 (m, 3H), 7.15-7.08 (m, 7H), 7.02-6.97 (m, 2H), 6.92-6.87 (m, 1H), 4.27 (s, 2H), 2.78 (s, 3H).

LCMS: M+H: 299.6.

Example 9

2-BENZYL-3-(4-PHENOXYPHENYL)-7-TRIFLUOROMETHYL-2H-INDAZOLE

This compound was prepared similarly to that of Example 1.

(CDCl$_3$) δ=7.64 (d, 1H), 7.57 (d, 1H), 7.32 (t, 2H), 7.18 (m, 5H), 7.10 (t, 1H), 7.01 (m, 7H), 5.60 (s, 2H).

LCMS: M+H: 445.4.

Example 10

3-[4-(2-BENZYL-7-TRIFLUOROMETHYL-2H-INDAZOL-3-YL)-PHENOXY]-BENZOIC ACID

This compound was prepared similarly to that of Example 3.

(CDCl$_3$) δ=7.85 (d, 2H), 7.81 (d, 1H), 7.73-7.67 (m, 2H), 7.53 (t, 1H), 7.45 (d, 2H), 7.36-7.31 (m, 1H), 7.29-7.14 (m, 6H), 7.02 (d, 2H), 5.75 (s, 2H).

LCMS: M+H: 489.5, 2M+H: 977.6; M−H: 487.4, 2M−H: 975.5.

Example 11

{4-[4-(2-BENZYL-7-TRIFLUOROMETHYL-2H-INDAZOL-3-YL)-PHENOXY]-PHENOXY}-ACETIC ACID

This compound was prepared similarly to that of Example 3.

(CDCl$_3$) δ=7.72 (d, 1H), 7.65 (d, 1H), 7.26 (m, 6H), 7.07 (m, 7H), 6.96 (d, 2H), 5.69 (s, 2H), 4.68 (s, 2H).

LCMS: M+H: 519.5, M−H: 517.4.

Example 12

{4-[4-(2-BENZYL-7-TRIFLUOROMETHYL-2H-INDAZOL-3-YL)-PHENOXYMETHYL]-PHENOXY}-ACETIC ACID

This compound was prepared similarly to that of Example 2.

(CDCl$_3$) δ=7.63 (d, 1H), 7.57 (d, 1H), 7.31 (d, 2H), 7.18 (m, 5H), 6.99 (m, 5H), 6.89 (d, 2H), 5.59 (s, 2H), 4.98 (s, 2H), 4.60 (s, 2H).

LCMS: M+H: 533.3, M−H: 531.2.

Example 13

{3-[4-(2-BENZYL-7-TRIFLUOROMETHYL-2H-INDAZOL-3-YL)-PHENOXYMETHYL]-PHENOXY}-ACETIC ACID

This compound was prepared similarly to that of Example 2.

(CDCl$_3$) δ=7.63 (d, 1H), 7.57 (d, 1H), 7.26 (t, 1H), 7.21-7.14 (m, 5H), 7.04-6.95 (m, 7H), 6.80 (d, 1H), 5.60 (s, 2H), 5.03 (s, 2H), 4.60 (s, 2H).

LCMS: +H, 533.3; M−H: 531.2.

Example 14

{3-[4-(2-BENZYL-7-TRIFLUOROMETHYL-2H-INDAZOL-3-YL)-PHENOXYMETHYL]-PHENYL}-ACETIC ACID

This compound was prepared similarly to that of Example 2.

(MeOD) δ=7.84 (d, 1H), 7.77 (d, 1H), 7.51 (d, 2H), 7.46-7.40 (m, 4H), 7.35-7.30 (m, 3H), 7.28-7.19 (m, 3H), 7.10-7.06 (m, 2H), 5.78 (s, 2H), 5.24 (s, 2H), 3.71 (s, 2H).

LCMS: M+H: 517.4; M−H: 515.3.

Example 15

3-[4-(2-BENZYL-7-TRIFLUOROMETHYL-2H-INDAZOL-3-YL)-PHENOXYMETHYL]-BENZOIC ACID

This compound was prepared similarly to that of Example 2.

(MeOD) δ=8.04 (s, 1H), 7.89 (d, 1H), 7.64 (d, 1H), 7.58 (t, 2H), 7.40 (t, 1H), 7.24 (d, 2H), 7.15-7.09 (m, 3H), 7.07-7.03 (m, 3H), 6.91-6.86 (m, 2H), 5.78 (s, 2H), 5.12 (s, 2H).

LCMS: M+H: 503.3; M−H: 501.2.

Example 16

{4-[3-(2-BENZYL-7-TRIFLUOROMETHYL-2H-INDAZOL-3-YL)-BENZYLOXYMETHYL]-PHENOXY}-ACETIC ACID

This compound was prepared similarly to that of Example 7.

(CDCl$_3$) δ=7.71 (d, 1H), 7.65 (d, 1H), 7.47 (d, 2H), 7.34 (s, 1H), 7.31-7.25 (m, 2H), 7.24-7.20 (m, 3H), 7.14-7.06 (m, 3H), 6.90 (d, 2H), 5.67 (s, 2H), 4.65 (s, 2H), 4.54 (s, 2H), 4.50 (s, 2H).

LCMS: M+H: 547.4; M−H: 545.3.

Example 17

{3-[3-(2-BENZYL-7-TRIFLUOROMETHYL-2H-INDAZOL-3-YL)-BENZYLOXYMETHYL]-PHENOXY}-ACETIC ACID

This compound was prepared similarly to that of Example 7.

(CDCl$_3$) δ=7.71 (d, 1H), 7.65 (d, 1H), 7.50-7.46 (m, 2H), 7.36 (s, 1H), 7.31-7.27 (m, 1H), 7.24-7.20 (m, 3H), 7.14-7.06 (m, 3H), 6.96 (t, 2H), 6.84 (d, 1H), 5.68 (s, 2H), 4.64 (s, 2H), 4.56 (s, 2H), 4.54 (s, 2H).

LCMS: M+H: 547.7; M−H: 545.3.

Example 18

3-[3-(2-BENZYL-7-TRIFLUOROMETHYL-2H-INDAZOL-3-YL)-BENZYLOXYMETHYL]-BENZOIC ACID

This compound was prepared similarly to that of Example 7.

(MeOD) δ=8.01 (s, 1H), 7.94 (d, 1H), 7.75 (d, 1H), 7.68 (d, 1H), 7.56-7.50 (m, 3H), 7.45-7.40 (m, 2H), 7.39-7.35 (m, 1H), 7.22-7.14 (m, 4H), 6.99 (d, 2H), 5.70 (s, 2H), 4.59 (d, 4H).

LCMS: M+H: 517.4; M−H: 515.3.

Example 19

2-BENZYL-3-(4-METHOXY-2-METHYLPHENYL)-7-TRIFLUOROMETHYL-2H-INDAZOLE

This compound was prepared similarly to that of Example 1.

(CDCl$_3$) δ=7.64 (d, 1H), 7.50 (d, 1H), 7.24-7.16 (m, 3H), 7.10-7.00 (m, 4H), 6.88-6.82 (m, 2H), 5.55 (d, 1H), 5.47 (d, 1H), 3.89 (s, 3H), 1.79 (s, 3H).

LCMS: M+H: 397.2.

Example 20

2-BENZYL-3-(2-METHOXYPHENYL)-7-TRIFLUOROMETHYL-2H-INDAZOLE

This compound was prepared similarly to that of Example 1.

(CDCl$_3$) δ=7.67-7.60 (m, 2H), 7.50 (dt, 1H), 7.23-7.14 (m, 4H), 7.10-6.98 (m, 5H), 5.66 (d, 1H), 5.56 (d, 1H), 3.63 (s, 3H).

LCMS: M+H: 383.2.

Example 21

2-BENZYL-3-O-TOLYL-7-TRIFLUOROMETHYL-2H-INDAZOLE

This compound was prepared similarly to that of Example 1.

(CDCl$_3$) δ=7.65 (d, 1H), 7.50 (d, 1H), 7.44 (dt, 1H), 7.35-7.27 (m, 2H), 7.24-7.12 (m, 4H), 7.07 (t, 1H), 7.04-6.97 (m, 2H), 5.56 (d, 1H), 5.49 (d, 1H), 1.81 (s, 3H).

LCMS: M+H: 367.0.

Example 22

2-BENZYL-3-(2,4-DIMETHYLPHENYL)-7-TRIFLUOROMETHYL-2H-INDAZOLE

This compound was prepared similarly to that of Example 1.

(CDCl$_3$) δ=7.65 (d, 1H), 7.50 (d, 1H), 7.24-6.99 (m, 9H), 5.57 (d, 1H), 5.47 (d, 1H), 2.44 (s, 3H), 1.80 (s, 3H).
LCMS: M+H: 381.5.

Example 23

2-BENZYL-3-BIPHENYL-4-YL-7-TRIFLUOROMETHYL-2H-INDAZOLE

This compound was prepared similarly to that of Example 1.

(CDCl$_3$) δ=7.82 (d, 1H), 7.75 (d, 2H), 7.72-7.66 (m, 2H), 7.52 (t, 2H), 7.49-7.40 (m, 3H), 7.34-7.25 (m, 3H), 7.20-7.12 (m, 3H), 5.76 (s, 2H).
LCMS: M+H: 429.5.

Example 24

2-BENZYL-7-TRIFLUOROMETHYL-3-(2-VINYLPHENYL)-2H-INDAZOLE

This compound was prepared similarly to that of Example 1.

(CDCl$_3$) δ=7.62 (d, 1H), 7.53 (d, 1H), 7.43-7.34 (m, 2H), 7.20 (dt, 1H), 7.09-7.01 (m, 3H), 7.00-6.92 (m, 2H), 6.88-6.82 (m, 2H), 6.06 (dd, 1H), 5.55 (d, 1H), 5.50 (d, 1H), 5.30 (d, 1H), 4.98 (d, 1H).
LCMS: M+H: 379.4.

Example 25

2-BENZYL-7-TRIFLUOROMETHYL-3-(3-TRIFLUOROMETHYLPHENYL)-2H-INDAZOLE

This compound was prepared similarly to that of Example 1.

(CDCl$_3$) δ=7.65 (d, 1H), 7.61-7.56 (m, 2H), 7.53 (t, 1H), 7.48 (s, 1H), 7.44 (d, 1H), 7.20-7.12 (m, 3H), 7.05 (t, 1H), 7.03-6.97 (m, 2H), 5.57 (d, 2H).
LCMS: M+H: 421.4.

Example 26

2-BENZYL-3-(4-FLUOROPHENYL)-7-TRIFLUOROMETHYL-2H-INDAZOLE

This compound was prepared similarly to that of Example 1.

(CDCl$_3$) δ=7.60-7.53 (m, 2H), 7.24-7.19 (m, 2H), 7.18-7.12 (m, 3H), 7.11-7.05 (m, 2H), 7.02 (t, 1H), 7.00-6.95 (m, 2H), 5.55 (s, 2H).
LCMS: M+H: 371.0.

Example 27

2-BENZYL-3-(3-CHLOROPHENYL)-7-TRIFLUOROMETHYL-2H-INDAZOLE

This compound was prepared similarly to that of Example 1.

(CDCl$_3$) δ=7.59 (d, 1H), 7.55 (d, 1H), 7.37-7.33 (m, 1H), 7.30 (t, 1H), 7.25-7.21 (m, 1H), 7.19-7.10 (m, 4H), 7.05-6.97 (m, 3H), 5.56 (s, 2H).
LCMS: M+H: 387.5.

Example 28

2-BENZYL-3-(3-METHOXYPHENYL)-7-TRIFLUOROMETHYL-2H-INDAZOLE

This compound was prepared similarly to that of Example 1.

(CDCl$_3$) δ=7.76 (d, 1H), 7.66 (d, 1H), 7.42 (t, 1H), 7.31-7.22 (m, 3H), 7.16-7.10 (m, 3H), 7.07-7.02 (m, 1H), 7.01-6.96 (m, 1H), 6.88-6.85 (m, 1H), 5.72 (s, 2H), 3.72 (s, 3H).
LCMS: M+H: 383.3.

Example 29

BENZYL-[4-(2-BENZYL-7-TRIFLUOROMETHYL-2H-INDAZOL-3-YL)-PHENYL]-METHYLAMINE

This compound was prepared similarly to that of Example 4.

(CDCl$_3$) δ=7.67 (d, 1H), 7.53 (d, 1H), 7.30-7.25 (m, 2H), 7.23-7.10 (m, 8H), 7.05-6.95 (m, 3H), 6.76-6.70 (m, 2H), 5.60 (s, 2H), 4.53 (s, 2H), 3.03 (s, 3H).
LCMS: M+COO$^-$: 516.5.

Example 30

2-(2-BENZYL-7-TRIFLUOROMETHYL-2H-INDAZOL-3-YL)-PHENOL

This compound was prepared similarly to that of Example 1.

(acetone) δ=8.96 (s, br, 1H), 7.73 (d, 1H), 7.68 (d, 1H), 7.46-7.41 (m, 1H), 7.28 (dd, 1H), 7.25-7.14 (m, 5H), 7.11-7.06 (m, 2H), 7.03 (dt, 1H), 5.69 (d, 2H).
LCMS: M+H: 369.2; M–H: 367.0.

Example 31

3-(4-METHOXY-2-METHYLPHENYL)-2-(4-METHYL-BENZYL)-7-TRIFLUOROMETHYL-2H-INDAZOLE

This compound was prepared similarly to that of Example 1.

(CDCl$_3$) δ=7.63 (d, 1H), 7.49 (d, 1H), 7.08-6.99 (m, 4H), 6.94 (d, 2H), 6.89-6.86 (m, 1H), 6.86-6.82 (m, 1H), 5.51 (d, 1H), 5.41 (d, 1H), 3.89 (s, 3H), 2.28 (s, 3H), 1.81 (s, 3H).
LCMS: M+H: 411.5.

Example 32

2-(2,4-DIMETHYLBENZYL)-3-(4-METHOXY-2-METHYLPHENYL)-7-TRIFLUOROMETHYL-2H-INDAZOLE

This compound was prepared similarly to that of Example 1.

(CDCl$_3$) δ=7.63 (d, 1H), 7.50 (d, 1H), 7.09-7.03 (m, 2H), 6.90-6.85 (m, 2H), 6.84-6.77 (m, 2H), 6.57 (d, 1H), 5.56 (d, 1H), 5.43 (d, 1H), 3.88 (s, 3H), 2.24 (s, 3H), 2.12 (s, 3H), 1.85 (s, 3H).
LCMS: M+H: 425.3.

Example 33

3-(4-METHOXY-2-METHYL-PHENYL)-7-TRIFLUOROMETHYL-2-(2,4,6-TRIMETHYL-BENZYL)-2H-INDAZOLE

This compound was prepared similarly to that of Example 1.

(CDCl$_3$) δ=7.59 (d, 1H), 7.47 (d, 1H), 7.06-7.00 (m, 2H), 6.89-6.85 (m, 1H), 6.82-6.78 (m, 1H), 6.75 (s, 2H), 5.62 (d, 1H), 5.51 (d, 1H), 3.89 (s, 3H), 2.24 (s, 3H), 2.12 (s, 6H), 1.93 (s, 3H).

LCMS: M+H: 439.7.

Example 34

2-BENZYL-3-(4-BROMOPHENYL)-7-TRIFLUOROMETHYL-2H-INDAZOLE

This compound was prepared similarly to that of Example 1.

(CDCl$_3$) δ=7.62-7.57 (m, 2H), 7.57-7.53 (m, 2H), 7.23-7.17 (m, 3H), 7.16-7.12 (m, 2H), 7.06 (t, 1H), 7.03-6.98 (m, 2H), 5.59 (s, 2H).

LCMS: M+H: 433.4($^{81}$Br); 431.3($^{79}$Br).

Example 35

2-BENZYL-3-(3-BROMOPHENYL)-7-TRIFLUOROMETHYL-2H-INDAZOLE

This compound was prepared similarly to that of Example 1.

(CDCl$_3$) δ=7.60 (d, 1H), 7.56 (d, 1H), 7.53-7.49 (m, 1H), 7.40-7.36 (m, 1H), 7.25 (t, 1H), 7.20-7.12 (m, 4H), 7.06-6.99 (m, 3H), 5.56 (s, 2H).

LCMS: M+H: 431.3($^{79}$Br).

Example 36

4-[4-(2-BENZYL-7-TRIFLUOROMETHYL-2H-INDAZOL-3-YL)-BENZYL]-BENZOIC ACID

This compound was prepared similarly to that of Example 5.

(acetone) δ=8.08-8.03 (m, 2H), 7.85 (d, 1H), 7.76-7.72 (m, 1H), 7.56-7.47 (m, 6H), 7.32-7.21 (m, 4H), 7.15-7.11 (m, 2H), 5.79 (s, 2H), 4.23 (s, 2H).

LCMS: M+H: 487.4; M−H: 485.3.

Example 37

4-[3-(2-BENZYL-7-TRIFLUOROMETHYL-2H-INDAZOL-3-YL)-BENZYL]-BENZOIC ACID

This compound was prepared similarly to that of Example 5.

(acetone) δ=8.03-7.99 (m, 2H), 7.83 (d, 1H), 7.74 (d, 1H), 7.57 (t, 1H), 7.53-7.45 (m, 3H), 7.40 (d, 2H), 7.31-7.26 (m, 3H), 7.23 (t, 1H), 7.12-7.07 (m, 2H), 5.77 (s, 2H), 4.18 (s, 2H).

LCMS: M+H: 487.4; M−H: 485.3.

Example 38

3-[4-(2-BENZYL-7-TRIFLUOROMETHYL-2H-INDAZOL-3-YL)-BENZYL]-BENZOIC ACID

This compound was prepared similarly to that of Example 5.

(acetone) δ=8.06 (s, 1H), 7.98 (d, 1H), 7.84 (d, 1H), 7.73 (d, 1H), 7.59 (d, 1H), 7.54-7.46 (m, 5H), 7.31-7.25 (m, 3H), 7.22 (t, 1H), 7.14-7.09 (m, 2H), 5.78 (s, 2H), 4.21 (s, 2H).

LCMS: M+H: 487.4; M−H: 485.6.

Example 39

3-[3-(2-BENZYL-7-TRIFLUOROMETHYL-2H-INDAZOL-3-YL)-BENZYL]-BENZOIC ACID

This compound was prepared similarly to that of Example 5.

(acetone) δ=8.02 (s, 1H), 7.96-7.92 (m, 1H), 7.84 (d, 1H), 7.74 (d, 1H), 7.59-7.43 (m, 6H), 7.32-7.26 (m, 3H), 7.23 (t, 1H), 7.12-7.07 (m, 2H), 5.77 (s, 2H), 4.20 (s, 2H).

LCMS: M+H: 487.4; M−H: 485.6.

Example 40

{4-[4-(2-BENZYL-7-TRIFLUOROMETHYL-2H-INDAZOL-3-YL)-BENZYL]-PHENYL}-ACETIC ACID

This compound was prepared similarly to that of Example 5.

(acetone) δ=7.84 (d, 1H), 7.74 (d, 1H), 7.46-7.53 (m, 4H), 7.25-7.35 (m, 7H), 7.22 (t, 1H), 7.10-7.15 (m, 2H), 5.78 (s, 2H), 4.11 (s, 2H), 3.65 (s, 2H).

LCMS: M+H: 501.5; M−H: 499.4.

Example 41

{4-[3-(2-BENZYL-7-TRIFLUOROMETHYL-2H-INDAZOL-3-YL)-BENZYL]-PHENYL}-ACETIC ACID

This compound was prepared similarly to that of Example 5.

(acetone) δ=7.83 (d, 1H), 7.74 (d, 1H), 7.57-7.52 (m, 1H), 7.50-7.47 (m, 1H), 7.46-7.42 (m, 2H), 7.32-7.27 (m, 5H), 7.25-7.21 (m, 3H), 7.12-7.07 (m, 2H), 5.76 (s, 2H), 4.08 (s, 2H), 3.63 (s, 2H).

LCMS: M+H: 501.5; M−H: 499.4.

Example 42

N-BENZYL-N-[4-(2-BENZYL-7-TRIFLUOROMETHYL-2H-INDAZOL-3-YL)-PHENYL]-AMINE

This compound was prepared similarly to that of Example 4.

(CDCl$_3$) δ=7.63 (d, 1H), 7.53 (d, 1H), 7.33-7.19 (m, 5H), 7.19-7.11 (m, 3H), 7.07 (d, 2H), 7.14-6.94 (m, 3H), 6.65 (d, 2H), 5.57 (s, 2H), 4.30 (s, 2H).

LCMS: M+H: 458.6; M−H: 456.2.

Example 43

BENZYL-[3-(2-BENZYL-7-TRIFLUOROM-ETHYL-2H-INDAZOL-3-YL)-PHENYL]-AMINE

This compound was prepared similarly to that of Example 4.

(CDCl$_3$) δ=7.52 (d, 2H), 7.29-7.10 (m, 10H), 7.01-6.92 (m, 3H), 6.69 (d, 1H), 6.63 (d, 1H), 6.48 (s, 1H), 5.53 (s, 2H), 4.15 (s, 2H).

LCMS: M+H: 458.6; M–H: 456.5.

Example 44

2-(2,4-DIMETHYL-BENZYL)-3-PHENYL-7-TRI-FLUOROMETHYL-2H-INDAZOLE

This compound was prepared similarly to that of Example 1.

(CDCl$_3$) δ=7.65 (d, 1H), 7.60 (d, 1H), 7.40 (m, 3H), 7.30 (m, 2H), 7.05 (t, 1H), 6.87 (s, 1H), 6.78 (d, 1H), 6.41 (d, 1H), 5.57 (s, 2H), 2.19 (s, 3H), 2.13 (s, 3H).

LCMS: M+H: 381.5.

Example 45

3-PHENYL-7-TRIFLUOROMETHYL-2-(2,4,6-TRIMETHYL-BENZYL)-2H-INDAZOLE

This compound was prepared similarly to that of Example 1.

(CDCl$_3$) δ=7.58 (d, 1H), 7.49 (d, 1H), 7.42 (m, 3H), 7.32 (m, 2H), 6.97 (t, 1H), 6.67 (s, 2H), 5.58 (s, 2H), 2.14 (s, 3H), 2.04 (s, 6H).

LCMS: M+H: 395.2.

Example 46

METHYL 3-({3-[2-BENZYL-7-(TRIFLUOROM-ETHYL)-2H-INDAZOL-3-YL]PHENOXY}METHYL)BENZOATE

This compound was prepared similarly to that of Example 2.

(CDCl$_3$) δ=8.06 (s, 1H), 7.99 (d, 1H), 7.83-7.75 (m, 2H), 7.58 (d, 1H), 7.45 (t, 1H), 7.41 (t, 1H), 7.28-7.25 (m, 3H), 7.15-7.12 (m, 4H), 6.98 (d, 1H), 6.89 (m, 1H), 5.66 (s, 2H), 5.00 (s, 2H), 3.94 (s, 3H).

LCMS: M+H: 517.4.

Example 47

2-BENZYL-3-[3-(BENZYLOXY)PHENYL]-7-(TRIFLUOROMETHYL)-2H-INDAZOLE

This compound was prepared similarly to that of Example 2.

(CDCl3) δ=7.53-7.50 (m, 2H), 7.28-7.19 (m, 8H), 7.17-7.12 (m, 4H), 7.03-6.95 (m, 4H), 6.86 (d, 1H), 6.75-6.83 (m, 1H), 5.50 (s, 2H), 4.87 (s, 2H).

LCMS: M+H: 459.5.

Example 48

[4-({3-[2-BENZYL-7-TRIFLUOROMETHYL)-2H-INDAZOL-3-YL]PHENOXY}METHYL)PHENYL] ACETIC ACID

This compound was prepared similarly to that of Example 2.

(CDCl$_3$) δ=3.67 (s, 2H), 4.95 (s, 2H), 5.68 (s, 2H), 6.90 (m, 1H), 6.97 (m, 1H), 7.06-7.13 (m, 4H), 7.23-7.28 (m, 3H), 7.29-732 (m, 2H), 7.33-7.37 (m, 2H), 7.40 (t, 1H), 7.66(m, 2H).

LCMS: M+H: 517.4.

Example 49

3-({3-[2-BENZYL-7-(TRIFLUOROMETHYL)-2H-INDAZOL-3-YL]PHENOXY}METHYL) BEN-ZOIC ACID

This compound was prepared similarly to that of Example 2.

(CDCl$_3$) δ=5.00 (s, 2H), 5.68 (s, 2H), 6.89 (m, 1H), 7.01 (d, 1H), 7.08-7.13 (m, 4H), 7.25-7.30 (m, 3H), 7.42 (t, 1H), 7.51 (t, 1H), 7.62 (t, 2H), 7.65 (d, 1H), 8.08 (d, 1H), 8.12 (s, 1H).

LCMS: M+H: 503.3; M–H: 501.2.

Example 50

4-({3-[2-BENZYL-7-(TRIFLUOROMETHYL)-2H-INDAZOL-3-YL]PHENOXY}METHYL) BEN-ZOIC ACID

This compound was prepared similarly to that of Example 2.

(CDCl$_3$) δ=5.02 (s, 2H), 5.67 (s, 2H), 6.85 (s, 1H), 6.97 (m, 1H), 7.05-7.15 (m, 4H), 7.40-7.50 (m, 3H), 7.54 (m, 1H), 7.63 (d, 2H), 8.12 (m, 4H).

LCMS: M+H: 503.3; M–H: 501.2.

Example 51

[4-({3-[2-BENZYL-7-TRIFLUOROMETHYL)-2H-INDAZOL-3-YL]PHENOXY}METHYL)PHENYL] PROPIONIC ACID

This compound was prepared similarly to that of Example 2.

(CDCl$_3$) δ=1.53 (d, 3H), 3.74 (q, 1H), 4.93 (s, 2H), 5.65 (s, 2H), 6.89 (m, 1H), 6.96 (dt, 1H), 7.04-7.12 (m, 4H), 7.22-7.26 (m, 3H), 7.35 (m, 4H), 7.39 (t, 1H), 7.65 (m, 2H).

LCMS: M+H: 531.2; M–H: 529.1.

Example 52

{3-[3-(2-BENZYL-7-TRIFLUOROMETHYL-2H-INDAZOL-3-YL)-PHENOXYMETHYL])-PHE-NOXY}-ACETIC ACID

This compound was prepared similarly to that of Example 2.

(CD$_3$OD) δ=4.50 (d, 2H), 4.92 (d, 2H), 5.55 (d, 2H), 6.78 (dt, 1H), 6.85-6.92 (m, 6H), 7.03-7.08 (m, 2H), 7.10-7.20 (m, 4H), 7.32 (t, 1H), 7.56 (d, 1H), 7.58 (s, 1H).

LCMS: M+H: 533.3; M–H: 531.5.

Example 53

{4-[3-(2-BENZYL-7-TRIFLUOROMETHYL-2H-INDAZOL-3-YL)-PHENOXYMETHYL])-PHENOXY}-ACETIC ACID

This compound was prepared similarly to that of Example 2.

(CD$_3$OD) δ=4.55 (s, 2H), 4.86 (s, 2H), 5.57 (s, 2H), 6.82-6.93 (m, 6H), 7.02-7.10 (m, 2H), 7.11-7.17 (m, 3H), 7.22 (d, 2H), 7.33 (t, 1H), 7.58 (m, 2H).
LCMS: M+H: 533.3; M−H: 531.2.

Example 54

2-BENZYL-3-PHENYL-7-TRIFLUOROMETHYL-2H-INDAZOLE

This compound was prepared similarly to that of Example 1.

(CD$_3$OD) δ=5.62 (s, 2H), 6.90 (m, 2H), 7.08 (t, 1H), 7.13 (m, 3H), 7.31(m, 2H), 7.43 (m, 3H), 7.53 (d, 1H), 7.62 (d, 1H).
LCMS: M+H: 353.2.

Example 55

2-(3-METHOXYBENZYL)-3-PHENYL-7-TRIFLUOROMETHYL-2H-INDAZOLE

This compound was prepared similarly to that of Example 1.

(CD$_3$OD) δ=3.51 (s, 3H), 5.50 (s, 2H), 6.38 (d, 1H), 6.46 (s, 1H), 6.62 (m, 1H), 7.01 (m, 2H), 7.29 (m, 2H), 7.36 (m, 3H), 7.55 (d, 1H), 7.61 (d, 1H).
LCMS: M+H: 383.2.

Example 56

2-(3-FLUOROBENZYL)-3-PHENYL-7-TRIFLUOROMETHYL-2H-INDAZOLE

This compound was prepared similarly to that of Example 1.

(CD$_3$OD), δ=5.68 (s, 2H), 6.79 (d, 1H), 6.85 (d, 1H), 6.96 (m, 1H), 7.55 (t, 1H), 7.23 (m, 1H), 7.37 (m, 2H), 7.49-7.55 (m, 3H), 7.67 (d, 1H), 7.73 (d, 1H).
LCMS: M+H: 371.0.

Example 57

2-(2-NITROBENZYL)-3-PHENYL-7-TRIFLUOROMETHYL-2H-INDAZOLE

This compound was prepared similarly to that of Example 1.

(CD$_3$OD) δ=6.12 (s, 2H), 6.63 (d, 1H), 7.19 (t, 1H), 7.35 (m, 2H), 7.49 (m, 4H), 7.57 (t, 1H), 7.70 (d, 1H), 7.80 (d, 1H), 8.15 (d, 1H).
LCMS: M+H: 398.2; M−H: 395.8.

Example 58

2-(3,5-DIFLUOROBENZYL)-3-PHENYL-7-TRIFLUOROMETHYL-2H-INDAZOLE

This compound was prepared similarly to that of Example 1.

(CDCl$_3$) δ=5.67 (s, 2H), 6.61 (d, 2H), 6.68 (m, 1H), 7.15 (t, 1H), 7.37 (m, 2H), 7.52 (m, 3H), 7.68 (d, 1H), 7.75 (d, 1H).
LCMS: M+H: 389.4; M−H: 387.4.

Example 59

8-(3-PHENYL-7-TRIFLUOROMETHYL-INDAZOL-2-YL-METHYL)-QUINOLINE

This compound was prepared similarly to that of Example 1.

(CDCl$_3$) δ=6.46 (s, 2H), 7.02 (d, 1H), 7.15 (t, 1H), 7.32-7.42 (m, 7H), 7.70 (d, 1H), 7.75 (d, 1H), 7.83 (d, 1H), 8.16 (d, 1H), 8.85 (m, 1H).
LCMS: M+H: 404.4.

Example 60

2-(4-METHYLBENZYL)-3-PHENYL-7-TRIFLUOROMETHYL-2H-INDAZOLE

This compound was prepared similarly to that of Example 1.

(CD$_3$OD) δ=2.12 (s, 3H), 5.53 (s, 2H), 6.77 (d, 2H), 6.93 (d, 2H), 7.04 (t, 1H), 7.27 (m, 2H), 7.42 (m, 3H), 7.55 (d, 1H), 7.62 (d, 1H).
LCMS: M+H: 367.2.

Example 61

2-(2-TRIFLUOROMETHYLBENZYL)-3-PHENYL-7-TRIFLUOROMETHYL-2H-INDAZOLE

This compound was prepared similarly to that of Example 1.

(CD$_3$OD) δ=5.83 (s, 2H), 6.50 (d, 1H), 7.16 (t, 1H), 7.27-7.32 (m, 2H), 7.35-7.43 (m, 5H), 7.62 (d, 1H), 7.66 (d, 1H), 7.74 (d, 1H).
LCMS: M+H: 421.4.

Example 62

2-(4-BROMOBENZYL)-3-PHENYL-7-TRIFLUOROMETHYL-2H-INDAZOLE

This compound was prepared similarly to that of Example 1.

(CD$_3$OD) δ=5.55 (s, 2H), 6.81 (d, 2H), 7.06 (t, 1H), 7.25 (d, 2H), 7.33 (m, 2H), 7.42 (m, 3H), 7.58 (d, 1H), 7.62 (d, 1H).
LCMS: M+H: 431.4.

Example 63

2-(2-DIFLUOROMETHOXYBENZYL)-3-PHENYL-7-TRIFLUOROMETHYL-2H-INDAZOLE

This compound was prepared similarly to that of Example 1.

(CDCl$_3$) δ=5.77 (s, 2H), 6.32-6.62 (t, 1H), 6.83 (d, 1H), 7.10 (m, 2H), 7.13 (t, 1H), 7.30 (m, 1H), 7.40 (m, 2H), 7.50 (m, 3H), 7.66 (d, 1H), 7.78 (d, 1H).
LCMS: M+H: 419.4.

Example 64

2-(3-DIFLUOROMETHOXYBENZYL)-3-PHENYL-7-TRIFLUOROMETHYL-2H-INDAZOLE

This compound was prepared similarly to that of Example 1.

(CDCl$_3$) δ=5.68 (s, 2H), 6.27-6.57 (t, 1H), 6.87 (s, 1H), 6.95 (d, 1H), 7.03 (d, 1H), 7.15 (t, 1H), 7.25 (m, 1H), 7.37 (m, 2H), 7.50 (m, 3H), 7.66 (d, 1H), 7.73 (d, 1H).
LCMS: M+H: 419.4.

Example 65

2-(3-TRIFLUOROMETHOXYLBENZYL)-7-TRIFLUOROMETHYL-3-PHENYL-2H-INDAZOLE

This compound was prepared similarly to that of Example 1.

(CDCl$_3$) δ=5.65 (s, 2H), 6.93 (s, 1H), 7.02-7.12 (m, 3H), 7.25 (t, 1H), 7.33 (m, 2H), 7.47 (m, 3H), 7.62 (d, 1H), 7.70 (d, 1H).
LCMS: M+H: 437.2.

Example 66

2-(3,5-DIMETHYLBENZYL)-3-PHENYL-7-TRIFLUOROMETHYL-2H-INDAZOLE

This compound was prepared similarly to that of Example 1.

(CDCl$_3$) δ=2.20 (2, 6H), 5.65 (s, 2H), 6.73 (s, 2H), 6.88 (s, 1H),), 7.13 (t, 1H), 7.42 (m, 2H), 7.53 (m, 3H), 7.68 (d, 1H), 7.78 (d, 1H).
LCMS: M+H: 381.4.

Example 67

2-NAPHTHALEN-1-YLMETHYL-3-PHENYL-7-TRIFLUOROMETHYL-2H-INDAZOLE

This compound was prepared similarly to that of Example 1.

(CD$_3$OD) δ=5.80 (s, 2H), 7.08-7.13 (m, 2H), 7.29 (s, 1H), 7.32 (m, 2H), 7.40 (m, 2H), 7.44 (m, 3H), 7.58 (m, 1H), 7.62 (d, 1H), 7.67-7.72 (m, 3H).
LCMS: M+H: 403.4.

Example 68

2-(2-CHLORO-4-FLUOROBENZYL)-3-PHENYL-7-TRIFLUOROMETHYL-2H-INDAZOLE

This compound was prepared similarly to that of Example 1.

(CDCl$_3$) δ=5.74 (s, 2H), 6.77 (m, 1H), 6.90 (td, 1H), 7.11 (dd, 1H), 7.17 (t, 1H), 7.35 (m, 2H), 7.48 (m, 3H), 7.68 (d, 1H), 7.81 (d, 1H).
LCMS: M+H: 405.4.

Example 69

3-PHENYL-2-(3-PYRROL-1-YL-BENZYL)-7-TRIFLUOROMETHYL-2H-INDAZOLE

This compound was prepared similarly to that of Example 1.

(CDCl$_3$) δ=5.73 (s, 2H), 6.31 (m, 2H), 6.95-7.03 (m, 3H), 7.14 (t, 1H), 7.28-7.34 (m, 3H), 7.40 (m, 2H), 7.53 (m, 3H), 7.67 (d, 1H), 7.75 (d, 1H).
LCMS: M+H: 418.4.

Example 70

2-(2-BROMOBENZYL)-3-PHENYL-7-TRIFLUOROMETHYL-2H-INDAZOLE

This compound was prepared similarly to that of Example 1.

(CDCl$_3$) δ=5.75 (s, 2H), 6.67 (d, 1H), 7.08-7.18 (m, 3H), 7.35 (m, 2H), 7.48 (m, 3H), 7.54 (d, 1H), 7.70 (d, 1H), 7.75 (d, 1H).
LCMS: M+H: 431.3.

Example 71

2-(2-METHYLBENZYL)-3-PHENYL-7-TRIFLUOROMETHYL-2H-INDAZOLE

This compound was prepared similarly to that of Example 1.

(CDCl$_3$) δ=2.20 (s, 3H), 5.67 (s, 2H), 6.60 (d, 1H), 7.07 (m, 1H), 7.12-7.18 (m, 3H), 7.37 (m, 2H), 7.48-7.54 (m, 3H), 7.69 (d, 1H), 7.80 (d, 1H).
LCMS: M+H: 367.1.

Example 72

2-(2,5-DICHLOROBENZYL)-7-TRIFLUOROMETHYL-3-PHENYL-2H-INDAZOLE

This compound was prepared similarly to that of Example 1.

(CDCl$_3$) δ=5.64 (s, 2H), 6.76 (d, 1H), 7.18 (m, 2H), 7.28 (m, 1H), 7.37 (m, 2H), 7.51 (m, 3H), 7.71 (d, 1H), 7.81 (d, 1H).
LCMS: M+H: 423.2.

Example 73

2-(2-METHYL-5-FLUOROBENZYL)-3-PHENYL-7-TRIFLUOROMETHYL-2H-INDAZOLE

This compound was prepared similarly to that of Example 1.

(CDCl$_3$) δ=2.15 (s, 3H), 5.58 (s, 2H), 6.27 (d, 1H), 6.95 (t, 1H), 7.09 (dd, 1H),), 7.15 (t, 1H), 7.32 (m, 2H), 7.52 (m, 3H), 7.67 (d, 1H), 7.80 (d, 1H).
LCMS: M+H: 385.0.

Example 74

2-(6-CHLORO-2-FLUORO-3-METHYLBENZYL)-3-PHENYL-7-TRIFLUOROMETHYL-2H-INDAZOLE

This compound was prepared similarly to that of Example 1.

(CDCl$_3$) δ=2.17 (s, 3H), 5.87 (s, 2H), 7.02 (m, 2H), 7.13 (t, 1H), 7.48-7.55 (m, 5H), 7.62 (d, 1H), 7.71 (d, 1H).
LCMS: M+H: 419.2.

Example 75

2-BIPHENYL-3-YLMETHYL-3-PHENYL-7-TRIFLUOROMETHYL-2H-INDAZOLE

This compound was prepared similarly to that of Example 1.

(CDCl$_3$) δ=5.58 (s, 2H), 6.98 (d, 1H), 7.04 (t, 1H), 7.23 (t, 2H), 7.30-7.38 (m, 5H), 7.42-7.47 (m, 6H), 7.58 (d, 1H), 7.66 (d, 1H).
LCMS: M+H: 429.4.

Example 76

2-BENZYL-3-BUTYL-7-TRIFLUOROMETHYL-2H-INDAZOLE

This compound was prepared similarly to that of Example 1.

(CDCl$_3$) δ=0.86 (t, 3H), 1.30 (m, 2H), 1.51 (m, 2H), 2.92 (t, 2H), 5.69 (s, 2H), 7.07 (t, 1H), 7.13 (d, 2H), 7.29 (m, 3H), 7.61 (d, 1H), 7.77 (d, 1H).
LCMS: M+H: 333.5.

Example 77

2-BENZYL-3-ISOBUTYL-7-TRIFLUOROMETHYL-2H-INDAZOLE

This compound was prepared similarly to that of Example 1.

(CDCl$_3$) δ=0.90 (d, 6H), 1.93 (m, 1H), 2.31 (d, 2H), 5.73 (s, 2H), 7.10 (t, 1H), 7.14 (d, 2H), 7.30 (m, 3H), 7.62 (d, 1H), 7.77 (d, 1H).
LCMS: M+H: 333.2.

Example 78

2-BENZYL-3-CYCLOPENTYL-7-TRIFLUOROMETHYL-2H-INDAZOLE

This compound was prepared similarly to that of Example 1.

(CDCl$_3$) δ=1.68 (m, 2H), 1.90 (m, 6H), 3.47 (m, 1H), 5.75 (s, 2H), 7.06 (t, 1H), 7.11 (d, 2H), 7.30 (m, 3H), 7.61 (d, 1H), 7.87 (d, 1H).
LCMS: M+H: 345.2.

Example 79

2-BENZYL-3-CYCLOHEXANYL-7-TRIFLUOROMETHYL-2H-INDAZOLE

This compound was prepared similarly to that of Example 1.

(CDCl$_3$) δ=1.19-1.30 (m, 4H), 1.78-1.92 (m, 6H), 2.98 (t, 1H), 5.75 (s, 2H), 7.01 (t, 1H), 7.15 (d, 2H), 7.32 (m, 3H), 7.55 (d, 1H), 7.96 (d, 1H).
LCMS: M+H: 359.3.

Example 80

[3-(2-BENZYL-7-TRIFLUOROMETHYL-2H-INDAZOL-3-YL)-PHENYL]-METHANOL

This compound was prepared similarly to that of Example 7.

(CDCl$_3$) δ=7.61 (m, 2H), 7.39 (m, 2H), 7.23 (m, 6H), 7.02 (m, 3H), 5.59 (s, 2H), 4.64 (s, 2H), 2.05 (s, br, 1H)
LCMS: M+H: 383.3.

Example 81

[3-(2-BENZYL-7-TRIFLUOROMETHYL-2H-INDAZOL-3-YL)-PHENYL]-PHENYLAMINE

This compound was prepared similarly to that of Example 4.

(CDCl$_3$) δ=5.62 (s, 2H), 6.82 (d, 1H), 6.90 (t, 1H), 6.94 (s, 1H), 6.95-7.05 (m, 5H), 7.09 (d, 1H), 7.12-7.20 (m, 5H), 7.28 (t, 1H), 7.56 (d, 1H), 7.66 (d, 1H).
LCMS: M+H: 444.5; M–H: 442.7.

Example 82

3-(2-BENZYL-7-TRIFLUOROMETHYL-2H-INDAZOL-3-YL)-PHENOL

This compound was prepared similarly to that of Example 2.

(acetone) δ=8.73 (s, br, 1H), 7.86 (d, 1H), 7.71 (d, 1H), 7.45-7.40 (m, 1H), 7.33-7.24 (m, 3H), 7.22 (t, 1H), 7.17-7.12 (m, 2H), 7.07-7.01 (m, 3H), 5.78 (s, 2H).
LCMS: M+H: 369.2; M–H: 367.0.

Example 83

2-(2-CHLORO-BENZYL)-3-PHENYL-7-TRIFLUOROMETHYL-2H-INDAZOLE

This compound was prepared similarly to that of Example 1.

(CDCl$_3$) δ=7.81 (d, 1H), 7.69 (d, 1H), 7.51-7.45 (m, 3H), 7.38-7.33 (m, 3H), 7.22 (t, 1H), 7.16 (q, 2H), 6.69 (d, 1H), 5.80 (s, 2H).
LCMS: M+H: 387.2.

Example 84

2-NAPHTHALEN-1-YLMETHYL-3-PHENYL-7-TRIFLUOROMETHYL-2H-INDAZOLE

This compound was prepared similarly to that of Example 1.

(CDCl$_3$) δ=8.02-7.97 (m, 1H), 7.89-7.83 (m, 1H), 7.81-7.73 (m, 2H), 7.68 (d, 1H), 7.53-7.48 (m, 2H), 7.42 (m, 3H), 7.36 (d, 2H), 7.29 (t, 1H), 7.95 (t, 1H), 6.69 (d, 1H), 6.20 (s, 2H).
LCMS: M+H: 403.4.

Example 85

2-BENZYL-3-NAPHTALEN-2-YL-7-TRIFLUOROMETHYL-2H-INDAZOLE

This compound was prepared similarly to that of Example 1.

(CDCl$_3$) δ=7.98-7.91 (m, 2H), 7.83-7.75 (m, 3H), 7.68 (d, 1H), 7.62-7.55 (m, 2H), 7.46 (d, 1H), 7.30-7.23 (m, 3H), 7.16-7.11 (m, 3H), 5.73 (s, 2H).
LCMS: M+H: 403.4.

Example 86

2-BENZYL-3-(4-METHOXY-3-METHYLPHENYL)-7-TRIFLUOROMETHYL-2H-INDAZOLE

This compound was prepared similarly to that of Example 1.

(CDCl₃) δ=7.65 (d, 1H), 7.56 (d, 1H), 7.19 (m, 3H), 7.05 (m, 5H), 6.84 (d, 1H), 5.59 (s, 2H), 3.83 (s, 3H), 2.16 (s, 3H).
LCMS: M+H: 397.4.

Example 87

2-BENZYL-3-METHYLPHENYL-7-TRIFLUOROMETHYL-2H-INDAZOLE

This compound was prepared similarly to that of Example 1.

(CDCl₃) δ=7.65 (d, 1H), 7.57 (d, 1H), 7.27(m, 6H), 7.05 (m, 5H), 5.60 (s, 2H), 2.31 (s, 3H).
LCMS: M+H: 367.1.

Example 88

2-BENZYL-3-(2,3-DIMETHYLPHENYL)-7-TRIFLUOROMETHYL-2H-INDAZOLE

This compound was prepared similarly to that of Example 1.

(CDCl₃) δ=7.56 (d, 1H), 7.42 (d, 1H), 7.24 (d, 1H), 7.11 (m, 4H), 6.98 (t, 1H), 6.91 (m, 3H), 5.42 (dd, 2H), 2.24 (s, 3H), 1.59 (s, 3H).
LCMS: M+H: 381.5.

Example 89

2-(2-BENZYL-7-TRIFLUOROMETHYL-2H-INDAZOL-3-YL)-BENZALDEHYDE

This compound was prepared similarly to that of Example 1.

(CDCl₃) δ=9.34 (s, 1H), 8.04 (d, 1H), 7.73-7.65 (m, 3H), 7.46 (d, 1H), 7.31 (dd, 1H), 7.21-7.09 (m, 4H), 6.94 (d, 2H), 5.59 (s, 2H).
LCMS: M+H: 381.2.

Example 90

2-BENZYL-3-(2-ISOPROPYL-PHENYL)-7-TRIFLUOROMETHYL-2H-INDAZOLE

This compound was prepared similarly to that of Example 1.

(CDCl₃) δ=7.55 (d, 1H), 7.41 (t, 2H), 7.36 (d, 1H), 7.15 (t, 1H), 7.12-7.07 (m, 3H), 7.00-6.91 (m, 4H), 5.40 (dd, 2H), 2.41-7.31 (m, 1H), 0.96 (d, 3H).
LCMS: M+H: 395.0.

Example 91

2-BENZYL-3-(2-CYCLOHEXYL-PHENYL)-7-TRIFLUOROMETHYL-2H-INDAZOLE

This compound was prepared similarly to that of Example 1.

(CDCl₃) δ=7.69 (d, 1H), 7.56-7.49 (m, 2H), 7.46 (d, 1H), 7.30-7.25 (m, 1H), 7.25-7.20 (m, 3H), 7.10 (t, 1H), 7.08-7.02 (m, 3H), 5.54 (dd, 2H), 2.08 (m, 1H), 172 (d, 1H), 1.67-1.53 (m, 3H), 1.42-1.27 (m, 2H), 1.20-1.07 (m, 2H), 0.99-0.84 (m, 2H).
LCMS: M+H: 435.5.

Example 92

2-BENZYL-3-(2-BENZYLPHENYL)-7-TRIFLUOROMETHYL-2H-INDAZOLE

This compound was prepared similarly to that of Example 1.

(CDCl₃) δ=7.52 (d, 1H), 7.36-7.28 (m, 2H), 7.20 (d, 1H), 7.16 (t, 1H), 7.12-7.06 (m, 3H), 7.03-7.95 (m, 3H), 6.94-6.87 (m, 4H), 6.53 (d, 2H), 5.06 (dd, 2H) 3.37 (dd, 2H).
LCMS: M+H: 443.9.

Example 93

2-BENZYL-3-[2-(1,1,2,2-TETRAFLUOROETHOXY)-PHENYL]-7-TRIFLUOROMETHYL-2H-INDAZOLE

This compound was prepared similarly to that of Example 1.

(CDCl₃) δ=7.65 (d, 1H), 7.56 (t, 2H), 7.51 (d, 1H), 7.34 (t, 1H), 7.22-7.16 (m, 4H), 7.11 (t, 1H), 7.06-6.99 (m, 2H), 5.58 (dd, 2H), 5.32 (tt, 1H).
LCMS: M+H: 469.7.

Example 94

2-BENZYL-3-(2-CHLORO-5-FLUORO-PHENYL)-7-TRIFLUOROMETHYL-2H-INDAZOLE

This compound was prepared similarly to that of Example 1.

(CDCl₃) δ=7.67 (d, 1H), 7.54 (d, 1H), 7.39-7.35 (m, 1H), 7.30-7.23 (m, 3H), 7.16-7.08 (m, 3H), 6.90 (td, 1H), 6.35 (dd, 1H), 5.67 (s, 2H).
LCMS: M+H: 419.3; M−H: 417.4.

Example 95

2-BENZYL-3-(9H-FLOUREN-2-YL)-7-TRIFLUOROMETHYL-2H-INDAZOLE

This compound was prepared similarly to that of Example 1.

(CDCl₃) δ=7.90 (d, 1H), 7.86 (d, 1H), 7.78 (d, 1H), 7.67 (d, 1H), 7.60 (d, 1H), 7.50 (s, 1H), 7.44 (t, 1H), 7.41-7.35 (m, 2H), 7.29-7.22 (m, 3H), 7.16-7.10 (m, 3H), 5.73 (s, 2H), 3.95 (s, 2H).
LCMS: M+H: 441.5; M−H: 439.4.

Example 96

2-BENZYL-3-(4-BENZYLPHENYL)-7-TRIFLUOROMETHYL-2H-INDAZOLE

This compound was prepared similarly to that of Example 1.

(CDCl₃) δ=7.61 (d, 1H), 7.52 (d, 1H), 7.25-7.06 (m, 12H), 6.99-6.92 (m, 3H), 5.56 (s, 2H), 3.94 (s, 2H)
LCMS: M+H: 443.6. .

Example 97

3-(2-BENZYL-7-TRIFLUOROMETHYL-2H-IN-DAZOL-3-YL)-BENZALDEHYDE

This compound was prepared similarly to that of Example 1.

(CDCl$_3$) δ=9.99 (s, 1H), 7.99 (dt, 1H), 7.83 (t, 1H), 7.67 (q, 3H), 7.60 (dt, 1H), 7.26-7.23 (m, 3H), 7.15 (t, 1H), 7.09-7.04 (m, 2H), 5.68 (s, 2H).

LCMS: M+H: 381.5.

Example 98

2-BENZYL-3-(3-[1,3-DIOXOLAN-2-YL-PHE-NYL)-7-TRIFLUOROMETHYL INDAZOLE

This compound was prepared similarly to that of Example 1.

(CDCl$_3$) δ=7.73 (d, 1H), 7.66 (d, 1H), 7.60 (d, 1H), 7.51 (t, 2H), 7.37 (d, 1H), 7.29-7.22 (m, 3H), 7.15-7.10 (m, 3H), 5.82 (s, 2H), 5.68 (s, 2H), 4.08-4.01 (m, 4H).

LCMS: M+H: 335.6; M–H: 333.1.

Example 99

2-BENZYL-3-(4'-METHOXY-BIPHENYL-4-YL)-7-TRIFLUOROMETHYL INDAZOLE

This compound was prepared similarly to that of Example 1.

(CDCl$_3$) δ=7.79 (d, 1H), 7.67 (t, 3H), 7.60 (d, 2H), 7.42 (d, 1H), 7.30-7.23 (m, 3H), 7.16-7.11 (m, 3H), 7.03 (d, 2H), 5.73 (s, 2H), 3.88 (s, 3H).

LCMS: M+H: 495.5.

Example 100

4'-(2-BENZYL-7-TRIFLUOROMETHYL-2H-IN-DAZOL-3-YL)-BIPHENYL-4-OL

This compound was prepared similarly to that of Example 1.

(CDCl$_3$) δ=7.79 (d, 1H), 7.67 (d, 3H), 7.55 (d, 2H), 7.42 (d, 2H), 7.30-7.23 (m, 3H), 7.17-7.11 (m, 3H), 6.95 (d, 2H), 5.74 (s, 2H).

LCMS: M+H: 445.4; M–H: 443.6.

Example 101

2-ALLYL-3-(2,4-DIMETHOXYPHENYL)-7-(TRI-FLUOROMETHYL)-2H-INDAZOLE

Sodium hydride (60% in oil, 0.025 g, 1.04 mmol) was added in one portion to a solution of 3-(2,4-dimethoxyphenyl)-7-(trifluoromethyl)-1H-indazole (0.150 g, 0.49 mmol) in DMF. After the gas evolution ceased, allyl bromide (0.07 mL, 0.7 mmol) was added and the reaction mixture was stirred at ambient temperature to 50° C. overnight. The cool reaction mixture was partitioned with EtOAc and 1 N HCl. The organic phase was washed with brine and dried (Na$_2$SO$_4$). The resulting residue was purified by flash chromatography or by HPLC chromatography through silica gel columns, 150×12 mm (Biotage, Charlottesville, Va.), at 10 mL/min with methyl-t-butyl ether/hexane (gradient elution, 1:9 to 1:1) to give the title compound (0.062 g) as a white solid.

$^1$H NMR (DMSO-d$_6$): δ 3.75 (s, 3H), 3.86 (s, 3H), 4.87-4.99 (m, 3H), 5.13 (d, 1H), 5.90-5.99 (m, 1H), 6.72 (d, 1H), 6.79 (s, 1H), 7.12 (t, 1H), 7.31 (d, 1H), 7.61-7.68 (m, 2H), MS (ESI) m/z 363 ([M+H]$^+$).

Example 102

3-(2,4-DIMETHOXYPHENYL)-2-PROPYL-7-(TRIFLUOROMETHYL)-2H-INDAZOLE

Prepared according to Example 101 from 3-(2,4-dimethoxyphenyl)-7-(trifluoromethyl)-1H-indazole and 1-iodopropane.

$^1$H NMR (DMSO-d$_6$): δ 0.74 (t, 3H), 1.76-1.85 (m, 2H), 3.87 (s, 3H), 4.10-4.26 (m, 2H), 6.74 (d, 1H), 6.80 (s, 1H), 7.32 (d, 1H), 7.59.7.66 (m, 2H), MS (ESI) m/z 365 ([M+H]$^+$.

Example 103

7-CHLORO-2-ISOPROPYL-3-(4-METHOXY-2-METHYLPHENYL)-2H-INDAZOLE

Prepared according to Example 101 from 7-chloro-3-(4-methoxy-2-methylphenyl)-1H-indazole (0.150 g, 0.52 mmol), sodium hydride (60% in oil, 0.025 g, 1.04 mmol) and 2-iodopropane (0.07 mL, 0.7 mmol) to give the title compound (0.059 g) as a white solid.

$^1$H NMR (DMSO-d$_6$): δ 1.46 (s, 6H), 1.99 (s, 3H), 3.83 (s, 3H), 4.42-4.47 (m, 1H), 6.94-6.98 (m, 2H), 7.04 (s, 1H), 7.20 (dd, 1H, J=0.61 and 8.25 Hz), 7.26 (d, 1H), 7.35 (dd, 1H, J=0.76 and 7.17 Hz), MS (ESI) m/z 315 ([M+H]$^+$).

Example 104

7-CHLORO-3-(4-METHOXY-2-METHYLPHE-NYL)-2-PROPYL-2H-INDAZOLE

Prepared according to Example 101 from 7-chloro-3-(4-methoxy-2-methylphenyl)-1H-indazole (0.150 g, 0.52 mmol), sodium hydride (60% in oil, 0.025 g, 1.04 mmol) and 1-propyl iodide (0.07 mL, 0.7 mmol) to give the title compound (0.056 g) as a white solid.

$^1$H NMR (DMSO-d$_6$): δ 0.71 (t, 3H), 1.79 (m, 2H), 2.00 (s, 3H), 3.83 (s, 3H), 4.04-4.09 (m, 1H), 4.20-4.25 (m, 1H), 6.94-6.98 (m, 2H), 7.00 (s, 1H), 7.22 (d, 1H), 7.27 (d, 1H), 7.35 (d, 1H), MS (ESI) m/z 315 ([M+H]$^+$).

Example 105

2-CYCLOPENTYL-3-(2,4-DIMETHOXYPHE-NYL)-7-(TRIFLUOROMETHYL)-2H-INDAZOLE

Prepared according to Example 101 from 3-(2,4-methoxyphenyl)-7-trifluoromethyl-H-indazole (2.00 g, 6.20 mmol), sodium hydride (60% in oil, 0.297 g, 7.44 mmol) and cyclopentyl bromide (1.00 mL, 9.30 mmol) to give the title compound (0.892 g) as a white solid.

$^1$H NMR (DMSO-d$_6$): δ 1.61 (m, 2H), 1.97 (m, 4H) 2.11 (m, 1H), 2.18 (m, 1H), 3.76 (s, 3H), 3.87 (s, 3H), 4.69 (m, 1H), 6.74 (dd, 1H, J=8.4 and 2.3 Hz), 6.79 (d, 1H, J=2.3 Hz), 7.09 (t, 1H, J=7.6 Hz), 7.31 (d, 1H, J=8.4 Hz), 7.58 (d, 1H, J=8.4 Hz), 7.63 (d, 1H, J=7.0 Hz), MS (EI) m/z 390; Anal. calcd for C$_{21}$H$_{21}$F$_3$N$_2$O$_2$: C, 64.61; H, 5.42 N, 7.18 Found: C, 64.29; H, 5.48 N, 6.86.

Example 106

3-(2,4-DIMETHOXYPHENYL)-2-ISOBUTYL-7-(TRIFLUOROMETHYL)-2H-INDAZOLE

Prepared according to Example 101 from 3-(2,4-methoxyphenyl)-7-trifluoromethyl-H-indazole (2.00 g, 6.20 mmol), sodium hydride (60% in oil, 0.297 g, 7.44 mmol) and 1-iodo-2-methylpropane (1.07 mL, 9.30 mmol) to give the title compound (0.768 g) as a white solid.

mp 111-112° C.; $^1$H NMR (DMSO-d$_6$): δ 0.66 (d, 3H, J=6.7 Hz.), 0.76 (d, 3H, J=6.7 Hz) 2.19 (m, 1H), 3.75 (s, 3H), 3.87 (s, 3H), 3.97 (m, 1H), 4.16 (m, 1H), 6.74 (dd, 1H, J=8.4 and 2.3 Hz), 6.79 (d, 1H, J=2.1 Hz), 7.11 (t, 1H, J=7.8 Hz), 7.31 (d, 1H, J=8.4 Hz), 7.60 (d, 1H, J=8.3 Hz), 7.65 (d, 1H, J=7.0 Hz), MS (ESI) m/z 379 ([M+H]+); Anal. calcd for $C_{20}H_{21}F_3N_2O_2$: C, 63.48; H, 5.59 N, 7.40 Found: C, 63.37H, 5.66 N, 7.36.

Example 107

2-(CYCLOHEXYLMETHYL)-3-(2,4-DIMETHOXYPHENYL)-7-(TRIFLUOROMETHYL)-2H-INDAZOLE

Prepared according to Example 101 from 3-(2,4-methoxyphenyl)-7-trifluoromethyl-H-indazole (1.82 g, 5.64 mmol), sodium hydride (60% in oil, 0.451 g, 11.28 mmol) and (bromomethyl)cyclohexane (4.00 g, 22.5 mmol) to give the title compound (0.967 g) as a white solid.

mp 156-157° C.; $^1$H NMR (DMSO-d$_6$): δ 0.73 (m, 1H), 0.82 (m, 1H) 1.03 (m, 2H) 1.23 (m, 1H) 1.30 (m, 1H), 1.50 (m, 4H) 1.88 (m, 1H), 3.75 (s, 3H), 3.87 (s, 3H), 3.99 (m, 1H), 4.18 (m, 1H), 6.74 (dd, 1H, J=8.4 and 2.3 Hz), 6.79 (d, 1H, J=2.1 Hz), 7.10 (t, 1H, J=7.8 Hz), 7.31 (d, 1H, J=8.4 Hz), 7.59 (d, 1H, J=8.3 Hz), 7.64 (d, 1H, J=7.0 Hz, MS (ESI) m/z 419 ([M+H]+); Anal. calcd for $C_{23}H_{25}F_3N_2O_2$: C, 66.02; H, 6.02 N, 6.69 Found: C, 66.03; H, 6.05 N, 6.64.

Example 108

3-(2,4-DIMETHOXYPHENYL)-2-(2-ETHYLBUTYL)-7-(TRIFLUOROMETHYL)-2H-INDAZOLE

Prepared according to Example 101 from 3-(2,4-methoxyphenyl)-7-trifluoromethyl-H-indazole (2.00 g, 6.20 mmol), sodium hydride (60% in oil, 0.496 g, 12.4 mmol) and 1-bromo-2-ethylbutane (3.07 g, 18.6 mmol) to give the title compound (0.540 g) as a white solid.

$^1$H NMR (DMSO-d$_6$): 60.60 (t, 3H, J=7.3 Hz), 0.67 (t, 3h, J=7.3 Hz), 1.12 (m, 4H), 1.79 (m, 1H), 3.76 (s, 3H), 3.86 (s, 3H), 4.12 (dd, 1H, J=13.6 and 7.3 Hz), 4.24 (dd, 1H, J=13.6 and 7.0 Hz), 6.74 (dd, 1H, J=8.4 and 2.1 Hz), 6.79 (d, 1H, J=2.0 Hz), 7.11 (t, 1H, J=7.8 Hz), 7.32 (d, 1H, J=8.2 Hz), 7.60 (d, 1H, J=8.4 Hz), 7.65 (d, 1H, J=7.0 Hz), MS (ESI) m/z 407 ([M+H]+); Anal. calcd for $C_{22}H_{25}F_3N_2O_2$: C, 65.01; H, 6.20 N, 6.89 Found: C, 64.90; H, 6.22 N, 6.73.

Example 109

2-CYCLOBUTYL-3-(2,4-DIMETHOXYPHENYL)-7-(TRIFLUOROMETHYL)-2H-INDAZOLE

Prepared according to Example 101 from 3-(2,4-methoxyphenyl)-7-trifluoromethyl-H-indazole (2.38 g, 7.40 mmol), sodium hydride (60% in oil, 0.592 g, 14.8 mmol) and bromocyclobutane (3.00 g, 22.2 mmol) to give the title compound (0.896 g) as a white solid.

mp 51-52° C.; $^1$H NMR (DMSO-d$_6$): δ 1.80 (m, 2H), 2.25 (m, 1H), 2.39 (m, 1H), 2.74 (m, 2H), 3.75 (s, 3H), 3.87 (s, 3H), 4.85 (m, 1H), 6.74 (dd, 1H, J=8.4 and 2.1 Hz), 6.80 (d, 1H, J=2.1 Hz), 7.11 (t, 1H, J=7.6 Hz), 7.28 (d, 1H, J=8.4 Hz), 7.61 (d, 1H, J=8.3 Hz), 7.66 (d, 1H, J=7.0 Hz), MS (ESI) m/z 377 ([M+H]+); Anal. calcd for $C_{20}H_{19}F_3N_2O_2$: C, 63.82; H, 5.09 N, 7.44 Found: C, 64.11; H, 5.14 N, 7.15.

Example 110

3-(2,4-DIMETHOXYPHENYL)-2-(1-ETHYLPROPYL)-7-(TRIFLUOROMETHYL)-2H-INDAZOLE

Prepared according to Example 101 from 3-(2,4-methoxyphenyl)-7-trifluoromethyl-H-indazole (2.50 g, 7.75 mmol), sodium hydride (60% in oil, 0.62 g, 15.5 mmol) and 3-bromopentane (3.51 g, 23 mmol) to give the title compound (0.674 g) as a white solid.

mp 138-139° C.; $^1$H NMR (DMSO-d$_6$): δ 0.51 (t, 3H, J=7.3 Hz), 0.76 (t, 3h, J=7.3 Hz), 1.90 (m, 2H), 2.07 (m, 2H), 3.73 (s, 3H), 3.87 (s, 3H), 4.00 (m, 1H), 6.74 (dd, 1H, J=8.4 and 2.3 Hz), 6.79 (d, 1H, J=2.1 Hz), 7.10 (t, 1H, J=7.8 Hz), 7.23 (d, 1H, J=8.2 Hz), 7.58 (d, 1H, J=8.4 Hz), 7.63 (d, 1H, J=7.2 Hz, MS (ESI) m/z 393 ([M+H]+); Anal. calcd for $C_{21}H_{23}F_3N_2O_2$: C, 64.28; H, 5.91; N, 7.14 Found: C, 64.04H, 5.77 N, 6.92.

Example 111

2,3-DIPHENYL-7-(TRIFLUOROMETHYL)-2H-INDAZOLE

3-Phenyl-7-trifluoromethylindazole (0.2 g, 0.76 mmol), phenyl boronic acid (186 mg, 1.53 mmol), copper II acetate (208 mg, 1.14 mmol), and pyridine (93 uL, 1.14 mmol) in 6 mL methylene chloride were stirred at room temperature for 72 hours. The reaction mixture was filtered through Celite®, poured into NH$_4$Cl (sat. soln.) and extracted with EtOAc. The combined organic layers were dried with Na$_2$SO$_4$, concentrated and the resulting residue was purified by HPLC (10-100% CH$_3$CN—H$_2$O) to provide the desired compound as a white solid (40 mg).

MS (ESI) m/z 339 ([M+H]$^+$); HRMS: calcd for $C_{20}H_{13}F_3N_2$, 338.1031; found (ESI), 339.1062.

Example 112

3-PHENYL-2-(2-PHENYLETHYL)-7-(TRIFLUOROMETHYL)-2H-INDAZOLE

This compound was prepared similarly to that of Example 1.

MS (ESI) m/z 367 ([M+H]$^+$); Anal. Calcd for $C_{22}H_{17}F_3N_2$: C, 72.12; H, 4.68; N, 7.65. Found: C, 71.96; H, 4.42; N, 7.58.

Example 113

2-(4-FLUOROBENZYL)-3-PHENYL-7-(TRIFLUOROMETHYL)-2H-INDAZOLE

This compound was prepared similarly to that of Example 1.

MS (ESI) m/z 371 ([M+H]$^+$); HRMS: calcd for C$_{21}$H$_{14}$F$_4$N$_2$ 370.3492 found (ESI), 370.3487.

Example 114

2-(2-CHLORO-6-FLUOROBENZYL)-3-PHENYL-7-(TRIFLUOROMETHYL)-2H-INDAZOLE

This compound was prepared similarly to that of Example 1.

MS (ESI) m/z 405/407 ([M+H]$^+$), MS (ESI) m/z 403/405 ([M−H]$^−$); HRMS: calcd for C$_{21}$H$_{13}$ClF$_4$N$_2$, 404.7942; found (ESI), 404.7938.

Example 115

2-(4-CHLORO-2-FLUOROBENZYL)-3-PHENYL-7-(TRIFLUOROMETHYL)-2H-INDAZOLE

This compound was prepared similarly to that of Example 1.

MS (ESI) m/z 405/407 ([M+H]$^+$); HRMS: calcd for C$_{21}$H$_{13}$ClF$_4$N$_2$, 404.0703; found (ESI), 463.0855.

Example 116

2-PHENYL-3-PIPERIDIN-1-YL-7-TRIFLUOROMETHYL-2H-INDAZOLE

Preparation of 2-azido-3-trifluoromethyl-benzoic acid (compound of formula (IX))

A mixture of 1.67 g (10 mmol) of 2-amino-3-(trifluoromethyl)-benzoic acid (compound of formula (VIII)) with 40 ml of 6N HCl was cooled down to 5° C. and a solution of 760 mg of NaNO$_2$ (11 mmol) in 17 ml of water were added dropwise in such a way that the temperature of the reaction mixture did not exceed 7° C. The resulting solution was stirred at this temperature for 30 minutes and then added slowly to a solution of 20.5 g of NaOAc and 715 mg (11 mmol) of NaN$_3$ in 40 ml of water. The reaction mixture was stirred overnight at room temperature. The product was extracted with CH$_2$Cl$_2$ three times. The solvent was removed in vacuo and the residue dried in a desiccator over P$_2$O$_5$ affording the required compound in quantitative yield.

(DMSO-d$_6$) δ=13.84 (s, br, 1H), 8.06 (dd, 1H), 7.87 (dd, 1H), 7.42 (t, 1H).

LCMS: M−H: 229.8.

Preparation of 2-azido-N-phenyl-3-trifluoromethyl-benzamide (compound of formula (X))

2-Azido-3-trifluoromethyl-benzoic acid (460 mg, 2 mmol, compound IX) was dissolved in 2 ml of SOCl$_2$ and the reaction mixture was heated at 80° C. for 1 hour. The remaining SOCl$_2$ was evaporated in vacuo and the residue was coevaporated with dry benzene. Dry CH$_2$Cl$_2$ (2 ml) was added followed by a dropwise addition of 200 μl of aniline (2 mmol). The reaction mixture was stirred at room temperature for 1 hour. Saturated aq. NaHCO$_3$ was added and the product was extracted with CH$_2$Cl$_2$. The resulting amide was purified by recrystallization from methanol. The yield was 521 mg (86%).

(CDCl$_3$) δ=8.01 (s, br, 1H), 7.85 (d, 1H), 7.72 (d, 1H), 7.57-7.55 (m, 2H), 7.34-7.30 (m, 3H), 7.13 (t, 1H).

LCMS: M+H: 307.4.

Preparation of 3-chloro-2-phenyl-7-trifluoromethyl-2H-indazole (compound of formula (XI))

2-Azido-N-phenyl-3-trifluoromethyl-benzamide (310 mg, 1 mmol, compound of formula (X)) was heated in 2 ml of SOCl$_2$ in a sealed vial at 100° C. for 4 hours. After evaporation of SOCl$_2$ in vacuo the residue was purified by column chromatography on silica (n-heptane/ethyl acetate, 50:50, as eluent). Yield: 212 mg (72%).

(CDCl$_3$) δ=7.76 (d, 1H), 7.66-7.60 (m, 3H), 7.51-7.42 (m, 3H), 7.14 (t, 1H).

LCMS: M+H: 297.2; 299.2.

Preparation of 2-phenyl-3-piperidin-1-yl-7-trifluoromethyl-2H-indazole (compound of Formula (I))

3-Chloro-2-phenyl-7-trifluoromethyl-2H-indazole (21 mg, 0.07 mmol, compound of formula (XI)) was dissolved in 0.5 ml of DMSO and 100 μl of piperidine (1 mmol) were added. The reaction mixture was stirred overnight at 110° C. After cooling to room temperature, 10 volumes of water were added. The supernatant was removed and the residue was purified by column chromatography on silica (n-heptane/ethyl acetate, 50:50, as eluent) to provide the title compound as a white solid (9 mg, 37%).

(CDCl$_3$) δ=7.92 (d, 1H), 7.79-7.77 (m, 2H), 7.48-7.46 (m, 1H), 7.43-7.40 (m, 2H), 7.34-7.30 (m, 1H), 6.88 (t, 1H), 3.15-3.13 (m, 4H), 1.55-1.49 (m, 6H).

LCMS: M+H: 346.0.

Example 117

2-CYCLOPENTYL-7-FLUORO-3-(4-METHOXYPHENYL)-2H-INDAZOLE

Prepared according to Example 116 from 7-fluoro-3-(4-methoxyphenyl)-1H-indazole (0.75 g, 3.1 mmol), sodium hydride (60% in oil, 0.124 g, 3.1 mmol) and cyclopentylbromide (0.36 mL, 3.3 mmol) to give the title compound (0.055 g) as a white solid.

$^1$H NMR-(DMSO-d$_6$, 400 MHz) d: 1.70 (m, 2H), 1.89 (m, 2H), 2.14 (m, 4H), 3.82 (s, 3H), 5.27 (m, 1H), 7.08 (d, 2H), 7.15 (m, 1H), 7.23 (m, 1H), 7.815 (d, 1H) 7.855 (d, 2H); MS (ESI+, m/z): 311 [M+H]$^+$.

Example 118

3-(4-METHOXYPHENYL)-7-METHYL-1H-INDAZOLE

A solution of (2-fluoro-3-methylphenyl)-(4-methoxy-phenyl)-methanone (3.6 g, 14.7 mmol), hydrazine hydrate (4.3 mL, 140 mmol) and DMAP (1.8 g, 14.7 mmol) in pyridine was heated at 100 C for 24-48 hrs. The cooled reaction mixture was partitioned with EtOAc and 1 N HCl. The organic phase was washed with brine and dried (Na$_2$SO$_4$). The resulting residue was purified by flash chromatography to give the product (1.7 g) as a yellow solid.

$^1$H NMR (DMSO-d$_6$): δ 2.52 (s, 3H), 3.81 (s, 3H), 7.06 (m, 3H), 7.13 (d, 1H), 7.81 (d, 1H), 7.89 (d, 2H), 13.132 (s, 1H); MS (APCI) m/z 239 ([M+H]$^+$).

Example 119

3-(4-METHOXYPHENYL)-7-TRIFLUOROMETHYL-1H-INDAZOLE

Prepared as in Example 104 from (2-fluoro-3-trifluoromethylphenyl)-(4-methoxy-phenyl)-methanone (3.6 g, 14.7 mmol), hydrazine hydrate (4.3 mL, 140 mmol) and DMAP (1.8 g, 14.7 mmol) to give the product (1.7 g) as a yellow solid.
$^1$H NMR (DMSO-d$_6$, 300 MHz): δ 2.52 (s, 3H), 3.82 (s, 3H), 7.07 (d, 2H), 7.18 (t, 1H), 7.48 (d, 1H), 7.91 (d, 2H), 8.0 (d, 1H), 13.132 (s, 1H); MS (APCI) m/z 239 ([M+H]$^+$).

Example 120

7-CHLORO-3-(4-METHOXYPHENYL)-1H-INDAZOLE

Prepared as in Example 104 from (3-chloro-2-fluoro-phenyl)-(4-methoxy-phenyl)-methanone (0.84 g, 3.2 mmol), hydrazine hydrate (1.0 mL, 32 mmol) and DMAP (0.39 g, 3.2 mmol) to give the product (0.75 g) as a solid.
$^1$H NMR (DMSO-d$_6$): δ 3.81 (s, 3H), 7.06 (d, 2H), 7.13 (d, 1H), 7.81 (d, 1H), 7.89 (d, 2H), 13.52 (s, 1H); MS (APCI) m/z 259 ([M+H]$^+$).

Example 121

7-FLUORO-3-(4-METHOXYPHENYL)-1H-INDAZOLE

Prepared as in Example 104 from (2,3-difluorophenyl)-(4-methoxy-phenyl)-methanone (1.1 g, 4.4 mmol), hydrazine hydrate (1.37 mL, 44 mmol) and DMAP (0.54 g, 4.4 mmol) to give the product (0.85 g) as a white solid.
$^1$H NMR (DMSO-d$_6$): δ 3.82 (s, 3H), 7.06 (d, 3H), 7.1-7.25 (m, 2H), 7.83 (d, 1H), 7.92 (d, 2H), 13.53 (s, 1H); MS (APCI) m/z 243 ([M+H]$^+$).

Example 122

7-FLUORO-3-(4-METHOXY-3-METHYLPHENYL)-1H-INDAZOLE

Prepared as in Example 104 from (2,3-difluorophenyl)-(4-methoxy-3-methyl-phenyl)-methanone (0.9 g, 3.45 mmol), hydrazine hydrate (1.06 mL, 34 mmol) and DMAP (0.42 g, 3.45 mmol) to give the product (0.80 g) as a yellow solid.
$^1$H NMR (DMSO-d$_6$): δ 2.247 (s, 3H), 3.845 (s, 3H), 7.07 (d, 1H), 7.13 (m, 1H), 7.22 (m, 1H), 7.75 (m, 2H), 7.83 (d, 1H), 13.62 (broad s, 1H); MS (ESI) m/z 257 ([M+H]$^+$).

Example 123

3-(2,4-DIMETHOXYPHENYL)-7-(TRIFLUOROMETHYL)-1H-INDAZOLE

Prepared as in Example 104 from (2,4-dimethoxyphenyl)[2-fluoro-3-(trifluoromethyl)phenyl]methanone (1.50 g, 5.17 mmol), hydrazine hydrate (1.61 mL, 51.7 mmol) and DMAP (0.632 g, 5.17 mmol) to give the product (0.619 g) as a yellow solid.
$^1$H NMR (DMSO-d$_6$): δ 3.78 (s, 3H), 3.83 (s, 3H), 6.66 (dd, 1H, J=2.38 and 8.33 Hz), 6.75 (s, 1H), 7.24 (t, 1H), 7.43 (d, 1H), 7.72 (d, 1H), 7.89 (d, 1H); MS (APCI) m/z 323 ([M+H]$^+$); Anal. calcd for C$_{16}$H$_{13}$F$_3$N$_2$O$_2$: C, 59.63; H, 4.07 N, 8.69 Found: C, 59.91H, 4.08 N, 7.95.

Example 124

3-(4-METHOXY-2-METHYLPHENYL)-7-(TRIFLUOROMETHYL)-1H-INDAZOLE

Prepared as in Example 104 from [2-fluoro-3-(trifluoromethyl)phenyl](4-methoxy-2-methylphenyl)methanone (1.34 g, 4.90 mmol), hydrazine hydrate (1.61 mL, 51.7 mmol) and DMAP (0.632 g, 5.17 mmol) to give the product (0.620 g) as a yellow solid.
$^1$H NMR (DMSO-d$_6$): δ 2.31 (s, 3H), 3.81 (s, 3H), 6.92 (d, 1H), 6.98 (s, 1H), 7.29 (t, 1H), 7.41 (d, 1H), 7.70 (d, 1H), 7.90 (d, 1H); MS (APCI) m/z 307 ([M+H]$^+$); Anal. calcd for C$_{16}$H$_{13}$F$_3$N$_2$O: C, 62.74; H, 4.28 N, 9.15 Found: C, 62.35; H, 4.01; N, 9.34.

Example 125

3-(2,4-DIMETHOXYPHENYL)-7-FLUORO-1H-INDAZOLE

Prepared as in Example 104 from (2,4-dimethoxyphenyl)[2,3-difluorophenyl]methanone (1.60 g, 5.8 mmol), hydrazine hydrate (1.79 mL, 5702 mmol) and DMAP (0.632 g, 57.5 mmol) to give the product (1.66 g) as a yellow solid.
$^1$H NMR (DMSO-d$_6$): δ 3.77 (s, 3H), 3.83 (s, 3H), 6.65 (dd, 1H, J=2.13 and 8.40 Hz), 6.72 (s, 1H), 7.02-7.05 (m, 1H), 7.13-7.17 (m, 1H), 7.41 (t, 1H), 13.54 (broad s, 1H)
MS (ESI) m/z 273 ([M+H]$^+$).

Example 126

7-FLUORO-3-(4-METHOXY-2-METHYLPHENYL)-1H-INDAZOLE

Prepared as in Example 104 from [2-fluoro-3-(trifluoromethyl)phenyl](4-methoxy-2-methylphenyl)methanone (1.34 g, 4.90 mmol), hydrazine hydrate (1.61 mL, 51.7 mmol) and DMAP (0.632 g, 5.17 mmol) to give the product (0.620 g) as a yellow solid.
$^1$H NMR (DMSO-d$_6$): δ 2.30 (s, 3H), 3.80 (s, 3H), 6.89 (dd, 1H, J=2.44 and 8.39 Hz), 6.95 (s, 1H), 7.06-7.11 (m, 1H), 7.19-7.22 (m, 1H), 7.38-7.40 (m, 2H), 13.64 (broad s, 1H), MS (ESI) m/z 257 ([M+H]$^+$).

Example 127

7-CHLORO-3-(4-METHOXY-2-METHYLPHENYL)-1H-INDAZOLE

Prepared as in Example 104 from [2-fluoro-3-chlorophenyl](4-methoxy-2-methylphenyl)methanone (1.26 g, 4.52 mmol), hydrazine hydrate (1.61 mL, 51.7 mmol) and DMAP (0.632 g, 5.17 mmol) to give the product (0.613 g) as a yellow solid.
$^1$H NMR (DMSO-d$_6$): δ 2.31 (s, 3H), 3.81 (s, 3H), 6.89 (dd, 1H, J=2.57 and 8.53 Hz), 6.96 (s, 1H), 7.13 (t, 1H), 7.39 (d, 1H), 7.47 (d, 1H), 7.54 (d, 1H), 13.62 (broad s, 1H), MS (ESI) m/z 273 ([M+H]$^+$).

Example 128

7-CHLORO-3-(2,4-DIMETHOXYPHENYL)-1H-INDAZOLE

Prepared as in Example 104 from (2,4-dimethoxyphenyl)[2-fluoro-3-chlorophenyl]methanone (1.20 g, 4.1 mmol), hydrazine hydrate (1.61 mL, 51.7 mmol) and DMAP (0.632 g, 5.17 mmol) to give the product (0.618 g) as a yellow solid.
$^1$H NMR (DMSO-d$_6$): δ 3.77 (s, 3H), 3.83 (s, 3H), 6.65 (dd, 1H, J=2.18 and 8.33 Hz), 6.73 (s, 1H), 7.07 (t, 1H), 7.41 (d, 1H), 7.55 (d, 1H), 13.52 (broad s, 1H), MS (ESI) m/z 289 ([M+H]$^+$).

Example 129

4-[2-(2,4-DIMETHYL-BENZYL)-7-TRIFLUOROMETHYL-2H-INDAZOL-3-YL]-3-METHYLPHENOL

This compound was prepared similarly to that of Example 1.

$^1$H NMR (CDCl$_3$): δ 7.66 (d, 1H), 7.52 (d, 1H), 7.10 (t, 1H), 6.96-6.68 (m, 6H), 6.53 (d, 1H), 5.56 (d, 1H), 5.42 (d, 1H), 2.20 (s, 3H), 2.06 (s, 3H), 1.76 (s, 3H).
LCMS: M+H: 411.5.

Example 130

4-(2-BENZYL-7-TRIFLUOROMETHYL-2H-INDAZOL-3-YL)-PHENOL

This compound was prepared similarly to that of Example 2.

$^1$H NMR (acetone-d$_6$): δ 5.71 (s, 2H), 7.01-7.06 (m, 2H), 7.12 (d, 2H), 7.17 (t, 1H), 7.21-7.31 (m, 3H), 7.35-7.40 (m, 2H), 7.67 (d, 1H), 7.80 (d, 1H), 8.84 (s, br, 1H).
LCMS: M+H: 369.2; M–H: 367.0.

Example 131

4-[2-BENZYL-7-(TRIFLUOROMETHYL)-2H-INDAZOL-3-YL]-3-METHOXYPHENOL

Prepared according to Example 116 from 3-(2,4-dimethoxyphenyl)-7-(trifluoromethyl)-1H-indazole and benzyl bromide.

$^1$H NMR (CDCl$_3$): δ 3.558 (s, 3H), 5.55 (q, 2H), 6.52 (m, 2H), 7.09 (m, 2H), 7.18 (m, 4H), 7.263 (d, 1H), 7.56 (t, 2H) MS (ESI) m/z 399 ([M+H]$^+$).

Example 132

4-(2-CYCLOPENTYL-7-FLUORO-2H-INDAZOL-3-YL)PHENOL

A solution of 2-cyclopentyl-7-fluoro-3-(4-methoxyphenyl)-2H-indazole (0.055 g, 0.177 mmol) in CH$_2$Cl$_2$ containing excess equivalents of cyclohexene (0.3 mL) at −78° C. was treated with boron tribromide (0.70 mL, 0.74 mmol, 4 eq.) and slowly allowed to warm to ambient temperature. The reaction mixture was quenched by dropwise addition of CH$_3$OH to the cooled reaction mixture. The solvent was removed in vacuo and the residue partitioned with EtOAc and 1 N HCl. The organic phase was washed with brine and dried (Na$_2$SO$_4$). Removal of the solvent in vacuo afforded the crude product. Pure product was obtained by crystallization or flash chromatography through water deactivated silica gel to give the product (0.03 g) as an amber solid.

$^1$H NMR (DMSO-d$_6$): δ 1.63 (m, 2H), 1.94 (m, 2H), 2.118 (m, 4H), 4.96 (m, 1H), 6.98 (m, 4H), 7.25 (d 1H), 7.36 (d, 2H), 9.925 (s, 1H), MS (ESI) m/z 297 ([M+H]$^+$).

Example 133

4-(7-CHLORO-2-ISOPROPYL-2H-INDAZOL-3-YL)-3-METHYLPHENOL

Prepared according to Example 128 from 7-chloro-2-isopropyl-3-(4-methoxy-2-methylphenyl)-2H-indazole (0.05 g, 0.16 mmol), boron tribromide (0.19 mL, 2.0 mmol) and 1.0 mL of cyclohexene to give the product (0.016 g) as a white solid.

$^1$H NMR (DMSO-d$_6$): δ 1.45 (d, 6H), 1.93 (s, 3H), 4.43-4.48 (m, 1H), 6.77 (dd, 1H, J=2.29 and 8.24 Hz), 6.83 (s, 1H), 6.96 (t, 1H), 7.12 (d, 1H), 7.20 (d, 1H), 7.34 (d, 1H), 9.78 (broad s, 1H), MS (ESI) m/z 301 ([M+H]$^+$).

Example 134

4-(7-CHLORO-2-PROPYL-2H-INDAZOL-3-YL)-3-METHYLPHENOL

Prepared according to Example 128 from 7-chloro-3-(4-methoxy-2-methylphenyl)-2-propyl-2H-indazole (0.04 g, 0.13 mmol), boron tribromide (0.20 mL, 2.10 mmol) and 1.0 mL of cyclohexene to give the product (0.023 g) as a white solid.

$^1$H NMR (DMSO-d$_6$): δ 0.71 (t, 3H), 1.76-1.81 (m, 2H), 1.93 (s, 3H), 4.03-4.08 (m, 1H), 4.19-4.24 (m, 1H), 6.77 (dd, 1H, J=2.29 and 8.24 Hz), 6.82 (s, 1H), 6.96 (t, 1H), 7.12 (d, 1H), 7.22 (d, 1H), 7.34 (d, 1H), 9.78 (broad s, 1H), MS (ESI) m/z 301 ([M+H]$^+$).

Example 135

2-(2-CHLORO-4-FLUORO-BENZYL)-3-(4-FLUORO-PHENYL)-7-TRIFLUOROMETHYL-2H-INDAZOLE

Preparation of 2-fluoro-N-methoxy-N-methyl-3-trifluoromethyl-benzamide

Ten grams (10 g 65 mmol) of 2-fluoro-3-(trifluoromethyl) benzoic acid and oxalyl chloride in 10 mL of anhydrous CH$_2$Cl$_2$ were treated with a few drops of DMF, and stirred at ambient temperature for 1 hour (gas evolution ceased). N,O-Dimethyhydroxylamine hydrochloride (16.8 g, 174 mmol) was added followed by 16 ml of pyridine. The reaction mixture was stirred overnight, then washed successively with H$_2$O, 2 N HCl, and brine. The resulting solution was dried over sodium sulfate. Evaporation of solvents in vacuo gave 13.3 g of product as an oil, which was pure enough to be used in the next step without further purification.

(CDCl$_3$) δ: 7.68 (t, 1H), 7.62 (t, 1H), 7.30 (t, 1H), 3.52 (s, br, 3H), 3.35 (s, br, 3H).
LCMS: M+H: 252.3.

Preparation of (2-fluoro-3-trifluoromethyl-phenyl)-(4-fluoro-phenyl)-methanone 2M Et$_2$O solution of 4-fluorophenylmagnesium bromide (32.5 ml; 65 mmol) was added to a solution of 12.8 g (65 mmol) of 2-fluoro-N-methoxy-N-methyl-3-trifluoromethyl-benzamide in 150 ml of THF at 0° C. The reaction mixture was heated overnight at 50° C. The reaction mixture was partitioned with EtOAc and H$_2$O. The organic phases were washed with brine and dried over Na$_2$SO$_4$. The resulting ketone (135 mg) was obtained after flash chromatographic purification using hexane/CH$_2$Cl$_2$ (3:1, v/v) as an eluent.

$^1$HNMR (DMSO-d$_6$) δ: 7.43 (t, 2H), 7.61 (t, 1H), 7.9 (m, 3H), 8.06 (t, 1H).

Preparation of 3-(4-Fluoro-phenyl)-7-trifluoromethyl-1H-indazole (2-Fluoro-3-trifluoromethyl-phenyl)-(4-fluoro-phenyl)-methanone (6.58 g, 23 mmol) was dissolved in 20 ml of pyridine. Hydrazine hydrate (7.36 mL, 230 mmol) and 4-(dimethylamino)-pyridine (2.8 g, 23 mmol) were added. The reaction mixture was stirred overnight at 110° C. After cooling to room temperature, EtOAc and 2N HCl were added. The organic phase was washed three times with brine, dried over $NaSO_4$ and concentrated under vacuum. Purification of the crude product by plug filtration (silica gel, $CH_2Cl_2$) provided 5.18 g product as a white solid.

$^1$HNMR (DMSO-$d_6$) δ: 7.39 (t, 3H), 7.82 (d, 1H), 8.04 (dt, 2H), 8.37 (d, 1H), 13.8 (s 1H).

Preparation of 2-(2-Chloro-4-fluoro-benzyl)-3-(4-fluoro-phenyl)-7-trifluoromethyl-2H-indazole To a solution of 3-(4-fluoro-phenyl)-7-trifluoromethyl-1H-indazole (6.43 g, 23 mmol) in 20 mL DMF was added 2-chloro-4-fluoro benzyl bromide (7.0 g, 31 mmol). The reaction mixture was heated overnight at 120° C. After cooling to room temperature, ethyl acetate was added and the solution was washed three times with brine. The organic layer was dried over $NaSO_4$ and concentrated. Flash chromatography (hexane/$CH_2Cl_2$, 1:1, as eluent) afforded 4.1 g of pure product. Three grams (3 g) of product were recrystallized from 10 mL of isopropanol to recover 1.98 g of crystalline product, mp 78° C.

$^1$HNMR (DMSO-$d_6$) δ: 5.77 (s, 2H), 6.92 (dt, 1H), 7.15 (dt, 1H), 7.24 (t, 1H), 7.43 (m, 3H), 7.63 (m, 2H), 7.76 (d, 1H), 7.83 (d, 1H).

MS (ES, m/z): [423/425]$^+$.

Example 136

2-(2-FLUOROBENZYL)-3-(4-FLUOROPHENYL)-7-(TRIFLUOROMETHYL)-2H-INDAZOLE

This compound was prepared similarly to that of Example 1.

MS (ESI) m/z 389; mp 89-90° C.

Example 137

2-(2-CHLOROBENZYL)-3-(4-FLUOROPHENYL)-7-(TRIFLUOROMETHYL)-2H-INDAZOLE

This compound was prepared similarly to that of Example 1.

MS (ESI) m/z 405.

Example 138

2-(3,4-DIFLUOROBENZYL)-3-(4-FLUOROPHENYL)-7-(TRIFLUOROMETHYL)-2H-INDAZOLE

This compound was prepared similarly to that of Example 1.

MS (ESI) m/z 407.

Example 139

3-(4-FLUOROPHENYL)-2-(2,4,6-TRIFLUOROBENZYL)-7-(TRIFLUOROMETHYL)-2H-INDAZOLE

This compound was prepared similarly to that of Example 1.

MS (ESI) m/z 425; mp 125° C.

Example 140

2-(4-FLUOROBENZYL)-3-(4-FLUOROPHENYL)-7-(TRIFLUOROMETHYL)-2H-INDAZOLE

This compound was prepared similarly to that of Example 1.

MS (ESI) m/z 389.

Example 141

2-(4-CHLOROBENZYL)-3-(4-FLUOROPHENYL)-7-(TRIFLUOROMETHYL)-2H-INDAZOLE

This compound was prepared similarly to that of Example 1.

MS (ESI) m/z 405.

Example 142

2-(2,4-DIFLUOROBENZYL)-3-(4-FLUOROPHENYL)-7-(TRIFLUOROMETHYL)-2H-INDAZOLE

This compound was prepared similarly to that of Example 1.

MS (ESI) m/z 407.

Example 143

2-(2,4-DIMETHYLBENZYL)-3-(4-FLUOROPHENYL)-7-(TRIFLUOROMETHYL)-2H-INDAZOLE

This compound was prepared similarly to that of Example 1.

MS (ESI) m/z 399.

Example 144

METHYL 2-(2,4-DIMETHYLBENZYL)-3-(4-FLUOROPHENYL)-2H-INDAZOLE-7-CARBOXYLATE

A solution of 2-(2,4-dimethylbenzyl)-3-(4-fluorophenyl)-7-(trifluoromethyl)-2H-indazole (0.43 g, 1.08 mmol) in 10 mL of methylene chloride containing 0.1 mL of cyclohexene was treated with boron tribromide (0.48 mL, 4.3 mmol) at −78° C. The reaction mixture was allowed to warm to room temperature. The reaction mixture was quenched by the slow addition of methanol. The reaction mixture was partitioned with 2 N HCl and the organic phase was washed with brine. The oranic phase was concentrated in vacuo and purified by flash chromatography (silica gel 60; $CH_2Cl_2$ then $CH_2Cl_2$-EtOAc, 7:3) to give 0.43 g of the title compound as a white solid.

MS (ESI) m/z 389.

Example 145

2-(2,4-DIMETHYLBENZYL)-3-(4-FLUOROPHENYL)-2H-INDAZOLE-7-CARBOXYLIC ACID

A solution of methyl 2-(2,4-dimethylbenzyl)-3-(4-fluorophenyl)-2H-indazole-7-carboxylate (0.195 g, 0.5 mmol) in 5 mL methanol was treated with 1 mL of 1N NaOH and stirred at 50° C. for 1 hour. The solution was neutralized with dilute HCl and partitioned with ethyl acetate and H₂O. The organic phase was dried (Na₂SO₄) and concentrated in vacuo to give 0.95 mg of the title compound as a yellow solid.

MS (ESI) m/z 375.

Example 146

[2-(2,4-DIMETHYLBENZYL)-3-(4-FLUOROPHE-NYL)-2H-INDAZOL-7-YL]METHANOL

A solution of methyl 2-(2,4-dimethylbenzyl)-3-(4-fluorophenyl)-2H-indazole-7-carboxylate (0.100 g, 0.25 mmol) and lithium aluminum (0.1 g, 0.25 mmol) in 5 mL THF was stirred at ambient temperature for 1 hour. Excess hydride was decomposed by the addition of 0.1 mL H₂O, 0.1 mL 1N NaOH, 0.3 mL H₂O and 100 mg of Na₂SO₄. The solids were filtered and the filtrate concentrated in vacuo to give 0.09 g of product as a light yellow solid.

MS (ESI) m/z 361.

Example 147

ETHYL 1-{4-[2-(2,4-DIMETHYLBENZYL)-7-(TRIFLUOROMETHYL)-2H-INDAZOL-3-YL]PHENYL}PIPERIDINE-4-CARBOXYLATE

A solution of 2-(2,4-dimethylbenzyl)-3-(4-fluorophenyl)-7-(trifluoromethyl)-2H-indazole (0.187 g, 0.47 mmol), ethyl isonipicotate (77 uL, 0.5 mmol) and potassium t-butoxide (0.056 g, 0.5 mmol) in DMA was heated at 120° C. for 72 hours. The reaction mixture was partitioned with ethyl acetate and H₂O. The organic phase was adsorbed on silica gel and purified by flash chromatography (CH₂Cl₂) to give 0.008 g product.

MS (ESI) m/z 536.

Example 148

2-BENZYL-3-(4-CHLOROPHENYL)-7-(TRIF-LUOROMETHYL)-2H-INDAZOLE

This compound was prepared similarly to that of Example 1.

MS (ESI) m/z 387.

Example 149

1-{4-[2-BENZYL-7-(TRIFLUOROMETHYL)-2H-INDAZOL-3-YL]PHENYL}PIPERIDINE-4-CAR-BOXAMIDE

A solution of 2-benzyl-3-(4-chlorophenyl)-7-(trifluoromethyl)-2H-indazole (0.1 g, 0.25 mmol), isonipecotamide (0.039 g, 0.3 mmol), tris-(dibenzylidineacetone)dipalladium (0) (14 mg), 2-dicyclohexylphosphino-2'-(N,N-dimethylamino)biphenyl (47 mg) and sodium t-butoxide (0.029 g, 0.3 mmol) in 2 mL of dimethoxyethane was heated at 150° C. for 5 minutes in a microwave (Emory's Optimizer, Personal Chemistry). The reaction mixture was concentrated in vacuo. The residue was purified by flash chromatography (CH₂Cl₂-CH₃OH, 19:1) to give the product (0.034 g) as an off-white solid.

MS (ESI) m/z 479.

Example 150

ETHYL 1-{4-[2-BENZYL-7-(TRIFLUOROM-ETHYL)-2H-INDAZOL-3-YL]PHENYL}PIPERIDINE-4-CARBOXYLATE

This compound was prepared similarly to that of Example 149.

MS (ESI) m/z 508.

Example 151

(1-{4-[2-BENZYL-7-(TRIFLUOROMETHYL)-2H-INDAZOL-3-YL]PHENYL}PIPERIDIN-4-YL)METHANOL

This compound was prepared similarly to that of Example 149.

MS (ESI) m/z 466.

Example 152

3-(4-CHLOROPHENYL)-2-(2,4,6-TRIFLUO-ROBENZYL)-7-(TRIFLUOROMETHYL)-2H-IN-DAZOLE

This compound was prepared similarly to that of Example 1.

MS (ES) m/z 441.1.

Example 153

2-(2-CHLORO-4-FLUOROBENZYL)-3-(4-CHLO-ROPHENYL)-7-(TRIFLUOROMETHYL)-2H-IN-DAZOLE

This compound was prepared similarly to that of Example 1.

MS (ES) m/z 439.1.

Example 154

2-(4-CHLORO-2-FLUOROBENZYL)-3-(4-CHLO-ROPHENYL)-7-(TRIFLUOROMETHYL)-2H-IN-DAZOLE

This compound was prepared similarly to that of Example 1.

MS (ES) m/z 439.1.

Example 155

3-(4-CHLOROPHENYL)-2-(2,4-DIMETHYLBEN-ZYL)-7-(TRIFLUOROMETHYL)-2H-INDAZOLE

This compound was prepared similarly to that of Example 1.

MS (ES) m/z 415.2.

Example 156

2-(4-CHLORO-2-FLUOROBENZYL)-3-(4-FLUO-ROPHENYL)-7-(TRIFLUOROMETHYL)-2H-IN-DAZOLE

This compound was prepared similarly to that of Example 1.

MS (ES) m/z 423.1.

Example 157

2-(2-CHLORO-6-FLUOROBENZYL)-3-(4-CHLOROPHENYL)-7-(TRIFLUOROMETHYL)-2H-INDAZOLE

This compound was prepared similarly to that of Example 1.
MS (ES) m/z 439.2.

Example 158

2-(2-CHLORO-6-FLUOROBENZYL)-3-(4-FLUOROPHENYL)-7-(TRIFLUOROMETHYL)-2H-INDAZOLE

This compound was prepared similarly to that of Example 1.
ms (ES) m/z 423.2.

Example 159

4-[2-(2,4-DIMETHYLBENZYL)-7-(TRIFLUOROMETHYL)-2H-INDAZOL-3-YL]-3-METHYLPHENOL

A solution of 2-(2,4-Dimethylbenzyl)-3-(4-methoxy-2-methylphenyl)-7-trifluoromethyl-2H-indazole (0.27 g, 0.63 mmol) and tetrabutylammonium iodide (0.7 g, 1.9 mmol) in 10 mL of $CH_2Cl_2$ was cooled to –78° C. and treated with boron trichloride 1M in $CH_2Cl_2$ (1.9 mL, 1.9 mmol). The reaction mixture was allowed to warm to ambient temperature. The reaction mixture was partitioned with 1N HCl and the organic phase was concentrated in vacuo. The residue was purified by flash chromatography to give 0.18 g of title compound as a white solid.
MS (ES) m/z 409.2.

Example 160

(1-{4-[2-BENZYL-7-(TRIFLUOROMETHYL)-2H-INDAZOL-3-YL]PHENYL}PIPERIDIN-3-YL)METHANOL

This compound was prepared similarly to that of Example 149.
MS (ES) m/z 466.

Example 161

2-(1-{4-[2-BENZYL-7-(TRIFLUOROMETHYL)-2H-INDAZOL-3-YL]PHENYL}PIPERIDIN-4-YL)ETHANOL

This compound was prepared similarly to that of Example 149.
MS (ES) m/z 480.

Example 162

2-BENZYL-3-(4-PIPERIDIN-1-YLPHENYL)-7-(TRIFLUOROMETHYL)-2H-INDAZOLE

This compound was prepared similarly to that of Example 149.
MS (ES) m/z 436.

Example 163

2-BENZYL-3-(4-PYRROLIDIN-1-YLPHENYL)-7-(TRIFLUOROMETHYL)-2H-INDAZOLE

This compound was prepared similarly to that of Example 149.
MS (ES) m/z 422.

Example 164

1-{4-[2-BENZYL-7-(TRIFLUOROMETHYL)-2H-INDAZOL-3-YL]PHENYL}PYRROLIDIN-3-OL

This compound was prepared similarly to that of Example 149.
MS (ESI) m/z 438.

Example 165

1-BENZYL-N-{4-[2-BENZYL-7-(TRIFLUOROMETHYL)-2H-INDAZOL-3-YL]PHENYL}PYRROLIDIN-3-AMINE

This compound was prepared similarly to that of Example 149.
MS (ESI) m/z 527.

Example 166

1-{4-[2-BENZYL-7-(TRIFLUOROMETHYL)-2H-INDAZOL-3-YL]PHENYL}PIPERIDINE-4-CARBOXYLIC ACID

A solution of ethyl 1-{4-[2-benzyl-7-(trifluoromethyl)-2H-indazol-3-yl]phenyl}piperidine-4-carboxylate (0.06 g, 0.12 mmol) in 5 mL of methanol containing 1 mL of 1 N NaOH was stirred overnight at ambient temperature. The reaction mixture was neutralized with dilute HCl and partitioned with ethyl acetate and $H_2O$. The organic phase was dried ($Na_2SO_4$) and concentrated in vacuo. The residue was triturated with petroleum ether to give the title compound as an amber solid (0.049 g).
MS (ES) m/z 478.2.

Example 167

(1-{4-[2-(2,4,6-TRIFLUOROBENZYL)-7-(TRIFLUOROMETHYL)-2H-INDAZOL-3-YL]PHENYL}PIPERIDIN-3-YL)METHANOL

This compound was prepared similarly to that of Example 149.
MS (ESI) m/z 520.

Example 168

(1-{4-[2-(2,4,6-TRIFLUOROBENZYL)-7-(TRIFLUOROMETHYL)-2H-INDAZOL-3-YL]PHENYL}PIPERIDIN-4-YL)METHANOL

This compound was prepared similarly to that of Example 149.
MS (ESI) m/z 520.

Example 169

((3R)-1-{4-[2-(2,4,6-TRIFLUOROBENZYL)-7-(TRIFLUOROMETHYL)-2H-INDAZOL-3-YL]PHENYL}PIPERIDIN-3-YL)METHANOL

The racemic compound of Example 169 was resolved by chiral HPLC to give the title compound.

$[\alpha]_D^{25}$=−6.6° (c=0.010 g/mL, CHCl$_3$); MS (ES) m/z 520.1.

Example 170

((3S)-1-{4-[2-(2,4,6-TRIFLUOROBENZYL)-7-(TRIFLUOROMETHYL)-2H-INDAZOL-3-YL]PHENYL}PIPERIDIN-3-YL)METHANOL

The racemic compound of Example 169 was resolved by chiral HPLC to give the title compound.

MS (ES) m/z 520.1.

Example 171

ETHYL 1-{4-[2-(2,4,6-TRIFLUOROBENZYL)-7-(TRIFLUOROMETHYL)-2H-INDAZOL-3-YL]PHENYL}PIPERIDINE-4-CARBOXYLATE

This compound was prepared similarly to that of Example 149.

MS (ES) m/z 562.4.

Example 172

1-{4-[2-(2,4,6-TRIFLUOROBENZYL)-7-(TRIFLUOROMETHYL)-2H-INDAZOL-3-YL]PHENYL}PYRROLIDIN-3-OL

This compound was prepared similarly to that of Example 149.

MS (ESI) m/z 492.

Example 173

1-BENZYL-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.

MS m/z 581.

Example 174

N-METHYL-1-{4-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.

MS (ES) m/z 519.2.

Example 175

3-[4-(2-METHYLPIPERIDIN-1-YL)PHENYL]-2-(2,4,6-TRIFLUOROBENZYL)-7-(TRIFLUOROMETHYL)-2H-INDAZOLE

This compound was prepared similarly to that of Example 149.

MS (ES) m/z 504.2.

Example 176

3-[4-(3-METHYLPIPERIDIN-1-YL)PHENYL]-2-(2,4,6-TRIFLUOROBENZYL)-7-(TRIFLUOROMETHYL)-2H-INDAZOLE

This compound was prepared similarly to that of Example 149.

MS (ES) m/z 504.2; mp 103° C.

Example 177

3-[4-(4-METHYLPIPERIDIN-1-YL)PHENYL]-2-(2,4,6-TRIFLUOROBENZYL)-7-(TRIFLUOROMETHYL)-2H-INDAZOLE

This compound was prepared similarly to that of Example 149.

MS (ES) m/z 504.2.

Example 178

1-{4-[2-(2,4,6-TRIFLUOROBENZYL)-7-(TRIFLUOROMETHYL)-2H-INDAZOL-3-YL]PHENYL}PIPERIDIN-3-OL

This compound was prepared similarly to that of Example 149.

MS m/z 506.

Example 179

(1-{4-[2-(2,4-DIMETHYLBENZYL)-7-(TRIFLUOROMETHYL)-2H-INDAZOL-3-YL]PHENYL}PIPERIDIN-3-YL)METHANOL

This compound was prepared similarly to that of Example 149.

MS (ES) m/z 494.2.

Example 180

(1-{4-[2-(2,4-DIMETHYLBENZYL)-7-(TRIFLUOROMETHYL)-2H-INDAZOL-3-YL]PHENYL}PIPERIDIN-4-YL)METHANOL

This compound was prepared similarly to that of Example 149.

MS m/z 494.

Example 181

ETHYL 1-{4-[2-(2,4-DIMETHYLBENZYL)-7-(TRIFLUOROMETHYL)-2H-INDAZOL-3-YL]PHENYL}PIPERIDINE-3-CARBOXYLATE

This compound was prepared similarly to that of Example 149.
MS (ES) m/z 536.2.

Example 182

2-(1-{4-[2-(2,4,6-TRIFLUOROBENZYL)-7-(TRIFLUOROMETHYL)-2H-INDAZOL-3-YL]PHENYL}PIPERIDIN-4-YL)ETHANOL

This compound was prepared similarly to that of Example 149.
MS (ES) m/z 534.2.

Example 183

4-PHENYL-1-{4-[2-(2,4,6-TRIFLUOROBENZYL)-7-(TRIFLUOROMETHYL)-2H-INDAZOL-3-YL]PHENYL}PIPERIDIN-4-OL

This compound was prepared similarly to that of Example 149.
MS (ES) m/z 582.2.

Example 184

TERT-BUTYL [(1-{4-[2-(2,4,6-TRIFLUOROBENZYL)-7-(TRIFLUOROMETHYL)-2H-INDAZOL-3-YL]PHENYL}PIPERIDIN-4-YL)METHYL]CARBAMATE

This compound was prepared similarly to that of Example 149.
MS (ES) m/z 619.3.

Example 185

8-{4-[2-(2,4,6-TRIFLUOROBENZYL)-7-(TRIFLUOROMETHYL)-2H-INDAZOL-3-YL]PHENYL}-1,4-DIOXA-8-AZASPIRO[4.5]DECANE

This compound was prepared similarly to that of Example 149.
MS (ESI) m/z 548.

Example 186

(3S)-1-BENZYL-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.
MS (ESI) m/z 581.

Example 187

(3R)-1-BENZYL-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.
MS (ES) m/z 581.0.

Example 188

METHYL ((3R)-1-{4-[2-(2,4,6-TRIFLUOROBENZYL)-7-(TRIFLUOROMETHYL)-2H-INDAZOL-3-YL]PHENYL}PIPERIDIN-3-YL)ACETATE

This compound was prepared similarly to that of Example 149.
mp 103° C.; MS (ES) m/z 562.0.

Example 189

1-{4-[2-(2,4,6-TRIFLUOROBENZYL)-7-(TRIFLUOROMETHYL)-2H-INDAZOL-3-YL]PHENYL}PIPERIDIN-4-ONE

A solution of 8-{4-[2-(2,4,6-trifluorobenzyl)-7-(trifluoromethyl)-2H-indazol-3-yl]phenyl}-1,4-dioxa-8-azaspiro[4.5]decane (0.195 g, 0.36 mmol) in 2 mL of formic acid was heated at 70° C. for 2 hours. The solvent was evaporated and the residue purified by flash chromatography ($CH_2Cl_2$-EtOAc, 19:1) to give 0.1 g of the title compound.
MS (ES) m/z 503.9.

Example 190

((3R)-1-{4-[2-(2,4,6-TRIFLUOROBENZYL)-7-(TRIFLUOROMETHYL)-2H-INDAZOL-3-YL]PHENYL}PIPERIDIN-3-YL)ACETIC ACID

A solution of methyl ((3R)-1-{4-[2-(2,4,6-trifluorobenzyl)-7-(trifluoromethyl)-2H-indazol-3-yl]phenyl}piperidin-3-yl)acetate (0.045 g, 0.08 mmol) in $CH_3OH$-THF (1:1, v/v) containing 0.5 mL of 1 N NaOH was stirred overnight at ambient temperature. Then it was neutralized with dilute acid and partitioned with ethyl acetate and brine. The organic phase was dried ($Na_2SO_4$) and concentrated in vacuo. The crude product was crystallized from ether/petroleum ether to give 0.036 g of title compound as a pale yellow solid.
MS (ESI) m/z 548; $[\alpha]_D^{25}$=−4.5° (c=0.012 g/mL, $CHCl_3$).

Example 191

1-{4-[2-(2,4,6-TRIFLUOROBENZYL)-7-(TRIFLUOROMETHYL)-2H-INDAZOL-3-YL]PHENYL}-N-[4-(TRIFLUOROMETHYL)BENZYL]PIPERIDIN-4-AMINE

This compound was prepared similarly to that of Example 149.
MS (ES) m/z 663.0.

Example 192

ETHYL 1-{4-[2-(2,4,6-TRIFLUOROBENZYL)-7-(TRIFLUOROMETHYL)-2H-INDAZOL-3-YL]PHENYL}PIPERIDINE-2-CARBOXYLATE

This compound was prepared similarly to that of Example 149.
MS (ES) m/z 562.0.

Example 193

ETHYL 1-{4-[2-(2,4,6-TRIFLUOROBENZYL)-7-(TRIFLUOROMETHYL)-2H-INDAZOL-3-YL]PHENYL}PIPERIDINE-3-CARBOXYLATE

This compound was prepared similarly to that of Example 149.
MS (ES) m/z 562.0.

Example 194

TERT-BUTYL ((3S)-1-{4-[2-(2,4,6-TRIFLUOROBENZYL)-7-(TRIFLUOROMETHYL)-2H-INDAZOL-3-YL]PHENYL}PYRROLIDIN-3-YL)CARBAMATE

This compound was prepared similarly to that of Example 149.
MS (ES) m/z 591.0.

Example 195

TERT-BUTYL ((3R)-1-{4-[2-(2,4,6-TRIFLUOROBENZYL)-7-(TRIFLUOROMETHYL)-2H-INDAZOL-3-YL]PHENYL}PYRROLIDIN-3-YL)CARBAMATE

This compound was prepared similarly to that of Example 149.
MS (ES) m/z 591.0.

Example 196

(3S)-1-CYCLOHEXYL-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.
MS (ESI) m/z 573.

Example 197

(3S)-1-{4-[2-(2,4,6-TRIFLUOROBENZYL)-7-(TRIFLUOROMETHYL)-2H-INDAZOL-3-YL]PHENYL}PYRROLIDIN-3-AMINE

A solution of tert-butyl ((3S)-1-{4-[2-(2,4,6-trifluorobenzyl)-7-(trifluoromethyl)-2H-indazol-3-yl]phenyl}pyrrolidin-3-yl)carbamate (0.05 g, 0.085 mmol) in 1 mL $CH_2Cl_2$ was treated with 0.1 mL of trifluoroacetic acid and stirred at ambient temperature overnight. Then the reaction mixture was partitioned with extra $CH_2Cl_2$ and saturated $NaHCO_3$. The organic phase was isolated and dried ($Na_2SO_4$). The sovent was evaporated and the residue treated with excess HCl in diethyl ether. The solids were collected and dried to give 0.32 g of the title compound as the HCl salt.
MS (ESI) m/z 491.

Example 198

(3R)-1-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 197.
MS (ESI) m/z 491.

Example 199

(3S)-1-(3-METHYLBUT-2-ENYL)-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.
MS m/z 559.

Example 200

(3R)-1-(3-METHYLBUT-2-ENYL)-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.
MS m/z 559.

Example 201

(3R)-N-{4-[2-(2,4,6-TRIFLUOROBENZYL)-7-(TRIFLUOROMETHYL)-2H-INDAZOL-3-YL]PHENYL}-1-(3,3,3-TRIFLUOROPROPYL)PYRROLIDIN-3-AMINE

This compound was prepared similarly to that of Example 149.
MS (ES) m/z 585.0.

Example 202

(3R)-1-(2-METHYLPROP-2-ENYL)-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.
MS (ES) m/z 545.0.

Example 203

(3R)-1-[(2E)-PENT-2-ENYL]-N-{4-[2-(2,4,6-TRIFLUOROBENZYL)-7-(TRIFLUOROMETHYL)-2H-INDAZOL-3-YL]PHENYL}PYRROLIDIN-3-AMINE

This compound was prepared similarly to that of Example 149.
MS (ESI) m/z 559.

Example 204

(3R)-1-HEXYL-N-{4-[2-(2,4,6-TRIFLUOROBEN-ZYL)-7-(TRIFLUOROMETHYL)-2H-INDAZOL-3-YL]PHENYL}PYRROLIDIN-3-AMINE

This compound was prepared similarly to that of Example 149.
MS (ESI) m/z 575.

Example 205

(3R)-1-CYCLOPENTYL-N-{4-[2-(2,4,6-TRIFLUO-ROBENZYL)-7-(TRIFLUOROMETHYL)-2H-IN-DAZOL-3-YL]PHENYL}PYRROLIDIN-3-AMINE

This compound was prepared similarly to that of Example 149.
MS (ES) m/z 559.1.

Example 206

(3R)-1-ISOPROPYL-N-{4-[2-(2,4,6-TRIFLUO-ROBENZYL)-7-(TRIFLUOROMETHYL)-2H-IN-DAZOL-3-YL]PHENYL}PYRROLIDIN-3-AMINE

This compound was prepared similarly to that of Example 149.
MS (ESI) m/z 533.

Example 207

(3S)-1-HEXYL-N-{4-[2-(2,4,6-TRIFLUOROBEN-ZYL)-7-(TRIFLUOROMETHYL)-2H-INDAZOL-3-YL]PHENYL}PYRROLIDIN-3-AMINE

This compound was prepared similarly to that of Example 149.
MS (ESI) m/z 575.

Example 208

(3S)-N-{4-[2-(2,4,6-TRIFLUOROBENZYL)-7-(TRIFLUOROMETHYL)-2H-INDAZOL-3-YL]PHENYL}-1-(3,3,3-TRIFLUOROPROPYL)PYR-ROLIDIN-3-AMINE

This compound was prepared similarly to that of Example 149.
MS (ESI) m/z 587.

Example 209

(3S)-1-(2-METHYLPROP-2-ENYL)-N-{4-[2-(2,4,6-TRIFLUOROBENZYL)-7-(TRIFLUOROM-ETHYL)-2H-INDAZOL-3-YL]PHENYL}PYRROLIDIN-3-AMINE

This compound was prepared similarly to that of Example 149.
MS (ESI) m/z 545.

Example 210

(3S)-1-[(2E)-PENT-2-ENYL]-N-{4-[2-(2,4,6-TRIF-LUOROBENZYL)-7-(TRIFLUOROMETHYL)-2H-INDAZOL-3-YL]PHENYL}PYRROLIDIN-3-AMINE

This compound was prepared similarly to that of Example 149.
MS (ESI) m/z 559.

Example 211

(3S)-1-CYCLOPENTYL-N-{4-[2-(2,4,6-TRIFLUO-ROBENZYL)-7-(TRIFLUOROMETHYL)-2H-IN-DAZOL-3-YL]PHENYL}PYRROLIDIN-3-AMINE

This compound was prepared similarly to that of Example 149.
MS (ESI) m/z 559.

Example 212

(3S)-1-ISOBUTYL-N-{4-[2-(2,4,6-TRIFLUO-ROBENZYL)-7-(TRIFLUOROMETHYL)-2H-IN-DAZOL-3-YL]PHENYL}PYRROLIDIN-3-AMINE

This compound was prepared similarly to that of Example 149.
MS (ESI) m/z 547.

Example 213

METHYL ((3S)-1-{4-[2-(2,4,6-TRIFLUOROBEN-ZYL)-7-(TRIFLUOROMETHYL)-2H-INDAZOL-3-YL]PHENYL}PIPERIDIN-3-YL)ACETATE

This compound was prepared similarly to that of Example 149.
MS (ES) m/z 562.0; mp 103° C.

Example 214

((3S)-1-{4-[2-(2,4,6-TRIFLUOROBENZYL)-7-(TRIFLUOROMETHYL)-2H-INDAZOL-3-YL]PHENYL}PIPERIDIN-3-YL)ACETIC ACID

This compound was prepared similarly to that of Example 190.
MS (ES) m/z 546.0.

Example 215

3-(4-BROMOPHENYL)-2-(2-CHLORO-4-FLUO-ROBENZYL)-7-(TRIFLUOROMETHYL)-2H-IN-DAZOLE

This compound was prepared similarly to that of Example 1.
MS m/z 483.

Example 216

METHYL ((3R)-1-{4-[2-(2-CHLORO-4-FLUO-ROBENZYL)-7-(TRIFLUOROMETHYL)-2H-IN-DAZOL-3-YL]PHENYL}PIPERIDIN-3-YL)AC-ETATE

This compound was prepared similarly to that of Example 149.
MS (ES) m/z 560.0.

Example 217

((3R)-1-{4-[2-(2-CHLORO-4-FLUOROBENZYL)-7-(TRIFLUOROMETHYL)-2H-INDAZOL-3-YL]PHENYL}PIPERIDIN-3-YL)ACETIC ACID

This compound was prepared similarly to that of Example 190.
MS (ES) m/z 543.9.

Example 218

3-(4-BROMOPHENYL)-2-(2,4-DIFLUOROBEN-ZYL)-7-(TRIFLUOROMETHYL)-2H-INDAZOLE

This compound was prepared similarly to that of Example 1.
MS (ES) m/z 467.0.

Example 219

3-(4-BROMOPHENYL)-2-(2,6-DICHLOROBEN-ZYL)-7-(TRIFLUOROMETHYL)-2H-INDAZOLE

This compound was prepared similarly to that of Example 1.
MS (ES) m/z 498.9.

Example 220

METHYL ((3R)-1-{4-[2-(2,6-DICHLOROBEN-ZYL)-7-(TRIFLUOROMETHYL)-2H-INDAZOL-3-YL]PHENYL}PIPERIDIN-3-YL)ACETATE

This compound was prepared similarly to that of Example 149.
MS (ES) m/z 576.1.

Example 221

METHYL ((3R)-1-{4-[2-(2,4-DIFLUOROBEN-ZYL)-7-(TRIFLUOROMETHYL)-2H-INDAZOL-3-YL]PHENYL}PIPERIDIN-3-YL)ACETATE

This compound was prepared similarly to that of Example 149.
MS (ES) m/z 544.2.

Example 222

((3R)-1-{4-[2-(2,4-DIFLUOROBENZYL)-7-(TRIF-LUOROMETHYL)-2H-INDAZOL-3-YL]PHENYL}PIPERIDIN-3-YL)ACETIC ACID

This compound was prepared similarly to that of Example 190.
MS (ES) m/z 528.1.

Example 223

((3R)-1-{4-[2-(2,6-DICHLOROBENZYL)-7-(TRIF-LUOROMETHYL)-2H-INDAZOL-3-YL]PHENYL}PIPERIDIN-3-YL)ACETIC ACID

This compound was prepared similarly to that of Example 190.
MS (ES) m/z 562.1.

Example 224

3-(3-BROMOPHENYL)-2-(2,4,6-TRIFLUO-ROBENZYL)-7-(TRIFLUOROMETHYL)-2H-IN-DAZOLE

This compound was prepared similarly to that of Example 1.
MS (ESI) m/z 485.

Example 225

2-(2,4,6-TRIFLUOROBENZYL)-7-(TRIFLUO-ROMETHYL)-3-{3-[(TRIMETHYLSILYL)ETHY-NYL]PHENYL}-2H-INDAZOLE

A solution of 3-(3-bromophenyl)-2-(2,4,6-trifluorobenzyl)-7-(trifluoromethyl)-2H-indazole (2.0 g, 4.1 mmol) and trimethylsilyl-acetylene-tributyltin in 30 mL of toluene was degassed. Palladium-tetrakis-triphenylphosphine (0.046 g, 0.4 mmol) was added and the mixture heated at reflux for 18 hours. The reaction mixture was concentrated in vacuo and purified by flash chromatography (silica 60, hexane-ethyl acetate, 9:1) to give the title compound (1.8 g) as a white solid.
MS (ESI) m/z 503.

Example 226

3-(3-ETHYNYLPHENYL)-2-(2,4,6-TRIFLUO-ROBENZYL)-7-(TRIFLUOROMETHYL)-2H-IN-DAZOLE

A mixture of 2-(2,4,6-trifluorobenzyl)-7-(trifluoromethyl)-3-{3-[(trimethylsilyl)-ethynyl]phenyl}-2H-indazole (1.78 g, 3.54 mmol) and potassium carbonate (0.49 g, 3.54 mmol) in 50 mL of methanol was heated at 50° C. for 2 hours. The reaction mixture was concentrated in vacuo and the residue partitioned between ethyl acetate and $H_2O$. The organic phase was dried ($Na_2SO_4$) and concentrated in vacuo to give 1.4 g of a white solid, which was purified by flash chromatography (silica gel 60, hexane-ethyl acetate, 4:1) to give 1.1 g of the title compound.
MS (ESI) m/z 431.

Example 227

(3R)-1-(2,4-DIMETHOXYBENZOYL)-N-{4-[2-(2,4,6-TRIFLUOROBENZYL)-7-(TRIFLUOROM-ETHYL)-2H-INDAZOL-3-YL]PHENYL}PYRROLIDIN-3-AMINE

This compound was prepared similarly to that of Example 149.
MS (ESI) m/z 655.

Example 228

ETHYL 3-({3-[2-(2,4,6-TRIFLUOROBENZYL)-7-(TRIFLUOROMETHYL)-2H-INDAZOL-3-YL] PHENYL}ETHYNYL)BENZOATE

A solution of 3-(3-ethynylphenyl)-2-(2,4,6-trifluorobenzyl)-7-(trifluoromethyl)-2H-indazole (0.103 g, 0.24 mmol), ethyl 3-iodobenzoate (0.042 mL, 0.25 mmol), tetrabutylammonium acetate (0.108 g, 0.36 mmol) and 8.8 mg of tris-(dibenzylidineacetone)-dipalladium in 2 mL of dry DMF was stirred at ambient temperature for 3 hours. The reaction mixture was partitioned with ethyl acetate and $H_2O$. The organic phase was concentrated in vacuo and purified by flash chromatography (silica 60, $CH_2Cl_2$-hexane, 1:1) to give the title compound (0.065 g).

MS (ESI) m/z 579.

Example 229

ETHYL 3-(2-{3-[2-(2,4,6-TRIFLUOROBENZYL)-7-(TRIFLUOROMETHYL)-2H-INDAZOL-3-YL] PHENYL}ETHYL)BENZOATE

A mixture of ethyl 3-({3-[2-(2,4,6-trifluorobenzyl)-7-(trifluoromethyl)-2H-indazol-3-yl]phenyl}ethynyl)benzoate (0.035 g, 0.06 mmol) and palladium dimethylamine complex (3.5 mg) (ref. Sajiki et. al. *JOC*, 1998, 63, 7990) in 1 mL of methanol was hydrogenated at atmospheric pressure for 24 hours. The catalyst was filtered and washed with methanol. The combined filtrates were evaporated to give 35 mg of product as an oil, which solidified on standing.

MS (ES+, [M+H]+m/z 550.8.

Example 230

3-({3-[2-(2,4,6-TRIFLUOROBENZYL)-7-(TRIFLUOROMETHYL)-2H-INDAZOL-3-YL] PHENYL}ETHYNYL)BENZOIC ACID

A solution of ethyl 3-({3-[2-(2,4,6-trifluorobenzyl)-7-(trifluoromethyl)-2H-indazol-3-yl]phenyl}ethynyl)benzoate (0.19 g, 0.33 mmol) in $CH_3OH$-THF (1:1, v/v) containing 1.0 mL of 1 N NaOH was stirred overnight at ambient temperature, then neutralized with dilute acid and partitioned with ethyl acetate and brine. The organic phase was dried ($Na_2SO_4$) and concentrated in vacuo to give 0.15 g of the title compound as a white solid.

MS (ES) m/z 550.8.

Example 231

3-(2-{3-[2-(2,4,6-TRIFLUOROBENZYL)-7-(TRIFLUOROMETHYL)-2H-INDAZOL-3-YL] PHENYL}ETHYL)BENZOIC ACID

The compound was prepared using the same conditions outlined in Example 230.

MS (ESI) m/z 555.

Example 232

N-METHYL-3-({3-[2-(2,4,6-TRIFLUOROBENZYL)-7-(TRIFLUOROMETHYL)-2H-INDAZOL-3-YL]PHENYL}ETHYNYL)BENZAMIDE

A solution of 3-({3-[2-(2,4,6-trifluorobenzyl)-7-(trifluoromethyl)-2H-indazol-3-yl]phenyl}ethynyl)benzoic acid (0.042 g, 0.076 mmol), methyl amine-HCl (0.006 g, 0.076 mmol) and carbonyl diimidazole (0.013 g, 0.076 mmol) in 2 mL DMF was stirred at ambient temperature overnight. The reaction mixture was partitioned with ethyl acetate and $H_2O$. The organic phase was concentrated in vacuo and purified by flash chromatography (silica 60, $CH_2Cl_2$—$CH_3OH$, 25:1) to give 0.017 g of the product.

MS (ES) m/z 564.0.

Example 233

3-(3-{[3-(MORPHOLIN-4-YLCARBONYL)PHENYL]ETHYNYL}PHENYL)-2-(2,4,6-TRIFLUOROBENZYL)-7-(TRIFLUOROMETHYL)-2H-INDAZOLE

This compound was prepared similarly to that of Example 232.

MS (ES) m/z 620.1.

Example 234

TERT-BUTYL 4-[3-({3-[2-(2,4,6-TRIFLUOROBENZYL)-7-(TRIFLUOROMETHYL)-2H-INDAZOL-3-YL]PHENYL}ETHYNYL)BENZOYL] PIPERAZINE-1-CARBOXYLATE

This compound was prepared similarly to that of Example 232.

MS (ES) m/z 719.1.

Example 235

N-METHYL-3-(2-{3-[2-(2,4,6-TRIFLUOROBENZYL)-7-(TRIFLUOROMETHYL)-2H-INDAZOL-3-YL]PHENYL}ETHYL)BENZAMIDE

This compound was prepared similarly to that of Example 232.

MS (ES) m/z 568.1.

Example 236

3-(3-{2-[3-(MORPHOLIN-4-YLCARBONYL)PHENYL]ETHYL}PHENYL)-2-(2,4,6-TRIFLUOROBENZYL)-7-(TRIFLUOROMETHYL)-2H-INDAZOLE

This compound was prepared similarly to that of Example 232.

MS (ESI) m/z 624.

Example 237

TERT-BUTYL 4-[3-(2-{3-[2-(2,4,6-TRIFLUOROBENZYL)-7-(TRIFLUOROMETHYL)-2H-INDAZOL-3-YL]PHENYL}ETHYL)BENZOYL]PIPERAZINE-1-CARBOXYLATE

This compound was prepared similarly to that of Example 232.

MS (ES) m/z 723.2.

Example 238

3-{3-[(2,5-DICHLOROPHENYL)ETHYNYL]PHENYL}-2-(2,4,6-TRIFLUOROBENZYL)-7-(TRIFLUOROMETHYL)-2H-INDAZOLE

This compound was prepared similarly to that of Example 228.

MS (ES) m/z 574.9.

Example 239

3-{3-[(2,4-DICHLOROPHENYL)ETHYNYL]PHENYL}-2-(2,4,6-TRIFLUOROBENZYL)-7-(TRIFLUOROMETHYL)-2H-INDAZOLE

This compound was prepared similarly to that of Example 228.

MS (ES) m/z 574.9.

Example 240

2-(2,4,6-TRIFLUOROBENZYL)-7-(TRIFLUOROMETHYL)-3-(3-{[2-(TRIFLUOROMETHYL)PHENYL]ETHYNYL}PHENYL)-2H-INDAZOLE

This compound was prepared similarly to that of Example 228.

MS (ES) m/z 575.1.

Example 241

3-{3-[2-(2,4-DICHLOROPHENYL)ETHYL]PHENYL}-2-(2,4,6-TRIFLUOROBENZYL)-7-(TRIFLUOROMETHYL)-2H-INDAZOLE

This compound was prepared similarly to that of Example 229.

MS (ESI) m/z 579.

Example 242

2-(2,4,6-TRIFLUOROBENZYL)-7-(TRIFLUOROMETHYL)-3-(3-{2-[2-(TRIFLUOROMETHYL)PHENYL]ETHYL}PHENYL)-2H-INDAZOLE

This compound was prepared similarly to that of Example 229.

MS (ESI) m/z 579.

Example 243

3-{3-[2-(2,5-DICHLOROPHENYL)ETHYL]PHENYL}-2-(2,4,6-TRIFLUOROBENZYL)-7-(TRIFLUOROMETHYL)-2H-INDAZOLE

This compound was prepared similarly to that of Example 229.

MS (ES) m/z 579.1.

Example 244

3-[3-(2-PHENYLETHYL)PHENYL]-2-(2,4,6-TRIFLUOROBENZYL)-7-(TRIFLUOROMETHYL)-2H-INDAZOLE

This compound was prepared similarly to that of Example 229.

MS (ES) m/z 511.2.

Example 245

3-(3-{[2-CHLORO-5-(TRIFLUOROMETHYL)PHENYL]ETHYNYL}PHENYL)-2-(2,4,6-TRIFLUOROBENZYL)-7-(TRIFLUOROMETHYL)-2H-INDAZOLE

This compound was prepared similarly to that of Example 228.

MS (ES) m/z 609.0.

Example 246

3-{3-[(2-BROMO-5-FLUOROPHENYL)ETHYNYL]PHENYL}-2-(2,4,6-TRIFLUOROBENZYL)-7-(TRIFLUOROMETHYL)-2H-INDAZOLE

This compound was prepared similarly to that of Example 228.

MS (ES) m/z 602.9.

Example 247

3-(3-{2-[2-CHLORO-5-(TRIFLUOROMETHYL)PHENYL]ETHYL}PHENYL)-2-(2,4,6-TRIFLUOROBENZYL)-7-(TRIFLUOROMETHYL)-2H-INDAZOLE

This compound was prepared similarly to that of Example 229.

MS (ES) m/z 613.0.

Example 248

3-{3-[2-(3-FLUOROPHENYL)ETHYL]PHENYL}-2-(2,4,6-TRIFLUOROBENZYL)-7-(TRIFLUOROMETHYL)-2H-INDAZOLE

This compound was prepared similarly to that of Example 229.

MS (ES) m/z 529.

Example 249

3-{3-[2-(2-BROMO-5-FLUOROPHENYL)ETHYL]PHENYL}-2-(2,4,6-TRIFLUOROBENZYL)-7-(TRIFLUOROMETHYL)-2H-INDAZOLE

This compound was prepared similarly to that of Example 229.
MS (ES) m/z 608.

Example 250

4-AMINO-3-({3-[2-(2,4,6-TRIFLUOROBENZYL)-7-(TRIFLUOROMETHYL)-2H-INDAZOL-3-YL]PHENYL}ETHYNYL)BENZONITRILE

This compound was prepared similarly to that of Example 229.
MS (ES) m/z 547.1.

Example 251

3-{3-[(3-CHLORO-2-FLUOROPHENYL)ETHYNYL]PHENYL}-2-(2,4,6-TRIFLUOROBENZYL)-7-(TRIFLUOROMETHYL)-2H-INDAZOLE

This compound was prepared similarly to that of Example 228.
MS (ES) m/z 559.0.

Example 252

[3-({3-[2-(2,4,6-TRIFLUOROBENZYL)-7-(TRIFLUOROMETHYL)-2H-INDAZOL-3-YL]PHENYL}ETHYNYL)PHENYL]METHANOL

This compound was prepared similarly to that of Example 228.
MS (ES) m/z 537.1.

Example 253

4-AMINO-3-(2-{3-[2-(2,4,6-TRIFLUOROBENZYL)-7-(TRIFLUOROMETHYL)-2H-INDAZOL-3-YL]PHENYL}ETHYL)BENZONITRILE

This compound was prepared similarly to that of Example 229.
MS (ES) m/z 551.1.

Example 254

3-{3-[(2,3-DICHLOROPHENYL)ETHYNYL]PHENYL}-2-(2,4,6-TRIFLUOROBENZYL)-7-(TRIFLUOROMETHYL)-2H-INDAZOLE

This compound was prepared similarly to that of Example 228.
MS (ES) m/z 575.0.

Example 255

3-{3-[2-(3-CHLORO-2-FLUOROPHENYL)ETHYL]PHENYL}-2-(2,4,6-TRIFLUOROBENZYL)-7-(TRIFLUOROMETHYL)-2H-INDAZOLE

This compound was prepared similarly to that of Example 229.
MS (ES) m/z 563.0.

Example 256

[3-(2-{3-[2-(2,4,6-TRIFLUOROBENZYL)-7-(TRIFLUOROMETHYL)-2H-INDAZOL-3-YL]PHENYL}ETHYL)PHENYL]METHANOL

This compound was prepared similarly to that of Example 229.
MS (ES) m/z 541.1.

Example 257

3-{3-[2-(2,3-DICHLOROPHENYL)ETHYL]PHENYL}-2-(2,4,6-TRIFLUOROBENZYL)-7-(TRIFLUOROMETHYL)-2H-INDAZOLE

This compound was prepared similarly to that of Example 229.
MS (ES) m/z 576.

Example 258

N-[3-({3-[2-(2,4,6-TRIFLUOROBENZYL)-7-(TRIFLUOROMETHYL)-2H-INDAZOL-3-YL]PHENYL}ETHYNYL)PHENYL]MORPHOLINE-4-CARBOXAMIDE

Preparation of N-(3-iodophenyl)morpholine-4-carboxamide

A solution of 3-iodophenylisocyanate (0.1 g, 0.41 mmol) and morpholine (0.04 mL, 0.45 mmol) in 2 mL dioxane were heated at 100° C. overnight. The solvent was evaporated and the resulting product was used without purification.
MS (ES) m/z 331.0.

Preparation of N-[3-({3-[2-(2,4,6-trifluorobenzyl)-7-(trifluoromethyl)-2h-indazol-3-yl]phenyl}ethynyl)phenyl]morpholine-4-carboxamide The title compound was obtained by reaction of N-(3-iodophenyl)morpholine-4-carboxamide with the alkyne of Example 228.
MS (ES) m/z 635.2.

Example 259

TERT-BUTYL 4-({[3-({3-[2-(2,4,6-TRIFLUOROBENZYL)-7-(TRIFLUOROMETHYL)-2H-INDAZOL-3-YL]PHENYL}ETHYNYL)PHENYL]AMINO}CARBONYL)PIPERAZINE-1-CARBOXYLATE

This compound was prepared similarly to that of Example 258.
MS (ES) m/z 734.3.

Example 260

2-METHYL-N-[3-({3-[2-(2,4,6-TRIFLUOROBEN-ZYL)-7-(TRIFLUOROMETHYL)-2H-INDAZOL-3-YL]PHENYL}ETHYNYL)PHENYL]PIPERIDINE-1-CARBOXAMIDE

This compound was prepared similarly to that of Example 258.
MS (ES) m/z 647.2.

Example 261

3-METHYL-N-[3-({3-[2-(2,4,6-TRIFLUOROBEN-ZYL)-7-(TRIFLUOROMETHYL)-2H-INDAZOL-3-YL]PHENYL}ETHYNYL)PHENYL]PIPERIDINE-1-CARBOXAMIDE

This compound was prepared similarly to that of Example 258.
MS (ES) m/z 647.2.

Example 262

4-METHYL-N-[3-({3-[2-(2,4,6-TRIFLUOROBEN-ZYL)-7-(TRIFLUOROMETHYL)-2H-INDAZOL-3-YL]PHENYL}ETHYNYL)PHENYL]PIPERIDINE-1-CARBOXAMIDE

This compound was prepared similarly to that of Example 258.
MS (ES) m/z 647.2.

Example 263

3-(HYDROXYMETHYL)-N-[3-({3-[2-(2,4,6-TRIF-LUOROBENZYL)-7-(TRIFLUOROMETHYL)-2H-INDAZOL-3-YL]PHENYL}ETHYNYL)PHENYL]PIPERIDINE-1-CARBOXAMIDE

This compound was prepared similarly to that of Example 258.
MS (ES) m/z 663.3.

Example 264

N-ISOPROPYL-N'-[3-({3-[2-(2,4,6-TRIFLUO-ROBENZYL)-7-(TRIFLUOROMETHYL)-2H-IN-DAZOL-3-YL]PHENYL}ETHYNYL)PHENYL]UREA

This compound was prepared similarly to that of Example 258.
MS (ES) m/z 607.2.

Example 265

N,N-DIPROPYL-N'-[3-({3-[2-(2,4,6-TRIFLUO-ROBENZYL)-7-(TRIFLUOROMETHYL)-2H-IN-DAZOL-3-YL]PHENYL}ETHYNYL)PHENYL]UREA

This compound was prepared similarly to that of Example 258.
MS (ES) m/z 649.3.

Example 266

N-METHYL-N'-[3-({3-[2-(2,4,6-TRIFLUOROBEN-ZYL)-7-(TRIFLUOROMETHYL)-2H-INDAZOL-3-YL]PHENYL}ETHYNYL)PHENYL]UREA

This compound was prepared similarly to that of Example 258.
MS (ESI) m/z 579.

Example 267

N,N-DIMETHYL-N'-[3-({3-[2-(2,4,6-TRIFLUO-ROBENZYL)-7-(TRIFLUOROMETHYL)-2H-IN-DAZOL-3-YL]PHENYL}ETHYNYL)PHENYL]UREA

This compound was prepared similarly to that of Example 258.
MS (ES) m/z 593.2.

Example 268

3-[3-(PYRIDIN-3-YLETHYNYL)PHENYL]-2-(2,4,6-TRIFLUOROBENZYL)-7-(TRIFLUOROM-ETHYL)-2H-INDAZOLE

This compound was prepared similarly to that of Example 228.
MS (ES) m/z 508.1.

Example 269

3-[3-(PYRIDIN-4-YLETHYNYL)PHENYL]-2-(2,4,6-TRIFLUOROBENZYL)-7-(TRIFLUOROM-ETHYL)-2H-INDAZOLE

This compound was prepared similarly to that of Example 228.
MS (ES) m/z 508.1.

Example 270

N-(METHYLSULFONYL)-N-[3-({3-[2-(2,4,6-TRI-FLUOROBENZYL)-7-(TRIFLUOROMETHYL)-2H-INDAZOL-3-YL]PHENYL}ETHYNYL)PHE-NYL]METHANESULFONAMIDE

This compound was prepared similarly to that of Example 228.
MS (ES) m/z 678.1.

Example 271

METHYL [3-({3-[2-(2,4,6-TRIFLUOROBENZYL)-7-(TRIFLUOROMETHYL)-2H-INDAZOL-3-YL]PHENYL}ETHYNYL)PHENYL]CARBAMATE

This compound was prepared similarly to that of Example 228.
MS (ES) m/z 580.1.

Example 272

1-METHYL-3-[3-({3-[2-(2,4,6-TRIFLUOROBEN-ZYL)-7-(TRIFLUOROMETHYL)-2H-INDAZOL-3-YL]PHENYL}ETHYNYL)PHENYL]IMIDAZOLI-DIN-2-ONE

This compound was prepared similarly to that of Example 228.
MS (ES) m/z 605.2.

Example 273

6-METHYL-2-({3-[2-(2,4,6-TRIFLUOROBEN-ZYL)-7-(TRIFLUOROMETHYL)-2H-INDAZOL-3-YL]PHENYL}ETHYNYL)PYRIDIN-3-OL

This compound was prepared similarly to that of Example 228.
MS (ES) m/z 538.1.

Example 274

3-[3-(PYRIDIN-2-YLETHYNYL)PHENYL]-2-(2,4,6-TRIFLUOROBENZYL)-7-(TRIFLUOROMETHYL)-2H-INDAZOLE

This compound was prepared similarly to that of Example 228.
MS (ES) m/z 508.1.

Example 275

METHYL 5-CYANO-2-{3-[2-(2,4,6-TRIFLUOROBENZYL)-7-(TRIFLUOROMETHYL)-2H-INDAZOL-3-YL]PHENYL}-1H-INDOLE-1-CARBOXYLATE

This compound was prepared similarly to that of Example 228.
MS (ES) m/z 603.7.

Example 276

2-({3-[2-(2,4,6-TRIFLUOROBENZYL)-7-(TRIFLUOROMETHYL)-2H-INDAZOL-3-YL]PHENYL}ETHYNYL)PYRIDIN-3-OL

This compound was prepared similarly to that of Example 228.
MS (ES) m/z 524.1.

Example 277

TERT-BUTYL 6-METHYL-5-{3-[2-(2,4,6-TRIFLUOROBENZYL)-7-(TRIFLUOROMETHYL)-2H-INDAZOL-3-YL]PHENOXY}-1H-INDOLE-1-CARBOXYLATE

This compound was prepared similarly to that of Example 3.
MS (ES) m/z 652.2.

Example 278

TERT-BUTYL 6-FLUORO-5-{3-[2-(2,4,6-TRIFLUOROBENZYL)-7-(TRIFLUOROMETHYL)-2H-INDAZOL-3-YL]PHENOXY}-1H-INDOLE-1-CARBOXYLATE

This compound was prepared similarly to that of Example 3.
MS (ES) m/z 656.2.

Example 279

4-FLUORO-2-({3-[2-(2,4,6-TRIFLUOROBENZYL)-7-(TRIFLUOROMETHYL)-2H-INDAZOL-3-YL]PHENYL}ETHYNYL)ANILINE

This compound was prepared similarly to that of Example 228.
MS (ES) m/z 538.1.

Example 280

4-CHLORO-2-FLUORO-6-({3-[2-(2,4,6-TRIFLUOROBENZYL)-7-(TRIFLUOROMETHYL)-2H-INDAZOL-3-YL]PHENYL}ETHYNYL)ANILINE

This compound was prepared similarly to that of Example 228.
MS (ES) m/z 571.9.

Example 281

METHYL [4-FLUORO-2-({3-[2-(2,4,6-TRIFLUOROBENZYL)-7-(TRIFLUOROMETHYL)-2H-INDAZOL-3-YL]PHENYL}ETHYNYL) PHENYL] CARBAMATE

This compound was prepared similarly to that of Example 228.
MS (ES) m/z 596.1.

Example 282

3-[3-(5-FLUORO-1H-INDOL-2-YL)PHENYL]-2-(2,4,6-TRIFLUOROBENZYL)-7-(TRIFLUOROMETHYL)-2H-INDAZOLE

A solution of methyl [4-fluoro-2-({3-[2-(2,4,6-trifluorobenzyl)-7-(trifluoromethyl)-2H-indazol-3-yl]phenyl}ethynyl)phenyl]carbamate (0.07 g, 0.12 mmol) and tetrabutylammonium fluoride (0.24 mL, 0.24 mmol, 1M solution in THF) in 2 mL THF was heated at 60° C. for 21 hours. The reaction mixture was concentrated in vacuo and the residue purified by normal phase HPLC (silica, hexane-EtOAC, 19:1) to give 0.045 g of product as a white solid.
MS (ES) m/z 539.7.

Example 283

3-[3-(5-FLUORO-1-METHYL-1H-INDOL-2-YL)PHENYL]-2-(2,4,6-TRIFLUOROBENZYL)-7-(TRIFLUOROMETHYL)-2H-INDAZOLE

A solution of 3-[3-(5-fluoro-1H-indol-2-yl)phenyl]-2-(2,4,6-trifluorobenzyl)-7-(trifluoromethyl)-2H-indazole (0.03 g, 0.056 mmol) in 2 mL THF was treated with sodium hydride (0.004 g, 0.1 mmol, 60% in oil). The reaction mixture was stirred for 20 minutes and treated with iodomethane (0.007 mL, 0.1 mmol). Stirring was continued for 1 hour. The reaction mixture was concentrated and purified by normal phase HPLC (silica, hexane-EtOAct, 19:1) to give 0.01 g of product as a white solid.
MS (ES) m/z 553.6.

Example 284

1-BENZYL-7-CHLORO-3-(4-METHOXY-2-METHYLPHENYL)-1H-INDAZOLE

This compound was prepared similarly to that of Example 1.

MS (ESI) m/z 363.

Example 285

7-CHLORO-2-(2-FLUOROBENZYL)-3-(4-METHOXY-2-METHYLPHENYL)-2H-INDAZOLE

This compound was prepared similarly to that of Example 1.

MS (ESI) m/z 381.

Example 286

7-CHLORO-2-(4-FLUOROBENZYL)-3-(4-METHOXY-2-METHYLPHENYL)-2H-INDAZOLE

This compound was prepared similarly to that of Example 1.

MS (ESI) m/z 381.

Example 287

2-BENZYL-7-CHLORO-3-(2,4-DIMETHOXYPHENYL)-2H-INDAZOLE

This compound was prepared similarly to that of Example 1.

MS (ESI) m/z 379.

Example 288

7-CHLORO-3-(2,4-DIMETHOXYPHENYL)-2-(2-FLUOROBENZYL)-2H-INDAZOLE

This compound was prepared similarly to that of Example 1.

MS (ESI) m/z 397.

Example 289

7-CHLORO-3-(2,4-DIMETHOXYPHENYL)-2-(4-FLUOROBENZYL)-2H-INDAZOLE

This compound was prepared similarly to that of Example 1.

MS (ESI) m/z 397.

Example 290

2-BENZYL-7-FLUORO-3-(4-METHOXY-2-METHYLPHENYL)-2H-INDAZOLE

This compound was prepared similarly to that of Example 1.

MS (ESI) m/z 347.

Example 291

7-FLUORO-2-(2-FLUOROBENZYL)-3-(4-METHOXY-2-METHYLPHENYL)-2H-INDAZOLE

This compound was prepared similarly to that of Example 1.

MS (ESI) m/z 365.

Example 292

7-FLUORO-2-(4-FLUOROBENZYL)-3-(4-METHOXY-2-METHYLPHENYL)-2H-INDAZOLE

This compound was prepared similarly to that of Example 1.

MS (ESI) m/z 365.

Example 293

2-(2-CHLORO-6-FLUOROBENZYL)-7-FLUORO-3-(4-METHOXY-2-METHYLPHENYL)-2H-INDAZOLE

This compound was prepared similarly to that of Example 1.

MS (ESI) m/z 399.

Example 294

2-(2-CHLOROBENZYL)-7-FLUORO-3-(4-METHOXY-2-METHYLPHENYL)-2H-INDAZOLE

This compound was prepared similarly to that of Example 1.

MS (ESI) m/z 381.

Example 295

2-(2,4-DIFLUOROBENZYL)-7-FLUORO-3-(4-METHOXY-2-METHYLPHENYL)-2H-INDAZOLE

This compound was prepared similarly to that of Example 1.

MS (ESI) m/z 383.

Example 296

2-BENZYL-3-(2,4-DIMETHOXYPHENYL)-7-FLUORO-2H-INDAZOLE

This compound was prepared similarly to that of Example 1.

MS (ESI) m/z 363.

Example 297

3-(2,4-DIMETHOXYPHENYL)-7-FLUORO-2-(2-FLUOROBENZYL)-2H-INDAZOLE

This compound was prepared similarly to that of Example 1.

MS (ESI) m/z 381.

Example 298

3-(2,4-DIMETHOXYPHENYL)-7-FLUORO-2-(4-FLUOROBENZYL)-2H-INDAZOLE

This compound was prepared similarly to that of Example 1.

MS (ESI) m/z 381.

Example 299

2-(2-CHLORO-6-FLUOROBENZYL)-3-(2,4-DIMETHOXYPHENYL)-7-FLUORO-2H-INDAZOLE

This compound was prepared similarly to that of Example 1.

MS (ESI) m/z 415.

Example 300

2-(2-CHLOROBENZYL)-3-(2,4-DIMETHOXYPHENYL)-7-FLUORO-2H-INDAZOLE

This compound was prepared similarly to that of Example 1.

MS (ESI) m/z 397.

Example 301

2-(2,4-DIFLUOROBENZYL)-3-(2,4-DIMETHOXYPHENYL)-7-FLUORO-2H-INDAZOLE

This compound was prepared similarly to that of Example 1.

MS (ESI) m/z 399.

Example 302

2-(3,4-DIFLUOROBENZYL)-3-(2,4-DIMETHOXYPHENYL)-7-FLUORO-2H-INDAZOLE

This compound was prepared similarly to that of Example 1.

MS (ESI) m/z 399.

Example 303

2-(4-CHLOROBENZYL)-3-(2,4-DIMETHOXYPHENYL)-7-FLUORO-2H-INDAZOLE

This compound was prepared similarly to that of Example 1.

MS (ESI) m/z 397.

Example 304

3-(3,4-DIFLUOROPHENYL)-2-(3-METHYLBENZYL)-7-(TRIFLUOROMETHYL)-2H-INDAZOLE

This compound was prepared similarly to that of Example 1.

MS (ESI) m/z 403.

Example 305

2-BENZYL-3-(3,4-DIFLUOROPHENYL)-7-(TRIFLUOROMETHYL)-2H-INDAZOLE

This compound was prepared similarly to that of Example 1.

MS (ESI) m/z 389.

Example 306

3-(3,4-DIFLUOROPHENYL)-2-(2-FLUOROBENZYL)-7-(TRIFLUOROMETHYL)-2H-INDAZOLE

This compound was prepared similarly to that of Example 1.

MS (ESI) m/z 407.

Example 307

3-(3,4-DIFLUOROPHENYL)-2-(2,4,6-TRIFLUOROBENZYL)-7-(TRIFLUOROMETHYL)-2H-INDAZOLE

This compound was prepared similarly to that of Example 1.

MS (ESI) m/z 443.

Example 308

2-(2,4-DIFLUOROBENZYL)-3-(3,4-DIFLUOROPHENYL)-7-(TRIFLUOROMETHYL)-2H-INDAZOLE

This compound was prepared similarly to that of Example 1.

MS (ESI) m/z 425.

Example 309

2-(3,4-DICHLOROBENZYL)-3-(3,4-DIFLUOROPHENYL)-7-(TRIFLUOROMETHYL)-2H-INDAZOLE

This compound was prepared similarly to that of Example 1.

MS (ESI) m/z 457.

Example 310

3-(4-CHLOROPHENYL)-2-(3,4-DICHLOROBENZYL)-7-(TRIFLUOROMETHYL)-2H-INDAZOLE

This compound was prepared similarly to that of Example 1.

MS (ES) m/z 455.1.

Example 311

3-(4-CHLOROPHENYL)-7-(TRIFLUOROMETHYL)-2-[4-(TRIFLUOROMETHYL)BENZYL]-2H-INDAZOLE

This compound was prepared similarly to that of Example 1.

MS (ES) m/z 455.1.

Example 312

3-(4-CHLOROPHENYL)-7-(TRIFLUOROM-
ETHYL)-2-[2-(TRIFLUOROMETHYL)BENZYL]-
2H-INDAZOLE

This compound was prepared similarly to that of Example 1.

MS (ES) m/z 455.1.

Example 313

3-(4-CHLOROPHENYL)-2-(2,4-DIMETHYLBEN-
ZYL)-7-(TRIFLUOROMETHYL)-2H-INDAZOLE

This compound was prepared similarly to that of Example 1.

MS (ES) m/z 415.2.

Example 314

3-(4-CHLOROPHENYL)-2-(2,4-DIFLUOROBEN-
ZYL)-7-(TRIFLUOROMETHYL)-2H-INDAZOLE

This compound was prepared similarly to that of Example 1.

MS (ES) m/z 423.1.

Example 315

3-(4-CHLOROPHENYL)-2-(2-FLUOROBENZYL)-
7-(TRIFLUOROMETHYL)-2H-INDAZOLE

This compound was prepared similarly to that of Example 1.

MS (ES) m/z 405.1.

Example 316

2-(4-CHLOROBENZYL)-3-(4-CHLOROPHE-
NYL)-7-(TRIFLUOROMETHYL)-2H-INDAZOLE

This compound was prepared similarly to that of Example 1.

MS (ES) m/z 421.1.

Example 317

2-(2-CHLOROBENZYL)-3-(4-CHLOROPHE-
NYL)-7-(TRIFLUOROMETHYL)-2H-INDAZOLE

This compound was prepared similarly to that of Example 1.

MS (ES) m/z 421.1.

Example 318

2-BENZYL-3-(2,4-DIFLUOROPHENYL)-7-(TRIF-
LUOROMETHYL)-2H-INDAZOLE

This compound was prepared similarly to that of Example 1.

MS (ES) m/z 389.2.

Example 319

3-(2,4-DIFLUOROPHENYL)-2-(2,4,6-TRIFLUO-
ROBENZYL)-7-(TRIFLUOROMETHYL)-2H-IN-
DAZOLE

This compound was prepared similarly to that of Example 1.

MS (ES) m/z 443.1.

Example 320

3-(4-CHLOROPHENYL)-2-(3-METHOXYBEN-
ZYL)-7-(TRIFLUOROMETHYL)-2H-INDAZOLE

This compound was prepared similarly to that of Example 1.

MS (ESI) m/z 417.

Example 321

3-(3-CHLOROPHENYL)-2-(2,4,6-TRIFLUO-
ROBENZYL)-7-(TRIFLUOROMETHYL)-2H-IN-
DAZOLE

This compound was prepared similarly to that of Example 1.

MS (ES) m/z 441.1.

Example 322

2-(4-CHLORO-2-FLUOROBENZYL)-3-(3-CHLO-
ROPHENYL)-7-(TRIFLUOROMETHYL)-2H-IN-
DAZOLE

This compound was prepared similarly to that of Example 1.

MS (ES) m/z 439.1.

Example 323

2-(2-CHLOROBENZYL)-3-(3-CHLOROPHE-
NYL)-7-(TRIFLUOROMETHYL)-2H-INDAZOLE

This compound was prepared similarly to that of Example 1.

MS (ES) m/z 421.1.

Example 324

2-(4-CHLOROBENZYL)-3-(3-CHLOROPHE-
NYL)-7-(TRIFLUOROMETHYL)-2H-INDAZOLE

This compound was prepared similarly to that of Example 1.

MS (ES) m/z 421.1.

Example 325

3-(4-CHLOROPHENYL)-2-(3-METHYLBEN-
ZYL)-7-(TRIFLUOROMETHYL)-2H-INDAZOLE

This compound was prepared similarly to that of Example 1.

MS (ESI) m/z 401.

Example 326

3-(4-CHLOROPHENYL)-2-(3-NITROBENZYL)-7-(TRIFLUOROMETHYL)-2H-INDAZOLE

This compound was prepared similarly to that of Example 1.

MS (ESI) m/z 432.

Example 327

3-(4-CHLOROPHENYL)-2-(2-METHYLBENZYL)-7-(TRIFLUOROMETHYL)-2H-INDAZOLE

This compound was prepared similarly to that of Example 1.

MS (ESI) m/z 401.

Example 328

3-(4-CHLOROPHENYL)-2-(4-METHOXYBENZYL)-7-(TRIFLUOROMETHYL)-2H-INDAZOLE

This compound was prepared similarly to that of Example 1.

MS (ESI) m/z 417.

Example 329

3-(4-CHLOROPHENYL)-2-(2,6-DICHLOROBENZYL)-7-(TRIFLUOROMETHYL)-2H-INDAZOLE

This compound was prepared similarly to that of Example 1.

MS (ESI) m/z 455.

Example 330

2-(4-TERT-BUTYLBENZYL)-3-(4-CHLOROPHENYL)-7-(TRIFLUOROMETHYL)-2H-INDAZOLE

This compound was prepared similarly to that of Example 1.

MS (ESI) m/z 443.

Example 331

3-(3-CHLOROPHENYL)-2-(2-FLUOROBENZYL)-7-(TRIFLUOROMETHYL)-2H-INDAZOLE

This compound was prepared similarly to that of Example 1.

MS (ESI) m/z 405.

Example 332

3-(3-CHLOROPHENYL)-2-(2,4-DIFLUOROBENZYL)-7-(TRIFLUOROMETHYL)-2H-INDAZOLE

This compound was prepared similarly to that of Example 1.

MS (ESI) m/z 423.

Example 333

3-(3-CHLOROPHENYL)-2-(2,4-DIMETHYLBENZYL)-7-(TRIFLUOROMETHYL)-2H-INDAZOLE

This compound was prepared similarly to that of Example 1.

MS (ESI) m/z 415.

Example 334

3-(3-CHLOROPHENYL)-7-(TRIFLUOROMETHYL)-2-[4-(TRIFLUOROMETHYL)BENZYL]-2H-INDAZOLE

This compound was prepared similarly to that of Example 1.

MS (ESI) m/z 455.

Example 335

3-(3-CHLOROPHENYL)-2-(3,4-DICHLOROBENZYL)-7-(TRIFLUOROMETHYL)-2H-INDAZOLE

This compound was prepared similarly to that of Example 1.

MS (ESI) m/z 455.

Example 336

3-(3-CHLOROPHENYL)-2-(3,4-DIFLUOROBENZYL)-7-(TRIFLUOROMETHYL)-2H-INDAZOLE

This compound was prepared similarly to that of Example 1.

MS (ESI) m/z 423.

Example 337

3-(3-CHLOROPHENYL)-2-(3-METHOXYBENZYL)-7-(TRIFLUOROMETHYL)-2H-INDAZOLE

This compound was prepared similarly to that of Example 1.

MS (ESI) m/z 417.

Example 338

3-(3-CHLOROPHENYL)-2-(3-METHYLBENZYL)-7-(TRIFLUOROMETHYL)-2H-INDAZOLE

This compound was prepared similarly to that of Example 1.

MS (ESI) m/z 401.

Example 339

3-(3-CHLOROPHENYL)-2-(3-NITROBENZYL)-7-(TRIFLUOROMETHYL)-2H-INDAZOLE

This compound was prepared similarly to that of Example 1.

MS (ESI) m/z 432.

Example 340

3-(3-CHLOROPHENYL)-2-(2-METHYLBENZYL)-7-(TRIFLUOROMETHYL)-2H-INDAZOLE

This compound was prepared similarly to that of Example 1.
MS (ESI) m/z 401.

Example 341

(1-{4-[2-(2-METHYLBENZYL)-7-(TRIFLUOROMETHYL)-2H-INDAZOL-3-YL]PHENYL}PIPERIDIN-3-YL)METHANOL

This compound was prepared similarly to that of Example 149.
MS (ESI) m/z 480.

Example 342

2-(2-FLUOROBENZYL)-3-[3-(4-METHYLPIPERIDIN-1-YL)PHENYL]-7-(TRIFLUOROMETHYL)-2H-INDAZOLE

This compound was prepared similarly to that of Example 149.
MS (ESI) m/z 468;

Example 343

(1-{3-[2-(3,4-DIFLUOROBENZYL)-7-(TRIFLUOROMETHYL)-2H-INDAZOL-3-YL]PHENYL}PIPERIDIN-3-YL)METHANOL

This compound was prepared similarly to that of Example 149.
MS (ESI) m/z 502.

Example 344

(1-{3-[2-(3-METHYLBENZYL)-7-(TRIFLUOROMETHYL)-2H-INDAZOL-3-YL]PHENYL}PIPERIDIN-4-YL)METHANOL

This compound was prepared similarly to that of Example 149.
MS (ESI) m/z 480.

Example 345

(1-{4-[2-(2,4-DIFLUOROBENZYL)-7-(TRIFLUOROMETHYL)-2H-INDAZOL-3-YL]PHENYL}PIPERIDIN-3-YL)METHANOL

This compound was prepared similarly to that of Example 149.
MS m/z 502.

Example 346

(1-{4-[2-(2-METHYLBENZYL)-7-(TRIFLUOROMETHYL)-2H-INDAZOL-3-YL]PHENYL}PIPERIDIN-4-YL)METHANOL

This compound was prepared similarly to that of Example 149.
MS (ESI) m/z 480.

Example 347

(1-{3-[2-(2,4-DIFLUOROBENZYL)-7-(TRIFLUOROMETHYL)-2H-INDAZOL-3-YL]PHENYL}PIPERIDIN-4-YL)METHANOL

This compound was prepared similarly to that of Example 149.
MS (ESI) m/z 502.

Example 348

(1-{3-[2-(2,4,6-TRIFLUOROBENZYL)-7-(TRIFLUOROMETHYL)-2H-INDAZOL-3-YL]PHENYL}PIPERIDIN-3-YL)METHANOL

This compound was prepared similarly to that of Example 149.
MS (ESI) m/z 520.

Example 349

(1-{3-[2-(2,4-DIFLUOROBENZYL)-7-(TRIFLUOROMETHYL)-2H-INDAZOL-3-YL]PHENYL}PIPERIDIN-3-YL)METHANOL

This compound was prepared similarly to that of Example 149.
MS (ESI) m/z 502.

Example 350

(1-{3-[2-(3-METHYLBENZYL)-7-(TRIFLUOROMETHYL)-2H-INDAZOL-3-YL]PHENYL}PIPERIDIN-3-YL)METHANOL

This compound was prepared similarly to that of Example 149.
MS (ESI) m/z 480.

Example 351

(1-{3-[2-(2,4,6-TRIFLUOROBENZYL)-7-(TRIFLUOROMETHYL)-2H-INDAZOL-3-YL]PHENYL}PIPERIDIN-4-YL)METHANOL

This compound was prepared similarly to that of Example 149.
MS (ESI) m/z 520.

Example 352

(1-{3-[2-(3,4-DIFLUOROBENZYL)-7-(TRIFLUOROMETHYL)-2H-INDAZOL-3-YL]PHENYL}PIPERIDIN-4-YL)METHANOL

This compound was prepared similarly to that of Example 149.
MS (ESI) m/z 502.

Example 353

8-{4-[2-(2,4,6-TRIFLUOROBENZYL)-7-(TRIFLUOROMETHYL)-2H-INDAZOL-3-YL]PHENYL}-1,4-DIOXA-8-AZASPIRO[4.5]DECANE

This compound was prepared similarly to that of Example 149.
MS (ESI) m/z 548.

Example 354

N-(2-PHENYLETHYL)-1-{4-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 609.

Example 355

3-[4-(4-MORPHOLIN-4-YLPIPERIDIN-1-YL)PHENYL]-2-(2,4,6-TRIFLUOROBENZYL)-7-(TRIFLUOROMETHYL)-2H-INDAZOLE

This compound was prepared similarly to that of Example 149.
MS (ES) m/z 575.0.

Example 356

7-{4-[2-(2,4,6-TRIFLUOROBENZYL)-7-(TRIFLUOROMETHYL)-2H-INDAZOL-3-YL]PHENYL}-1,4-DIOXA-7-AZASPIRO[4.5]DECANE

This compound was prepared similarly to that of Example 149.
MS (ES) m/z 548.

Example 357

7-{3-[2-(2,4,6-TRIFLUOROBENZYL)-7-(TRIFLUOROMETHYL)-2H-INDAZOL-3-YL]PHENYL}-1,4-DIOXA-7-AZASPIRO[4.5]DECANE

This compound was prepared similarly to that of Example 149.
MS (ES) m/z 548.

Example 358

8-{3-[2-(2,4,6-TRIFLUOROBENZYL)-7-(TRIFLUOROMETHYL)-2H-INDAZOL-3-YL]PHENYL}-1,4-DIOXA-8-AZASPIRO[4.5]DECANE

This compound was prepared similarly to that of Example 149.
MS (ES) m/z 548.

Example 359

1-{3-[2-(2,4,6-TRIFLUOROBENZYL)-7-(TRIFLUOROMETHYL)-2H-INDAZOL-3-YL]PHENYL}PIPERIDIN-4-ONE

This compound was prepared similarly to that of Example 149.
MS (ES) m/z 504.0.

Example 360

3-[3-(3-MORPHOLIN-4-YLPIPERIDIN-1-YL)PHENYL]-2-(2,4,6-TRIFLUOROBENZYL)-7-(TRIFLUOROMETHYL)-2H-INDAZOLE

This compound was prepared similarly to that of Example 149.
MS (ES) m/z 575.2.

Example 361

N-BUTYL-1-{4-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 561.

Example 362

N,N-DIPROPYL-1-{4-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ES) m/z 589.2.

Example 363

N-PHENYL-1-{4-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 581.

Example 364

3-{4-[4-(4-METHYLPIPERAZIN-1-YL)PIPERIDIN-1-YL]PHENYL}-2-(2,4,6-TRIFLUOROBENZYL)-7-(TRIFLUOROMETHYL)-2H-INDAZOLE

This compound was prepared similarly to that of Example 149.
MS (ESI) m/z 588.

Example 365

N-(CYCLOHEXYLMETHYL)-1-{4-[2-(2,4,6-TRI-FLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 601.

Example 366

N-HENYL-1-{3-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 581.

Example 367

N-(CYCLOHEXYLMETHYL)-1-{3-[2-(2,4,6-TRI-FLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 601.

Example 368

3-{3-[4-(4-METHYLPIPERAZIN-1-YL)PIPERIDIN-1-YL]PHENYL}-2-(2,4,6-TRIFLUOROBENZYL)-7-(TRIFLUOROMETHYL)-2H-INDAZOLE

This compound was prepared similarly to that of Example 149.
MS (ESI) m/z 588.

Example 369

N-BUTYL-1-{3-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 561.

Example 370

3-[3-(4-MORPHOLIN-4-YLPIPERIDIN-1-YL)PHENYL]-2-(2,4,6-TRIFLUOROBENZYL)-7-(TRIFLUOROMETHYL)-2H-INDAZOLE

This compound was prepared similarly to that of Example 149.
MS (ESI) m/z 575.

Example 371

N-(2-PHENYLETHYL)-1-{3-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 609.

Example 372

N-ETHYL-N-METHYL-1-{3-[2-(2,4,6-TRIFLUOROBENZYL)-7-(TRIFLUOROMETHYL)-2H-INDAZOL-3-YL]PHENYL}PIPERIDIN-4-AMINE

This compound was prepared similarly to that of Example 149.
MS (ESI) m/z 547.

Example 373

1-{3-[2-(2,4,6-TRIFLUOROBENZYL)-7-(TRIFLUOROMETHYL)-2H-INDAZOL-3-YL]PHENYL}PIPERIDIN-4-OL

This compound was prepared similarly to that of Example 149.
MS (ESI) m/z 506.

Example 374

3-(1-BENZOTHIEN-2-YL)-2-(2,4,6-TRIFLUOROBENZYL)-7-(TRIFLUOROMETHYL)-2H-INDAZOLE

A solution of 3-bromo-5-trifluoroindazole (1.8 g, 9.3 mmol) and 2,4,6-trifluorobenzyl bromide (2.19, 9.3 mmol) in 20 mL DMF was heated at 110° C. for 48 hours. The reaction mixture was partitioned with EtOAc and $H_2O$. The organic phase was concentrated in vacuo and the residue purified by flash chromatography (hexane-EtOAc: 9:1) to give the intermediate 2-(2,4,6-trifluorobenzyl-3-bromo-5-trifluoroindazole. Then a solution of 2-(2,4,6-trifluorobenzyl-3-bromo-5-trifluoroindazole (0.15 g, 0.37 mmol), 2-benzothiophene boronic acid (0.37 g, 0.21 mmol), palladium dichloro-diphenylphosphonoferrocene (0.02 g. 0.024 mmol) and potassium phosphate (0.222 g, 1.05 mmol) in ethylene glycol dimethylether (10 mL) was heated at 84° C. for 12 hours. The reaction mixture was partitioned with EtOAc and $H_2O$. The organic phase was concentrated in vacuo and the residue purified by flash chromatography (hexane-EtOAc, 10:1) to give the title compound
MS (ES) m/z 463.0.

Example 375

3-(1H-INDOL-5-YL)-2-(2,4,6-TRIFLUOROBENZYL)-7-(TRIFLUOROMETHYL)-2H-INDAZOLE

This compound was prepared similarly to that of Example 374.
MS (ESI) m/z 446.

Example 376

3-DIBENZO[B,D]THIEN-4-YL-2-(2,4,6-TRIFLUOROBENZYL)-7-(TRIFLUOROMETHYL)-2H-INDAZOLE

This compound was prepared similarly to that of Example 374.
MS (ES) m/z 513.0.

Example 377

3-(2-NAPHTHYL)-2-(2,4,6-TRIFLUOROBENZYL)-7-(TRIFLUOROMETHYL)-2H-INDAZOLE

This compound was prepared similarly to that of Example 374.
MS (ES) m/z 457.1.

Example 378

3-[2-(2-FLUORO-4-METHOXYPHENYL)-1H-INDOL-6-YL]-2-(2,4,6-TRIFLUOROBENZYL)-7-(TRIFLUOROMETHYL)-2H-INDAZOLE

This compound was prepared similarly to that of Example 374.
MS (ES) m/z 568.1.

Example 379

3-[1-(2,4-DICHLOROBENZYL)-1H-INDOL-5-YL]-2-(2,4,6-TRIFLUOROBENZYL)-7-(TRIFLUOROMETHYL)-2H-INDAZOLE

A solution of 3-(1H-indol-5-yl)-2-(2,4,6-trifluorobenzyl)-7-(trifluoromethyl)-2H-indazole (0.025 g, 0.056 mmol) and sodium hydride (60% in oil, 0.003 g, 0.07 mmol) in 1 mL DMF was stirred at ambient temperature under nitrogen for 20 minutes. 2,4-dichlorobenzyl bromide (0.081 g, 0.42 mmol) was added to the reaction mixture, which was stirred overnight and then partitioned between EtOAc and H$_2$O. The organic phase was concentrated and purified by normal phase HPLC (silica, hexane-EtOAc, 4:1) to provide the title compound.
MS (ES) m/z 604.0.

Example 380

3-{1-[5-CHLORO-2-(TRIFLUOROMETHYL)BENZYL]-1H-INDOL-5-YL}-2-(2,4,6-TRIFLUOROBENZYL)-7-(TRIFLUOROMETHYL)-2H-INDAZOLE

This compound was prepared similarly to that of Example 379.
MS (ES) m/z 638.0.

Example 381

3-[1-(2-CHLOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 570.0.

Example 382

3-[1-(2-FLUOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 554.1.

Example 383

3-[1-(2,4-DIFLUOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 572.

Example 384

3-(1-BENZYL-1H-INDOL-5-YL)-2-(2,4,6-TRIFLUOROBENZYL)-7-(TRIFLUOROMETHYL)-2H-INDAZOLE

This compound was prepared similarly to that of Example 379.
MS (ES) m/z 536.1.

Example 385

3-[1-(4-CHLOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 570.0.

Example 386

3-[1-(2-CHLORO-6-FLUOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 588.0.

Example 387

3-[1-(2,6-DICHLOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 604.0.

Example 388

3-[1-(2,6-DIFLUOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 572.1.

Example 389

3-[1-(2-CHLORO-4-FLUOROBENZYL)-1H-INDOL-5-YL]-2-(2,4,6-TRIFLUOROBENZYL)-7-(TRIFLUOROMETHYL)-2H-INDAZOLE

This compound was prepared similarly to that of Example 379.
MS (ES) m/z 588.0.

Example 390

3-[1-(2-FLUOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 554.0.

Example 391

3-[1-(2,6-DIFLUOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 572.1.

Example 392

3-[1-(2-CHLORO-4-FLUOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 588.0.

Example 393

3-[1-(2-CHLOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 570.0.

Example 394

3-[1-(2-CHLORO-6-FLUOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 588.0.

Example 395

3-[1-(2,4-DIFLUOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 572.1.

Example 396

3-[1-(2,6-DICHLOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 601.9.

Example 397

3-[1-(4-CHLOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 570.0.

Example 398

3-{1-[5-CHLORO-2-(TRIFLUOROMETHYL)BENZYL]-1H-INDOL-6-YL}-2-(2,4,6-TRIFLUOROBENZYL)-7-(TRIFLUOROMETHYL)-2H-INDAZOLE

This compound was prepared similarly to that of Example 379.
MS (ES) m/z 638.1.

Example 399

3-(1-BENZYL-1H-INDOL-6-YL)-2-(2,4,6-TRIFLUOROBENZYL)-7-(TRIFLUOROMETHYL)-2H-INDAZOLE

This compound was prepared similarly to that of Example 379.
MS (ES) m/z 536.1.

Example 400

3-[1-(2,4-DICHLOROBENZYL)-1H-INDOL-6-YL]-2-(2,4,6-TRIFLUOROBENZYL)-7-(TRIFLUOROMETHYL)-2H-INDAZOLE

This compound was prepared similarly to that of Example 379.
MS (ES) m/z 604.0.

Example 401

3-[2-(2,4,6-TRIFLUOROBENZYL)-7-(TRIFLUOROMETHYL)-2H-INDAZOL-3-YL]PHENOL

This compound was prepared similarly to that of Example 379.
MS (ES) m/z 423.1.

Example 402

2-{[3-[1-(2,6-DICHLOROBENZYL)-1H-INDOL-6-YL]-7-(TRIFLUOROMETHYL)-2H-INDAZOL-2-YL]METHYL}-3,5-DIFLUOROPHENOL

This compound was prepared similarly to that of Example 379.
MS (ES) m/z 603.1.

Example 403

2-{[3-[1-(2-CHLORO-6-FLUOROBENZYL)-1H-INDOL-6-YL]-7-(TRIFLUOROMETHYL)-2H-INDAZOL-2-YL]METHYL}-3,5-DIFLUOROPHENOL

This compound was prepared similarly to that of Example 379.
MS (ES) m/z 586.1.

Example 404

N,N-DIMETHYL-4-{3-[1-(2,4,6-TRIFLUOROBENZYL)-7-(TRIFLUOROMETHYL)-1H-INDAZOL-3-YL]PHENOXY}BENZENESULFONAMIDE

A solution of 3-[2-(2,4,6-trifluorobenzyl)-7-(trifluoromethyl)-1H-indazol-3-yl]phenol (0.09 g, 0.21 mmol, prepared similarly to that of Example 1), 4-fluoro-N,N-dimethyl-benzenesulfonamide (0.087 g, 0.42 mmol) and potassium carbonate (0.06 g, 0.42 mmol) in 1 mL DMF was heated at 150° C. for 3 hours, and then partitioned between EtOAc and $H_2O$. The organic phase was concentrated and purified by normal phase chromatography (silica, hexane-EtOAc, 4:1) to provide the title compound.
MS (ES) m/z 605.8.

Example 405

3-{3-[4-(MORPHOLIN-4-YLSULFONYL)PHENOXY]PHENYL}-2-(2,4,6-TRIFLUOROBENZYL)-7-(TRIFLUOROMETHYL)-2H-INDAZOLE

This compound was prepared similarly to that of Example 404.
MS (ES) m/z 648.

Example 406

N-PROPYL-4-{3-[2-(2,4,6-TRIFLUOROBENZYL)-7-(TRIFLUOROMETHYL)-2H-INDAZOL-3-YL]PHENOXY}BENZENESULFONAMIDE

This compound was prepared similarly to that of Example 404.
MS (ESI) m/z 620.

Example 407

3-{3-[4-(PYRROLIDIN-1-YLSULFONYL)PHENOXY]PHENYL}-2-(2,4,6-TRIFLUOROBENZYL)-7-(TRIFLUOROMETHYL)-2H-INDAZOLE

This compound was prepared similarly to that of Example 404.
MS (ES) m/z 632.2.

Example 408

3-{3-[4-(PIPERIDIN-1-YLSULFONYL)PHENOXY]PHENYL}-1-(2,4,6-TRIFLUOROBENZYL)-7-(TRIFLUOROMETHYL)-1H-INDAZOLE

This compound was prepared similarly to that of Example 404.
MS (ESI) m/z 646.

Example 409

N,N-DIETHYL-4-{3-[1-(2,4,6-TRIFLUOROBENZYL)-7-(TRIFLUOROMETHYL)-1H-INDAZOL-3-YL]PHENOXY}BENZENESULFONAMIDE

This compound was prepared similarly to that of Example 404.
MS (ES) m/z 634.3.

Example 410

N-ETHYL-N-METHYL-4-{3-[1-(2,4,6-TRIFLUOROBENZYL)-7-(TRIFLUOROMETHYL)-1H-INDAZOL-3-YL]PHENOXY}BENZENESULFONAMIDE

This compound was prepared similarly to that of Example 404.
MS (ES) m/z 620.3.

Example 411

7-FLUORO-2-(4-FLUOROBENZYL)-3-(4-FLUOROPHENYL)-2H-INDAZOLE

This compound was made in a similar manner as for Example 1.
MS (ESI) m/z 339.

Example 412

7-FLUORO-2-(2-FLUOROBENZYL)-3-(4-FLUO-ROPHENYL)-2H-INDAZOLE

This compound was made in a similar manner as for Example 1.
MS (ESI) m/z 339.

Example 413

2-(2,4-DIFLUOROBENZYL)-7-FLUORO-3-(4-FLUOROPHENYL)-2H-INDAZOLE

This compound was made in a similar manner as for Example 1.
MS (ESI) m/z 357.

Example 414

2-(3,4-DIFLUOROBENZYL)-7-FLUORO-3-(4-FLUOROPHENYL)-2H-INDAZOLE

This compound was made in a similar manner as for Example 1.
MS (ESI) m/z 357.

Example 415

2-(4-CHLOROBENZYL)-7-FLUORO-3-(4-FLUO-ROPHENYL)-2H-INDAZOLE

This compound was made in a similar manner as for Example 1.
MS (ESI) m/z 355.

Example 416

7-CHLORO-2-(4-CHLOROBENZYL)-3-(4-FLUO-ROPHENYL)-2H-INDAZOLE

This compound was made in a similar manner as for Example 1.
MS (ESI) m/z 371.

Example 417

7-CHLORO-2-(4-FLUOROBENZYL)-3-(4-FLUO-ROPHENYL)-2H-INDAZOLE

This compound was made in a similar manner as for Example 1.
MS (ESI) m/z 355.

Example 418

7-CHLORO-2-(3,4-DIFLUOROBENZYL)-3-(4-FLUOROPHENYL)-2H-INDAZOLE

This compound was made in a similar manner as for Example 1.
MS (ESI) m/z 373.

Example 419

7-CHLORO-2-(2,4-DIFLUOROBENZYL)-3-(4-FLUOROPHENYL)-2H-INDAZOLE

This compound was made in a similar manner as for Example 1.
MS (ESI) m/z 373.

Example 420

7-CHLORO-2-(2-FLUOROBENZYL)-3-(4-FLUO-ROPHENYL)-2H-INDAZOLE

This compound was made in a similar manner as for Example 1.
MS (ESI) m/z 355.

Example 421

1-[2-(2,4-DIFLUOROBENZYL)-3-(4-FLUO-ROPHENYL)-2H-INDAZOL-7-YL]PIPERIDINE-4-CARBOXAMIDE

This compound was made in a similar manner as for Example 149.
MS (ESI) m/z 465.

Example 422

2-(2,4-DIFLUOROBENZYL)-3-(4-FLUOROPHE-NYL)-7-MORPHOLIN-4-YL-2H-INDAZOLE

This compound was made in a similar manner as for Example 149.
MS (ESI) m/z 424.

Example 423

2-(2,4-DIFLUOROBENZYL)-3-(4-FLUOROPHE-NYL)-7-PIPERIDIN-1-YL-2H-INDAZOLE

This compound was made in a similar manner as for Example 149.
MS (ESI) m/z 422.

Example 424

2-(2,4-DIFLUOROBENZYL)-3-(4-FLUOROPHE-NYL)-N,N-DIMETHYL-2H-INDAZOL-7-AMINE

This compound was made in a similar manner as for Example 149.
MS (ESI) m/z 382.

Example 425

2-(2,4-DIFLUOROBENZYL)-N-ETHYL-3-(4-FLUOROPHENYL)-2H-INDAZOL-7-AMINE

This compound was made in a similar manner as for Example 149.
MS (ESI) m/z 382.

Example 426

2-(2,4-DIFLUOROBENZYL)-3-(4-FLUOROPHE-NYL)-7-PYRROLIDIN-1-YL-2H-INDAZOLE

This compound was made in a similar manner as for Example 149.
mp 112-114° C.; MS (ESI) m/z 408.

Example 427

2-(2,4-DIFLUOROBENZYL)-3-(4-FLUOROPHE-
NYL)-2H-INDAZOLE-7-CARBONITRILE

This compound was made in a similar manner as for Example 149.
MS (ESI) m/z 364.

Example 428

7-CHLORO-2-(2,4-DICHLOROBENZYL)-3-(4-
FLUOROPHENYL)-2H-INDAZOLE

This compound was made in a similar manner as for Example 1.
MS (ES) m/z 405.1.

Example 429

7-CHLORO-2-(2-CHLORO-4-FLUOROBENZYL)-
3-(4-FLUOROPHENYL)-2H-INDAZOLE

This compound was made in a similar manner as for Example 1.
MS (ES) m/z 389.1.

Example 430

7-CHLORO-2-(2-CHLORO-6-FLUOROBENZYL)-
3-(4-FLUOROPHENYL)-2H-INDAZOLE

This compound was made in a similar manner as for Example 1.
MS (ES) m/z 389.1.

Example 431

7-CHLORO-2-(2,6-DIFLUOROBENZYL)-3-(4-
FLUOROPHENYL)-2H-INDAZOLE

This compound was made in a similar manner as for Example 1.
MS (ES) m/z 373.1.

Example 432

7-CHLORO-3-(4-FLUOROPHENYL)-2-(2,4,6-TRI-
FLUOROBENZYL)-2H-INDAZOLE

This compound was made in a similar manner as for Example 1.
MS (ES) m/z 391.1.

Example 433

7-CHLORO-2-(2,4-DIMETHYLBENZYL)-3-(4-
FLUOROPHENYL)-2H-INDAZOLE

This compound was made in a similar manner as for Example 1.
MS (ES) m/z 365.2.

Example 434

2-(2,4-DIFLUOROBENZYL)-3-PYRIDIN-2-YL-7-
(TRIFLUOROMETHYL)-2H-INDAZOLE

Picolinic acid (12.3 g, 100 mmol), N,N-carbonyldiimidazole (17.8 g, 110 mmol) and anhydrous $CH_2Cl_2$ (150 mL) were combined and stirred at room temperature for 60 minutes. To the reaction mixture was added a solution of N,O-dimethylhydroxylamine hydrochloride (10.7 gr, 0.11 mole), anhydrous $CH_2Cl_2$ (50 mL) and diisopropylethylamine (20 mL), and stirring continued overnight. The reaction mixture was concentrated in vacuo and purified by flash chromatography (silica gel 60, MeOH/$CH_2Cl_2$, 9:1) to afford pyridine-2-carboxylic acid methoxy-methyl-amide (a pale yellow liquid, 15.9 g, 95%); ESI) m/z 167.

Then a solution of pyridine-2-carboxylic acid methoxy-methyl-amide (1.5 g, 9 mmoles) was allowed to react with 2-flouro-3-trifluoromethylphenylmagnesium bromide (2.72 g, 10 mmoles) in THF (30 mL) at 60° C. overnight. The reaction mixture was cooled and diluted with ethyl acetate and ammonium chloride. The organic portion was washed with brine and dried over $MgSO_4$ and stripped to afford a crude product, which was purified by chromatography with $CH_2Cl_2$ to give (6-fluoro-5-trifluoromethyl-cyclohexa-2,4-dienyl)-pyridin-2-yl-methanone as a colorless liquid (1.6 gr., 65%).

Next, a solution of (6-fluoro-5-trifluoromethyl-cyclohexa-2,4-dienyl)-pyridin-2-yl-methanone (1.5 g, 5.6 mmol), 4-dimethylaminopyridine (0.5 g) and hydrazine hydrate (5 mL) in pyridine (20 mL) was heated at 100° C. overnight. The reaction mixture was cooled and diluted with brine and EtOAc. The organics were washed with water (3×25 mL), then brine (25 mL) and dried over $MgSO_4$. The reaction mixture was concentrated in vacuo and purified by flash chromatography (silica gel 60, EtOAc/$CH_2Cl_2$, 19:1) to afford 3-pyridin-2-yl-7-(trifluoromethyl)-2H-indazole as a pale yellow solid (1.1 g, 76%).

Then a solution of 3-pyridin-2-yl-7-(trifluoromethyl)-2H-indazole (0.183 g, 0.7 mmol) and 2,4,6-trifluorobenzyl bromide (0.203 g, 0.9 mmol) in DMF (5 mL) was heated at 120° C. After 5 days, the reaction mixture was partitioned with EtOAc and water. Organics were washed with water (3×), then brine and dried over $MgSO_4$, then stripped and the resulting crude product was flashed by reverse phase HPLC to afford the title compound (0.033 g, 5%).
MS m/z 390.

Example 435

2-(2-CHLORO-4-FLUOROBENZYL)-3-(PYRI-
DIN-2-YLMETHYL)-7-(TRIFLUOROMETHYL)-
2H-INDAZOLE

This compound was made in a similar manner as for Example 434.
MS (ESI) m/z 420.

Example 436

2-(2,4-DIFLUOROBENZYL)-3-(PYRIDIN-2-YLM-
ETHYL)-7-(TRIFLUOROMETHYL)-2H-INDA-
ZOLE

This compound was made in a similar manner as for Example 434.
MS (ESI) m/z 404.

Example 437

2-(2-CHLORO-6-FLUOROBENZYL)-3-(PYRIDIN-2-YLMETHYL)-7-(TRIFLUOROMETHYL)-2H-INDAZOLE

This compound was made in a similar manner as for Example 434.
MS (ESI) m/z 420.

Example 438

2-(2,6-D FLUOROBENZYL)-3-(PYRIDIN-2-YLMETHYL)-7-(TRIFLUOROMETHYL)-2H-INDAZOLE

This compound was made in a similar manner as for Example 434.
MS (ESI) m/z 404.

Example 439

3-(PYRIDIN-2-YLMETHYL)-2-(2,4,6-TRIFLUOROBENZYL)-7-(TRIFLUOROMETHYL)-2H-INDAZOLE

This compound was made in a similar manner as for Example 434.
MS (ESI) m/z 422.

Example 440

2-(2,6-DICHLOROBENZYL)-3-(PYRIDIN-2-YLMETHYL)-7-(TRIFLUOROMETHYL)-2H-INDAZOLE

This compound was made in a similar manner as for Example 434.
MS (ESI) m/z 436.

Example 441

2-(2,6-DIFLUOROBENZYL)-3-PYRIDIN-2-YL-7-(TRIFLUOROMETHYL)-2H-INDAZOLE

This compound was made in a similar manner as for Example 434.
MS (ES) m/z 390.1.

Example 442

2-(2-METHYLPHENYL)-3-PYRIDIN-2-YL-7-(TRIFLUOROMETHYL)-2H-INDAZOLE

A solution of 3-pyridin-2-yl-7-(trifluoromethyl)-2H-indazole (0.2633 g, 1 mmol), 2-methylphenylboronic acid (0.271 g, 2 mmol), copper(II)acetate (0.181 g, 1 mmol) and pyridine (0.161 mL, 2 mmol) in 20 mL of methylene chloride was stirred at ambient temperature for 2 hours. The reaction mixture was concentrated in vacuo and purified by flash chromatography (silica gel 60, methylene chloride-ethyl acetate, 3:1) to give the title compound (0.08 g).
MS (ES) m/z 354.0.

Example 443

3-(4-BROMOPHENYL)-2-(2,4,6-TRIFLUOROBENZYL)-7-(TRIFLUOROMETHYL)-2H-INDAZOLE

This compound was made in a similar manner as for Example 1.
MS m/z 485.

Example 444

{3-[2-(2,4,6-TRIFLUOROBENZYL)-7-(TRIFLUOROMETHYL)-2H-INDAZOL-3-YL]PHENYL}AMINE

Combined in a large microwave vial were 3-(3-chlorophenyl)-2-(2,4,6-trifluorobenzyl)-7-(trifluoromethyl)-2H-indazole (1.0 g, 2.3 mmol), benzophenone-diphenylimine (0.500 g, 2.8 mmol), sodium t-butoxide (0.260 mg, 2.8 mmoles), tris dibenzylideneacetone-dipalladium (0.150 g, 0.16 mmoles), dicyclohexyl-dimethylamino-biphenyl (0.25 g, 0.63 mmol) and dimethoxyethane (8 mL), which were then ran in a microwave (Emory's Optimizer, Personal Chemistry) at 150° C. for 10 minutes. The reaction mixture was diluted with ethyl acetate and water; then the organics were washed with water and brine and dried over magnesium sulfate. The solvent was removed and the crude material purified by flash chromatography (silica 60, 10% ethyl acetate/hexane) to afford N-(diphenylmethylene)-N-{3-[2-(2,4,6-trifluorobenzyl)-7-(trifluoromethyl)-2H-indazol-3-yl]phenyl}amine as a pale yellow solid (0.82 gr, 62%).

Then a solution of N-(diphenylmethylene)-N-{3-[2-(2,4,6-trifluorobenzyl)-7-(trifluoromethyl)-2H-indazol-3-yl]phenyl}amine (0.77 g, 1.31 mmol) in methanol (10 mL) was treated with sodium acetate (0.25 g, 3 mmol) and hydroxylamine hydrochloride (0.15 g, 2.2 mmol), and stirred at room temperature for 2 hours. The methanol was evaporated and the residue slurried in ether, the inorganic solid filtered off, and the ether stripped to afford crude product, which was purified by flash chromatography (silica 60, 10% hexane/ethyl acetate) to afford the title compound (0.28 g, 50%).
MS (ESI) m/z 422.

Example 445

{4-[2-(2,4,6-TRIFLUOROBENZYL)-7-(TRIFLUOROMETHYL)-2H-INDAZOL-3-YL]PHENYL}AMINE

This compound was made in a similar manner as for Example 444.
MS (ES) m/z 422.0.

Example 446

N-ISOBUTYL-N'-{4-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS m/z 521; MS m/z 519.

Example 447

N-(PIPERIDIN-4-YLMETHYL)-N'-{4-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS m/z 560.

Example 448

N-(2-METHOXYBENZYL)-N'-{4-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS m/z 585; MS m/z 583.

Example 449

N,N-DIPROPYL-N'-{4-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS m/z 549; MS m/z 547.

Example 450

N-(TETRAHYDROFURAN-2-YLMETHYL)-N'-{4-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS (ESI) m/z 549; MS (ESI) m/z 547.

Example 451

N-(4-BROMOPHENYL)-N'-{4-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS (ESI) m/z 619; MS (ESI) m/z 617.

Example 452

N-(PYRIDIN-4-YLMETHYL)-N'-{4-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS (ESI) m/z 556; MS (ESI) m/z 554.

Example 453

2-(2,4-DICHLOROBENZYL)-3-PYRIDIN-2-YL-7-(TRIFLUOROMETHYL)-2H-INDAZOLE

This compound was made in a similar manner as for Example 434.
MS (ES) m/z 421.9.

Example 454

2-(2,4-DIMETHYLBENZYL)-3-PYRIDIN-2-YL-7-(TRIFLUOROMETHYL)-2H-INDAZOLE

This compound was made in a similar manner as for Example 434.
MS (ES) m/z 382.0.

Example 455

3-PYRIDIN-2-YL-2-(2,4,6-TRIFLUOROBENZYL)-7-(TRIFLUOROMETHYL)-2H-INDAZOLE

This compound was made in a similar manner as for Example 434.
MS (ES) m/z 407.9.

Example 456

2-(2-CHLOROBENZYL)-3-PYRIDIN-2-YL-7-(TRIFLUOROMETHYL)-2H-INDAZOLE

This compound was made in a similar manner as for Example 434.
MS (ES) m/z 387.9.

Example 457

2-(4-CHLOROBENZYL)-3-PYRIDIN-2-YL-7-(TRIFLUOROMETHYL)-2H-INDAZOLE

This compound was made in a similar manner as for Example 434.
MS (ES) m/z 387.9.

Example 458

2-(2-CHLORO-6-FLUOROBENZYL)-3-PYRIDIN-2-YL-7-(TRIFLUOROMETHYL)-2H-INDAZOLE

This compound was made in a similar manner as for Example 434.
MS (ES) m/z 405.9.

Example 459

2-(2-CHLORO-4-FLUOROBENZYL)-3-PYRIDIN-2-YL-7-(TRIFLUOROMETHYL)-2H-INDAZOLE

This compound was made in a similar manner as for Example 434.
MS (ES) m/z 405.9.

Example 460

N-(2-FLUOROPHENYL)-N'-{3-[2-(2,4,6-TRIFLUOROBENZYL)-7-(TRIFLUOROMETHYL)-2H-INDAZOL-3-YL]PHENYL}UREA

This compound was made in a similar manner as for Example 258.
MS (ES) m/z 556.8.

Example 461

N-(2-CHLOROPHENYL)-N'-{4-[2-(2,4,6-TRIF-LUOROBENZYL)-7-(TRIFLUOROMETHYL)-2H-IDAZOL-3-YL]PHENYL}UREA

This compound was made in a similar manner as for Example 258.
MS (ES) m/z 572.8.

Example 462

N-PHENYL-N-{3-[2,4,6-TRIFLUOROBENZYL)-7-(TRIFLUOROMETHYL)-2H-INDAZOL-3-YL]PHENYL}UREA

This compound was made in a similar manner as for Example 258.
MS (ES) m/z 538.8.

Example 463

N-(2-CHLOROPHENYL)-N'-{3-[2-(2,4,6-TRIF-LUOROBENZYL)-7-(TRIFLUOROMETHYL)-2H-INDAZOL-3-YL]PHENYL}UREA

This compound was made in a similar manner as for Example 258.
MS (ES) m/z 572.8.

Example 464

N-(2-FLUOROPHENYL)-N'-{4-[2-(2,4,6-TRIFLUO-ROBENZYL)-7-(TRIFLUOROMETHYL)-2H-INDAZOL-3-YL]PHENYL}UREA

This compound was made in a similar manner as for Example 258.
MS (ES) m/z 556.8.

Example 465

N-PHENYL-N'-{4-[2-(2,4,6-TRIFLUOROBEN-ZYL)-7-(TRIFLUOROMETHYL)-2H-INDAZOL-3-YL]PHENYL}UREA

This compound was made in a similar manner as for Example 258.
MS (ES) m/z 538.8.

Example 466

3-(4-PIPERAZIN-1-YLPHENYL)-2-(2,4,6-TRIF-LUOROBENZYL)-7-(TRIFLUOROMETHYL)-2H-INDAZOLE

This compound was made in a similar manner as for Example 149.
MS (ES) m/z 491.0.

Example 467

3-[4-(4-BENZOYLPIPERAZIN-1-YL)PHENYL]-2-(2,4,6-TRIFLUOROBENZYL)-7-(TRIFLUOROM-ETHYL)-2H-INDAZOLE

Combined in a vial were 3-(4-piperazin-1-ylphenyl)-2-(2, 4,6-trifluorobenzyl)-7-(trifluoromethyl)-2H-indazole (0.10 g, 0.2 mmol), benzoyl chloride (0.030 g, 0.22 mmol), and diisopropylethylamine (0.2 mL) and THF (2 mL), which were stirred overnight at room temperature. Then the reaction mixture was diluted with ethyl acetate and water, and the organics washed with water and brine, then dried over magnesium sulfate. The crude product was purified by flash chromatography (silica 60, 5% EtOAc/CH$_2$Cl$_2$) to provide the title compound (0.06 g, 50%).
MS (ESI) m/z 595.

Example 468

3-{4-[4-(2-CHLOROBENZOYL)PIPERAZIN-1-YL]PHENYL}-2-(2,4,6-TRIFLUOROBENZYL)-7-(TRIFLUOROMETHYL)-2H-INDAZOLE

This compound was made in a similar manner as for Example 467.
MS (ESI) m/z 629.

Example 469

3-{4-[4-(2-THIENYLCARBONYL)PIPERAZIN-1-YL]PHENYL}-2-(2,4,6-TRIFLUOROBENZYL)-7-(TRIFLUOROMETHYL)-2H-INDAZOLE

This compound was made in a similar manner as for Example 467.
MS (ES) m/z 601.0.

Example 470

3-{4-[4-(2-METHOXYBENZOYL)PIPERAZIN-1-YL]PHENYL}-2-(2,4,6-TRIFLUOROBENZYL)-7-(TRIFLUOROMETHYL)-2H-INDAZOLE

This compound was made in a similar manner as for Example 467.
MS (ES) m/z 625.1.

Example 471

3-{4-[4-(3-METHOXYBENZOYL)PIPERAZIN-1-YL]PHENYL}-2-(2,4,6-TRIFLUOROBENZYL)-7-(TRIFLUOROMETHYL)-2H-INDAZOLE

This compound was made in a similar manner as for Example 467.
MS (ES) m/z 625.1.

Example 472

3-{4-[4-(4-METHOXYBENZOYL) PIPERAZIN-1-YL]PHENYL}-2-(2,4,6-TRIFLUOROBENZYL)-7-(TRIFLUOROMETHYL)-2H-INDAZOLE

This compound was made in a similar manner as for Example 467.
MS (ES) m/z 625.1.

Example 473

3-(4-CHLOROPYRIDIN-2-YL)-7-(TRIFLUOROM-ETHYL)-1H-INDAZOLE

This compound was made in a similar manner as for Example 434.
MS (ESI) m/z 298.

Example 474

N-(2,5-DIFLUOROBENZYL)-2-[2-(2,4-DIFLUOROBENZYL)-7-(TRIFLUOROMETHYL)-2H-INDAZOL-3-YL]PYRIDIN-4-AMINE

This compound was made in a similar manner as for Example 444.
MS (ESI) m/z 531.

Example 475

2-[2-(2,4-DIFLUOROBENZYL)-7-(TRIFLUOROMETHYL)-2H-INDAZOL-3-YL]-N-(2,5-DIMETHYLBENZYL)PYRIDIN-4-AMINE

This compound was made in a similar manner as for Example 444.
MS (ES) m/z 521.2.

Example 476

N-(3,5-DIFLUOROBENZYL)-2-[2-(2,4-DIFLUOROBENZYL)-7-(TRIFLUOROMETHYL)-2H-INDAZOL-3-YL]PYRIDIN-4-AMINE

This compound was made in a similar manner as for Example 444.
MS (ES) m/z 529.1.

Example 477

N-(1H-INDOL-5-YLMETHYL)-3-[2-(2,4,6-TRIFLUOROBENZYL)-7-(TRIFLUOROMETHYL)-2H-INDAZOL-3-YL]ANILINE

A solution of ({3-[2-(2,4,6-trifluorobenzyl)-7-(trifluoromethyl)-2H-indazol-3-yl]phenyl}amine (0.1 g, 0.24 mmol), indole 5-carboxaldehyde (0.035 g, 0.24 mmol), sodium formate (0.189 g, 3 mmol) and sodium cyanoborohydride (0.188 g, 3 mmol) in methanol (3 mL) was heated at 60° C. overnight. The reaction mixture was cooled, and concentrated in vacuo. The residue was partitioned with ethyl acetate and ammonium hydroxide. The organic phase was concentrated in vacuo to afford crude product, which was purified by flash chromatography (silic gel 60, methylene chloride) to afford the title compound (0.031 g, 24%).
MS (ES) m/z 551.2.

Example 478

N-[(1-METHYL-1H-INDOL-5-YL)METHYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ES) m/z 565.2.

Example 479

{3-[2-(2,4-DIFLUOROBENZYL)-7-(TRIFLUOROMETHYL)-2H-INDAZOL-3-YL]PHENYL}AMINE

This compound was made in a similar manner as for Example 444.
MS (ES) m/z 404.1.

Example 480

{3-[2-(2,4-DIFLUOROBENZYL)-7-(TRIFLUOROMETHYL)-2H-INDAZOL-3-YL]PHENYL}[(1-METHYL-1H-INDOL-2-YL)METHYL]AMINE

This compound was made in a similar manner as for Example 477.
MS (ESI) m/z 547; MS (ESI) m/z 545.

Example 481

N-(2-FLUORO-4-METHOXYBENZYL)-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ESI) m/z 560.

Example 482

N-(2,5-DIMETHYLBENZYL)-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ES) m/z 540.2.

Example 483

N-[2-FLUORO-5-(TRIFLUOROMETHYL)BENZYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ESI) m/z 598.

Example 484

N-[2-FLUORO-3-(TRIFLUOROMETHYL)BENZYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ESI) m/z 598.

Example 485

N-(2,5-DIMETHYLBENZYL)-4-[2-(2,4,6-TRIFLUOROBENZYL)-7-(TRIFLUOROMETHYL)-2H-INDAZOL-3-YL]ANILINE

This compound was made in a similar manner as for Example 477.
MS (ESI) m/z 540.

Example 486

N-[2-FLUORO-5-(TRIFLUOROMETHYL)BEN-ZYL]-4-[2-(2,4,6-TRIFLUOROBENZYL)-7-(TRIF-LUOROMETHYL)-2H-INDAZOL-3-YL]ANILINE

This compound was made in a similar manner as for Example 477.
MS (ES) m/z 596.2.

Example 487

N-(PYRIDIN-2-YLMETHYL)-3-[2-(2,4,6-TRIF-LUOROBENZYL)-7-(TRIFLUOROMETHYL)-2H-INDAZOL-3-YL]ANILINE

This compound was made in a similar manner as for Example 477.
MS (ES) m/z 513.1.

Example 488

N-(1H-INDOL-7-YLMETHYL)-3-[2-(2,4,6-TRIF-LUOROBENZYL)-7-(TRIFLUOROMETHYL)-2H-INDAZOL-3-YL]ANILINE

This compound was made in a similar manner as for Example 477.
MS (ES) m/z 549.2.

Example 489

N-(PYRIDIN-3-YLMETHYL)-3-[2-(2,4,6-TRIFLUO-ROBENZYL)-7-(TRIFLUOROMETHYL)-2H-INDAZOL-3-YL]ANILINE
This compound was made in a similar manner as for Example 477.
MS (ES) m/z 513.1.

Example 490

N-(1H-INDOL-4-YLMETHYL)-3-[2-(2,4,6-TRIF-LUOROBENZYL)-7-(TRIFLUOROMETHYL)-2H-INDAZOL-3-YL]ANILINE

This compound was made in a similar manner as for Example 477.
MS (ES) m/z 551.1.

Example 491

N-(PYRIDIN-4-YLMETHYL)-3-[2-(2,4,6-TRIF-LUOROBENZYL)-7-(TRIFLUOROMETHYL)-2H-INDAZOL-3-YL]ANILINE

This compound was made in a similar manner as for Example 477.
MS (ES) m/z 513.1.

Example 492

N-[(5-CHLORO-2-THIENYL)METHYL]-3-[2-(2,4,6-TRIFLUOROBENZYL)-7-(TRIFLUOROM-ETHYL)-2H-INDAZOL-3-YL]ANILINE

This compound was made in a similar manner as for Example 477.
MS (ES) m/z 552.0.

Example 493

N-[(5-BROMO-2-THIENYL)METHYL]-3-[2-(2,4,6-TRIFLUOROBENZYL)-7-(TRIFLUOROM-ETHYL)-2H-INDAZOL-3-YL]ANILINE

This compound was made in a similar manner as for Example 477.
MS (ES) m/z 596.0.

Example 494

N-[(4-BROMO-2-THIENYL)METHYL]-3-[2-(2,4,6-TRIFLUOROBENZYL)-7-(TRIFLUOROM-ETHYL)-2H-INDAZOL-3-YL]ANILINE

This compound was made in a similar manner as for Example 477.
MS (ES) m/z 596.0.

Example 495

N-[(5-METHYL-2-THIENYL)METHYL]-3-[2-(2,4,6-TRIFLUOROBENZYL)-7-(TRIFLUOROM-ETHYL)-2H-INDAZOL-3-YL]ANILINE

This compound was made in a similar manner as for Example 477.
MS (ES) m/z 532.1.

Example 496

N-[(3-METHYL-2-THIENYL)METHYL]-3-[2-(2,4,6-TRIFLUOROBENZYL)-7-(TRIFLUOROM-ETHYL)-2H-INDAZOL-3-YL]ANILINE

This compound was made in a similar manner as for Example 477.
MS (ES) m/z 532.1.

Example 497

N-[(1-ETHYL-1H-INDOL-5-YL)METHYL]-3-[2-(2,4,6-TRIFLUOROBENZYL)-7-(TRIFLUOROM-ETHYL)-2H-INDAZOL-3-YL]ANILINE

This compound was made in a similar manner as for Example 477.
MS (ES) m/z 579.1.

Example 498

N-[(1-PROPYL-1H-INDOL-5-YL)METHYL]-3-[2-(2,4,6-TRIFLUOROBENZYL)-7-(TRIFLUOROM-ETHYL)-2H-INDAZOL-3-YL]ANILINE

This compound was made in a similar manner as for Example 477.
MS (ES) m/z 593.1.

Example 499

N-[(1-BUTYL-1H-INDOL-5-YL)METHYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ESI) m/z 607.

Example 500

N-[(3-METHYL-1-BENZOTHIEN-2-YL)METHYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ES) m/z 582.0.

Example 501

N-[(2-METHYL-1H-IMIDAZOL-5-YL)METHYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ES) m/z 514.0.

Example 502

N-(2-NAPHTHYLMETHYL)-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ES) m/z 562.0.

Example 503

N-[(1-SEC-BUTYL-1H-INDOL-5-YL)METHYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ES) m/z 607.1.

Example 504

N-[(1-ISOPROPYL-1H-INDOL-5-YL)METHYL]-3-[2-(2,4,6-TRIFLUOROBENZYL)-7-(TRIFLUOROMETHYL)-2H-INDAZOL-3-YL]ANILINE

This compound was made in a similar manner as for Example 477.
MS (ES) m/z 593.2.

Example 505

3-(4-ETHYNYLPHENYL)-2-(2,4,6-TRIFLUOROBENZYL)-7-(TRIFLUOROMETHYL)-2H-INDAZOLE

This compound was made in a similar manner as for Example 229.
MS (ES) m/z 431.1.

Example 506

ETHYL 3-({4-[2-(2,4,6-TRIFLUOROBENZYL)-7-(TRIFLUOROMETHYL)-2H-INDAZOL-3-YL]PHENYL}ETHYNYL)BENZOATE

This compound was made in a similar manner as for Example 229.
MS (ES) m/z 579.1.

Example 507

3-({4-[2-(2,4,6-TRIFLUOROBENZYL)-7-(TRIFLUOROMETHYL)-2H-INDAZOL-3-YL]PHENYL}ETHYNYL)BENZOIC ACID

This compound was made in a similar manner as for Example 229.
MS (ESI) m/z 551.

Example 508

TERT-BUTYL 4-[3-({4-[2-(2,4,6-TRIFLUOROBENZYL)-7-(TRIFLUOROMETHYL)-2H-INDAZOL-3-YL]PHENYL}ETHYNYL)BENZOYL]PIPERAZINE-1-CARBOXYLATE

This compound was made in a similar manner as for Example 229.
MS (ES) m/z 719.2.

Example 509

3-(4-{[2-CHLORO-5-(TRIFLUOROMETHYL)PHENYL]ETHYNYL}PHENYL)-2-(2,4,6-TRIFLUOROBENZYL)-7-(TRIFLUOROMETHYL)-2H-INDAZOLE

This compound was made in a similar manner as for Example 229.
$^1$H NMR (CDCl$_3$): δ 5.70 (2H, s), 6.58-6.65 (2H, m), 7.21 (1H, t, J=2.7 Hz), 7.51-7.56 (3H, m), 7.59-7.63 (2H, m), 7.68-7.70 (1H, d, J=8.5 Hz), 7.76-7.78 (2H, m), 7.88 (1H, d, J=2.1 Hz).

Example 510

3-{4-[(2,4-DIFLUOROPHENYL)ETHYNYL]PHENYL}-2-(2,4,6-TRIFLUOROBENZYL)-7-(TRIFLUOROMETHYL)-2H-INDAZOLE

This compound was made in a similar manner as for Example 229.
$^1$H NMR (CDCl$_3$): δ 5.70 (2H, s), 6.58-6.63 (2H, m), 6.89-6.95 (2H, m), 7.09-7.13 (1H, m), 7.48-7.54 (3H, m), 7.58-7.62 (1H, m), 7.67-7.74 (3H, m).

Example 511

3-{4-[(3,5-DIMETHYLPHENYL)ETHYNYL]PHENYL}-2-(2,4,6-TRIFLUOROBENZYL)-7-(TRIFLUOROMETHYL)-2H-INDAZOLE

This compound was made in a similar manner as for Example 229.

$^1$H NMR (CDCl$_3$): δ 2.34 (6H, s), 5.70 (2H, s), 6.58-6.64 (2H, m), 7.02 (1H, s), 7.09-7.13 (1H, m), 7.22 (2H, s), 7.47 (2H, d, J=7.9 Hz), 7.61 (1H, d, J=7.9 Hz), 7.69 (3H, m).

Example 512

3-{4-[(3-CHLORO-2-FLUOROPHENYL)ETHYNYL]PHENYL}-2-(2,4,6-TRIFLUOROBENZYL)-7-(TRIFLUOROMETHYL)-2H-INDAZOLE

This compound was made in a similar manner as for Example 229.

$^1$H NMR (CDCl$_3$): δ 5.70 (2H, s), 6.57-6.64(2H, m), 7.09-7.14 (2H, m), 7.40-7.49 (2H, m), 7.51 (2H, d, J=8.1 Hz), 7.62 (1H, d, J=7.0 Hz), 7.69 (1H, d, J=8.5 Hz), 7.74 (2H, dd, J=6.6 Hz, J=1.6 Hz).

Example 513

3-{4-[(2,3-DICHLOROPHENYL)ETHYNYL]PHENYL}-2-(2,4,6-TRIFLUOROBENZYL)-7-(TRIFLUOROMETHYL)-2H-INDAZOLE

This compound was made in a similar manner as for Example 229.

$^1$H NMR (CDCl$_3$): δ 5.70 (2H, s), 6.58-6.64(2H, m), 7.10-7.14 (1H, m), 7.21-7.25 (2H, m), 7.46-7.54 (3H, m), 7.62 (1H, d, J=7.1 Hz), 7.69 (1H, d, J=8.4 Hz), 7.76 (2H, dd, J=6.7 Hz, J=1.8 Hz).

Example 514

3-{4-[(2,3-DIMETHYLPHENYL)ETHYNYL]PHENYL}-2-(2,4,6-TRIFLUOROBENZYL)-7-(TRIFLUOROMETHYL)-2H-INDAZOLE

This compound was made in a similar manner as for Example 229.

$^1$H NMR (CDCl$_3$): δ 2.33 (3H, s), 2.51 (3H, s), 5.70 (2H, s), 6.58-6.65(2H, m), 7.10-7.16 (3H, m), 7.42 (1H, d, J=7.4 Hz), 7.48-7.52 (2H, m), 7.61-763 (1H, m), 7.70-7.74 (3H, m).

Example 515

5-{3-[2-(4-CHLORO-2-FLUOROBENZYL)-7-(TRIFLUOROMETHYL)-2H-INDAZOL-3-YL]PHENOXY}-3,4-DIHYDRONAPHTHALEN-1(2H)-ONE

This compound was made in a similar manner as for Example 3.

MS (ES) m/z 565.1.

Example 516

3-(3-BROMOPHENYL)-2-(4-CHLORO-2-FLUOROBENZYL)-7-(TRIFLUOROMETHYL)-2H-INDAZOLE

This compound was made in a similar manner as for Example 1.

MS (ES) m/z 482.9.

Example 517

3-(3-BROMOPHENYL)-2-(2-CHLORO-4-FLUOROBENZYL)-7-(TRIFLUOROMETHYL)-2H-INDAZOLE

This compound was made in a similar manner as for Example 1.

MS (ES) m/z 482.9.

Example 518

2-BENZYL-3-PHENYL-2H-INDAZOLE-7-CARBOXYLIC ACID METHOXY-METHYL-AMIDE

2-Benzyl-3-phenyl-7-trifluoromethyl-2H-indazole (353 mg, 1 mmol), prepared similarly to that of Example 1, was treated with 3 ml of 70% aq H$_2$SO$_4$ at 90° C. for 4 hours. After cooling, 10 volumes of water were added and the product was extracted with dichloromethane. Flash column chromatography (SiO$_2$, dichloromethane as an eluant) afforded 2-benzyl-3-phenyl-2H-indazole-7-carboxylic acid in 60% yield. The 2-benzyl-3-phenyl-2H-indazole-7-carboxylic acid (1.64 g, 5 mmol) was dissolved in 20 ml of pyridine followed by addition of 1-(-3-dimethylaminopropyl)-3-ethylcarbodiimide hydrochloride (1.34 g, 7 mmol) and N,O-dimethyhydroxylamine hydrochloride (585 mg, 6 mmol). The reaction mixture was stirred at room temperature overnight. Pyridine was evaporated and the residue was shaken with 0.5M aq HCl and dichloromethane. The product was extracted with dichloromethane, and flash column chromatography (SiO$_2$, dichloromethane as an eluant) afforded 2-benzyl-3-phenyl-2H-indazole-7-carboxylic acid methoxy-methyl-amide in 79% yield.

LCMS: M+H: 372.2.

Example 519

1-(2-BENZYL-3-PHENYL-2H-INDAZOL-7-YL)ETHANONE

2-Benzyl-3-phenyl-2H-indazole-7-carboxylic acid (0.5 mmol, 160 mg, see preparation of Example 518) was dissolved in 5 ml of dry THF at 0° C. Two milliliters (2 ml) of MeLi (1.6M solution in THF) were added dropwise and the mixture was stirred overnight at room temperature. The reaction mixture was quenched with aq NH$_4$Cl solution and the product was extracted with EtOAc, and then flash column chromatography (SiO$_2$, dichloromethane as an eluant) afforded 1-(2-benzyl-3-phenyl-2H-indazol-7-yl)ethanone in 61% yield.

LCMS: M+H: 327.5.

Example 520

2-(2-BENZYL-3-PHENYL-2H-INDAZOL-7-YL) PROPAN-2-OL

Ninety milligrams (90 mg; 0.24 mmol) of 2-benzyl-3-phenyl-2H-indazole-7-carboxylic acid methyl ester, prepared from 2-benzyl-3-phenyl-2H-indazole-7-carboxylic acid (see preparation of Example 518), were dissolved in THF and 0.5 ml of 3M MeMgBr in THF (1.4 mmol) were added. The reaction mixture was stirred at room temperature for 2 hours. The reaction mixture was quenched with aq $NH_4Cl$ solution and product was extracted with EtOAc, and then flash column chromatography ($SiO_2$, dichloromethane as an eluant) afforded 2-(2-benzyl-3-phenyl-2H-indazol-7-yl)propan-2-ol in 86% yield.

LCMS: M+H: 343.4.

Example 521

2-BENZYL-7-ISOPROPENYL-3-PHENYL-2H-INDAZOLE

Fifty milligrams (50 mg; 0.15 mmol) of 2-(2-benzyl-3-phenyl-2H-indazol-7-yl)propan-2-ol (Example 520) were dissolved in 2 ml of toluene followed by the addition of 11 mg of TsOH. The mixture was heated at 110° C. for 1 hour. After cooling, the resulting solution was filtered through $SiO_2$ plug affording, after evaporation, 45 mg of pure 2-benzyl-7-isopropenyl-3-phenyl-2H-indazole. Yield: 94%.

LCMS: M+H: 325.4.

Example 522

2-BENZYL-7-ISOPROPYL-3-PHENYL-2H-INDAZOLE

Thirty milligrams (30 mg; 0.092 mmol) of 2-benzyl-7-isopropenyl-3-phenyl-2H-indazole (Example 521) were dissolved in 2 ml of dry ethanol followed by the addition of 30 mg of $PtO_2$. The reaction mixture was stirred under $H_2$ atmosphere at room temperature for 2 hours, then filtered and the EtOH evaporated. Flash column chromatography ($SiO_2$, dichloromethane/heptane, 1:1, as an eluant) afforded 2-benzyl-7-isopropyl-3-phenyl-2H-indazole in 80% yield.

LCMS: M+H: 327.5.

Example 523

2-BENZYL-3-{3-[(2,5-DIFLUOROPHENOXY) METHYL]PHENYL}-7-(TRIFLUOROMETHYL)-2H-INDAZOLE

Thirty-eight milligrams (38 mg; 0.1 mmol) of [3-(2-benzyl-7-trifluoromethyl-2H-indazol-3-yl)-phenyl]-methanol (see preparation of Example 7) were dissolved in 1 ml of dichloromethane followed by the addition of 28 µl of Et3N (0.2 mmol). The mixture was cooled to −30° C. and 12 µl of MsCl were added. Stirring continued at 0° C. for 1.5 hours. To the resulting solution, 85 mg of $Cs_2CO_3$ (0.25 mmol) were added followed by the addition of 65 mg (0.5 mmol) of 2,5-difluorophenol. Then the reaction mixture was stirred at room temperature overnight. The reaction mixture was quenched with 1M aq HCl and product was extracted with dichloromethane. Flash column chromatography ($SiO_2$, dichloromethane/heptane, 1:1, as an eluant) afforded 2-benzyl-3-{3-[(2,5-difluorophenoxy)methyl]phenyl}-7-(trifluoromethyl)-2H-indazole in 41% yield.

LCMS: M+H: 495.8.

Example 524

N-BENZYL-3-({3-[2-(4-CHLORO-2-FLUOROBENZYL)-7-(TRIFLUOROMETHYL)-2H-INDAZOL-3-YL]PHENOXY}METHYL)BENZAMIDE

Fifty-seven milligrams (57 mg; 0.1 mmol) of 3-[3-(2-(4-chloro-2-fluorobenzyl)-7-(trifluoromethyl)-2H-indazol-3-yl)-phenoxymethyl]-benzoic acid methyl ester (prepared similarly to that of 4-[4-(2-benzyl-7-trifluoromethyl-2H-indazol-3-yl)-phenoxymethyl]-benzoic acid methyl ester in preparation of Example 2) were dissolved in 2 ml of dry THF followed by the addition of 110 µl of benzylamine (1 mmol). The reaction mixture was cooled to −30° C. and 450 µl of 2M solution of butylmagnesiumbromide in ether were added dropwise. Then the reaction mixture was stirred for 30 min at −30° C. and left overnight at 0° C. The reaction mixture was quenched with aq $NH_4Cl$ solution and product was extracted with EtOAc. Flash column chromatography ($SiO_2$, dichloromethane as an eluant) afforded N-benzyl-3-({3-[2-(4-chloro-2-fluorobenzyl)-7-(trifluoromethyl)-2H-indazol-3-yl]phenoxy}methyl)benzamide in 66% yield.

LCMS: M+H: 644.6.

Example 525

2-BENZYL-3-[4-(BENZYLOXY)PHENYL]-7-(TRIFLUOROMETHYL)-2H-INDAZOLE 4-(2-Benzyl-7-trifluoromethyl-2H-indazole-3-yl)-phenol (10 mg, 1 eq) was treated with benzylbromide (10 µL, 3 eq) and potassium carbonate (19 mg, 5 eq) in acetone (1 mL). The reaction mixture was heated at 60° C. until completion of the reaction, as judged by TLC. Volatiles were removed in vacuo and the residue treated with a water/dichloromethane mixture followed by extraction with dichloromethane. Purification by flash chromatography (silica, ethyl acetate/n-heptane, 1:9) gave the title compound in 89% yield.

LCMS: M+H: 459.5.

Example 526

2-[4-({4-[2-BENZYL-7-(TRIFLUOROMETHYL)-2H-INDAZOL-3-YL]PHENOXY}METHYL)PHENYL]PROPANOIC ACID

The title compound was prepared by treating 4-(2-benzyl-7-trifluoromethyl-2H-indazole-3-yl)-phenol (20 mg, 1 eq) with 2-(4-bromomethyl-phenyl)-propionic acid (39 mg, 3 eq) and potassium carbonate (37 mg, 5 eq) in DMF (2 mL) at 150° C. overnight. After cooling, water was added and the pH adjusted to 1 (aq. HCl, 2M) followed by extraction with dichloromethane. Purification by preparative HPLC gave the desired product in 45% yield.

LCMS: M+H: 531.5.

Example 527

1-[4-({3-[2-BENZYL-7-(TRIFLUOROMETHYL)-2H-INDAZOL-3-YL]PHENOXY}METHYL)PHENYL]CYCLOPENTANECARBOXYLIC ACID

This compound was prepared similarly to that of Example 525 by treating 3-(2-benzyl-7-trifluoromethyl-2H-indazole- 3-yl)-phenol (20 mg, 1 eq) with 1-(4-bromomethyl-phenyl)-cyclopentanecarboxylic acid methyl ester (48 mg, 3 eq) and potassium carbonate (37 mg, 5 eq) in acetone (1.5 mL). The latter reagent was obtained by heating 1-p-tolyl-cyclopentanecarboxylic acid in methanol and a catalytic amount of sulphuric acid. Subsequent α-bromination was accomplished by refluxing the ester (100 mg, 1 eq) with NBS (82 mg, 1 eq) and benzoyl peroxide (5 mg, 3%) in carbon tetrachloride (2 mL) for one hour. The reaction mixture was cooled, water was added and product extracted with dichloromethane. The residue was purified by flash chromatography (ethyl acetate/n-heptane, 1:9, as an eluent). Then the resulting compound was hydrolyzed with aq LiOH (1M, 40 eq)/THF 1:1 and purified by preparative HPLC, affording the desired product in 48% yield.

LCMS: M+H: 571.4.

Example 528

2-[4-({3-[2-BENZYL-7-(TRIFLUOROMETHYL)-2H-INDAZOL-3-YL]PHENOXY}METHYL)PHENYL]-2-METHYLPROPANOIC ACID

This compound was prepared similarly to that of Example 525 by treating 3-(2-benzyl-7-trifluoromethyl-2H-indazole-3-yl)-phenol (23 mg, 1 eq) with 2-(4-bromomethyl-phenyl)-2-methyl-propionic acid methyl ester (17 mg, 1 eq) and potassium carbonate (26 mg, 3 eq) in acetone (2 mL). The latter reagent was obtained by heating p-tolyl-acetic acid in methanol and a catalytic amount of sulphuric acid. Subsequent methylation was accomplished by treating the obtained ester (50 mg, 1 eq) with sodium hydride (26 mg, 2.2 eq) and methyl iodide (41 μL, 2.2 eq) in THF (1 mL). Then α-bromination was accomplished by refluxing the ester (16 mg, 1 eq) with NBS (15 mg, 1 eq) and benzoyl peroxide (1 mg, 3%) in carbon tetrachloride (1.5 mL) overnight. The reaction mixture was cooled, water was added and product extracted with dichloromethane. The residue was purified by flash chromatography (ethyl acetate/n-heptane, 1:9, as an eluent). Then the resulting compound was then hydrolyzed with aq LiOH (1M, 40 eq)/THF, 1:1, and purified by preparative HPLC, affording the desired product in 26% yield.

LCMS: M+H: 545.3.

Example 529

2-BENZYL-3-(3-{[4-(1H-TETRAZOL-5-YL)BENZYL]OXY}PHENYL)-7-(TRIFLUOROMETHYL)-2H-INDAZOLE 4-({3-[2-Benzyl-7-(trifluoromethyl)-2H-indazol-3-yl]phenoxy}methyl)benzonitrile (37 mg, 1 eq) was treated with trimethylsilyl azide (21 μL, 2 eq) and di-n-butyltin oxide (5 mg, 0.3 eq) in toluene (2.5 mL) at 100° C. until full conversion. After cooling, most of the solvent was removed in vacuo and the residue was taken in methanol. Purification by flash chromatography, eluent 10% methanol in dichloromethane, afforded the title compound in 87% yield.

LCMS: M+H: 527.6, M−H: 525.8.

Example 530

{4-[3-(2-BENZYL-7-TRIFLUOROMETHYL-2H-INDAZOL-3-YL)-PHENOXYMETHYL]-BENZYL}-PHOSPHONIC ACID MONOETHYL ESTER

{4-[3-(2-Benzyl-7-trifluoromethyl-2H-indazol-3-yl)-phenoxymethyl]-benzyl}-phosphonic acid diethyl ester was obtained by a similar procedure to that described for Example 525. It was dissolved (45 mg, 1 eq) in acetonitrile (2 mL) and treated with bromotrimethylsilane (48 μL, 5 eq) at room temperature for two hours. The reaction mixture was quenched with water and concentrated. Purification by preparative HPLC provided the title compound in 35% yield.

LCMS: M+H: 581.3, M−H: 579.5.

Example 531

{3-[2-(4-CHLORO-2-FLUOROBENZYL)-7-(TRIFLUOROMETHYL)-2H-INDAZOL-3-YL]PHENOXY}(PHENYL)ACETIC ACID

3-[2-(4-Chloro-2-fluoro-benzyl)-7-trifluoromethyl-2H-indazol-3-yl]-phenol (25 mg, 1 eq) was treated with bromophenyl-acetic acid methyl ester (41 mg, 3 eq) and cesium carbonate (95 mg, 5 eq) in dichloromethane (2 mL) until the reaction mixture was completed as judged by TLC. Water was added followed by extraction with dichloromethane. Subsequently, the ester was hydrolyzed in aq. LiOH (1M, 15 eq)/THF 1:1. Purification by flash chromatography, eluent: 2-5% methanol in dichloromethane, afforded the title compound in 55% yield.

LCMS: M+H: 555.2, M−H: 553.4.

Example 532

2-(4-CHLORO-2-FLUOROBENZYL)-3-[3-(2-PHENYLETHYL)PHENYL]-7-(TRIFLUOROMETHYL)-2H-INDAZOLE

To a suspension of benzyl-phosphonic acid diethyl ester (20 μL, 1 eq) and sodium hydride (6 mg, 1.5 eq) in DMPU (0.5 mL), 3-[2-(4-chloro-2-fluoro-benzyl)-7-trifluoromethyl-2H-indazol-3-yl]-benzaldehyde (45 mg, 1 eq) was added. The reaction mixture was stirred for 45 minutes at room temperature, quenched with water and extracted with diethyl ether. The volatiles were removed and the residue purified by flash chromatography (silica, ethyl acetate/n-heptane, 2:8). The product obtained was dissolved in ethanol (2 mL) and hydrogenated at 1 atm using 7% platinum oxide as a catalyst. Filtration through Celite® and flash chromatography, eluent: dichloromethane/n-hepatane, 1:1, furnished the title compound in 11% overall yield.

LCMS: M+H: 509.3.

Example 533

2-BENZYL-3-ETHYL-7-(TRIFLUOROMETHYL)-2H-INDAZOLE

This compound was prepared similarly to that of Example 1.

LCMS: M+H: 305.6.

Example 534

3-(4-BROMOPHENYL)-2-METHYL-7-(TRIFLUOROMETHYL)-2H-INDAZOLE

This compound was prepared similarly to that of Example 1.

LCMS: M+H: 355.1.

Example 535

2-(4-CHLORO-2-FLUOROBENZYL)-3-{3-[(2,3-DIMETHYLPHENOXY)METHYL]PHENYL}-7-(TRIFLUOROMETHYL)-2H-INDAZOLE

This compound was prepared similarly to that of Example 523.
LCMS: M+H: 539.6.

Example 536

2-(4-CHLORO-2-FLUOROBENZYL)-3-(3-{[2-CHLORO-5-(TRIFLUOROMETHYL)PHENOXY]METHYL}PHENYL)-7-(TRIFLUOROMETHYL)-2H-INDAZOLE

This compound was prepared similarly to that of Example 523.
LCMS: M+H: 613.1.

Example 537

2-(4-CHLORO-2-FLUOROBENZYL)-3-(3-{[2-CHLORO-3-(TRIFLUOROMETHYL)PHENOXY]METHYL}PHENYL)-7-(TRIFLUOROMETHYL)-2H-INDAZOLE

This compound was prepared similarly to that of Example 523.
LCMS: M+H: 613.1.

Example 538

2-(4-CHLORO-2-FLUOROBENZYL)-3-{3-[(1-NAPHTHYLOXY)METHYL]PHENYL}-7-(TRIFLUOROMETHYL)-2H-INDAZOLE

This compound was prepared similarly to that of Example 523.
LCMS: M+H: 561.2.

Example 539

3-{3-[(2-TERT-BUTYL-5-METHYLPHENOXY)METHYL]PHENYL}-2-(4-CHLORO-2-FLUOROBENZYL)-7-(TRIFLUOROMETHYL)-2H-INDAZOLE

This compound was prepared similarly to that of Example 523.
LCMS: M+H: 581.3.

Example 540

2-(4-CHLORO-2-FLUOROBENZYL)-3-{3-[(4-FLUORO-2-METHYLPHENOXY)METHYL]PHENYL}-7-(TRIFLUOROMETHYL)-2H-INDAZOLE

This compound was prepared similarly to that of Example 523.
LCMS: M+H: 543.5.

Example 541

2-(4-CHLORO-2-FLUOROBENZYL)-3-{3-[(2,6-DIMETHYLPHENOXY)METHYL]PHENYL}-7-(TRIFLUOROMETHYL)-2H-INDAZOLE

This compound was prepared similarly to that of Example 523.
LCMS: M+H: 539.6.

Example 542

5-({3-[2-(4-CHLORO-2-FLUOROBENZYL)-7-(TRIFLUOROMETHYL)-2H-INDAZOL-3-YL]BENZYL}OXY)-3,4-DIHYDRONAPHTHALEN-1(2H)-ONE

This compound was prepared similarly to that of Example 523.
LCMS: M+H: 579.5.

Example 543

2-(4-CHLORO-2-FLUOROBENZYL)-3-(3-{[(3,3-DIMETHYL-2,3-DIHYDRO-1-BENZOFURAN-7-YL)OXY]METHYL}PHENYL)-7-(TRIFLUOROMETHYL)-2H-INDAZOLE

This compound was prepared similarly to that of Example 523.
LCMS: M+H: 581.3.

Example 544

3-{3-[(2-TERT-BUTYLPHENOXY)METHYL]PHENYL}-2-(4-CHLORO-2-FLUOROBENZYL)-7-(TRIFLUOROMETHYL)-2H-INDAZOLE

This compound was prepared similarly to that of Example 523.
LCMS: M+H: 567.2.

Example 545

2-(4-CHLORO-2-FLUOROBENZYL)-3-{3-[(2,3-DIMETHOXYPHENOXY)METHYL]PHENYL}-7-(TRIFLUOROMETHYL)-2H-INDAZOLE

This compound was prepared similarly to that of Example 523.
LCMS: M+H: 571.1.

Example 546

2-(4-CHLORO-2-FLUOROBENZYL)-3-{3-[(2,6-DICHLOROPHENOXY)METHYL]PHENYL}-7-(TRIFLUOROMETHYL)-2H-INDAZOLE

This compound was prepared similarly to that of Example 523.
LCMS: M+H: 579.5.

Example 547

2-(4-CHLORO-2-FLUOROBENZYL)-3-{3-[(2,6-DIMETHOXYPHENOXY)METHYL]PHENYL}-7-(TRIFLUOROMETHYL)-2H-INDAZOLE

This compound was prepared similarly to that of Example 523.
LCMS: M+H: 571.1.

Example 548

2-(4-CHLORO-2-FLUOROBENZYL)-3-{3-[(2,6-DIBROMOPHENOXY)METHYL]PHENYL}-7-(TRIFLUOROMETHYL)-2H-INDAZOLE

This compound was prepared similarly to that of Example 523.
LCMS: M+H: 669.2.

Example 549

3-{3-[(2-ALLYL-6-METHYLPHENOXY)METHYL]PHENYL}-2-(4-CHLORO-2-FLUOROBENZYL)-7-(TRIFLUOROMETHYL)-2H-INDAZOLE

This compound was prepared similarly to that of Example 523.
LCMS: M+H: 565.7.

Example 550

2-(4-CHLORO-2-FLUOROBENZYL)-3-{3-[(2,6-DIISOPROPYLPHENOXY)METHYL]PHENYL}-7-(TRIFLUOROMETHYL)-2H-INDAZOLE

This compound was prepared similarly to that of Example 523.
LCMS: M+H: 595.4.

Example 551

3-{3-[(2-TERT-BUTYL-6-METHYLPHENOXY)METHYL]PHENYL}-2-(4-CHLORO-2-FLUOROBENZYL)-7-(TRIFLUOROMETHYL)-2H-INDAZOLE

This compound was prepared similarly to that of Example 523.
LCMS: M+H: 581.3.

Example 552

3-{3-[(2-ALLYL-6-METHOXYPHENOXY)METHYL]PHENYL}-2-(4-CHLORO-2-FLUOROBENZYL)-7-(TRIFLUOROMETHYL)-2H-INDAZOLE

This compound was prepared similarly to that of Example 523.
LCMS: M+H: 581.3.

Example 553

2-(4-CHLORO-2-FLUOROBENZYL)-3-{3-[(2,5-DICHLOROPHENOXY)METHYL]PHENYL}-7-(TRIFLUOROMETHYL)-2H-INDAZOLE

This compound was prepared similarly to that of Example 523.
LCMS: M+H: 579.5.

Example 554

2-(4-CHLORO-2-FLUOROBENZYL)-3-{3-[(2,6-DIFLUOROPHENOXY)METHYL]PHENYL}-7-(TRIFLUOROMETHYL)-2H-INDAZOLE

This compound was prepared similarly to that of Example 523.
LCMS: M+H: 547.4.

Example 555

3-({3-[2-(4-CHLORO-2-FLUOROBENZYL)-7-(TRIFLUOROMETHYL)-2H-INDAZOL-3-YL]PHENOXY}METHYL)-N-PROPYLBENZAMIDE

This compound was prepared similarly to that of Example 524.
LCMS: M+H: 596.3.

Example 556

3-({3-[2-(4-CHLORO-2-FLUOROBENZYL)-7-(TRIFLUOROMETHYL)-2H-INDAZOL-3-YL]PHENOXY}METHYL)-N-CYCLOPROPYLBENZAMIDE

This compound was prepared similarly to that of Example 524.
LCMS: M+H: 594.5.

Example 557

2-(4-CHLORO-2-FLUOROBENZYL)-3-(3-{[3-(MORPHOLIN-4-YLCARBONYL)BENZYL]OXY}PHENYL)-7-(TRIFLUOROMETHYL)-2H-INDAZOLE

This compound was prepared similarly to that of Example 524.
LCMS: M+H: 624.5.

Example 558

3-({3-[2-(4-CHLORO-2-FLUOROBENZYL)-7-(TRIFLUOROMETHYL)-2H-INDAZOL-3-YL]PHENOXY}METHYL)-N-ISOPROPYLBENZAMIDE

This compound was prepared similarly to that of Example 524.
LCMS: M+H: 596.3.

Example 559

{4-[3-(2-BENZYL-7-TRIFLUOROMETHYL-2H-INDAZOL-3-YL)-PHENYLAMINO]-PHENYL}-ACETIC ACID

This compound was prepared similarly to that of Example 4.

LCMS: M+H: 502.4, 2M+H: 1003.7, M−H: 500.5, 2M−H: 1002.0.

Example 560

{4-[4-(2-BENZYL-7-TRIFLUOROMETHYL-2H-INDAZOL-3-YL)-PHENYLAMINO]-PHENYL}-ACETIC ACID

This compound was prepared similarly to that of Example 4.

LCMS: M+H: 502.4, M−H: 500.6.

Example 561

3-{4-[4-(2-BENZYL-7-TRIFLUOROMETHYL-2H-INDAZOL-3-YL)-PHENYLAMINO]-PHENYL}-PROPIONIC ACID

This compound was prepared similarly to that of Example 4.

LCMS: M+H: 516.8, M−H: 514.4.

Example 562

3-{4-[3-(2-BENZYL-7-TRIFLUOROMETHYL-2H-INDAZOL-3-YL)-PHENYLAMINO]-PHENYL}-PROPIONIC ACID

This compound was prepared similarly to that of Example 4.

LCMS: M+H: 516.8, M−H: 514.4.

Example 563

3-{3-[4-(2-BENZYL-7-TRIFLUOROMETHYL-2H-INDAZOL-3-YL)-PHENYLAMINO]-PHENYL}-PROPIONIC ACID

This compound was prepared similarly to that of Example 4.

LCMS: M+H: 516.8, M−H: 514.4.

Example 564

3-{3-[3-(2-BENZYL-7-TRIFLUOROMETHYL-2H-INDAZOL-3-YL)-PHENYLAMINO]-PHENYL}-PROPIONIC ACID

This compound was prepared similarly to that of Example 4.

LCMS: M+H: 516.8, M−H: 514.4.

Example 565

2-{4-[4-(2-BENZYL-7-TRIFLUOROMETHYL-2H-INDAZOL-3-YL)-PHENYLAMINO]-PHENOXY}-2-METHYL-PROPIONIC ACID

This compound was prepared similarly to that of Example 4.

LCMS: M+H: 546.8, M−H: 544.4.

Example 566

2-{4-[3-(2-BENZYL-7-TRIFLUOROMETHYL-2H-INDAZOL-3-YL)-PHENYLAMINO]-PHENOXY}-2-METHYL-PROPIONIC ACID

This compound was prepared similarly to that of Example 4.

LCMS: M+H: 546.8, M−H: 544.4.

Example 567

2-(4-{[4-(2-BENZYL-7-TRIFLUOROMETHYL-2H-INDAZOL-3-YL)-PHENYLAMINO]-METHYL}-PHENYL)-PROPIONIC ACID

This compound was prepared similarly to that of Example 4.

LCMS: M+H: 530.3, M−H: 528.5.

Example 568

{4-[4-(2-BENZYL-7-TRIFLUOROMETHYL-2H-INDAZOL-3-YL)-PHENYLAMINO]-PHENYL}-ACETIC ACID ETHYL ESTER

This compound was prepared similarly to that of Example 4.

LCMS: M+H: 530.3, M−H: 528.5.

Example 569

3-{3-[4-(2-BENZYL-7-TRIFLUOROMETHYL-2H-INDAZOL-3-YL)-PHENYLAMINO]-PHENYL}-PROPIONIC ACID METHYL ESTER

This compound was prepared similarly to that of Example 4.

LCMS: M+H: 530.3, M−H: 528.5.

Example 570

3-{3-[3-(2-BENZYL-7-TRIFLUOROMETHYL-2H-INDAZOL-3-YL)-PHENYLAMINO]-PHENYL}-PROPIONIC ACID METHYL ESTER

This compound was prepared similarly to that of Example 4.

LCMS: M+H: 530.3, M−H: 528.5.

Example 571

2-{4-[4-(2-BENZYL-7-TRIFLUOROMETHYL-2H-INDAZOL-3-YL)-PHENYLAMINO]-PHENOXY}-2-METHYL-PROPIONIC ACID METHYL ESTER

This compound was prepared similarly to that of Example 4.

LCMS: M+H: 560.3, M−H: 558.5.

Example 572

2-{4-[3-(2-BENZYL-7-TRIFLUOROMETHYL-2H-INDAZOL-3-YL)-PHENYLAMINO]-PHENOXY}-2-METHYL-PROPIONIC ACID METHYL ESTER

This compound was prepared similarly to that of Example 4.

LCMS: M+H: 560.3, M−H: 558.5.

Example 573

2-(4-{[4-(2-BENZYL-7-TRIFLUOROMETHYL-2H-INDAZOL-3-YL)-PHENYLAMINO]-METHYL}-PHENYL)-PROPIONIC ACID METHYL ESTER

This compound was prepared similarly to that of Example 4.

LCMS: M+H: 544.4, M−H: 542.6.

Example 574

2-(4-{[3-(2-BENZYL-7-TRIFLUOROMETHYL-2H-INDAZOL-3-YL)-PHENYLAMINO]-METHYL}-PHENYL)-PROPIONIC ACID METHYL ESTER

This compound was prepared similarly to that of Example 4.

LCMS: M+H: 544.4, M−H: 542.6.

Example 575

2-(4-{[3-(2-BENZYL-7-TRIFLUOROMETHYL-2H-INDAZOL-3-YL)-PHENYLAMINO]-METHYL}-PHENYL)-PROPIONIC ACID

This compound was prepared similarly to that of Example 4.

LCMS: M+H: 530.3, M−H: 528.5.

Example 576

3-{3-[3-(2-BENZYL-7-TRIFLUOROMETHYL-2H-INDAZOL-3-YL)-PHENYLAMINO]-PHENYL}-BUTYRIC ACID METHYL ESTER

This compound was prepared similarly to that of Example 4.

LCMS: M+H: 544.4, M−H: 542.6.

Example 577

3-{4-[3-(2-BENZYL-7-TRIFLUOROMETHYL-2H-INDAZOL-3-YL)-PHENYLAMINO]-PHENYL}-BUTYRIC ACID METHYL ESTER

This compound was prepared similarly to that of Example 4.

LCMS: M+H: 544.4, M−H: 542.6.

Example 578

(4-{[3-(2-BENZYL-7-TRIFLUOROMETHYL-2H-INDAZOL-3-YL)-PHENYLAMINO]-METHYL}-PHENYL)-ACETIC ACID METHYL ESTER

This compound was prepared similarly to that of Example 4.

LCMS: M+H: 530.3, M−H: 528.5.

Example 579

{3-[4-(2-BENZYL-7-TRIFLUOROMETHYL-2H-INDAZOL-3-YL)-PHENYLAMINO]-PHENYL}-ACETIC ACID METHYL ESTER

This compound was prepared similarly to that of Example 4.

LCMS: M+H: 516.5, M−H: 514.4.

Example 580

{3-[3-(2-BENZYL-7-TRIFLUOROMETHYL-2H-INDAZOL-3-YL)-PHENYLAMINO]-PHENYL}-ACETIC ACID METHYL ESTER

This compound was prepared similarly to that of Example 4.

LCMS: M+H: 516.5, M−H: 514.4.

Example 581

3-{3-[3-(2-BENZYL-7-TRIFLUOROMETHYL-2H-INDAZOL-3-YL)-PHENYLAMINO]-PHENYL}-BUTYRIC ACID

This compound was prepared similarly to that of Example 4.

LCMS: M+H: 530.3, M−H: 528.5.

Example 582

3-{4-[3-(2-BENZYL-7-TRIFLUOROMETHYL-2H-INDAZOL-3-YL)-PHENYLAMINO]-PHENYL}-BUTYRIC ACID

This compound was prepared similarly to that of Example 4.

LCMS: M+H: 530.3, M−H: 528.5.

Example 583

{3-[3-(2-BENZYL-7-TRIFLUOROMETHYL-2H-INDAZOL-3-YL)-PHENYLAMINO]-PHENYL}-ACETIC ACID

This compound was prepared similarly to that of Example 4.

LCMS: M+H: 502.4, M−H: 500.6.

Example 584

{3-[4-(2-BENZYL-7-TRIFLUOROMETHYL-2H-INDAZOL-3-YL)-PHENYLAMINO]-PHENYL}-ACETIC ACID

This compound was prepared similarly to that of Example 4.

LCMS: M+H: 502.4, M−H: 500.6.

Example 585

(4-{[3-(2-BENZYL-7-TRIFLUOROMETHYL-2H-INDAZOL-3-YL)-PHENYLAMINO]-METHYL}-PHENYL)-ACETIC ACID

This compound was prepared similarly to that of Example 4.

LCMS: M+H: 516.5, M−H: 514.4.

Example 586

3-(2-BENZYL-7-TRIFLUOROMETHYL-2H-INDAZOL-3-YL)-PHENYLAMINE

This compound was prepared similarly to that of Example 4.

LCMS: M+H: 368.3, M−H: 366.6.

Example 587

4-(2-BENZYL-7-TRIFLUOROMETHYL-2H-INDAZOL-3-YL)-PHENYLAMINE

This compound was prepared similarly to that of Example 4.

LCMS: M+H: 368.3, M−H: 366.1.

Example 588

(3-{[4-(2-BENZYL-7-TRIFLUOROMETHYL-2H-INDAZOL-3-YL)-PHENYLAMINO]-METHYL}-PHENYL)-ACETIC ACID ETHYL ESTER

This compound was prepared similarly to that of Example 4.

LCMS: M+H: 544.4, M−H: 542.6.

Example 589

(3-{[3-(2-BENZYL-7-TRIFLUOROMETHYL-2H-INDAZOL-3-YL)-PHENYLAMINO]-METHYL}-PHENYL)-ACETIC ACID ETHYL ESTER

This compound was prepared similarly to that of Example 4.

LCMS: M+H: 544.4, M−H: 542.6.

Example 590

1-(4-{[4-(2-BENZYL-7-TRIFLUOROMETHYL-2H-INDAZOL-3-YL)-PHENYLAMINO]-METHYL}-PHENYL)-CYCLOPROPANECARBOXYLIC ACID ETHYL ESTER

This compound was prepared similarly to that of Example 4.

LCMS: M+H: 566.1, M−H: 554.3.

Example 591

1-(4-{[3-(2-BENZYL-7-TRIFLUOROMETHYL-2H-INDAZOL-3-YL)-PHENYLAMINO]-METHYL}-PHENYL)-CYCLOPROPANECARBOXYLIC ACID METHYL ESTER

This compound was prepared similarly to that of Example 4.

LCMS: M+H: 566.1, M−H: 554.3.

Example 592

(3-{[4-(2-BENZYL-7-TRIFLUOROMETHYL-2H-INDAZOL-3-YL)-PHENYLAMINO]-METHYL}-PHENYL)-ACETIC ACID

This compound was prepared similarly to that of Example 4.

LCMS: M+H: 516.8, M−H: 514.4.

Example 593

(3-{[3-(2-BENZYL-7-TRIFLUOROMETHYL-2H-INDAZOL-3-YL)-PHENYLAMINO]-METHYL}-PHENYL)-ACETIC ACID

This compound was prepared similarly to that of Example 4.

LCMS: M+H: 516.5, M−H: 514.4.

Example 594

1-(4-{[3-(2-BENZYL-7-TRIFLUOROMETHYL-2H-INDAZOL-3-YL)-PHENYLAMINO]-METHYL}-PHENYL)-CYCLOPROPANECARBOXYLIC ACID

This compound was prepared similarly to that of Example 4.

LCMS: M+H: 542.6, M−H: 540.5.

Example 595

2-{3-[4-(2-BENZYL-7-TRIFLUOROMETHYL-2H-INDAZOL-3-YL)-PHENYLAMINO]-PHENYL}-PROPIONIC ACID METHYL ESTER

This compound was prepared similarly to that of Example 4.

LCMS: M+H: 530.3, M−H: 528.5.

Example 596

(4-{[4-(2-BENZYL-7-TRIFLUOROMETHYL-2H-INDAZOL-3-YL)-PHENYLAMINO]-METHYL}-PHENYL)-ACETIC ACID METHYL ESTER

This compound was prepared similarly to that of Example 4.

LCMS: M+H: 530.3, M−H: 528.5.

Example 597

2-{3-[4-(2-BENZYL-7-TRIFLUOROMETHYL-2H-INDAZOL-3-YL)-PHENYLAMINO]-PHENYL}-PROPIONIC ACID

This compound was prepared similarly to that of Example 4.

LCMS: M+H: 516.5, M−H: 514.4.

Example 598

(4-{[4-(2-BENZYL-7-TRIFLUOROMETHYL-2H-INDAZOL-3-YL)-PHENYLAMINO]-METHYL}-PHENYL)-ACETIC ACID

This compound was prepared similarly to that of Example 4.

LCMS: M+H: 516.5, M−H: 514.4.

Example 599

2-{3-[3-(2-BENZYL-7-TRIFLUOROMETHYL-2H-INDAZOL-3-YL)-PHENYLAMINO]-PHENYL}-PROPIONIC ACID METHYL ESTER

This compound was prepared similarly to that of Example 4.

LCMS: M+H: 530.3, M−H: 528.5.

Example 600

2-{3-[3-(2-BENZYL-7-TRIFLUOROMETHYL-2H-INDAZOL-3-YL)-PHENYLAMINO]-PHENYL}-PROPIONIC ACID

This compound was prepared similarly to that of Example 4.

LCMS: M+H: 516.5, M−H: 514.4.

Example 601

[3-(2-BENZYL-7-TRIFLUOROMETHYL-2H-INDAZOL-3-YL)-PHENYL]-(2,6-DIMETHYL-BENZYL)-AMINE

This compound was prepared similarly to that of Example 4.

LCMS: M+H: 486.5, M−H: 484.7.

Example 602

(3-{4-[2-(2,4,6-TRIFLUORO-BENZYL)-7-TRIFLUOROMETHYL-2H-INDAZOL-3-YL]-PHENYLAMINO}-PHENYL)-ACETIC ACID

This compound was prepared similarly to that of Example 4.

LCMS: M+H: 556.1, M−H: 554.3.

Example 603

2-{3-[4-(2-BENZYL-7-TRIFLUOROMETHYL-2H-INDAZOL-3-YL)-PHENYLAMINO]-PHENYL}-2-HYDROXY-PROPIONIC ACID

This compound was prepared similarly to that of Example 4.

LCMS: M+H: 532.4, M−H: 530.3.

Example 604

[4-(2-BENZYL-7-TRIFLUOROMETHYL-2H-INDAZOL-3-YL)-PHENYL]-(2,6-DIMETHYL-BENZYL)-AMINE

This compound was prepared similarly to that of Example 4.

LCMS: M+H: 486.5, M−H: 484.7.

Example 605

{3-[4-(1-METHYL-7-TRIFLUOROMETHYL-1H-INDAZOL-3-YL)-PHENYLAMINO]-PHENYL}-ACETIC ACID

This compound was prepared similarly to that of Example 4.

LCMS: M+H: 426.2, M−H: 424.4.

Example 606

{3-[4-(2-METHYL-7-TRIFLUOROMETHYL-2H-INDAZOL-3-YL)-PHENYLAMINO]-PHENYL}-ACETIC ACID

This compound was prepared similarly to that of Example 4.

LCMS: M+H: 426.2, M−H: 424.4.

Example 607

(4-{[4-(2-BENZYL-7-TRIFLUOROMETHYL-2H-INDAZOL-3-YL)-PHENYLAMINO]-METHYL}-3,5-DIMETHYL-PHENYL)-ACETIC ACID

This compound was prepared similarly to that of Example 4.

LCMS: M+H: 544.4, M−H: 542.6.

Example 608

(4-{[4-(2-BENZYL-7-TRIFLUOROMETHYL-2H-INDAZOL-3-YL)-PHENYLAMINO]-METHYL}-3,5-DIMETHYL-PHENYL)-ACETIC ACID

This compound was prepared similarly to that of Example 4.

LCMS: M+H: 544.4, M–H: 542.6.

Example 609

(3-{4-[2-(4-CHLORO-2-FLUORO-BENZYL)-7-TRIFLUOROMETHYL-2H-INDAZOL-3-YL]-PHENYLAMINO}-PHENYL)-ACETIC ACID

This compound was prepared similarly to that of Example 4.

LCMS: M+H: 554.3, M–H: 552.5.

Example 610

(3-{4-[2-(2,4-DIMETHYL-BENZYL)-7-TRIFLUOROMETHYL-2H-INDAZOL-3-YL]-PHENYLAMINO}-PHENYL)-ACETIC ACID

This compound was prepared similarly to that of Example 4.

LCMS: M+H: 530.3, M–H: 528.2.

Example 611

2-(4-CHLORO-2-FLUORO-BENZYL)-3-[3-(4-METHOXY-BENZYL)-PHENYL]-7-TRIFLUOROMETHYL-2H-INDAZOLE

This compound was prepared similarly to that of Example 5.

LCMS: M+H: 525.5.

Example 612

2-(4-CHLORO-2-FLUORO-BENZYL)-3-[3-(3,5-DIMETHOXY-BENZYL)-PHENYL]-7-TRIFLUOROMETHYL-2H-INDAZOLE

This compound was prepared similarly to that of Example 5.

LCMS: M+H: 555.2.

Example 613

2-(4-CHLORO-2-FLUORO-BENZYL)-3-[3-(3,5-DIMETHYL-BENZYL)-PHENYL]-7-TRIFLUOROMETHYL-2H-INDAZOLE

This compound was prepared similarly to that of Example 5.

LCMS: M+H: 523.9.

Example 614

2-(4-CHLORO-2-FLUORO-BENZYL)-3-[3-(2-METHOXY-BENZYL)-PHENYL]-7-TRIFLUOROMETHYL-2H-INDAZOLE

This compound was prepared similarly to that of Example 5.

LCMS: M+H: 525.5.

Example 615

2-(4-CHLORO-2-FLUORO-BENZYL)-3-[3-(3-METHOXY-BENZYL)-PHENYL]-7-TRIFLUOROMETHYL-2H-INDAZOLE

This compound was prepared similarly to that of Example 5.

LCMS: M+H: 525.5.

Example 616

2-(4-CHLORO-2-FLUORO-BENZYL)-3-[3-(2,3-DIMETHOXY-BENZYL)-PHENYL]-7-TRIFLUOROMETHYL-2H-INDAZOLE

This compound was prepared similarly to that of Example 5.

LCMS: M+H: 555.2.

Example 617

2-(4-CHLORO-2-FLUORO-BENZYL)-3-[3-(3,4-DIMETHOXY-BENZYL)-PHENYL]-7-TRIFLUOROMETHYL-2H-INDAZOLE

This compound was prepared similarly to that of Example 5.

LCMS: M+H: 555.2.

Example 618

2-(4-CHLORO-2-FLUORO-BENZYL)-3-[3-(4-CHLORO-2-FLUORO-BENZYL)-PHENYL]-7-TRIFLUOROMETHYL-2H-INDAZOLE

This compound was prepared similarly to that of Example 5.

LCMS: M+H: 547.4.

Example 619

2-(4-CHLORO-2-FLUORO-BENZYL)-3-[3-(2-CHLORO-4-FLUORO-BENZYL)-PHENYL]-7-TRIFLUOROMETHYL-2H-INDAZOLE

This compound was prepared similarly to that of Example 5.

LCMS: M+H: 549.5.

Example 620

2-(4-CHLORO-2-FLUORO-BENZYL)-3-[3-(2-FLUORO-4-TRIFLUOROMETHYL-BENZYL)-PHENYL]-7-TRIFLUOROMETHYL-2H-INDAZOLE

This compound was prepared similarly to that of Example 5.
LCMS: M+H: 581.3.

Example 621

3-[3-(2,4-BIS-TRIFLUOROMETHYL-BENZYL)-PHENYL]-2-(4-CHLORO-2-FLUORO-BENZYL)-7-TRIFLUOROMETHYL-2H-INDAZOLE

This compound was prepared similarly to that of Example 5.
LCMS: M+H: 631.7.

Example 622

2-(4-CHLORO-2-FLUORO-BENZYL)-3-[3-(2,4-DIFLUORO-BENZYL)-PHENYL]-7-TRIFLUOROMETHYL-2H-INDAZOLE

This compound was prepared similarly to that of Example 5.
LCMS: M+H: 531.2.

Example 623

3-[3-(2,5-BIS-TRIFLUOROMETHYL-BENZYL)-PHENYL]-2-(4-CHLORO-2-FLUORO-BENZYL)-7-TRIFLUOROMETHYL-2H-INDAZOLE

This compound was prepared similarly to that of Example 5.
LCMS: M+H: 631.7.

Example 624

2-(4-CHLORO-2-FLUORO-BENZYL)-3-[3-(2-FLUORO-3-METHYL-BENZYL)-PHENYL]-7-TRIFLUOROMETHYL-2H-INDAZOLE

This compound was prepared similarly to that of Example 5.
LCMS: M+H: 527.3.

Example 625

2-(4-CHLORO-2-FLUORO-BENZYL)-3-[3-(6-CHLORO-2-FLUORO-3-METHYL-BENZYL)-PHENYL]-7-TRIFLUOROMETHYL-2H-INDAZOLE

This compound was prepared similarly to that of Example 5.
LCMS: M+H: 562.1.

Example 626

2-(4-CHLORO-2-FLUORO-BENZYL)-3-[3-(3-DIFLUOROMETHOXY-BENZYL)-PHENYL]-7-TRIFLUOROMETHYL-2H-INDAZOLE

This compound was prepared similarly to that of Example 5.
LCMS: M+H: 561.2.

Example 627

2-(4-CHLORO-2-FLUORO-BENZYL)-3-[3-(2-CHLORO-5-TRIFLUOROMETHYL-BENZYL)-PHENYL]-7-TRIFLUOROMETHYL-2H-INDAZOLE

This compound was prepared similarly to that of Example 5.
LCMS: M+H: 597.2.

Example 628

2-(4-CHLORO-2-FLUORO-BENZYL)-3-[3-(4-METHANESULFONYL-BENZYL)-PHENYL]-7-TRIFLUOROMETHYL-2H-INDAZOLE

This compound was prepared similarly to that of Example 5.
LCMS: M+H: 573.5.

Example 629

2-(4-CHLORO-2-FLUORO-BENZYL)-3-[3-(2-METHYL-5-TRIFLUOROMETHYL-BENZYL)-PHENYL]-7-TRIFLUOROMETHYL-2H-INDAZOLE

This compound was prepared similarly to that of Example 5.
LCMS: M+H: 577.7.

Example 630

2-(4-CHLORO-2-FLUORO-BENZYL)-3-[3-(2-CHLORO-5-FLUORO-BENZYL)-PHENYL]-7-TRIFLUOROMETHYL-2H-INDAZOLE

This compound was prepared similarly to that of Example 5.
LCMS: M+H: 547.4.

Example 631

2-(4-CHLORO-2-FLUORO-BENZYL)-3-[3-(5-FLUORO-2-TRIFLUOROMETHYL-BENZYL)-PHENYL]-7-TRIFLUOROMETHYL-2H-INDAZOLE

This compound was prepared similarly to that of Example 5.
LCMS: M+H: 581.3.

Example 632

2-(4-CHLORO-2-FLUORO-BENZYL)-3-[3-(2,5-DICHLORO-BENZYL)-PHENYL]-7-TRIFLUOROMETHYL-2H-INDAZOLE

This compound was prepared similarly to that of Example 5.
LCMS: M+H: 565.4.

Example 633

2-(4-CHLORO-2-FLUORO-BENZYL)-3-[3-(5-CHLORO-2-TRIFLUOROMETHYL-BENZYL)-PHENYL]-7-TRIFLUOROMETHYL-2H-INDAZOLE

This compound was prepared similarly to that of Example 5.
LCMS: M+H: 597.2.

Example 634

(3-{3-[2-(4-CHLORO-2-FLUORO-BENZYL)-7-TRIFLUOROMETHYL-2H-INDAZOL-3-YL]-BENZYL}-PHENYL)-MORPHOLIN-4-YL-METHANONE

This compound was prepared similarly to that of Example 5.
LCMS: M+H: 608.6.

Example 635

N-BENZYL-3-{3-[2-(4-CHLORO-2-FLUORO-BENZYL)-7-TRIFLUOROMETHYL-2H-INDAZOL-3-YL]-BENZYL}-BENZAMIDE

This compound was prepared similarly to that of Example 5.
LCMS: M+H: 628.7.

Example 636

(3-{3-[2-(4-CHLORO-2-FLUORO-BENZYL)-7-TRIFLUOROMETHYL-2H-INDAZOL-3-YL]-BENZYL}-PHENYL)-PYRROLIDIN-1-YL-METHANONE

This compound was prepared similarly to that of Example 5.
LCMS: M+H: 592.7.

Example 637

(3-{3-[2-(4-CHLORO-2-FLUORO-BENZYL)-7-TRIFLUOROMETHYL-2H-INDAZOL-3-YL]-BENZYL}-PHENYL)-PIPERIDIN-1-YL-METHANONE

This compound was prepared similarly to that of Example 5.
LCMS: M+H: 606.5.

Example 638

3-{3-[2-(4-CHLORO-2-FLUORO-BENZYL)-7-TRIFLUOROMETHYL-2H-INDAZOL-3-YL]-BENZYL}-N,N-DIETHYL-BENZAMIDE

This compound was prepared similarly to that of Example 5.
LCMS: M+H: 594.5.

Example 639

3-{3-[2-(4-CHLORO-2-FLUORO-BENZYL)-7-TRIFLUOROMETHYL-2H-INDAZOL-3-YL]-BENZYL}-N-CYCLOPROPYL-BENZAMIDE

This compound was prepared similarly to that of Example 5.
LCMS: M+H: 578.6.

Example 640

3-{3-[2-(4-CHLORO-2-FLUORO-BENZYL)-7-TRIFLUOROMETHYL-2H-INDAZOL-3-YL]-BENZYL}-N-ISOPROPYL-BENZAMIDE

This compound was prepared similarly to that of Example 5.
LCMS: M+H: 580.4.

Example 641

3-{3-[2-(4-CHLORO-2-FLUORO-BENZYL)-7-TRIFLUOROMETHYL-2H-INDAZOL-3-YL]-BENZYL}-N-PROPYL-BENZAMIDE

This compound was prepared similarly to that of Example 5.
LCMS: M+H: 580.4.

Example 642

3-{3-[2-(4-CHLORO-2-FLUORO-BENZYL)-7-TRIFLUOROMETHYL-2H-INDAZOL-3-YL]-BENZYL}-N-ETHYL-BENZAMIDE

This compound was prepared similarly to that of Example 5.
LCMS: M+H: 566.6.

Example 643

3-{3-[2-(4-CHLORO-2-FLUORO-BENZYL)-7-TRIFLUOROMETHYL-2H-INDAZOL-3-YL]-BENZYL}-N-METHYL-BENZAMIDE

This compound was prepared similarly to that of Example 5.
LCMS: M+H: 552.5.

Example 644

2-BENZYL-3-[4-(3-METHOXYPHENOXY)PHENYL]-7-(TRIFLUOROMETHYL)-2H-INDAZOLE

This compound was prepared similarly to that of Example 3.
LCMS: M+H: 475.4.

Example 645

2-BENZYL-3-[4-(2,3-DIFLUOROPHENOXY)PHE-NYL]-7-(TRIFLUOROMETHYL)-2H-INDAZOLE

This compound was prepared similarly to that of Example 3.
LCMS: M+H: 481.4.

Example 646

2-BENZYL-3-[4-(4-CHLOROPHENOXY)PHE-NYL]-7-(TRIFLUOROMETHYL)-2H-INDAZOLE

This compound was prepared similarly to that of Example 3.
LCMS: M+H: 479.0.

Example 647

2-BENZYL-3-[4-(2,3-DIHYDRO-1H-INDEN-5-YLOXY)PHENYL]-7-(TRIFLUOROMETHYL)-2H-INDAZOLE

This compound was prepared similarly to that of Example 3.
LCMS: M+H: 485.6.

Example 648

2-BENZYL-3-[4-(2-FLUOROPHENOXY)PHE-NYL]-7-(TRIFLUOROMETHYL)-2H-INDAZOLE

This compound was prepared similarly to that of Example 3.
LCMS: M+H: 463.4.

Example 649

2-BENZYL-3-[4-(4-CHLORO-3-METHYLPHE-NOXY)PHENYL]-7-(TRIFLUOROMETHYL)-2H-INDAZOLE

This compound was prepared similarly to that of Example 3.
LCMS: M+H: 493.4.

Example 650

2-BENZYL-3-[4-(2-CHLOROPHENOXY)PHE-NYL]-7-(TRIFLUOROMETHYL)-2H-INDAZOLE

This compound was prepared similarly to that of Example 3.
LCMS: M+H: 479.0.

Example 651

3-{4-[2-BENZYL-7-(TRIFLUOROMETHYL)-2H-INDAZOL-3-YL]PHENOXY}-N,N-DIMETHYLA-NILINE

This compound was prepared similarly to that of Example 3.
LCMS: M+H: 488.3.

Example 652

2-BENZYL-3-[4-(3-NITROPHENOXY)PHENYL]-7-(TRIFLUOROMETHYL)-2H-INDAZOLE

This compound was prepared similarly to that of Example 3.
LCMS: M+H: 490.4.

Example 653

2-BENZYL-3-{4-[(7-METHOXY-2-NAPHTHYL)OXY]PHENYL}-7-(TRIFLUOROMETHYL)-2H-INDAZOLE

This compound was prepared similarly to that of Example 3.
LCMS: M+H: 525.8.

Example 654

2-BENZYL-3-[4-(4-FLUOROPHENOXY)PHE-NYL]-7-(TRIFLUOROMETHYL)-2H-INDAZOLE

This compound was prepared similarly to that of Example 3.
LCMS: M+H: 463.4.

Example 655

4-(4-{4-[2-BENZYL-7-(TRIFLUOROMETHYL)-2H-INDAZOL-3-YL]PHENOXY}BENZYL)PHE-NOL

This compound was prepared similarly to that of Example 3.
LCMS: M+H: 551.0.

Example 656

2-BENZYL-3-[4-(5,6,7,8-TETRAHYDRONAPH-THALEN-2-YLOXY)PHENYL]-7-(TRIFLUO-ROMETHYL)-2H-INDAZOLE

This compound was prepared similarly to that of Example 3.
LCMS: M+H: 499.0.

Example 657

7-{4-[2-BENZYL-7-(TRIFLUOROMETHYL)-2H-INDAZOL-3-YL]PHENOXY}QUINOLINE

This compound was prepared similarly to that of Example 3.
LCMS: M+H: 496.7.

Example 658

2-BENZYL-3-[4-(2,4-DICHLOROPHENOXY)PHENYL]-7-(TRIFLUOROMETHYL)-2H-INDA-ZOLE

This compound was prepared similarly to that of Example 3.
LCMS: M+H: 513.0.

Example 659

2-BENZYL-3-[4-(2-METHOXYPHENOXY)PHENYL]-7-(TRIFLUOROMETHYL)-2H-INDAZOLE

This compound was prepared similarly to that of Example 3.
LCMS: M+H: 475.4.

Example 660

2-BENZYL-3-[4-(3,5-DIFLUOROPHENOXY)PHENYL]-7-(TRIFLUOROMETHYL)-2H-INDAZOLE

This compound was prepared similarly to that of Example 3.
LCMS: M+H: 481.0.

Example 661

2-BENZYL-3-[4-(2,3-DIMETHYLPHENOXY)PHENYL]-7-(TRIFLUOROMETHYL)-2H-INDAZOLE

This compound was prepared similarly to that of Example 3.
LCMS: M+H: 473.3.

Example 662

2-BENZYL-3-[4-(3,5-DIMETHYLPHENOXY)PHENYL]-7-(TRIFLUOROMETHYL)-2H-INDAZOLE

This compound was prepared similarly to that of Example 3.
LCMS: M+H: 473.

Example 663

2-BENZYL-3-[4-(4-METHYLPHENOXY)PHENYL]-7-(TRIFLUOROMETHYL)-2H-INDAZOLE

This compound was prepared similarly to that of Example 3.
LCMS: M+H: 459.

Example 664

2-BENZYL-3-[4-(4-NITROPHENOXY)PHENYL]-7-(TRIFLUOROMETHYL)-2H-INDAZOLE

This compound was prepared similarly to that of Example 3.
LCMS: M+H: 490.

Example 665

2-BENZYL-3-{4-[(4'-NITROBIPHENYL-4-YL)OXY]PHENYL}-7-(TRIFLUOROMETHYL)-2H-INDAZOLE

This compound was prepared similarly to that of Example 3.
LCMS: M+H: 566.

Example 666

3-{4-[4-(4-ACETYLPIPERAZIN-1-YL)PHENOXY]PHENYL}-2-BENZYL-7-(TRIFLUOROMETHYL)-2H-INDAZOLE

This compound was prepared similarly to that of Example 3.
LCMS: M+H: 571.

Example 667

2-BENZYL-3-[4-(2,4-DIFLUOROPHENOXY)PHENYL]-7-(TRIFLUOROMETHYL)-2H-INDAZOLE

This compound was prepared similarly to that of Example 3.
LCMS: M+H: 481.0.

Example 668

2-BENZYL-3-[4-(3,4-DIMETHYLPHENOXY)PHENYL]-7-(TRIFLUOROMETHYL)-2H-INDAZOLE

This compound was prepared similarly to that of Example 3.
LCMS: M+H: 473.

Example 669

2-BENZYL-3-[4-(2-ISOPROPYLPHENOXY)PHENYL]-7-(TRIFLUOROMETHYL)-2H-INDAZOLE

This compound was prepared similarly to that of Example 3.
LCMS: M+H: 487.

Example 670

5-{4-[2-BENZYL-7-(TRIFLUOROMETHYL)-2H-INDAZOL-3-YL]PHENOXY}-3,4-DIHYDRONAPHTHALEN-1(2H)-ONE

This compound was prepared similarly to that of Example 3.
LCMS: M+H: 513.

Example 671

6-{4-[2-BENZYL-7-(TRIFLUOROMETHYL)-2H-INDAZOL-3-YL] PHENOXY}QUINOLINE

This compound was prepared similarly to that of Example 3.
LCMS: M+H: 496.

Example 672

2-BENZYL-3-[4-(2,6-DIMETHOXYPHENOXY)PHENYL]-7-(TRIFLUOROMETHYL)-2H-INDAZOLE

This compound was prepared similarly to that of Example 3.
LCMS: M+H: 505.

Example 673

2-BENZYL-3-[4-(2-METHYLPHENOXY)PHE-NYL]-7-(TRIFLUOROMETHYL)-2H-INDAZOLE

This compound was prepared similarly to that of Example 3.

LCMS: M+H: 459.

Example 674

2-BENZYL-3-[4-(3,4-DICHLOROPHENOXY) PHENYL]-7-(TRIFLUOROMETHYL)-2H-INDA-ZOLE

This compound was prepared similarly to that of Example 3.

LCMS: M+H: 513.

Example 675

2-BENZYL-3-[4-(3,4-DIFLUOROPHENOXY)PHE-NYL]-7-(TRIFLUOROMETHYL)-2H-INDAZOLE

This compound was prepared similarly to that of Example 3.

LCMS: M+H: 481.

Example 676

2-BENZYL-3-[4-(2,5-DIFLUOROPHENOXY)PHE-NYL]-7-(TRIFLUOROMETHYL)-2H-INDAZOLE

This compound was prepared similarly to that of Example 3.

LCMS: M+H: 481.

Example 677

8-{4-[2-BENZYL-7-(TRIFLUOROMETHYL)-2H-INDAZOL-3-YL]PHENOXY}QUINOLINE

This compound was prepared similarly to that of Example 3.

LCMS: M+H: 496.

Example 678

2-BENZYL-3-[4-(4-ETHYLPHENOXY)PHENYL]-7-(TRIFLUOROMETHYL)-2H-INDAZOLE

This compound was prepared similarly to that of Example 3.

LCMS: M+H: 473.

Example 679

2-BENZYL-3-[4-(2,6-DIFLUOROPHENOXY)PHE-NYL]-7-(TRIFLUOROMETHYL)-2H-INDAZOLE

This compound was prepared similarly to that of Example 3.

LCMS: M+H: 481.

Example 680

2-BENZYL-3-{4-[4-(BENZYLOXY)PHENOXY] PHENYL}-7-(TRIFLUOROMETHYL)-2H-INDA-ZOLE

This compound was prepared similarly to that of Example 3.

LCMS: M+H: 551.

Example 681

METHYL 3-{3-[2-BENZYL-7-(TRIFLUOROM-ETHYL)-2H-INDAZOL-3-YL] PHENOXY}BENZOATE

This compound was prepared similarly to that of Example 3.

LCMS: M+H: 503.7.

Example 682

2-BENZYL-3-[3-(3-METHOXYPHENOXY)PHE-NYL]-7-(TRIFLUOROMETHYL)-2H-INDAZOLE

This compound was prepared similarly to that of Example 3.

LCMS: M+H: 475.7.

Example 683

2-BENZYL-3-[3-(3,4-DICHLOROPHENOXY) PHENYL]-7-(TRIFLUOROMETHYL)-2H-INDA-ZOLE

This compound was prepared similarly to that of Example 3.

LCMS: M+H: 513.7.

Example 684

METHYL 3-(4-{3-[2-BENZYL-7-(TRIFLUOROM-ETHYL)-2H-INDAZOL-3-YL] PHENOXY}PHENYL)PROPANOATE

This compound was prepared similarly to that of Example 3.

LCMS: M+H: 531.7.

Example 685

1-(2-{3-[2-BENZYL-7-(TRIFLUOROMETHYL)-2H-INDAZOL-3-YL]PHENOXY}PHENYL)ETHA-NONE

This compound was prepared similarly to that of Example 3.

LCMS: M+H: 487.7.

Example 686

1-(3-{3-[2-BENZYL-7-(TRIFLUOROMETHYL)-2H-INDAZOL-3-YL]PHENOXY}PHENYL)ETHA-NONE

This compound was prepared similarly to that of Example 3.

LCMS: M+H: 487.7.

Example 687

2-BENZYL-3-[3-(3-METHYLPHENOXY)PHE-NYL]-7-(TRIFLUOROMETHYL)-2H-INDAZOLE

This compound was prepared similarly to that of Example 3.

LCMS: M+H: 459.7.

Example 688

2-BENZYL-3-[3-(2-CHLOROPHENOXY)PHE-NYL]-7-(TRIFLUOROMETHYL)-2H-INDAZOLE

This compound was prepared similarly to that of Example 3.

LCMS: M+H: 479.6.

Example 689

3-{3-[2-BENZYL-7-(TRIFLUOROMETHYL)-2H-INDAZOL-3-YL]PHENOXY}-N,N-DIMETHYLA-NILINE

This compound was prepared similarly to that of Example 3.

LCMS: M+H: 488.7.

Example 690

2-BENZYL-3-[3-(3-NITROPHENOXY)PHENYL]-7-(TRIFLUOROMETHYL)-2H-INDAZOLE

This compound was prepared similarly to that of Example 3.

LCMS: M+H: 490.7.

Example 691

2-BENZYL-3-[3-(2,3-DIM ETHYLPHENOXY)PHENYL]-7-(TRIFLUOROMETHYL)-2H-INDA-ZOLE

This compound was prepared similarly to that of Example 3.

LCMS: M+H: 473.8.

Example 692

2-BENZYL-3-{3-[2-(TRIFLUOROMETHOXY)PHENOXY]PHENYL}-7-(TRIFLUOROM-ETHYL)-2H-INDAZOLE

This compound was prepared similarly to that of Example 3.

LCMS: M+H: 529.7.

Example 693

2-BENZYL-3-[3-(2-TERT-BUTYLPHENOXY)PHENYL]-7-(TRIFLUOROMETHYL)-2H-INDA-ZOLE

This compound was prepared similarly to that of Example 3.

LCMS: M+H: 501.8.

Example 694

2-BENZYL-3-[3-(2-ISOPROPYLPHENOXY)PHE-NYL]-7-(TRIFLUOROMETHYL)-2H-INDAZOLE

This compound was prepared similarly to that of Example 3.

LCMS: M+H: 487.8.

Example 695

5-{3-[2-BENZYL-7-(TRIFLUOROMETHYL)-2H-INDAZOL-3-YL]PHENOXY}-3,4-DIHY-DRONAPHTHALEN-1(2H)-ONE

This compound was prepared similarly to that of Example 3.

LCMS: M+H: 513.7.

Example 696

7-{3-[2-BENZYL-7-(TRIFLUOROMETHYL)-2H-INDAZOL-3-YL]PHENOXY}QUINOLINE

This compound was prepared similarly to that of Example 3.

LCMS: M+H: 496.7.

Example 697

8-{3-[2-BENZYL-7-(TRIFLUOROMETHYL)-2H-INDAZOL-3-YL]PHENOXY}QUINOLINE

This compound was prepared similarly to that of Example 3.

LCMS: M+H: 496.7.

Example 698

2-BENZYL-3-{3-[3,5-BIS(TRIFLUOROMETHYL)PHENOXY]PHENYL}-7-(TRIFLUOROM-ETHYL)-2H-INDAZOLE

This compound was prepared similarly to that of Example 3.

LCMS: M+H: 581.6.

Example 699

2-BENZYL-3-{3-[(7-METHYL-1-NAPHTHYL)OXY]PHENYL}-7-(TRIFLUOROMETHYL)-2H-INDAZOLE

This compound was prepared similarly to that of Example 3.

LCMS: M+H: 509.7.

Example 700

4-{3-[2-BENZYL-7-(TRIFLUOROMETHYL)-2H-INDAZOL-3-YL]PHENOXY}ACRIDINE

This compound was prepared similarly to that of Example 3.

LCMS: M+H: 546.8.

Example 701

2-BENZYL-3-{3-[2-(BENZYLOXY)PHENOXY]PHENYL}-7-(TRIFLUOROMETHYL)-2H-INDAZOLE

This compound was prepared similarly to that of Example 3.

LCMS: M+H: 551.7.

Example 702

(2-{3-[2-BENZYL-7-(TRIFLUOROMETHYL)-2H-INDAZOL-3-YL]PHENOXY}PHENYL)(PHENYL)METHANONE

This compound was prepared similarly to that of Example 3.

LCMS: M+H: 549.7.

Example 703

2-BENZYL-3-[3-(BIPHENYL-2-YLOXY)PHENYL]-7-(TRIFLUOROMETHYL)-2H-INDAZOLE

This compound was prepared similarly to that of Example 3.

LCMS: M+H: 521.8.

Example 704

2-(2-{3-[2-BENZYL-7-(TRIFLUOROMETHYL)-2H-INDAZOL-3-YL]PHENOXY}PHENYL)-1,3-BENZOTHIAZOLE

This compound was prepared similarly to that of Example 3.

LCMS: M+H: 578.6.

Example 705

2-BENZYL-3-{3-[2-(1H-PYRROL-1-YL)PHENOXY]PHENYL}-7-(TRIFLUOROMETHYL)-2H-INDAZOLE

This compound was prepared similarly to that of Example 3.

LCMS: M+H: 510.7.

Example 706

2-BENZYL-3-[3-(3,4-DIFLUOROPHENOXY)PHENYL]-7-(TRIFLUOROMETHYL)-2H-INDAZOLE

This compound was prepared similarly to that of Example 3.

LCMS: M+H: 482.2.

Example 707

2-BENZYL-3-[3-(2,3-DIFLUOROPHENOXY)PHENYL]-7-(TRIFLUOROMETHYL)-2H-INDAZOLE

This compound was prepared similarly to that of Example 3.

LCMS: M+H: 482.2.

Example 708

2-BENZYL-3-[3-(2,5-DIFLUOROPHENOXY)PHENYL]-7-(TRIFLUOROMETHYL)-2H-INDAZOLE

This compound was prepared similarly to that of Example 3.

LCMS: M+H: 482.2.

Example 709

2-BENZYL-3-{3-[(7-METHOXY-2-NAPHTHYL)OXY]PHENYL}-7-(TRIFLUOROMETHYL)-2H-INDAZOLE

This compound was prepared similarly to that of Example 3.

LCMS: M+H: 526.3.

Example 710

1-(2-{3-[2-BENZYL-7-(TRIFLUOROMETHYL)-2H-INDAZOL-3-YL]PHENOXY}-4-METHOXYPHENYL)ETHANONE

This compound was prepared similarly to that of Example 3.

LCMS: M+H: 518.2.

Example 711

6-{3-[2-BENZYL-7-(TRIFLUOROMETHYL)-2H-INDAZOL-3-YL]PHENOXY}QUINOLINE

This compound was prepared similarly to that of Example 3.

LCMS: M+H: 497.2.

Example 712

2-BENZYL-3-[3-(3,5-DIMETHYLPHENOXY)PHENYL]-7-(TRIFLUOROMETHYL)-2H-INDAZOLE

This compound was prepared similarly to that of Example 3.

LCMS: M+H: 474.2.

Example 713

2-BENZYL-3-[3-(2-METHOXYPHENOXY)PHENYL]-7-(TRIFLUOROMETHYL)-2H-INDAZOLE

This compound was prepared similarly to that of Example 3.

LCMS: M+H: 476.2.

Example 714

2-BENZYL-3-[3-(1-NAPHTHYLOXY)PHENYL]-7-(TRIFLUOROMETHYL)-2H-INDAZOLE

This compound was prepared similarly to that of Example 3.

LCMS: M+H: 496.2.

Example 715

2-BENZYL-3-(3-{2-[(1E)-PROP-1-EN-1-YL]PHENOXY}PHENYL)-7-(TRIFLUOROMETHYL)-2H-INDAZOLE

This compound was prepared similarly to that of Example 3.

LCMS: M+H: 486.2.

Example 716

2-BENZYL-3-[3-(2-CYCLOPENTYLPHENOXY)PHENYL]-7-(TRIFLUOROMETHYL)-2H-INDAZOLE

This compound was prepared similarly to that of Example 3.

LCMS: M+H: 514.3.

Example 717

2-BENZYL-3-[3-(3,5-DIFLUOROPHENOXY)PHENYL]-7-(TRIFLUOROMETHYL)-2H-INDAZOLE

This compound was prepared similarly to that of Example 3.

LCMS: M+H: 482.2.

Example 718

2-BENZYL-3-[3-(3,5-DICHLOROPHENOXY)PHENYL]-7-(TRIFLUOROMETHYL)-2H-INDAZOLE

This compound was prepared similarly to that of Example 3.

LCMS: M+H: 515.1.

Example 719

2-BENZYL-3-[3-(3,5-DIMETHOXYPHENOXY)PHENYL]-7-(TRIFLUOROMETHYL)-2H-INDAZOLE

This compound was prepared similarly to that of Example 3.

LCMS: M+H: 506.2.

Example 720

2-(4-CHLORO-2-FLUOROBENZYL)-3-[3-(3-CHLOROPHENOXY)PHENYL]-7-(TRIFLUOROMETHYL)-2H-INDAZOLE

This compound was prepared similarly to that of Example 3.

LCMS: M+H: 533.2.

Example 721

2-(4-CHLORO-2-FLUOROBENZYL)-3-[3-(2-FLUOROPHENOXY)PHENYL]-7-(TRIFLUOROMETHYL)-2H-INDAZOLE

This compound was prepared similarly to that of Example 3.

LCMS: M+H: 517.3.

Example 722

6-{3-[2-(4-CHLORO-2-FLUOROBENZYL)-7-(TRIFLUOROMETHYL)-2H-INDAZOL-3-YL]PHENOXY}-2-NAPHTHONITRILE

This compound was prepared similarly to that of Example 3.

LCMS: M+H: 574.2.

Example 723

2-(4-CHLORO-2-FLUOROBENZYL)-3-[3-(5,6,7,8-TETRAHYDRONAPHTHALEN-1-YLOXY)PHENYL]-7-(TRIFLUOROMETHYL)-2H-INDAZOLE

This compound was prepared similarly to that of Example 3.

LCMS: M+H: 553.2.

Example 724

2-(4-CHLORO-2-FLUOROBENZYL)-3-[3-(2-ETHOXYPHENOXY)PHENYL]-7-(TRIFLUOROMETHYL)-2H-INDAZOLE

This compound was prepared similarly to that of Example 3.

LCMS: M+H: 543.2.

Example 725

1-(2-{3-[2-(4-CHLORO-2-FLUOROBENZYL)-7-(TRIFLUOROMETHYL)-2H-INDAZOL-3-YL]PHENOXY}PHENYL)PROPAN-1-ONE

This compound was prepared similarly to that of Example 3.

LCMS: M+H: 555.2.

Example 726

3-{3-[2-(1H-BENZIMIDAZOL-2-YL)PHENOXY]PHENYL}-2-(4-CHLORO-2-FLUOROBENZYL)-7-(TRIFLUOROMETHYL)-2H-INDAZOLE

This compound was prepared similarly to that of Example 3.

LCMS: M+H: 615.2.

Example 727

2-(4-CHLORO-2-FLUOROBENZYL)-3-[3-(2-PYRROLIDIN-1-YLPHENOXY)PHENYL]-7-(TRIFLUOROMETHYL)-2H-INDAZOLE

This compound was prepared similarly to that of Example 3.
LCMS: M+H: 568.2.

Example 728

2-BENZYL-3-{4-[(3-METHOXYBENZYL)OXY]PHENYL}-7-(TRIFLUOROMETHYL)-2H-INDAZOLE

This compound was prepared similarly to that of Example 525.
LCMS: M+H: 489.5.

Example 729

2-BENZYL-3-{4-[(2-CHLOROBENZYL)OXY]PHENYL}-7-(TRIFLUOROMETHYL)-2H-INDAZOLE

This compound was prepared similarly to that of Example 525.
LCMS: M+H: 493.4.

Example 730

2-BENZYL-7-(TRIFLUOROMETHYL)-3-(4-{[(2-(TRIFLUOROMETHYL)BENZYL]OXY}PHENYL)-2H-INDAZOLE

This compound was prepared similarly to that of Example 525.
LCMS: M+H: 527.6.

Example 731

2-BENZYL-3-{4-[(3-METHYLBENZYL)OXY]PHENYL}-7-(TRIFLUOROMETHYL)-2H-INDAZOLE

This compound was prepared similarly to that of Example 525.
LCMS: M+H: 473.6.

Example 732

2-BENZYL-3-{4-[(2-METHYLBENZYL)OXY]PHENYL}-7-(TRIFLUOROMETHYL)-2H-INDAZOLE

This compound was prepared similarly to that of Example 525.
LCMS: M+H: 473.3.

Example 733

2-BENZYL-3-{4-[(3-CHLOROBENZYL)OXY]PHENYL}-7-(TRIFLUOROMETHYL)-2H-INDAZOLE

This compound was prepared similarly to that of Example 525.
LCMS: M+H: 493.4.

Example 734

2-BENZYL-7-(TRIFLUOROMETHYL)-3-(4-{[3-(TRIFLUOROMETHYL)BENZYL]OXY}PHENYL)-2H-INDAZOLE

This compound was prepared similarly to that of Example 525.
LCMS: M+H: 527.6.

Example 735

2-BENZYL-3-(4-{[3,5-BIS(TRIFLUOROMETHYL)BENZYL]OXY}PHENYL)-7-(TRIFLUOROMETHYL)-2H-INDAZOLE

This compound was prepared similarly to that of Example 525.
LCMS: M+H: 595.4.

Example 736

2-BENZYL-3-{4-[(3,5-DIMETHYLBENZYL)OXY]PHENYL}-7-(TRIFLUOROMETHYL)-2H-INDAZOLE

This compound was prepared similarly to that of Example 525.
LCMS: M+H: 487.4.

Example 737

2-BENZYL-3-{4-[(2,6-DICHLOROBENZYL)OXY]PHENYL}-7-(TRIFLUOROMETHYL)-2H-INDAZOLE

This compound was prepared similarly to that of Example 525.
LCMS: M+H: 527.6.

Example 738

2-BENZYL-3-{4-[(3,5-DICHLOROBENZYL)OXY]PHENYL}-7-(TRIFLUOROMETHYL)-2H-INDAZOLE

This compound was prepared similarly to that of Example 525.
LCMS: M+H: 527.3.

Example 739

2-BENZYL-3-{3-[(3-METHOXYBENZYL)OXY]PHENYL}-7-(TRIFLUOROMETHYL)-2H-INDAZOLE

This compound was prepared similarly to that of Example 525.
LCMS: M+H: 489.5.

Example 740

2-BENZYL-3-{3-[(2-CHLOROBENZYL)OXY]PHENYL}-7-(TRIFLUOROMETHYL)-2H-INDAZOLE

This compound was prepared similarly to that of Example 525.
LCMS: M+H: 493.4.

Example 741

2-BENZYL-7-(TRIFLUOROMETHYL)-3-(3-{[2-(TRIFLUOROMETHYL) BENZYL]OXY}PHENYL)-2H-INDAZOLE

This compound was prepared similarly to that of Example 525.
LCMS: M+H: 527.6.

Example 742

2-BENZYL-3-{3-[(3-METHYLBENZYL)OXY]PHENYL}-7-(TRIFLUOROMETHYL)-2H-INDAZOLE

This compound was prepared similarly to that of Example 525.
LCMS: M+H: 473.3.

Example 743

2-BENZYL-3-{3-[(2-METHYLBENZYL)OXY]PHENYL}-7-(TRIFLUOROMETHYL)-2H-INDAZOLE

This compound was prepared similarly to that of Example 525.
LCMS: M+H: 473.3.

Example 744

2-BENZYL-7-(TRIFLUOROMETHYL)-3-(3-{[3-(TRIFLUOROMETHYL)BENZYL]OXY}PHENYL)-2H-INDAZOLE

This compound was prepared similarly to that of Example 525.
LCMS: M+H: 527.6.

Example 745

2-BENZYL-3-(3-{[3,5-BIS(TRIFLUOROMETHYL) BENZYL]OXY}PHENYL)-7-(TRIFLUOROMETHYL)-2H-INDAZOLE

This compound was prepared similarly to that of Example 525.
LCMS: M+H: 595.4.

Example 746

2-BENZYL-3-{3-[(3,5-DIMETHYLBENZYL)OXY]PHENYL}-7-(TRIFLUOROMETHYL)-2H-INDAZOLE

This compound was prepared similarly to that of Example 525.
LCMS: M+H: 487.4.

Example 747

2-BENZYL-3-{3-[(2,6-DICHLOROBENZYL)OXY]PHENYL}-7-(TRIFLUOROMETHYL)-2H-INDAZOLE

This compound was prepared similarly to that of Example 525.
LCMS: M+H: 527.3.

Example 748

2-BENZYL-3-{3-[(3,5-DICHLOROBENZYL)OXY]PHENYL}-7-(TRIFLUOROMETHYL)-2H-INDAZOLE

This compound was prepared similarly to that of Example 525.
LCMS: M+H: 527.3.

Example 749

1-[4-({3-[2-BENZYL-7-(TRIFLUOROMETHYL)-2H-INDAZOL-3-YL]PHENOXY}METHYL)PHENYL]CYCLOPROPANECARBOXYLIC ACID

This compound was prepared similarly to that of Example 527.
LCMS: M+H: 543.5, M−H: 541.4.

Example 750

2-BENZYL-3-{3-[(2,6-DIMETHYLBENZYL)OXY]PHENYL}-7-(TRIFLUOROMETHYL)-2H-INDAZOLE

This compound was prepared similarly to that of Example 525.
LCMS: M+H: 487.4.

Example 751

2-BENZYL-3-{3-[(2-FLUOROBENZYL)OXY]
PHENYL}-7-(TRIFLUOROMETHYL)-2H-INDA-
ZOLE

This compound was prepared similarly to that of Example 525.
LCMS: M+H: 477.2.

Example 752

2-BENZYL-3-{3-[(2-FLUORO-6-NITROBENZYL)
OXY]PHENYL}-7-(TRIFLUOROMETHYL)-2H-
INDAZOLE

This compound was prepared similarly to that of Example 525.
LCMS: M+H: 522.8.

Example 753

2-BENZYL-3-{3-[(2-CHLORO-6-FLUOROBEN-
ZYL)OXY]PHENYL}-7-(TRIFLUOROMETHYL)-
2H-INDAZOLE

This compound was prepared similarly to that of Example 525.
LCMS: M+H: 511.7.

Example 754

2-BENZYL-3-{3-[(2,6-DIFLUOROBENZYL)OXY]
PHENYL}-7-(TRIFLUOROMETHYL)-2H-INDA-
ZOLE

This compound was prepared similarly to that of Example 525.
LCMS: M+H: 495.8.

Example 755

2-BENZYL-3-{4-[(2-FLUOROBENZYL)OXY]
PHENYL}-7-(TRIFLUOROMETHYL)-2H-INDA-
ZOLE

This compound was prepared similarly to that of Example 525.
LCMS: M+H: 477.2.

Example 756

2-BENZYL-3-{4-[(2-CHLORO-6-FLUOROBEN-
ZYL)OXY]PHENYL}-7-(TRIFLUOROMETHYL)-
2H-INDAZOLE

This compound was prepared similarly to that of Example 525.
LCMS: M+H: 511.7.

Example 757

2-BENZYL-3-{4-[(2,6-DIFLUOROBENZYL)OXY]
PHENYL}-7-(TRIFLUOROMETHYL)-2H-INDA-
ZOLE

This compound was prepared similarly to that of Example 525.
LCMS: M+H: 495.8.

Example 758

[3-({3-[2-BENZYL-7-(TRIFLUOROMETHYL)-
2H-INDAZOL-3-YL]PHENOXY}METHYL)PHE-
NYL]ACETIC ACID

This compound was prepared similarly to that of Example 527.
LCMS: M+H: 517.4, M−H: 515.6.

Example 759

3-[2-BENZYL-7-(TRIFLUOROMETHYL)-2H-
INDAZOL-3-YL]PHENYL ACETATE

This compound was prepared similarly to that of Example 525.
LCMS: M+H: 411.2.

Example 760

2-BENZYL-3-{4-[(2-FLUORO-6-NITROBENZYL)
OXY]PHENYL}-7-(TRIFLUOROMETHYL)-2H-
INDAZOLE

This compound was prepared similarly to that of Example 525.
LCMS: M+H: 522.8.

Example 761

4-({3-[2-BENZYL-7-(TRIFLUOROMETHYL)-2H-
INDAZOL-3-YL]PHENOXY}METHYL)PHENYL
ACETATE

This compound was prepared similarly to that of Example 525.
LCMS: M+H: 517.4.

Example 762

DIETHYL [4-({3-[2-BENZYL-7-(TRIFLUOROM-
ETHYL)-2H-INDAZOL-3-YL]
PHENOXY}METHYL)BENZYL]PHOSPHONATE

This compound was prepared similarly to that of Example 525.
LCMS: M+H: 609.5.

Example 763

DIETHYL [4-({4-[2-BENZYL-7-(TRIFLUOROM-
ETHYL)-2H-INDAZOL-3-YL]
PHENOXY}METHYL)BENZYL]PHOSPHONATE

This compound was prepared similarly to that of Example 525.
LCMS: M+H: 609.5.

Example 764

4-({3-[2-BENZYL-7-(TRIFLUOROMETHYL)-2H-INDAZOL-3-YL]PHENOXY}METHYL)BENZONITRILE

This compound was prepared similarly to that of Example 525.
LCMS: M+H: 484.4.

Example 765

3-({3-[2-BENZYL-7-(TRIFLUOROMETHYL)-2H-INDAZOL-3-YL]PHENOXY}METHYL)BENZONITRILE

This compound was prepared similarly to that of Example 525.
LCMS: M+H: 484.4.

Example 766

4-({4-[2-BENZYL-7-(TRIFLUOROMETHYL)-2H-INDAZOL-3-YL]PHENOXY}METHYL)BENZONITRILE

This compound was prepared similarly to that of Example 525.
LCMS: M+H: 484.4.

Example 767

2-BENZYL-3-(3-{[3-(1H-TETRAZOL-5-YL)BENZYL]OXY}PHENYL)-7-(TRIFLUOROMETHYL)-2H-INDAZOLE

This compound was prepared similarly to that of Example 529.
LCMS: M+H: 527.6, M−H: 525.8.

Example 768

2-BENZYL-3-(4-{[4-(1H-TETRAZOL-5-YL)BENZYL]OXY}PHENYL)-7-(TRIFLUOROMETHYL)-2H-INDAZOLE

This compound was prepared similarly to that of Example 529.
LCMS: M+H: 527.6, M−H: 525.8.

Example 769

[4-({3-[2-BENZYL-7-(TRIFLUOROMETHYL)-2H-INDAZOL-3-YL]PHENOXY}METHYL)BENZYL]PHOSPHONIC ACID

This compound was prepared similarly to that of Example 530.
LCMS: M+H: 553.4, M−H: 551.9.

Example 770

{4-[4-(2-BENZYL-7-TRIFLUOROMETHYL-2H-INDAZOL-3-YL)-PHENOXYMETHYL]-BENZYL}-PHOSPHONIC ACID MONOETHYL ESTER

This compound was prepared similarly to that of Example 530.
LCMS: M+H: 581.3, M−H: 579.5.

Example 771

[4-({4-[2-BENZYL-7-(TRIFLUOROMETHYL)-2H-INDAZOL-3-YL]PHENOXY}METHYL)BENZYL]PHOSPHONIC ACID

This compound was prepared similarly to that of Example 530.
LCMS: M+H: 553.4, M−H: 551.6.

Example 772

2-(2,4-DIMETHYLBENZYL)-3-{3-[(2,6-DIMETHYLBENZYL)OXY]PHENYL}-7-(TRIFLUOROMETHYL)-2H-INDAZOLE

This compound was prepared similarly to that of Example 525.
LCMS: M+H: 515.6.

Example 773

3-{3-[(2,6-DIMETHYLBENZYL)OXY]PHENYL}-2-(2,4,6-TRIFLUOROBENZYL)-7-(TRIFLUOROMETHYL)-2H-INDAZOLE

This compound was prepared similarly to that of Example 525.
LCMS: M+H: 541.4.

Example 774

3-{3-[(2-FLUORO-6-NITROBENZYL)OXY]PHENYL}-2-(2,4,6-TRIFLUOROBENZYL)-7-(TRIFLUOROMETHYL)-2H-INDAZOLE

This compound was prepared similarly to that of Example 525.
LCMS: M+H: 576.5.

Example 775

2-(2,4-DIFLUOROBENZYL)-3-{3-[(2,6-DIMETHYLBENZYL)OXY]PHENYL}-7-(TRIFLUOROMETHYL)-2H-INDAZOLE

This compound was prepared similarly to that of Example 525.
LCMS: M+H: 523.7.

Example 776

2-(4-CHLORO-2-FLUOROBENZYL)-3-{3-[(2,6-DIMETHYLBENZYL)OXY]PHENYL}-7-(TRIFLUOROMETHYL)-2H-INDAZOLE

This compound was prepared similarly to that of Example 525.
LCMS: M+H: 539.6.

Example 777

2-(2-CHLORO-4-FLUOROBENZYL)-3-{3-[(2,6-DIMETHYLBENZYL)OXY]PHENYL}-7-(TRIFLUOROMETHYL)-2H-INDAZOLE

This compound was prepared similarly to that of Example 525.
LCMS: M+H: 539.6.

Example 778

2-BENZYL-3-{3-[(3,5-DIMETHOXYBENZYL)OXY]PHENYL}-7-(TRIFLUOROMETHYL)-2H-INDAZOLE

This compound was prepared similarly to that of Example 525.
LCMS: M+H: 519.5.

Example 779

2-BENZYL-3-{4-[(2,6-DIMETHYLBENZYL)OXY]PHENYL}-7-(TRIFLUOROMETHYL)-2H-INDAZOLE

This compound was prepared similarly to that of Example 525.
LCMS: M+H: 487.4.

Example 780

2-(2,4-DICHLOROBENZYL)-3-{3-[(2,6-DIMETHYLBENZYL)OXY]PHENYL}-7-(TRIFLUOROMETHYL)-2H-INDAZOLE

This compound was prepared similarly to that of Example 525.
LCMS: M+H: 555.2.

Example 781

2-BENZYL-3-{3-[(2,5-DIMETHYLBENZYL)OXY]PHENYL}-7-(TRIFLUOROMETHYL)-2H-INDAZOLE

This compound was prepared similarly to that of Example 525.
LCMS: M+H: 487.4.

Example 782

2-BENZYL-3-(3-{[2-FLUORO-6-(TRIFLUOROMETHYL)BENZYL]OXY}PHENYL)-7-(TRIFLUOROMETHYL)-2H-INDAZOLE

This compound was prepared similarly to that of Example 525.
LCMS: M+H: 545.3.

Example 783

2-[4-({3-[2-(2,4-DIMETHYLBENZYL)-7-(TRIFLUOROMETHYL)-2H-INDAZOL-3-YL]PHENOXY}METHYL)PHENYL]-2-METHYLPROPANOIC ACID

This compound was prepared similarly to that of Example 528.
LCMS: M+H: 573.8, M–H: 571.4.

Example 784

2-METHYL-2-[4-({3-[2-(2,4,6-TRIFLUOROBENZYL)-7-(TRIFLUOROMETHYL)-2H-INDAZOL-3-YL]PHENOXY}METHYL)PHENYL]PROPANOIC ACID

This compound was prepared similarly to that of Example 528.
LCMS: M+H: 599.6, M–H: 597.5.

Example 785

2-[4-({3-[2-(2,4-DIMETHYLBENZYL)-7-(TRIFLUOROMETHYL)-2H-INDAZOL-3-YL]PHENOXY}METHYL)PHENYL]PROPANOIC ACID

This compound was prepared similarly to that of Example 528.
LCMS: M+H: 559.4, M–H: 557.6.

Example 786

2-[4-({3-[2-(2,4,6-TRIFLUOROBENZYL)-7-(TRIFLUOROMETHYL)-2H-INDAZOL-3-YL]PHENOXY}METHYL)PHENYL]PROPANOIC ACID

This compound was prepared similarly to that of Example 528.
LCMS: M+H: 585.2, M–H: 583.4.

Example 787

2-(2,4-DIMETHYLBENZYL)-3-{3-[(2-FLUORO-6-NITROBENZYL)OXY]PHENYL}-7-(TRIFLUOROMETHYL)-2H-INDAZOLE

This compound was prepared similarly to that of Example 525.
LCMS: M+H: 550.7, M–H: 548.6.

Example 788

3-({3-[2-(2,4-DIMETHYLBENZYL)-7-(TRIFLUO-ROMETHYL)-2H-INDAZOL-3-YL]PHENOXY}METHYL)BENZONITRILE

This compound was prepared similarly to that of Example 525.
LCMS: M+H: 512.6.

Example 789

3-[3-(BENZYLOXY)PHENYL]-2-(2,4-DIMETH-YLBENZYL)-7-(TRIFLUOROMETHYL)-2H-INDAZOLE

This compound was prepared similarly to that of Example 525.
LCMS: M+H: 487.4.

Example 790

2-(4-CHLORO-2-FLUOROBENZYL)-3-{3-[(2-FLUORO-6-NITROBENZYL)OXY]PHENYL}-7-(TRIFLUOROMETHYL)-2H-INDAZOLE

This compound was prepared similarly to that of Example 525.
LCMS: M+H: 574.4, M−H: 572.3.

Example 791

3-({3-[2-(4-CHLORO-2-FLUOROBENZYL)-7-(TRIFLUOROMETHYL)-2H-INDAZOL-3-YL]PHENOXY}METHYL)BENZONITRILE

This compound was prepared similarly to that of Example 525.
LCMS: M+H: 536.3.

Example 792

2-{3-[2-(4-CHLORO-2-FLUOROBENZYL)-7-(TRIFLUOROMETHYL)-2H-INDAZOL-3-YL]PHENOXY}-2-(4-METHYLPHENYL)PROPANOIC ACID

This compound was prepared similarly to that of Example 528.
LCMS: M+H: 583.4, M−H: 581.3.

Example 793

2-[4-({3-[2-(4-CHLORO-2-FLUOROBENZYL)-7-(TRIFLUOROMETHYL)-2H-INDAZOL-3-YL]PHENOXY}METHYL)PHENYL]PROPANOIC ACID

This compound was prepared similarly to that of Example 528.
LCMS: M+H: 583.1, M−H: 581.3.

Example 794

2-[4-({3-[2-(4-CHLORO-2-FLUOROBENZYL)-7-(TRIFLUOROMETHYL)-2H-INDAZOL-3-YL]PHENOXY}METHYL)PHENYL]-2-METHYL-PROPANOIC ACID

This compound was prepared similarly to that of Example 528.
LCMS: M+H: 597.5, M−H: 595.4.

Example 795

2-(2,4-DIFLUOROBENZYL)-3-{4-[(2,6-DIMETH-YLBENZYL)OXY]PHENYL}-7-(TRIFLUOROM-ETHYL)-2H-INDAZOLE

This compound was prepared similarly to that of Example 525.
LCMS: M+H: 523.7.

Example 796

2-(2,4-DICHLOROBENZYL)-3-{4-[(2,6-DIMETH-YLBENZYL)OXY]PHENYL}-7-(TRIFLUOROM-ETHYL)-2H-INDAZOLE

This compound was prepared similarly to that of Example 525.
LCMS: M+H: 555.2.

Example 797

2-(4-CHLORO-2-FLUOROBENZYL)-3-{4-[(2,6-DIMETHYLBENZYL)OXY]PHENYL}-7-(TRIF-LUOROMETHYL)-2H-INDAZOLE

This compound was prepared similarly to that of Example 525.
LCMS: M+H: 539.6.

Example 798

2-(2-CHLORO-4-FLUOROBENZYL)-3-{4-[(2,6-DIMETHYLBENZYL)OXY]PHENYL}-7-(TRIF-LUOROMETHYL)-2H-INDAZOLE

This compound was prepared similarly to that of Example 525.
LCMS: M+H: 539.6.

Example 799

2-(2,4-DIMETHYLBENZYL)-3-{4-[(2,6-DIMETH-YLBENZYL)OXY]PHENYL}-7-(TRIFLUOROM-ETHYL)-2H-INDAZOLE

This compound was prepared similarly to that of Example 525.
LCMS: M+H: 515.6.

Example 800

2-BENZYL-3-(4-{[2-FLUORO-6-(TRIFLUOROM-ETHYL)BENZYL]OXY}PHENYL)-7-(TRIFLUO-ROMETHYL)-2H-INDAZOLE

This compound was prepared similarly to that of Example 525.
LCMS: M+H: 545.3.

Example 801

[4-({3-[2-BENZYL-7-(TRIFLUOROMETHYL)-2H-INDAZOL-3-YL]PHENOXY}METHYL)-3,5-DIMETHYLPHENYL]ACETIC ACID

This compound was prepared similarly to that of Example 2.
LCMS: M+H: 545.3.

Example 802

[4-({4-[2-BENZYL-7-(TRIFLUOROMETHYL)-2H-INDAZOL-3-YL]PHENOXY}METHYL)-3,5-DIMETHYLPHENYL]ACETIC ACID

This compound was prepared similarly to that of Example 801.
LCMS: M+H: 545.3.

Example 803

2-(4-CHLORO-2-FLUOROBENZYL)-3-{3-[(2,5-DIMETHYLBENZYL)OXY]PHENYL}-7-(TRIFLUOROMETHYL)-2H-INDAZOLE

This compound was prepared similarly to that of Example 525.
LCMS: M+H: 539.6.

Example 804

2-(2,4-DIMETHYLBENZYL)-3-{3-[(2,5-DIMETHYLBENZYL)OXY]PHENYL}-7-(TRIFLUOROMETHYL)-2H-INDAZOLE

This compound was prepared similarly to that of Example 525.
LCMS: M+H: 515.6.

Example 805

4-({3-[2-BENZYL-7-(TRIFLUOROMETHYL)-2H-INDAZOL-3-YL]PHENOXY}METHYL)-3,5-DIBROMOBENZOIC ACID

This compound was prepared similarly to that of Example 801.
LCMS: M+H: 661.0, M−H: 659.0.

Example 806

4-({4-[2-BENZYL-7-(TRIFLUOROMETHYL)-2H-INDAZOL-3-YL]PHENOXY}METHYL)-3,5-DIBROMOBENZOIC ACID

This compound was prepared similarly to that of Example 801.
LCMS: M+H: 661.0, M−H: 659.1.

Example 807

4-({3-[2-BENZYL-7-(TRIFLUOROMETHYL)-2H-INDAZOL-3-YL]PHENOXY}METHYL)-3,5-DIMETHYLBENZOIC ACID

This compound was prepared similarly to that of Example 801.
LCMS: M+H: 531.2, M−H: 529.3.

Example 808

2-BENZYL-3-{4-[(2,5-DIMETHYLBENZYL)OXY]PHENYL}-7-(TRIFLUOROMETHYL)-2H-INDAZOLE

This compound was prepared similarly to that of Example 525.
LCMS: M+H: 487.4.

Example 809

2-(2-CHLORO-4-FLUOROBENZYL)-3-{4-[(2,5-DIMETHYLBENZYL)OXY]PHENYL}-7-(TRIFLUOROMETHYL)-2H-INDAZOLE

This compound was prepared similarly to that of Example 525.
LCMS: M+H: 539.6.

Example 810

2-(2,4-DICHLOROBENZYL)-3-{4-[(2,5-DIMETHYLBENZYL)OXY]PHENYL}-7-(TRIFLUOROMETHYL)-2H-INDAZOLE

This compound was prepared similarly to that of Example 525.
LCMS: M+H: 555.2.

Example 811

3-{3-[(2,5-DIMETHYLBENZYL)OXY]PHENYL}-2-(2,4,6-TRIFLUOROBENZYL)-7-(TRIFLUOROMETHYL)-2H-INDAZOLE

This compound was prepared similarly to that of Example 525.
LCMS: M+H: 541.4.

Example 812

{4-[2-BENZYL-7-(TRIFLUOROMETHYL)-2H-INDAZOL-3-YL]PHENOXY}(3-METHYLPHENYL)ACETIC ACID

This compound was prepared similarly to that of Example 527.
LCMS: M+H: 517.4.

Example 813

{3-[2-BENZYL-7-(TRIFLUOROMETHYL)-2H-INDAZOL-3-YL]PHENOXY}(3-METHYLPHENYL)ACETIC ACID

This compound was prepared similarly to that of Example 527.
LCMS: M+H: 517.4, M–H: 515.3.

Example 814

2-BENZYL-3-[4-(2-NAPHTHYLMETHOXY)PHENYL]-7-(TRIFLUOROMETHYL)-2H-INDAZOLE

This compound was prepared similarly to that of Example 525.
LCMS: M+H: 509.6.

Example 815

2-BENZYL-3-[4-(1-NAPHTHYLMETHOXY)PHENYL]-7-(TRIFLUOROMETHYL)-2H-INDAZOLE

This compound was prepared similarly to that of Example 525.
LCMS: M+H: 509.3.

Example 816

2-BENZYL-3-{4-[(3-METHYL-2-NAPHTHYL)METHOXY]PHENYL}-7-(TRIFLUOROMETHYL)-2H-INDAZOLE

This compound was prepared similarly to that of Example 525.
LCMS: M+H: 523.7.

Example 817

2-BENZYL-3-[3-(2-NAPHTHYLMETHOXY)PHENYL]-7-(TRIFLUOROMETHYL)-2H-INDAZOLE

This compound was prepared similarly to that of Example 525.
LCMS: M+H: 509.3.

Example 818

2-BENZYL-3-[3-(1-NAPHTHYLMETHOXY)PHENYL]-7-(TRIFLUOROMETHYL)-2H-INDAZOLE

This compound was prepared similarly to that of Example 525.
LCMS: M+H: 509.6.

Example 819

2-BENZYL-3-{3-[(3-METHYL-2-NAPHTHYL)METHOXY]PHENYL}-7-(TRIFLUOROMETHYL)-2H-INDAZOLE

This compound was prepared similarly to that of Example 525.
LCMS: M+H: 523.7.

Example 820

2-BENZYL-3-{4-[(2-METHYL-1-NAPHTHYL)METHOXY]PHENYL}-7-(TRIFLUOROMETHYL)-2H-INDAZOLE

This compound was prepared similarly to that of Example 525.
LCMS: M+H: 523.7.

Example 821

3-[4-(9-ANTHRYLMETHOXY)PHENYL]-2-BENZYL-7-(TRIFLUOROMETHYL)-2H-INDAZOLE

This compound was prepared similarly to that of Example 525.
LCMS: M+H: 559.4.

Example 822

2-BENZYL-3-{3-[(2-METHYL-1-NAPHTHYL)METHOXY]PHENYL}-7-(TRIFLUOROMETHYL)-2H-INDAZOLE

This compound was prepared similarly to that of Example 525.
LCMS: M+H: 523.7.

Example 823

3-[3-(9-ANTHRYLMETHOXY)PHENYL]-2-BENZYL-7-(TRIFLUOROMETHYL)-2H-INDAZOLE

This compound was prepared similarly to that of Example 525.
LCMS: M+H: 559.4.

Example 824

2-(4-CHLORO-2-FLUOROBENZYL)-3-{4-[(2,5-DIMETHYLBENZYL)OXY]PHENYL}-7-(TRIFLUOROMETHYL)-2H-INDAZOLE

This compound was prepared similarly to that of Example 525.
LCMS: M+H: 539.6.

Example 825

2-(2,4-DIMETHYLBENZYL)-3-{4-[(2,5-DIMETH-YLBENZYL)OXY]PHENYL}-7-(TRIFLUOROM-ETHYL)-2H-INDAZOLE

This compound was prepared similarly to that of Example 525.
LCMS: M+H: 515.6.

Example 826

3-{4-[(2,5-DIMETHYLBENZYL)OXY]PHENYL}-2-(2,4,6-TRIFLUOROBENZYL)-7-(TRIFLUO-ROMETHYL)-2H-INDAZOLE

This compound was prepared similarly to that of Example 525.
LCMS: M+H: 541.4.

Example 827

2-(4-CHLORO-2-FLUOROBENZYL)-3-{3-[(2-METHYL-3-NITROBENZYL)OXY]PHENYL}-7-(TRIFLUOROMETHYL)-2H-INDAZOLE

This compound was prepared similarly to that of Example 525.
LCMS: M+H: 570.5.

Example 828

2-(4-CHLORO-2-FLUOROBENZYL)-3-{3-[(5-METHYL-2-NITROBENZYL)OXY]PHENYL}-7-(TRIFLUOROMETHYL)-2H-INDAZOLE

This compound was prepared similarly to that of Example 525.
LCMS: M+H: 570.5.

Example 829

2-(4-CHLORO-2-FLUOROBENZYL)-3-{3-[(2-CHLORO-5-NITROBENZYL)OXY]PHENYL}-7-(TRIFLUOROMETHYL)-2H-INDAZOLE

This compound was prepared similarly to that of Example 525.
LCMS: M+H: 590.3.

Example 830

2-(4-CHLORO-2-FLUOROBENZYL)-3-{3-[(2-FLUORO-3-METHYLBENZYL)OXY]PHENYL}-7-(TRIFLUOROMETHYL)-2H-INDAZOLE

This compound was prepared similarly to that of Example 525.
LCMS: M+H: 543.5.

Example 831

2-(4-CHLORO-2-FLUOROBENZYL)-3-(3-{[5-FLUORO-2-(TRIFLUOROMETHYL) BENZYL]OXY}PHENYL)-7-(TRIFLUOROMETHYL)-2H-INDAZOLE

This compound was prepared similarly to that of Example 525.
LCMS: M+H: 597.2.

Example 832

2-(4-CHLORO-2-FLUOROBENZYL)-3-(3-{[2-CHLORO-3-(TRIFLUOROMETHYL)BENZYL]OXY}PHENYL)-7-(TRIFLUOROMETHYL)-2H-INDAZOLE

This compound was prepared similarly to that of Example 525.
LCMS: M+H: 613.1.

Example 833

2-(4-CHLORO-2-FLUOROBENZYL)-3-{3-[(2-METHOXY-5-NITROBENZYL)OXY]PHENYL}-7-(TRIFLUOROMETHYL)-2H-INDAZOLE

This compound was prepared similarly to that of Example 525.
LCMS: M+H: 586.1.

Example 834

2-(4-CHLORO-2-FLUOROBENZYL)-3-(3-{[2-METHYL-5-(TRIFLUOROMETHYL)BENZYL]OXY}PHENYL)-7-(TRIFLUOROMETHYL)-2H-INDAZOLE

This compound was prepared similarly to that of Example 525.
LCMS: M+H: 593.6.

Example 835

3-{3-[(2-BROMO-5-METHOXYBENZYL)OXY]PHENYL}-2-(4-CHLORO-2-FLUOROBENZYL)-7-(TRIFLUOROMETHYL)-2H-INDAZOLE

This compound was prepared similarly to that of Example 525.
LCMS: M+H: 621.5.

Example 836

3-(3-{[2,5-BIS(TRIFLUOROMETHYL)BENZYL]OXY}PHENYL)-2-(4-CHLORO-2-FLUOROBEN-ZYL)-7-(TRIFLUOROMETHYL)-2H-INDAZOLE

This compound was prepared similarly to that of Example 525.
LCMS: M+H: 647.6.

Example 837

1-[3-({3-[2-(4-CHLORO-2-FLUOROBENZYL)-7-(TRIFLUOROMETHYL)-2H-INDAZOL-3-YL]PHENOXY}METHYL)-4-METHOXYPHENYL]ETHANONE

This compound was prepared similarly to that of Example 525.
LCMS: M+H: 584.3.

Example 838

2-(4-CHLORO-2-FLUOROBENZYL)-3-{3-[(2,5-DIFLUOROBENZYL)OXY]PHENYL}-7-(TRIFLUOROMETHYL)-2H-INDAZOLE

This compound was prepared similarly to that of Example 525.
LCMS: M+H: 547.7.

Example 839

3-{3-[(2-BROMO-5-FLUOROBENZYL)OXY]PHENYL}-2-(4-CHLORO-2-FLUOROBENZYL)-7-(TRIFLUOROMETHYL)-2H-INDAZOLE

This compound was prepared similarly to that of Example 525.
LCMS: M+H: 607.1.

Example 840

2-(4-CHLORO-2-FLUOROBENZYL)-3-{3-[(3-CHLORO-2-FLUOROBENZYL)OXY]PHENYL}-7-(TRIFLUOROMETHYL)-2H-INDAZOLE

This compound was prepared similarly to that of Example 525.
LCMS: M+H: 563.3.

Example 841

2-(4-CHLORO-2-FLUOROBENZYL)-3-(3-{[2-FLUORO-5-(TRIFLUOROMETHYL)BENZYL]OXY}PHENYL)-7-(TRIFLUOROMETHYL)-2H-INDAZOLE

This compound was prepared similarly to that of Example 525.
LCMS: M+H: 597.2.

Example 842

2-(4-CHLORO-2-FLUOROBENZYL)-3-{3-[(2,3,6-TRIFLUOROBENZYL)OXY]PHENYL}-7-(TRIFLUOROMETHYL)-2H-INDAZOLE

This compound was prepared similarly to that of Example 525.
LCMS: M+H: 565.4.

Example 843

2-(4-CHLORO-2-FLUOROBENZYL)-3-{3-[(2,5-DICHLOROBENZYL)OXY]PHENYL}-7-(TRIFLUOROMETHYL)-2H-INDAZOLE

This compound was prepared similarly to that of Example 525.
LCMS: M+H: 579.3.

Example 844

2-(4-CHLORO-2-FLUOROBENZYL)-3-(3-{[2-CHLORO-5-(TRIFLUOROMETHYL)BENZYL]OXY}PHENYL)-7-(TRIFLUOROMETHYL)-2H-INDAZOLE

This compound was prepared similarly to that of Example 525.
LCMS: M+H: 613.1.

Example 845

2-(4-CHLORO-2-FLUOROBENZYL)-3-(3-{[5-CHLORO-2-(TRIFLUOROMETHYL)BENZYL]OXY}PHENYL)-7-(TRIFLUOROMETHYL)-2H-INDAZOLE

This compound was prepared similarly to that of Example 525.
LCMS: M+H: 612.8.

Example 846

[4-({3-[2-(4-CHLORO-2-FLUOROBENZYL)-7-(TRIFLUOROMETHYL)-2H-INDAZOL-3-YL]PHENOXY}METHYL)PHENYL]ACETIC ACID

This compound was prepared similarly to that of Example 525.
LCMS: M+H: 569.6.

Example 847

METHYL [4-({3-[2-(4-CHLORO-2-FLUOROBENZYL)-7-(TRIFLUOROMETHYL)-2H-INDAZOL-3-YL]PHENOXY}METHYL)PHENYL]ACETATE

This compound was prepared similarly to that of Example 525.
LCMS: M+H: 583.4.

Example 848

2-(4-CHLORO-2-FLUOROBENZYL)-3-{3-[(6-CHLORO-2-FLUORO-3-METHYLBENZYL)OXY]PHENYL}-7-(TRIFLUOROMETHYL)-2H-INDAZOLE

This compound was prepared similarly to that of Example 525.
LCMS: M+H: 577.7.

Example 849

3-{3-[(2-CHLORO-3,6-DIFLUOROBENZYL)OXY]PHENYL}-2-(4-CHLORO-2-FLUOROBENZYL)-7-(TRIFLUOROMETHYL)-2H-INDAZOLE

This compound was prepared similarly to that of Example 525.
LCMS: M+H: 581.3.

Example 850

3-{3-[(3-CHLORO-2,6-DIFLUOROBENZYL)OXY]PHENYL}-2-(4-CHLORO-2-FLUOROBENZYL)-7-(TRIFLUOROMETHYL)-2H-INDAZOLE

This compound was prepared similarly to that of Example 525.
LCMS: M+H: 581.3.

Example 851

2-(4-CHLORO-2-FLUOROBENZYL)-3-{3-[(5-CHLORO-2-FLUOROBENZYL)OXY]PHENYL}-7-(TRIFLUOROMETHYL)-2H-INDAZOLE

This compound was prepared similarly to that of Example 525.
LCMS: M+H: 563.6.

Example 852

2-(4-CHLORO-2-FLUOROBENZYL)-3-{3-[(2,5-DIMETHOXYBENZYL)OXY]PHENYL}-7-(TRIFLUOROMETHYL)-2H-INDAZOLE

This compound was prepared similarly to that of Example 525.
LCMS: M+H: 571.4.

Example 853

2-(4-CHLORO-2-FLUOROBENZYL)-3-{3-[(5-FLUORO-2-METHYLBENZYL)OXY]PHENYL}-7-(TRIFLUOROMETHYL)-2H-INDAZOLE

This compound was prepared similarly to that of Example 525.
LCMS: M+H: 543.5.

Example 854

2-(4-CHLORO-2-FLUOROBENZYL)-3-{3-[(2,6-DIFLUORO-3-METHYLBENZYL)OXY]PHENYL}-7-(TRIFLUOROMETHYL)-2H-INDAZOLE

This compound was prepared similarly to that of Example 525.
LCMS: M+H: 561.2.

Example 855

2-(4-CHLORO-2-FLUOROBENZYL)-3-{3-[(2,6-DIFLUOROBENZYL)OXY]PHENYL}-7-(TRIFLUOROMETHYL)-2H-INDAZOLE

This compound was prepared similarly to that of Example 525.
LCMS: M+H: 547.7.

Example 856

2-(4-CHLORO-2-FLUOROBENZYL)-3-{3-[(2-CHLORO-6-FLUOROBENZYL)OXY]PHENYL}-7-(TRIFLUOROMETHYL)-2H-INDAZOLE

This compound was prepared similarly to that of Example 525.
LCMS: M+H: 563.3.

Example 857

2-(4-CHLORO-2-FLUOROBENZYL)-3-(3-{[2-METHOXY-5-(TRIFLUOROMETHOXY)BENZYL]OXY}PHENYL)-7-(TRIFLUOROMETHYL)-2H-INDAZOLE

This compound was prepared similarly to that of Example 525.
LCMS: M+H: 625.4.

Example 858

2-(4-CHLORO-2-FLUOROBENZYL)-3-{3-[(2,3-DIMETHOXYBENZYL)OXY]PHENYL}-7-(TRIFLUOROMETHYL)-2H-INDAZOLE

This compound was prepared similarly to that of Example 525.
LCMS: M+H: 571.4.

Example 859

3-[3-(BENZYLOXY)PHENYL]-2-(4-CHLORO-2-FLUOROBENZYL)-7-(TRIFLUOROMETHYL)-2H-INDAZOLE

This compound was prepared similarly to that of Example 525.
LCMS: M+H: 511.7.

Example 860

2-(4-CHLORO-2-FLUOROBENZYL)-3-{3-[(4-METHYLBENZYL)OXY]PHENYL}-7-(TRIFLUOROMETHYL)-2H-INDAZOLE

This compound was prepared similarly to that of Example 525.
LCMS: M+H: 525.8.

Example 861

2-(4-CHLORO-2-FLUOROBENZYL)-3-{3-[(2-CHLORO-5-FLUOROBENZYL)OXY]PHENYL}-7-(TRIFLUOROMETHYL)-2H-INDAZOLE

This compound was prepared similarly to that of Example 525.
LCMS: M+H: 563.6.

Example 862

2-(2,4-DIMETHYLBENZYL)-3-(3-{[5-FLUORO-2-(TRIFLUOROMETHYL) BENZYL]OXY}PHENYL)-7-(TRIFLUOROMETHYL)-2H-INDAZOLE

This compound was prepared similarly to that of Example 525.
LCMS: M+H: 573.8.

Example 863

[4-({3-[2-METHYL-7-(TRIFLUOROMETHYL)-2H-INDAZOL-3-YL]PHENOXY}METHYL)PHENYL]ACETIC ACID

This compound was prepared similarly to that of Example 531.
LCMS: M+H: 441.5, M−H: 439.7.

Example 864

2-(4-CHLORO-2-FLUOROBENZYL)-3-{3-[(2-CHLORO-6-FLUORO-3-METHYLBENZYL)OXY]PHENYL}-7-(TRIFLUOROMETHYL)-2H-INDAZOLE

This compound was prepared similarly to that of Example 525.
LCMS: M+H: 577.7.

Example 865

[4-({3-[7-(TRIFLUOROMETHYL)-1H-INDAZOL-3-YL]PHENOXY}METHYL)PHENYL]ACETIC ACID

This compound was prepared similarly to that of Example 531.
LCMS: M+H: 427.4, M−H: 425.9.

Example 866

2-{3-[2-(4-CHLORO-2-FLUOROBENZYL)-7-(TRIFLUOROMETHYL)-2H-INDAZOL-3-YL]PHENOXY}-2-PHENYLPROPANOIC ACID

This compound was prepared similarly to that of Example 531.
LCMS: M+H: 569.6, M−H: 567.5.

Example 867

{3-[2-(4-CHLORO-2-FLUOROBENZYL)-7-(TRIFLUOROMETHYL)-2H-INDAZOL-3-YL]PHENOXY}(3-METHYLPHENYL)ACETIC ACID

This compound was prepared similarly to that of Example 531.
LCMS: M+H: 569.6, M−H: 567.5.

Example 868

[4-({3-[2-(4-CHLORO-2-FLUOROBENZYL)-7-(TRIFLUOROMETHYL)-2H-INDAZOL-3-YL]PHENOXY}METHYL)-2,5-DIMETHYLPHENYL]ACETIC ACID

This compound was prepared similarly to that of Example 531.
LCMS: M+H: 597.5.

Example 869

[4-({3-[2-(2,4,6-TRIFLUOROBENZYL)-7-(TRIFLUOROMETHYL)-2H-INDAZOL-3-YL]PHENOXY}METHYL)PHENYL]ACETIC ACID

This compound was prepared similarly to that of Example 531.
LCMS: M+H: 571.4, M−H: 569.3.

Example 870

1-[4-({3-[2-(4-CHLORO-2-FLUOROBENZYL)-7-(TRIFLUOROMETHYL)-2H-INDAZOL-3-YL]PHENOXY}METHYL)PHENYL]CYCLOPROPANECARBOXYLIC ACID

This compound was prepared similarly to that of Example 527.
LCMS: M+H: 595.4, M−H: 593.6.

Example 871

3-(3-{[5-FLUORO-2-(TRIFLUOROMETHYL)BENZYL]OXY}PHENYL)-2-(2,4,6-TRIFLUOROBENZYL)-7-(TRIFLUOROMETHYL)-2H-INDAZOLE

This compound was prepared similarly to that of Example 525.
LCMS: M+H: 599.3.

Example 872

[3-({3-[2-(4-CHLORO-2-FLUOROBENZYL)-7-(TRIFLUOROMETHYL)-2H-INDAZOL-3-YL]PHENOXY}METHYL)-2,4-DIMETHYLPHENYL]ACETIC ACID

This compound was prepared similarly to that of Example 531.
LCMS: M+H: 597.5.

Example 873

[4-({3-[2-(2,4-DIMETHYLBENZYL)-7-(TRIFLUOROMETHYL)-2H-INDAZOL-3-YL]PHENOXY}METHYL)PHENYL]ACETIC ACID

This compound was prepared similarly to that of Example 531.
LCMS: M+H: 545.6, M–H: 543.5.

Example 874

2-[3-({4-[2-(2,4-DIMETHYLBENZYL)-7-(TRIFLUOROMETHYL)-2H-INDAZOL-3-YL]PHENYL}AMINO)PHENYL]-2-METHYLPROPANOIC ACID

This compound was prepared similarly to that of Example 4.
LCMS: M+H: 558.5.

Example 875

3-(3-{[5-CHLORO-2-(TRIFLUOROMETHYL)BENZYL]OXY}PHENYL)-2-(2,4,6-TRIFLUOROBENZYL)-7-(TRIFLUOROMETHYL)-2H-INDAZOLE

This compound was prepared similarly to that of Example 525.
LCMS: M+H: 615.5.

Example 876

3-(3-{[2-CHLORO-5-(TRIFLUOROMETHYL)BENZYL]OXY}PHENYL)-2-(2,4,6-TRIFLUOROBENZYL)-7-(TRIFLUOROMETHYL)-2H-INDAZOLE

This compound was prepared similarly to that of Example 525.
LCMS: M+H: 615.5.

Example 877

2-(4-CHLORO-2-FLUOROBENZYL)-3-{3-[2-(2,5-DIMETHYLPHENYL)ETHYL]PHENYL}-7-(TRIFLUOROMETHYL)-2H-INDAZOLE

This compound was prepared similarly to that of Example 532.
LCMS: M+H: 537.5.

Example 878

2-(4-CHLORO-2-FLUOROBENZYL)-3-{3-[2-(2,5-DICHLOROPHENYL)ETHYL]PHENYL}-7-(TRIFLUOROMETHYL)-2H-INDAZOLE

This compound was prepared similarly to that of Example 532.
LCMS: M+H: 577.7.

Example 879

2-(4-CHLORO-2-FLUOROBENZYL)-3-{3-[2-(2,5-DIFLUOROPHENYL)ETHYL]PHENYL}-7-(TRIFLUOROMETHYL)-2H-INDAZOLE

This compound was prepared similarly to that of Example 532.
LCMS: M+H: 545.3.

Example 880

2-(4-CHLORO-2-FLUOROBENZYL)-3-{3-[2-(5-CHLORO-2-FLUOROPHENYL)ETHYL]PHENYL}-7-(TRIFLUOROMETHYL)-2H-INDAZOLE

This compound was prepared similarly to that of Example 532.
LCMS: M+H: 561.2.

Example 881

2-(4-CHLORO-2-FLUOROBENZYL)-3-{3-[2-(2-CHLORO-5-FLUOROPHENYL)ETHYL]PHENYL}-7-(TRIFLUOROMETHYL)-2H-INDAZOLE

This compound was prepared similarly to that of Example 532.
LCMS: M+H: 561.2.

Example 882

2-(4-CHLORO-2-FLUOROBENZYL)-3-(3-{2-[2-FLUORO-5-(TRIFLUOROMETHYL)PHENYL]ETHYL}PHENYL)-7-(TRIFLUOROMETHYL)-2H-INDAZOLE

This compound was prepared similarly to that of Example 532.
LCMS: M+H: 595.4.

Example 883

2-(4-CHLORO-2-FLUOROBENZYL)-3-(3-{2-[3-(TRIFLUOROMETHOXY)PHENYL]ETHYL}PHENYL)-7-(TRIFLUOROMETHYL)-2H-INDAZOLE

This compound was prepared similarly to that of Example 532.
LCMS: M+H: 593.6.

Example 884

2-(4-CHLORO-2-FLUOROBENZYL)-3-{3-[2-(3-METHOXYPHENYL)ETHYL]PHENYL}-7-(TRIFLUOROMETHYL)-2H-INDAZOLE

This compound was prepared similarly to that of Example 532.
LCMS: M+H: 539.6.

Example 885

2-(4-CHLORO-2-FLUOROBENZYL)-3-(3-{2-[3-(DIFLUOROMETHOXY)PHENYL]ETHYL}PHENYL)-7-(TRIFLUOROMETHYL)-2H-INDAZOLE

This compound was prepared similarly to that of Example 532.
LCMS: M+H: 575.6.

Example 886

2-(4-CHLORO-2-FLUOROBENZYL)-3-(3-{2-[2-METHYL-5-(TRIFLUOROMETHYL) PHENYL]ETHYL}PHENYL)-7-(TRIFLUOROMETHYL)-2H-INDAZOLE

This compound was prepared similarly to that of Example 532.
LCMS: M+H: 591.5.

Example 887

3-(3-{2-[2,5-BIS(TRIFLUOROMETHYL)PHENYL]ETHYL}PHENYL)-2-(4-CHLORO-2-FLUOROBENZYL)-7-(TRIFLUOROMETHYL)-2H-INDAZOLE

This compound was prepared similarly to that of Example 532.
LCMS: M+H: 645.5.

Example 888

2-(4-CHLORO-2-FLUOROBENZYL)-3-{3-[2-(2,3-DIMETHOXYPHENYL)ETHYL]PHENYL}-7-(TRIFLUOROMETHYL)-2H-INDAZOLE

This compound was prepared similarly to that of Example 532.
LCMS: M+H: 569.6.

Example 889

2-(4-CHLORO-2-FLUOROBENZYL)-3-(3-{2-[2-CHLORO-5-(TRIFLUOROMETHYL)PHENYL]ETHYL}PHENYL)-7-(TRIFLUOROMETHYL)-2H-INDAZOLE

This compound was prepared similarly to that of Example 532.
LCMS: M+H: 611.3.

Example 890

2-(4-CHLORO-2-FLUOROBENZYL)-3-(3-{2-[5-CHLORO-2-(TRIFLUOROMETHYL)PHENYL]ETHYL}PHENYL)-7-(TRIFLUOROMETHYL)-2H-INDAZOLE

This compound was prepared similarly to that of Example 532.
LCMS: M+H: 611.3.

Example 891

2-(4-CHLORO-2-FLUOROBENZYL)-3-(3-{2-[5-FLUORO-2-(TRIFLUOROMETHYL)PHENYL]ETHYL}PHENYL)-7-(TRIFLUOROMETHYL)-2H-INDAZOLE

This compound was prepared similarly to that of Example 532.
LCMS: M+H: 595.4.

Example 892

(3-{3-[2-BENZYL-7-(TRIFLUOROMETHYL)-2H-INDAZOL-3-YL]PHENOXY}PHENYL)ACETIC ACID

Fifty milligrams (50 mg 0.094 mmol) of 2-benzyl-3-[4-(3-[1,3]dioxolan-2-yl-methyl-phenoxy)-phenyl]-7-trifluoromethyl-2H-indazole (this compound was prepared similarly to that of Example 3) in 600 µL acetone, was treated with 5 eq. of Jones reagent (3.6M $CrO_3$ in aq. $H_2SO_4$) at 0° C., while stirring for 2 hours at room temperature. The reaction mixture was quenched with ice/$NaHSO_3$ and extracted three times with $CH_2Cl_2$. The combined organic phases were dried, evaporated and the crude material was dissolved in 0.5 mL methanol. Twenty milligrams (20 mg) of LiOH were added and the reaction mixture was stirred at 70° C. for 2 hours. The reaction mixture was concentrated, diluted with NaCl (aq. sat.), acidified with 2 M HCl(aq) and extracted three times with $CH_2Cl_2$. The crude material was purified by HPLC using a gradient with acidic mobile phase on an ACE-C8 column to afford analytically pure product.
LCMS: M+H: 503.3, M−H: 501.5.

Example 893

2-{3-[2-BENZYL-7-(TRIFLUOROMETHYL)-2H-INDAZOL-3-YL]PHENOXY}BENZALDEHYDE

The preparation of this compound is was similar to that described for Example 3. 2-Benzyl-3-(3-bromo-phenyl)-7-trifluoromethyl-2H-indazole (60 mg, 0.139 mmol), cesium carbonate (272 mg, 0.835 mmol), CuI (80 mg, 0.417 mmol) and 2-hydroxy-benzaldehyde (51 mg, 0.417 mmol) were dissolved in 6 ml of dry pyridine. The reaction and work-up were carried out as described for Example 3.
LCMS: M+H: 473.3, M+COO⁻: 517.4.

Example 894

2-(3-{3-[2-BENZYL-7-(TRIFLUOROMETHYL)-2H-INDAZOL-3-YL]PHENOXY}PHENYL)-2-METHYLPROPANOIC ACID

Preparation of 2-(3-{3-[2-benzyl-7-(trifluoromethyl)-2H-indazol-3-yl]phenoxy}phenyl)-2-methyl-propanoic acid methyl ester 3-(2-Benzyl-7-trifluoromethyl-2H-indazol-3-yl)-phenol (96 mg, 0.26 mmol), 2-methyl-2-[3-(4,4,5,5-tetramethyl-[1,3,2]dioxaborolan-2-yl)-phenyl]-propionic acid methyl ester (80 mg, 0.26 mmol), $Cu(OAc)_2$ (47 mg, 0.26 mmol) and pyridine (42 µL, 0.52 mmol) were dissolved in 3 ml anhydrous $CH_2Cl_2$ and stirred at room temperature with crushed molsieves (4 Å) overnight. The reaction mixture was diluted with 1 M HCl (aq.) and the product was extracted three times with CH$_2$Cl$_2$. The combined organic phases were dried, evaporated and the crude material was purified by preparative HPLC using a gradient with an acidic mobile phase on an ACE-C8 column to afford 8.4 mg of analytically pure product.

LCMS: M+H: 546.5.

Preparation of 2-(3-{3-[2-benzyl-7-(trifluoromethyl)-2H-indazol-3-yl]phenoxy}phenyl)-2-methyl-propanoic acid This compound was obtained from 2-(3-{3-[2-benzyl-7-(trifluoromethyl)-2H-indazol-3-yl]phenoxy}phenyl)-2-methylpropanoic acid methyl ester in a similar manner as described for the preparation of Example 2.

LCMS: M+H: 531.5, M−H: 529.1.

Example 895

3-{4-[2-BENZYL-7-(TRIFLUOROMETHYL)-2H-INDAZOL-3-YL]PHENOXY}BENZALDEHYDE

Preparation of 2-Benzyl-3-[4-(3-[1,3]dioxolan-2-ylmethyl-phenoxy)-phenyl]-7-trifluoromethyl-2H-indazole This compound was prepared similarly to that of Example 3.

LCMS: M+H: 531.5.

Preparation of 3-{4-[2-benzyl-7-(trifluoromethyl)-2H-indazol-3-yl]phenoxy}benzaldehyde 2-benzyl-3-[4-(3-[1,3]dioxolan-2-ylmethyl-phenoxy)-phenyl]-7-trifluoromethyl-2H-indazole (14 mg, 0.0264 mmol) was treated with 6.6 mg PPTS in 1.5 ml acetone under reflux for 2 hrs. The reaction mixture was extracted with NaHCO$_3$ and CH$_2$Cl$_2$. The combined organic phases were dried, evaporated and the crude material was purified on a chromatotron using a gradient changing from 1:99 (EtOAc/heptane) to 3:7 (EtOAc/heptane) to afford 5 mg of analytically pure product.

LCMS: M+H: 487.0, M−H⁻: 485.6.

Example 896

(3-{4-[2-BENZYL-7-(TRIFLUOROMETHYL)-2H-INDAZOL-3-YL]PHENOXY}PHENYL)METHANOL

This compound was prepared from methyl 3-{4-[2-benzyl-7-(trifluoromethyl)-2H-indazol-3-yl]phenoxy}benzoate (Example 912; 30 mg, 0.060 mmol), which was dissolved in 1.5 ml diethylether and treated with LiAlH$_4$. The reaction mixture was stirred at room temperature overnight. The reaction mixture was quenched with water and stirred for 15 minutes. The slurry was filtered and the product extracted with Et$_2$O/NH$_4$Cl (aq, sat). After evaporation of the solvents, the crude material was purified by HPLC using a gradient with an acidic mobile phase on an ACE-C8 column to afford 19.6 mg of analytically pure product.

LCMS: M+H: 475.4, M+COO⁻: 519.5.

Example 897

3-{4-[2-BENZYL-7-(TRIFLUOROMETHYL)-2H-INDAZOL-3-YL]PHENOXY}-N-METHOXY-N-METHYLBENZAMIDE

Preparation of 3-{4-[2-benzyl-7-(trifluoromethyl)-2H-indazol-3-yl]phenoxy}benzoic acid This compound was prepared similarly to that of Example 3.

Preparation of 3-{4-[2-benzyl-7-(trifluoromethyl)-2H-indazol-3-yl]phenoxy}-N-methoxy-N-methyl-benzamide A reaction mixture of 3-{4-[2-benzyl-7-(trifluoromethyl)-2H-indazol-3-yl]phenoxy}benzoic acid (115.8 mg, 0.237 mmol), (3-dimethylamino-propyl)-ethyl-carbodiimide hydrochloride (86 mg, 0.356 mmol), O,N-dimethyl-hydroxylamine hydrochloride (69 mg, 0.711 mmol) and 0.3 mL of triethylamine dissolved in 2 mL CH$_2$Cl$_2$ was stirred at room temperature overnight. The reaction mixture was quenched with 1M HCl(aq) and the crude material was extracted with CH$_2$Cl$_2$. The crude material was purified with flash chromatography using EtOAc/heptane, 3:7, as eluent to afford 17 mg of analytically pure product.

LCMS: M+H: 532.2.

Example 898

3-{4-[2-BENZYL-7-(TRIFLUOROMETHYL)-2H-INDAZOL-3-YL]PHENOXY}-N,N-DIMETHYL-BENZAMIDE

This compound was prepared from Example 912. Methyl 3-{4-[2-benzyl-7-(trifluoromethyl)-2H-indazol-3-yl]phenoxy}benzoate (49 mg, 0.0971 mmol) was dissolved in a 2M solution of dimethylamine in methanol (1.5 mL), 0.5 mg of sodium cyanide was added and the reaction mixture was stirred at 60° C. overnight. The solvent was evaporated, the residue dissolved in CH$_2$Cl$_2$ and washed with brine. The combined organic phases were dried, evaporated and the crude material was purified by HPLC using a gradient with an acidic mobile phase on an ACE-C8 column to afford 9 mg of analytically pure product.

LCMS: M+H: 516.0.

Example 899

3-{4-[2-BENZYL-7-(TRIFLUOROMETHYL)-2H-INDAZOL-3-YL]PHENOXY}BENZAMIDE

3-{4-[2-benzyl-7-(trifluoromethyl)-2H-indazol-3-yl]phenoxy}benzoic acid (39 mg, 0.08 mmol) in 0.8 mL dioxane was added to NbCl$_5$ (64 mg, 0.238 mmol), followed by 0.95 mL NH$_3$ (0.5M in dioxane). The temperature was slowly raised to 50° C. and stirred for 2 days. The solvents were evaporated and the residue dissolved in CH$_2$Cl$_2$, followed by filtration of the precipitate. The residue was dissolved in CH$_2$Cl$_2$ and washed with brine. The combined organic phases were dried, evaporated and the crude material was purified by HPLC using a gradient with an acidic mobile phase on an ACE-C8 column to afford analytically pure product.

LCMS: M+H: 488.3, M−H: 486.5.

Example 900

5-{4-[2-(4-CHLORO-2-FLUOROBENZYL)-7-(TRIFLUOROMETHYL)-2H-INDAZOL-3-YL]PHENOXY}-1,2,3,4-TETRAHYDRONAPHTHA-LEN-1-OL

5-{4-[2-(4-chloro-2-fluorobenzyl)-7-(trifluoromethyl)-2H-indazol-3-yl]phenoxy}-3,4-dihydronaphthalen-1(2H)-one (14 mg, 0.025 mmol) dissolved in 1.5 mL THF was added to a slurry of LiAlH$_4$ in THF and stirred at room temperature for 2 hours. The reaction mixture was quenched with H$_2$O and stirred for 15 min. Filtration of the mixture was followed by extraction with CH$_2$Cl$_2$. The combined organic phases were dried, evaporated and the crude material was purified by HPLC using a gradient with an acidic mobile phase on an ACE-C8 column to afford 1.2 mg analytically pure product.

LCMS: M+H: 567.5, M+COO$^-$: 611.3.

Example 901

3-{4-[2-(4-CHLORO-2-FLUOROBENZYL)-7-(TRIFLUOROMETHYL)-2H-INDAZOL-3-YL]PHENOXY}-N,N-DIMETHYLBENZAMIDE

4-[2-(4-Chloro-2-fluoro-benzyl)-7-trifluoromethyl-2H-indazol-3-yl]-phenol (50 mg, 0.12 mmol), 3-(N,N-dimethyl-benzamide)-phenylboronic acid (0.24 mmol), Cu(OAc)$_2$ (22 mg, 0.12 mmol) and pyridine (2eq) were dissolved in 2 ml of anhydrous CH$_2$Cl$_2$. Molsieves (4 Å) were added and the reaction mixture was stirred for 3 days. The reaction mixture was extracted with NH$_4$CL(aq) and CH$_2$Cl$_2$. The combined organic phases were dried, evaporated and the crude material was purified by HPLC using a gradient with a neutral mobile phase on an ACE-C8 column to afford 17 mg analytically pure product.

LCMS: M+H: 568.8, M+COO$^-$: 571.2.

Example 902

2-(3-{4-[2-BENZYL-7-(TRIFLUOROMETHYL)-2H-INDAZOL-3-YL]PHENOXY}PHENYL)PROPAN-2-OL

Methyl 3-{4-[2-benzyl-7-(trifluoromethyl)-2H-indazol-3-yl]phenoxy}benzoate (10 mg, 0.02 mmol) was treated with MeMgBr (3M in Et$_2$O, 0.13 mL) in 2 ml of THF. The reaction mixture was stirred for 2 hours at room temperature before extraction with CH$_2$Cl$_2$/NH$_4$Cl. Purification by flash chromatography using CH$_2$Cl$_2$/heptane, 1:1, as eluent afforded 2 mg of analytical pure product.

LCMS: M+H: 503.3; M+COO$^-$: 547.4.

Example 903

5-{4-[2-(4-CHLORO-2-FLUOROBENZYL)-7-(TRIFLUOROMETHYL)-2H-INDAZOL-3-YL]PHENOXY}-1,2,3,4-TETRAHYDRONAPHTHA-LEN-1-OL

5-{4-[2-(4-chloro-2-fluorobenzyl)-7-(trifluoromethyl)-2H-indazol-3-yl]phenoxy}-3,4-dihydronaphthalen-1(2H)-one (330 mg, 0.58 mmol) dissolved in 10 mL of EtOH was added to a slurry of NaBH$_4$ in EtOH and stirred at room temperature overnight. The reaction mixture was quenched with H$_2$O and stirred for 15 min. Filtration of the mixture was followed by extraction with CH$_2$Cl$_2$. The combined organic phases were dried, evaporated and the crude material was purified by HPLC using a gradient with an acidic mobile phase on an ACE-C8 column to afford a racemic mixture. Separation of the two enatiomers afforded the analytically pure products of this Example 903 and Example 936.

LCMS: M+H: 567.5, M+Ac$^-$: 625.4.

Example 904

2-BENZYL-3-(3-PHENOXYPHENYL)-7-(TRIFLUOROMETHYL)-2H-INDAZOLE

This compound was prepared similarly to that of Example 3.

LCMS: M+H: 445.4, M+Ac$^-$: 503.3.

Example 905

2-BENZYL-3-[3-(4-METHOXYPHENOXY)PHENYL]-7-(TRIFLUOROMETHYL)-2H-INDAZOLE

This compound was prepared similarly to that of Example 3.

LCMS: M+H: 475.4, M+Ac$^-$: 533.3.

Example 906

2-BENZYL-3-{3-[3-(1,3-DIOXOLAN-2-YLMETHYL)PHENOXY]PHENYL}-7-(TRIFLUOROMETHYL)-2H-INDAZOLE

This compound was prepared similarly to that of Example 3.

LCMS: M+H: 531.1.

Example 907

METHYL 2-(4-{3-[2-BENZYL-7-(TRIFLUOROMETHYL)-2H-INDAZOL-3-YL]PHENOXY}PHENYL)-2-METHYLPROPANOATE

This compound was prepared similarly to that of Example 3.

LCMS: M+H: 545.3, M+COO$^-$: 589.7.

Example 908

3-{3-[2-BENZYL-7-(TRIFLUOROMETHYL)-2H-INDAZOL-3-YL]PHENOXY}-N,N-DIMETHYL-BENZAMIDE

This compound was prepared similarly to that of Example 894.

LCMS: M+H: 545.6, M+COO$^-$: 589.4.

Example 909

(3-{4-[2-BENZYL-7-(TRIFLUOROMETHYL)-2H-INDAZOL-3-YL]PHENOXY}PHENYL)ACETIC ACID

This compound was prepared similarly to that of Example 892.

LCMS: M+H: 503.3, M+−H, 501.2.

Example 910

2-BENZYL-3-{4-[3-(1,3-DIOXOLAN-2-YLM-ETHYL)PHENOXY]PHENYL}-7-(TRIFLUO-ROMETHYL)-2H-INDAZOLE

This compound was prepared similarly to that of Example 3.
LCMS: M+H: 531.2, M+COO−: 575.6.

Example 911

2-BENZYL-3-[4-(3,5-DIMETHYLPHENOXY)PHENYL]-7-(TRIFLUOROMETHYL)-2H-INDAZOLE

This compound was prepared similarly to that of Example 3.
LCMS: M+H: 473.3.

Example 912

METHYL 3-{4-[2-BENZYL-7-(TRIFLUOROM-ETHYL)-2H-INDAZOL-3-YL]PHENOXY}BENZOATE

This compound was prepared similarly to that of Example 3.
LCMS: M+H: 503.3, M+COO−: 547.7.

Example 913

3-{4-[2-BENZYL-7-(TRIFLUOROMETHYL)-2H-INDAZOL-3-YL]PHENOXY}-N-METHYLBEN-ZAMIDE

This compound was prepared from similarly to that of Example 898.
LCMS: M+H: 502.0, M+Ac−: 560.0.

Example 914

2-(2,4-DIMETHYLBENZYL)-3-[4-(2-METHOX-YPHENOXY)PHENYL]-7-(TRIFLUOROM-ETHYL)-2H-INDAZOLE

This compound was prepared similarly to that of Example 893.
LCMS: M+H: 503.3.

Example 915

3-[4-(2-METHOXYPHENOXY)PHENYL]-2-(2,4,6-TRIFLUOROBENZYL)-7-(TRIFLUOROM-ETHYL)-2H-INDAZOLE

This compound was prepared similarly to that of Example 893.
LCMS: M+H: 529.1, M+COO−: 573.2.

Example 916

2-(4-CHLORO-2-FLUOROBENZYL)-3-[4-(2-METHOXYPHENOXY)PHENYL]-7-(TRIFLUO-ROMETHYL)-2H-INDAZOLE

This compound was prepared similarly to that of Example 893.
LCMS: M+H: 527.3, M+COO−: 571.1.

Example 917

3-{4-[2-(2,4-DIMETHYLBENZYL)-7-(TRIFLUO-ROMETHYL)-2H-INDAZOL-3-YL]PHENOXY}-N,N-DIMETHYLANILINE

This compound was prepared similarly to that of Example 3.
LCMS: M+H: 516.8, M+COO−: 559.7.

Example 918

N,N-DIMETHYL-3-{4-[2-(2,4,6-TRIFLUO-ROBENZYL)-7-(TRIFLUOROMETHYL)-2H-IN-DAZOL-3-YL]PHENOXY}ANILINE

This compound was prepared similarly to that of Example 3.
LCMS: M+H: 542.6.

Example 919

3-{4-[2-(4-CHLORO-2-FLUOROBENZYL)-7-(TRIFLUOROMETHYL)-2H-INDAZOL-3-YL]PHENOXY}-N,N-DIMETHYLANILINE

This compound was prepared similarly to that of Example 3.
LCMS: M+H: 540.5, M+COO−: 584.6.

Example 920

3-{4-[2-(2,4-DIMETHYLBENZYL)-7-(TRIFLUO-ROMETHYL)-2H-INDAZOL-3-YL]PHENOXY}-N-METHOXY-N-METHYLBENZAMIDE

This compound was prepared similarly to that of Example 3.
LCMS: M+H: 560.3.

Example 921

N-METHOXY-N-METHYL-3-{4-[2-(2,4,6-TRIF-LUOROBENZYL)-7-(TRIFLUOROMETHYL)-2H-INDAZOL-3-YL]PHENOXY}BENZAMIDE

This compound was prepared similarly to that of Example 3.
LCMS: M+H: 586.1.

Example 922

3-{4-[2-(4-CHLORO-2-FLUOROBENZYL)-7-(TRIFLUOROMETHYL)-2H-INDAZOL-3-YL]PHENOXY}-N-METHOXY-N-METHYLBENZAMIDE

This compound was prepared similarly to that of Example 3.
LCMS: M+H: 584.3.

Example 923

5-{4-[2-(4-CHLORO-2-FLUOROBENZYL)-7-(TRIFLUOROMETHYL)-2H-INDAZOL-3-YL]PHENOXY}-3,4-DIHYDRONAPHTHALEN-1(2H)-ONE

This compound was prepared similarly to that of Example 893.
LCMS: M+H 565.2.

Example 924

2-BENZYL-3-{4-[2-(TRIFLUOROMETHOXY)PHENOXY]PHENYL}-7-(TRIFLUOROMETHYL)-2H-INDAZOLE

This compound was prepared similarly to that of Example 893.
LCMS: M+H: 529.3.

Example 925

2-BENZYL-3-[4-(1-NAPHTHYLOXY)PHENYL]-7-(TRIFLUOROMETHYL)-2H-INDAZOLE

This compound was prepared similarly to that of Example 893.
LCMS: M+H: 495.4.

Example 926

3-{4-[2-(4-CHLORO-2-FLUOROBENZYL)-7-(TRIFLUOROMETHYL)-2H-INDAZOL-3-YL]PHENOXY}BENZALDEHYDE

This compound was prepared similarly to that of Example 893.
LCMS: M+H 525.8.

Example 927

2-(4-CHLORO-2-FLUOROBENZYL)-3-[4-(5,6,7,8-TETRAHYDRONAPHTHALEN-1-YLOXY)PHENYL]-7-(TRIFLUOROMETHYL)-2H-INDAZOLE

This compound was prepared similarly to that of Example 893.
LCMS: M+H 551.6.

Example 928

3-{4-[2-(4-CHLORO-2-FLUOROBENZYL)-7-(TRIFLUOROMETHYL)-2H-INDAZOL-3-YL]PHENOXY}-N,N-DIETHYLBENZAMIDE

This compound was prepared similarly to that of Example 901.
LCMS: M+H: 596.3.

Example 929

2-(4-CHLORO-2-FLUOROBENZYL)-3-{4-[3-(PYRROLIDIN-1-YLCARBONYL)PHENOXY]PHENYL}-7-(TRIFLUOROMETHYL)-2H-INDAZOLE

This compound was prepared similarly to that of Example 901.
LCMS: M+H: 594.3.

Example 930

2-(4-CHLORO-2-FLUOROBENZYL)-3-{4-[3-(PIPERIDIN-1-YLCARBONYL)PHENOXY]PHENYL}-7-(TRIFLUOROMETHYL)-2H-INDAZOLE

This compound was prepared similarly to that of Example 901.
LCMS: M+H: 608.3.

Example 931

2-(4-CHLORO-2-FLUOROBENZYL)-3-{4-[3-(MORPHOLIN-4-YLCARBONYL)PHENOXY]PHENYL}-7-(TRIFLUOROMETHYL)-2H-INDAZOLE

This compound was prepared similarly to that of Example 901.
LCMS: M+H: 610.26.

Example 932

1-(3-{4-[2-(4-CHLORO-2-FLUOROBENZYL)-7-(TRIFLUOROMETHYL)-2H-INDAZOL-3-YL]PHENOXY}PHENYL)ETHANONE

This compound was prepared similarly to that of Example 893.
LCMS: M+H: 539.6, M+COO$^-$: 583.1.

Example 933

N,N-DIMETHYL-3-{4-[2-(2,4,6-TRIFLUOROBENZYL)-7-(TRIFLUOROMETHYL)-2H-INDAZOL-3-YL]PHENOXY}BENZAMIDE

This compound was prepared similarly to that of Example 901.
LCMS: M+H: 570.5, M+COO$^-$: 614.6.

Example 934

3-{4-[2-(2,4-DIMETHYLBENZYL)-7-(TRIFLUOROMETHYL)-2H-INDAZOL-3-YL]PHENOXY}-N,N-DIMETHYLBENZAMIDE

This compound was prepared similarly to that of Example 901.
LCMS: M+H: 544.4, M+Ac⁻: 602.6.

Example 935

2-(3-{4-[2-(4-CHLORO-2-FLUOROBENZYL)-7-(TRIFLUOROMETHYL)-2H-INDAZOL-3-YL]PHENOXY}PHENYL)PROPAN-2-OL

This compound was prepared similarly to that of Example 902.
LCMS: M+H: 555.2, M+COO⁻: 559.6.

Example 936

5-{4-[2-(4-CHLORO-2-FLUOROBENZYL)-7-(TRIFLUOROMETHYL)-2H-INDAZOL-3-YL]PHENOXY}-1,2,3,4-TETRAHYDRONAPHTHALEN-1-OL

This compound was prepared similarly to that of Example 903, and is the other enantiomer of Example 903.
LCMS: M+H: 567.5, M+COO⁻: 625.4.

Example 937

3-{4-[3-(PIPERIDIN-1-YLCARBONYL)PHENOXY]PHENYL}-2-(2,4,6-TRIFLUOROBENZYL)-7-(TRIFLUOROMETHYL)-2H-INDAZOLE

This compound was prepared similarly to that of Example 901.
LCMS: M+H: 610.4, M+COO⁻: 654.5.

Example 938

2-(3-{4-[2-(2,4,6-TRIFLUOROBENZYL)-7-(TRIFLUOROMETHYL)-2H-INDAZOL-3-YL]PHENOXY}PHENYL)PROPAN-2-OL

This compound was prepared similarly to that of Example 901.
LCMS: M+H: 557.3, M+Ac⁻: 615.5.

Example 939

3-{4-[3-(MORPHOLIN-4-YLCARBONYL)PHENOXY]PHENYL}-2-(2,4,6-TRIFLUOROBENZYL)-7-(TRIFLUOROMETHYL)-2H-INDAZOLE

This compound was prepared similarly to that of Example 901.
LCMS: M+H: 612.5.

By procedures similar to those in the preceding examples, the following examples (Examples 940 to 967) were prepared.

Example 940

5-{3-[2-(2-CHLORO-4-FLUOROBENZYL)-7-(TRIFLUOROMETHYL)-2H-INDAZOL-3-YL]PHENOXY}-3,4-DIHYDRONAPHTHALEN-1(2H)-ONE

MS (ES) m/z 564.6;
HPLC purity 99.6% at 210-370 nm, 12.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 941

2-(2-CHLORO-4-FLUOROBENZYL)-3-(4-METHOXYPHENYL)-7-(TRIFLUOROMETHYL)-2H-INDAZOLE

MS (ES) m/z 434.7.

Example 942

2-(4-CHLORO-2-FLUOROBENZYL)-3-(4-METHOXYPHENYL)-7-(TRIFLUOROMETHYL)-2H-INDAZOLE

MS (ES) m/z 434.8.

Example 943

3-(4-METHOXYPHENYL)-2-(2,4,6-TRIFLUOROBENZYL)-7-(TRIFLUOROMETHYL)-2H-INDAZOLE

MS (ES) m/z 437.0.

Example 944

5-{3-[2-(2-CHLORO-4-FLUOROBENZYL)-7-(TRIFLUOROMETHYL)-2H-INDAZOL-3-YL]PHENOXY}QUINOLINE

MS (ES) m/z 547.6.
HPLC purity 100% at 210-370 nm, 11.8 min.; Xterra RP18, 3.5 u, 150×4.6 mm column, 1.2 mL/min, 85/15-5/95 (Ammon. Form. Buff. Ph=3.5/ACN+MeOH) for 10 min., hold 4 min.

Example 945

5-{3-[2-(2-CHLORO-4-FLUOROBENZYL)-7-(TRIFLUOROMETHYL)-2H-INDAZOL-3-YL]PHENOXY}ISOQUINOLINE

MS (ES) m/z 547.7.
HPLC purity 97.4% at 210-370 nm, 11.8 min.; Xterra RP18, 3.5 u, 150×4.6 mm column, 1.2 mL/min, 85/15-5/95 (Ammon. Form. Buff. Ph=3.5/ACN+MeOH) for 10 min., hold 4 min.

Example 946

4-{3-[2-(2-CHLORO-4-FLUOROBENZYL)-7-(TRIFLUOROMETHYL)-2H-INDAZOL-3-YL]PHENOXY}QUINAZOLINE

MS (ES) m/z 548.6.
HPLC purity 98.5% at 210-370 nm, 11.1 min.; Xterra RP18, 3.5 u, 150×4.6 mm column, 1.2 mL/min, 85/15-5/95 (Ammon. Form. Buff. Ph=3.5/ACN+MeOH) for 10 min., hold 4 min.

Example 947

6-{3-[2-(2,4,6-TRIFLUOROBENZYL)-7-(TRIF-LUOROMETHYL)-2H-INDAZOL-3-YL]PHE-NOXY}-3,4-DIHYDRONAPHTHALEN-1(2H)-ONE

MS (ES) m/z 566.8.
HPLC purity 98.4% at 210-370 nm, 11.7 min.; Xterra RP18, 3.5 u, 150×4.6 mm column, 1.2 mL/min, 85/15-5/95 (Ammon. Form. Buff. Ph=3.5/ACN+MeOH) for 10 min., hold 4 min.

Example 948

2-(2-CHLORO-4-FLUOROBENZYL)-3-[3-(5,6,7,8-TETRAHYDRONAPHTHALEN-2-YLOXY)PHE-NYL]-7-(TRIFLUOROMETHYL)-2H-INDAZOLE
MS (ES) m/z 550.7.

HPLC purity 95.1% at 210-370 nm, 12.9 min.; Xterra RP18, 3.5 u, 150×4.6 mm column, 1.2 mL/min, 85/15-5/95 (Ammon. Form. Buff. Ph=3.5/ACN+MeOH) for 10 min., hold 4 min.

Example 949

2-(2-CHLORO-4-FLUOROBENZYL)-3-[3-(5,6,7,8-TETRAHYDRONAPHTHALEN-1-YLOXY)PHE-NYL]-7-(TRIFLUOROMETHYL)-2H-INDAZOLE

MS (ES) m/z 550.7.
HPLC purity 100% at 210-370 nm, 12.8 min.; Xterra RP18, 3.5 u, 150×4.6 mm column, 1.2 mL/min, 85/15-5/95 (Ammon. Form. Buff. Ph=3.5/ACN+MeOH) for 10 min., hold 4 min.

Example 950

2-{4-[2-(2,4,6-TRIFLUOROBENZYL)-7-(TRIF-LUOROMETHYL)-2H-INDAZOL-3-YL]PHE-NYL}-1H-INDOLE-5-CARBONITRILE

MS (ES) m/z 546.7.

Example 951

3-[4-(5-FLUORO-1H-INDOL-2-YL)PHENYL]-2-(2,4,6-TRIFLUOROBENZYL)-7-(TRIFLUOROM-ETHYL)-2H-INDAZOLE

MS (ES) m/z 539.7.

Example 952

5-{3-[2-(2,4,6-TRIFLUOROBENZYL)-7-(TRIF-LUOROMETHYL)-2H-INDAZOL-3-YL]PHE-NOXY}-3,4-DIHYDRONAPHTHALEN-1(2H)-ONE

MS (ES) m/z 566.8.
HPLC purity 100% at 210-370 nm, 11.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 953

6-{3-[2-(2-CHLORO-4-FLUOROBENZYL)-7-(TRIFLUOROMETHYL)-2H-INDAZOL-3-YL]PHENOXY}-3,4-DIHYDRONAPHTHALEN-1(2H)-ONE

MS (ES) m/z 564.7.
HPLC purity 99.3% at 210-370 nm, 12.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 954

3-[3-(5-BROMO-6-METHYL-1H-INDOL-2-YL)PHENYL]-2-(2,4,6-TRIFLUOROBENZYL)-7-(TRIFLUOROMETHYL)-2H-INDAZOLE

MS (ES) m/z 613.6.

Example 955

3-[4-(5-BROMO-6-METHYL-1H-INDOL-2-YL)PHENYL]-2-(2,4,6-TRIFLUOROBENZYL)-7-(TRIFLUOROMETHYL)-2H-INDAZOLE

MS (ESI, [M–H]–) m/z 711.7.

Example 956

1-METHYL-2-{4-[2-(2,4,6-TRIFLUOROBEN-ZYL)-7-(TRIFLUOROMETHYL)-2H-INDAZOL-3-YL]PHENYL}-1H-INDOLE-5-CARBONITRILE

HRMS: calcd for C31H18F6N4+H+, 561.15084; found (ESI, [M+H]+), 561.1509.

Example 957

3-[4-(5-FLUORO-1-METHYL-1H-INDOL-2-YL)PHENYL]-2-(2,4,6-TRIFLUOROBENZYL)-7-(TRIFLUOROMETHYL)-2H-INDAZOLE

HRMS: calcd for C30H18F7N3+H+, 554.14617; found (ESI, [M+H]+), 554.1463.

Example 958

6-{3-[2-(2,4,6-TRIFLUOROBENZYL)-7-(TRIF-LUOROMETHYL)-2H-INDAZOL-3-YL]PHE-NOXY}-3,4-DIHYDRONAPHTHALEN-1(2H)-ONE

MS (ES) m/z 566.8.

Example 959

2-{4-[2-(2,4,6-TRIFLUOROBENZYL)-7-(TRIF-LUOROMETHYL)-2H-INDAZOL-3-YL]PHE-NYL}-1H-INDOLE-5-CARBONITRILE

MS (ES) m/z 546.7.

Example 960

3-[4-(5-FLUORO-1H-INDOL-2-YL)PHENYL]-2-(2,4,6-TRIFLUOROBENZYL)-7-(TRIFLUOROMETHYL)-2H-INDAZOLE

MS (ES) m/z 539.7.

Example 961

5-{3-[2-(2,4,6-TRIFLUOROBENZYL)-7-(TRIFLUOROMETHYL)-2H-INDAZOL-3-YL]PHENOXY}-3,4-DIHYDRONAPHTHALEN-1(2H)-ONE

MS (ES) m/z 566.8.

Example 962

6-{3-[2-(2-CHLORO-4-FLUOROBENZYL)-7-(TRIFLUOROMETHYL)-2H-INDAZOL-3-YL]PHENOXY}-3,4-DIHYDRONAPHTHALEN-1(2H)-ONE

MS (ES) m/z 564.7.

Example 963

METHYL (5-{3-[2-(2-CHLORO-4-FLUOROBENZYL)-7-(TRIFLUOROMETHYL)-2H-INDAZOL-3-YL]PHENOXY}-1-HYDROXY-1,2,3,4-TETRAHYDRONAPHTHALEN-1-YL)ACETATE

MS (ESI) m/z 639.

Example 964

ETHYL [4-({3-[2-(2,4,6-TRIFLUOROBENZYL)-7-(TRIFLUOROMETHYL)-2H-INDAZOL-3-YL]PHENOXY}METHYL)PHENYL]ACETATE

MS (ES) m/z 598.8.

Example 965

(5-{3-[2-(2-CHLORO-4-FLUOROBENZYL)-7-(TRIFLUOROMETHYL)-2H-INDAZOL-3-YL]PHENOXY}-3,4-DIHYDRONAPHTHALEN-1-YL)ACETIC ACID

MS (ES) m/z 606.8.

Example 966

ETHYL [4-({4-[2-(4-CHLORO-2-FLUOROBENZYL)-7-(TRIFLUOROMETHYL)-2H-INDAZOL-3-YL]PHENOXY}METHYL)PHENYL]ACETATE

MS (ES) m/z 596.8.

Example 967

5-{3-[2-(4-CHLORO-2-FLUOROBENZYL)-7-(TRIFLUOROMETHYL)-2H-INDAZOL-3-YL]PHENOXY}-1,2,3,4-TETRAHYDRONAPHTHALEN-1-OL

MS (ES) m/z 566.8.

As those skilled in the art will appreciate, numerous changes and modifications may be made to the preferred embodiments of the invention without departing from the spirit of the invention. It is intended that all such variations fall within the scope of the invention. It is intended that each of the patents, applications, and printed publications including books mentioned in this patent document be hereby incorporated by reference in their entirety.

This application claims priority benefit of U.S. Provisional Application Ser. No. 60/598,573, filed Aug. 3, 2004, and 60/669,737, filed Apr. 8, 2005, each of which is hereby incorporated herein by reference in its entirety.

What is claimed is:

1. A compound having the Formula (I):

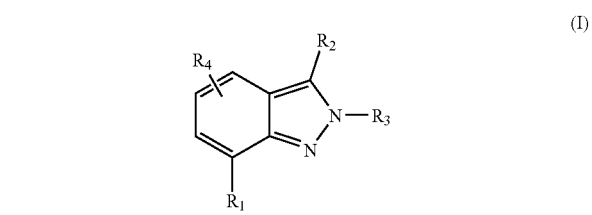

wherein:
  $R_1$ is $C_{1-6}$ alkyl, CN, $CO_2R_5$, $C(O)R_5$, $C_{2-6}$ alkenyl, $C_{3-8}$ cycloalkenyl, $C_{2-6}$ alkynyl, $NR_5R_6$, $C(O)NR_5R_6$, phenyl, thiophene, $C_{1-3}$ alkoxy, halogen, or $S(O)_kR_5$; wherein:
    said $C_{1-6}$ alkyl is optionally substituted with from 1 to 7 substituents independently
      selected from the group consisting of halogen and OH;
    k is 0, 1 or 2;
    each $R_5$ and each $R_6$ is independently H, $C_{1-6}$ alkyl, $C_{3-8}$ cycloalkyl, $S(O)_2$-alkyl or arylalkyl; or
    each $R_5$ and each $R_6$, together with the nitrogen atom to which they are attached, form independently:
      a) a 3 to 7 membered saturated ring that is optionally substituted with $C_{1-3}$ alkyl, $CH_2OH$, or $C(=O)NH_2$; or
      b) a 3 to 7 membered ring containing in its backbone one or two Additional heteroatoms that is optionally substituted with up to three substituents independently selected from the group consisting of =O, $C_{1-3}$ alkyl, $COC_{1-6}$ alkyl, and $CO_2C_{1-6}$ alkyl;
    provided that when $R_1$ is $S(O)_kR_5$, then said $R_5$ of said $S(O)_kR_5$ is not $S(O)_2$-alkyl;
  $R_2$ is $C_{3-8}$ alkyl, $C_{3-8}$ cycloalkyl, $C_{2-8}$ alkenyl, $C_{3-8}$ cycloalkenyl, $C_{2-8}$ alkynyl, aryl, arylalkyl, heteroaryl, or heteroarylalkyl, wherein said $C_{3-8}$ alkyl, said $C_{3-8}$ cycloalkyl and said arylalkyl are each optionally substituted with up to four substituents independently selected from the group consisting of halogen, CN and $OR_7$, and wherein said heteroaryl is optionally substituted with YD; or
  $R_2$ is phenyl substituted with up to four substituents independently selected from the group consisting of $C_{1-3}$ alkyl, $C_{2-8}$ alkenyl, $C_{2-8}$ alkynyl, $C_{1-3}$ alkoxy, $C_{3-8}$ cycloalkyl, halogen, OH, $CH_2OH$, CN, $NR_7R_8$, $N(R_7)C(O)NR_5R_6$, $S(O)_mR_7$, phenyl, $NO_2$, $C(O)R_7$, $OC(O)R_7$, $C(O)NR_7R_8$, $C(O)NR_7D$ and YD, providing any OH group present is not in the para position; wherein:
said $C_{1-3}$ alkyl and said $C_{1-3}$ alkoxy are each optionally substituted with from 1 to 7 fluorine atoms;
m is 0 to 2; and
$R_5$ and $R_6$ are as previously defined;
each $R_7$ and each $R_8$ is independently H or $C_{1-3}$ alkyl; or each $R_7$ and each $R_8$, together with the N atom to which they are attached, form independently:
a) a 3 to 7 membered saturated ring which is optionally substituted with $C_{1-3}$ alkyl, $CO_2R_{14}$, $CH_2CO_2R_{14}$, $OCH_2CO_2R_{14}$, $CH_2OCH_2CO_2R_{14}$, $C(O)NR_{14}R_{15}$, $CH_2OH$, or $CH_2CH_2OH$; or
b) a 3 to 7 membered ring containing in its backbone one or two additional heteroatoms that is optionally substituted with $CH_2CO_2R_{14}$; wherein $R_{14}$ and $R_{15}$ are each independently H or $C_{1-3}$ alkyl;
Y is a bond, $CH_2$, $CH_2CH_2$, $C_{2-4}$ alkynylenyl, —O—, $CH_2OCH_2$, $OCH_2$, $CH_2O$, —$N(R_7)$—, —$N(COR_7)$—, $S(O)_j$, —$N(R_7)CH_2$—, —$N(R_7)CONR_8$—, —$N(COR_7)CH_2$—, $S(O)_jCH_2$, —$CH_2N(R_7)CH_2$—, —$CH_2N(COR_7)CH_2$—, —$OCH_2O$—, —$OC(R_7)(CO_2R_8)$— or —$CH_2S(O)_jCH_2$—; wherein $R_7$ and $R_8$ are as previously defined; and j is 0, 1 or 2;
D is tetrahydronaphthalene, tetrahydronaphthalol, tetralone, naphthalene, anthracene, benzyl or phenyl, each of which is optionally substituted with up to five independently selected R groups;
each R is independently selected from the group consisting of $C_{1-6}$ alkyl, $C_{1-3}$ alkoxy, halogen, —C(=O)H, —C(O)—$C_{1-3}$ alkyl, $CH_2OH$, CN, $NH_2$, $NO_2$, $C_{2-4}$ alkenyl, $C_{2-4}$ alkynyl, $S(O)_jR_9$, and WX; wherein said $C_{1-6}$ alkyl and said $C_{1-3}$ alkoxy are each optionally substituted with from 1 to 7 fluorine atoms; and j is 0, 1 or 2; or
D is a heterocycloalkyl, heterocycloalkylalkyl, heteroarylalkyl, heteroaryl or arylalkyl group, each of which is optionally substituted with up to four independently selected $R_a$ groups;
each $R_a$ is independently selected from the group consisting of $C_{1-8}$ alkyl, phenyl, benzyl, $C_{3-8}$cycloalkyl $C_{7-11}$ arylalkyl, $C_{1-3}$ alkoxy, halogen, —C(=O)H, —C(O)—$C_{1-3}$ alkyl, $CH_2OH$, CN, $NO_2$, $NH_2$, OH, =O, $C_{2-6}$ alkenyl, $C_{2-4}$ alkynyl, $S(O)_jR_9$ and WX; wherein said $C_{1-8}$ alkyl, said $C_{2-6}$ alkenyl, said $C_{2-4}$ alkynyl and said $C_{1-3}$ alkoxy are each optionally substituted with from 1 to 7 fluorine atoms; and j is 0, 1 or 2;
W is a bond, —$CH_2$—, —$CH_2CH_2$—, —$NR_7$—, -Q-$N(R_7)$—, —$CHR_8$—, —$(CHR_8)_2$—, —$CHR_9$—, —$CR_9R_{10}$—, —CO—, —O—, —$OCH_2$—, —$OCHR_9$—, or —$OCR_9R_{10}$—; wherein $R_7$ and $R_8$ are as previously defined; and Q is $C_{1-6}$ alkylenyl;
each $R_9$ and each $R_{10}$ is independently $C_{1-3}$ alkyl or OH; or
any $R_9$ and $R_{10}$, together with the atom to which they are attached, can form a 3 to 7 membered saturated ring that optionally contains one O, N or S atom;
X is $CO_2R_{11}$, $COR_{11}$, $C(R_{11})_2OH$, $CO_2R_5$, $C(O)NR_5R_6$, $NR_5R_6$, $QNR_5CO_2R_6$, OH, $CH_2OH$, CN, $SO_2NR_5R_6$, $P(O)(OR_5)(OR_6)$, cycloalkylalkyl, aryl, arylalkyl, heterocycloalkyl or heteroaryl, wherein:
said aryl, said arylalkyl, said heterocycloalkyl and said heteroaryl are independently each optionally substituted with up to three substituents selected from the group consisting of $C_{1-3}$ alkyl, $C_{1-3}$ alkoxy, halogen, H, OH, $NO_2$ and benzyl that is optionally substituted with up to five halogen atoms; wherein said $C_{1-3}$ alkyl and said $C_{1-3}$ alkoxy are each optionally substituted with from 1 to 7 fluorine atoms;
Q is $C_{1-6}$ alkylenyl;
$R_{11}$ is H or $C_{1-6}$ alkyl; and
$R_5$ and $R_6$ are as previously defined;
$R_3$ is ZA; wherein:
Z is $CH_2$, or $CH_2CH_2$;
A is naphthyl, or phenyl;—wherein said phenyl is optionally substituted with up to five independently selected $R_{18}$ groups; wherein
each said $R_{18}$ is independently selected from the group consisting of $C_{1-6}$ alkyl, $C_{1-3}$ alkoxy, halogen, OH, $NO_2$, CN, phenyl, pyrrol-1-yl, $C(O)R_{12}$, $CO_2R_{12}$, $NR_{12}R_{13}$, $C(O)NR_{12}R_{13}$ and $S(O)_nR_{12}$; wherein said $C_{1-6}$ alkyl and said $C_{1-3}$ alkoxy are each optionally substituted with from 1 to 7 fluorine atoms; n is 0, 1 or 2; and $R_{12}$ and $R_{13}$ are each independently H or $C_{1-3}$ alkyl;
$R_{20}$ is H or $C_{1-3}$ alkyl; and
$R_4$ is H, halogen, methyl or methoxy.

2. A compound of claim 1 wherein $R_1$ is $C_{1-6}$ alkyl, CN, $CO_2R_5$, $NR_5R_6$, or halogen; wherein said $C_{1-6}$ alkyl is optionally substituted with from 1 to 7 substituents independently selected from the group consisting of halogen and OH; and $R_5$ and $R_6$ are as previously defined.

3. A compound of claim 1 wherein $R_1$ is CN, halogen, or $C_{1-6}$ alkyl substituted with from 1 to 7 fluorine atoms.

4. A compound of claim 1 wherein $R_1$ is $C_{1-3}$ perhaloalkyl.

5. A compound of claim 1 wherein $R_1$ is $CF_3$, F or Cl.

6. A compound of claim 1 wherein $R_1$ is $CF_3$.

7. A compound of claim 1 wherein:
$R_2$ is $C_{3-8}$ alkyl, $C_{3-8}$ cycloalkyl, aryl, arylalkyl, or heterocycloalkyl; wherein
said $C_{3-8}$ alkyl, said $C_{3-8}$ cycloalkyl and said arylalkyl are each optionally substituted with up to four substituents independently selected from the group consisting of halogen, CN and $OR_7$; and
said heteroaryl is optionally substituted with YD; wherein Y and D are as previously defined; or
$R_2$ is phenyl substituted with up to four substituents independently selected from the group consisting of $C_{1-3}$ alkyl, $C_{2-8}$ alkenyl, $C_{2-8}$ alkynyl, $C_{1-3}$ alkoxy, $C_{3-8}$ cycloalkyl, halogen, OH, $CH_2OH$, CN, $NR_7R_8$, $N(R_7)C(O)NR_5R_6$, $S(O)_mR_7$, phenyl, $NO_2$, $C(O)R_7$, $OC(O)R_7$, $C(O)NR_7R_8$, $C(O)NR_7D$ and YD, providing any OH group present is not in the para position; wherein said $C_{1-3}$ alkyl and said $C_{1-3}$ alkoxy are each optionally substituted with from 1 to 7 fluorine atoms.

8. A compound of claim 1 wherein:
$R_2$ is arylalkyl, heteroaryl or heteroarylalkyl, wherein:
said arylalkyl is optionally substituted with up to four substituents independently selected from the group consisting of halogen, CN and $OR_7$; and
said heteroaryl is optionally substituted with YD; or
$R_2$ is phenyl substituted with up to four substituents independently selected from the group consisting of $C_{1-3}$ alkyl, $C_{1-3}$ alkoxy, halogen, $CH_2OH$, CN, $NR_7R_8$, $N(R_7)$ CONR$_5$R$_6$, S(O)$_m$R$_7$, NO$_2$, and YD; wherein said C$_{1-3}$ alkyl and said C$_{1-3}$ alkoxy are each optionally substituted with from 1 to 7 fluorine atoms; m, R$_5$, R$_6$, R$_7$, and R$_8$ are as previously defined;

Y is a bond, CH$_2$, CH$_2$CH$_2$, C$_{2-4}$ alkynylenyl, —O—, OCH$_2$, CH$_2$O, —N(R$_7$)—, —N(R$_7$)CH$_2$—, —N(R$_7$)CONR$_8$—, —OCH$_2$O— or —OC(R$_7$)(CO$_2$R$_8$)—; wherein R$_7$ and R$_8$ are as previously defined;

D is benzyl or phenyl, each of which is optionally substituted with up to five independently selected R groups;
each R is independently selected from the group consisting of C$_{1-6}$ alkyl, C$_{1-3}$ alkoxy, halogen, —C(=O)H, —C(O)—C$_{1-3}$ alkyl, CH$_2$OH, CN, NO$_2$, C$_{2-4}$ alkenyl, C$_{2-4}$ alkynyl, S(O)$_j$R$_9$, and WX; wherein said C$_{1-6}$ alkyl and said C$_{1-3}$ alkoxy are each optionally substituted with from 1 to 7 fluorine atoms; and j, R$_9$ and WX are as previously defined; or D is a heterocycloalkyl, heteroarylalkyl, heteroaryl, or arylalkyl group, each of which is optionally substituted with up to four independently selected R$_a$ groups;
each R$_a$ is independently selected from the group consisting of C$_{1-8}$ alkyl, phenyl, benzyl, C$_{7-11}$ arylalkyl, C$_{1-3}$ alkoxy, halogen, C(O)H, CO(CH$_3$)$_2$, C(CH$_3$)$_2$OH, —C(O)—C$_{1-3}$ alkyl, CH$_2$OH, CN, NO$_2$, NH$_2$, OH, =O, C$_{2-6}$ alkenyl, C$_{2-4}$ alkynyl, S(O)$_j$R$_9$, and WX; wherein said C$_{1-8}$ alkyl, said C$_{2-6}$ alkenyl, C$_{2-4}$ alkynyl and said C$_{1-3}$ alkoxy are each optionally substituted with from 1 to 7 fluorine atoms; and j, R$_9$ and WX are as previously defined.

9. A compound of claim 1 wherein R$_2$ is phenyl substituted with an ortho or meta OH.

10. A compound of claim 1 wherein R$_2$ is phenyl substituted with a meta OH.

11. A compound of claim 1 wherein:
R$_2$ is phenyl substituted with up to four substituents independently selected from the group consisting of C$_{1-3}$ alkyl, C$_{2-8}$ alkenyl, C$_{2-8}$ alkynyl, C$_{1-3}$ alkoxy, C$_{3-8}$ cycloalkyl, halogen, OH, CH$_2$OH, CN, NR$_7$R$_8$—, N(R$_7$)C(O)NR$_5$R$_6$, S(O)$_m$R$_7$, phenyl, NO$_2$, C(O)R$_7$, OC(O)R$_7$, C(O)NR$_7$R$_8$, C(O)NR$_7$D and YD, providing any OH group present is not in the para position; wherein said C$_{1-3}$ alkyl and said C$_{1-3}$ alkoxy are each optionally substituted with from 1 to 7 fluorine atoms; and m, R$_5$, R$_6$, R$_7$, R$_8$, Y and D are as previously defined.

12. A compound of claim 1 wherein R$_2$ is phenyl substituted with YD.

13. A compound of claim 12 wherein Y is a bond, CH$_2$, CH$_2$CH$_2$, C$_{2-4}$ alkynylenyl, —O—, OCH$_2$, CH$_2$O, —N(R$_7$)—, —N(R$_7$)CH$_2$—, —N(R$_7$)CONR$_8$—, —OCH$_2$O— or —OC(R$_7$)(CO$_2$R$_8$).

14. A compound of claim 13 wherein D is benzyl or phenyl, each of which is optionally substituted with up to five independently selected R groups; each R is independently selected from the group consisting of C$_{1-6}$ alkyl, C$_{1-3}$ alkoxy, halogen, —C(=O)H, —C(O)—C$_{1-3}$ alkyl, C$_{1-6}$ alkyl, C$_{1-3}$ alkoxy, halogen, C(=O)H, C$_{1-3}$ acyl, CH$_2$OH, CN, NO$_2$, C$_{2-4}$ alkenyl, C$_{2-4}$ alkynyl, S(O)$_j$R$_9$, and WX; wherein said C$_{1-6}$ alkyl and said C$_{1-3}$ alkoxy are each optionally substituted with from 1 to 7 fluorine atoms; and j, R$_9$ and WX are as previously defined.

15. A compound of claim 14 wherein D is phenyl that is optionally substituted with up to four independently selected R groups; each R is independently selected from the group consisting of C$_{1-6}$ alkyl, —C(=O)H, —C(O)—C$_{1-3}$ alkyl, C$_{1-3}$ alkoxy, halogen, CH$_2$OH, CN, NO$_2$, C$_{2-4}$ alkenyl, C$_{2-4}$ alkynyl, and WX; wherein said C$_{1-6}$ alkyl and said C$_{1-3}$ alkoxy are each optionally substituted with from 1 to 7 fluorine atoms; and wherein WX is previously defined.

16. A compound of claim 1 wherein R$_2$ is phenyl substituted with C$_{1-3}$ perfluoroalkyl.

17. A compound of claim 1 wherein R or R$_a$ is C$_{1-3}$ perfluoroalkyl or C$_{1-3}$ perfluoroalkoxy.

18. A compound of claim 1 wherein R$_2$ is selected from the group consisting of 2,4-dimethoxyphenyl, phenyl, 4-methoxy-2-methylphenyl, 2-methoxyphenyl, 4-methoxyphenyl, 2-methylphenyl, 2,4-dimethylphenyl, 1,1'-biphenyl-4-yl, 4-methoxy-3,5-dimethylphenyl, 2-naphthyl, 2-vinylphenyl, 4-methoxy-3-methylphenyl, 3-methylphenyl, 2,3-dimethylphenyl, 3-(trifluoromethyl)phenyl, 4-fluorophenyl, 3-chlorophenyl, 3-methoxyphenyl, benzaldehyde-2-yl, 2-isopropylphenyl, 2-cyclohexylphenyl, 2-benzylphenyl, 2-(1,1,2,2-tetrafluoroethoxy)phenyl, 2-chloro-5-fluorophenyl, 9H-fluoren-2-yl, 4-benzylphenyl, benzaldehyde-3-yl, 3-hydroxyphenyl, butyl, isobutyl, pentyl, cyclopentyl, 2-hydroxyphenyl, 1,3-dioxolan-2-yl, 4'-methoxy-1,1'-biphenyl-4-yl, 1,1'-biphenyl-4-ol, cyclohexanyl, 4-methoxy-2-methylphenyl, 4-methoxy-2-methylphenyl, 4-bromophenyl, 3-bromophenyl, 3-(benzyloxy)phenyl, and 4-phenoxy-phenyl.

19. A compound of claim 1, wherein A is phenyl that is optionally substituted with up to five independently selected R$_{18}$ groups; wherein each said R$_{18}$ is independently selected from the group consisting of C$_{1-6}$ alkyl, C$_{1-3}$ alkoxy, halogen, OH, NO$_2$, CN, phenyl, pyrrol-1-yl, C(O)R$_{12}$, CO$_2$R$_{12}$, NR$_{12}$R$_{13}$, C(O)NR$_{12}$R$_{13}$, and S(O)$_n$R$_{12}$; wherein said C$_{1-6}$ alkyl and said C$_{1-3}$ alkoxy are each optionally substituted with from 1 to 7 fluorine atoms; and n, R$_{12}$ and R$_{13}$ are as previously defined.

20. A compound of claim 1 wherein
Z is CH$_2$; and
A is phenyl, wherein said phenyl is optionally substituted with up to five independently selected R$_{18}$ groups; wherein each said R$_{18}$ is independently selected from the group consisting of C$_{1-6}$ alkyl, C$_{1-3}$ alkoxy, halogen, OH, NO$_2$, and CN; wherein said C$_{1-6}$ alkyl and C$_{1-3}$ alkoxy are each optionally substituted with from 1 to 7 fluorine atoms.

21. A compound of claims 20 wherein R$_{18}$ is C$_{1-3}$ perfluoroalkyl.

22. A compound of claim 1 wherein R$_3$ is selected from the group consisting of benzyl, 3-methoxybenzyl, 2-naphthylmethyl, 4-methylbenzyl, 2-nitrobenzyl, 2-(trifluoromethyl)benzyl, 4-bromobenzyl, 3-(difluoromethoxy)benzyl, 3-(trifluoromethoxy)benzyl, 3,5-difluorobenzyl, 3,5-dimethylbenzyl, 2-chloro-4-fluorobenzyl, 3-(1H-pyrrol-1-yl)benzyl, 2-bromobenzyl, 2-methylbenzyl, 5-fluoro-2-methylbenzyl, 6-chloro-2-fluoro-3-methylbenzyl, 1,1'-biphenyl-3-ylmethyl, 2-chlorobenzyl, 1-naphthylmethyl, 2,5-dichlorobenzyl, (difluoromethoxy)benzyl, 3-fluorobenzyl, 4-methylbenzyl, 2,4-dimethylbenzyl, mesitylmethyl, 2,4-dimethylbenzyl, 2-phenylethyl, 2-chloro-6-fluorobenzyl, 4-chloro-2-fluorobenzyl, 4-fluorobenzyl, 4-(methylsulfonyl)benzyl.

23. A compound of claim 1 wherein R$_4$ is H or F.

24. The compound of claim 1 wherein:
R$_1$ is C$_{1-6}$ alkyl, CN, CO$_2$R$_5$, NR$_5$R$_6$, halogen; wherein said C$_{1-6}$ alkyl is optionally substituted with from 1 to 7 substituents independently selected from the group consisting of halogen and OH;
R$_5$ and R$_6$ are as previously defined;
R$_2$ is as previously defined;

Z is $CH_2$; and

A is phenyl, wherein said phenyl is optionally substituted with up to five independently selected $R_{18}$ groups; wherein each said $R_{18}$ is independently selected from the group consisting of $C_{1-6}$ alkyl, $C_{1-3}$ alkoxy, halogen, OH, $NO_2$, and CN; wherein said $C_{1-6}$ alkyl and said $C_{1-3}$ alkoxy are each optionally substituted with from 1 to 7 fluorine atoms; and $R_4$ is H or halogen.

25. A compound of claim 1 wherein:

$R_1$ is $C_{1-6}$ alkyl, CN, or halogen; wherein said $C_{1-6}$ alkyl is optionally substituted with from 1 to 7 fluorine atoms;

$R_2$ is arylalkyl, heteroaryl or heteroarylalkyl, wherein:
said arylalkyl is optionally substituted with up to four substituents independently selected from the group consisting of halogen, CN and $OR_7$; and
said heteroaryl is optionally substituted with YD;
wherein $R_7$, Y and D are as previously defined; or $R_2$ is phenyl substituted with up to four substituents independently selected from the group consisting of $C_{1-3}$ alkyl, $C_{1-3}$ alkoxy, halogen, $CH_2OH$, CN, $NR_7R_8$, $N(R_7)$ $CONR_5R_6$, $S(O)_mR_7$, $NO_2$ and YD; wherein said $C_{1-3}$ alkyl and said $C_{1-3}$ alkoxy are each optionally substituted with from 1 to 7 fluorine atoms; m, $R_5$, $R_6$, $R_7$, and $R_8$ are as previously defined;

Y is a bond, $CH_2$, $CH_2CH_2$, $C_{2-4}$ alkynenyl, —O—, $OCH_2$, $CH_2O$, —$N(R_7)$—, —$N(R_7)CH_2$—, —$N(R_7)$ $CONR_8$—, —$OCH_2O$— or —$OC(R_7)(CO_2R_8)$—;

D is benzyl or phenyl, each of which is optionally substituted with up to five independently selected R groups;
each R is independently selected from the group consisting of $C_{1-6}$ alkyl, $C_{1-3}$ alkoxy, halogen, C(=O)H, —C(O)—$C_{1-3}$ alkyl, $CH_2OH$, CN, $NO_2$, $C_{2-4}$ alkenyl, $C_{2-4}$ alkynyl, $S(O)_jR_9$, and WX; wherein said $C_{1-6}$ alkyl and said $C_{1-3}$ alkoxy are each optionally substituted with from 1 to 7 fluorine atoms; and j, $R_9$ and WX are as previously defined; or D is a heterocycloalkyl, heteroarylalkyl, heteroaryl, or arylalkyl group, each of which is optionally substituted with up to four independently selected $R_a$ groups;
each $R_a$ is independently selected from the group consisting of, $C_{1-8}$ alkyl, phenyl, benzyl, $C_{7-11}$ arylalkyl, $C_{1-3}$ alkoxy, halogen, C(O)H, —C(O)—$C_{1-3}$ alkyl, $CH_2OH$, CN, $NO_2$, $NH_2$, OH, =O, $C_{2-6}$ alkenyl, $C_{2-4}$ alkynyl, $S(O)_jR_9$, and WX; wherein said $C_{1-8}$ alkyl, said $C_{2-6}$ alkenyl, $C_{2-4}$ alkynyl and said $C_{1-3}$ alkoxy are each optionally substituted with from 1 to 7 fluorine atoms; and j, $R_9$ and WX are as previously defined;

Z is $CH_2$; and

A is phenyl, wherein said phenyl is optionally substituted with up to five independently selected $R_{18}$ groups; wherein each said $R_{18}$ is independently selected from the group consisting of $C_{1-6}$ alkyl, $C_{1-3}$ alkoxy, halogen, OH, $NO_2$, and CN, wherein said $C_{1-6}$ alkyl and $C_{1-3}$ alkoxy are each optionally substituted with from 1 to 7 fluorine atoms;and $R_4$ is H.

26. A compound of claim 25 wherein $R_{18}$ is $C_{1-3}$ perfluoroalkyl.

27. A compound of claim 26 wherein $R_2$ is phenyl substituted with $C_{1-3}$ perfluoroalkyl.

28. A compound of claim 27 wherein R or $R_a$ is $C_{1-3}$ perfluoroalkyl or $C_{1-3}$ perfluoroalkoxy.

29. A compound of any of claims 7 to 18 or 19 to 28 wherein $R_1$ is $CF_3$, F or Cl.

30. A compound of claim 1 selected from the group consisting of:
ae) 3-(4-Methoxy-2-methylphenyl)-2-(4-methyl-benzyl)-7-trifluoromethyl-2H-indazole;
af) 2-(2,4-Dimethylbenzyl)-3-(4-methoxy-2-methylphenyl)-7-trifluoromethyl-2H-indazole;
ag) 3-(4-Methoxy-2-methyl-phenyl)-7-trifluoromethyl-2-(2,4,6-trimethyl-benzyl)-2H-indazole;
ar) 2-(2,4-Dimethyl-benzyl)-3-phenyl-7-trifluoromethyl-2H-indazole;
as) 3-Phenyl-7-trifluoromethyl-2-(2,4,6-trimethyl-benzyl)-2H-indazole;
bc) 2-(3-Methoxybenzyl)-3-phenyl-7-trifluoromethyl-2H-indazole;
bd) 2-(3-Fluorobenzyl)-3-phenyl-7-trifluoromethyl-2H-indazole;
be) 2-(2-Nitrobenzyl)-3-phenyl-7-trifluoromethyl-2H-indazole;
bf) 2-(3,5-Difluorobenzyl)-3-phenyl-7-trifluoromethyl-2H-indazole;
bh) 2-(4-Methylbenzyl)-3-phenyl-7-trifluoromethyl-2H-indazole;
bi) 2-(2-Trifluoromethylbenzyl)-3-phenyl-7-trifluoromethyl-2H-indazole;
bj) 2-(4-Bromobenzyl)-3-phenyl-7-trifluoromethyl-2H-indazole;
bk) 2-(2-Difluoromethoxybenzyl)-3-phenyl-7-trifluoromethyl-2H-indazole;
bl) 2-(3-Difluoromethoxybenzyl)-3-phenyl-7-trifluoromethyl-2H-indazole;
bn) 2-(3-Trifluoromethoxylbenzyl)-7-trifluoromethyl-3-phenyl-2H-indazole;
bn) 2-(3,5-Dimethylbenzyl)-3-phenyl-7-trifluoromethyl-2H-indazole;
bo) 2-Naphthalen-1-ylmethyl-3-phenyl-7-trifluoromethyl-2H-indazole;
bp) 2-(2-Chloro-4-fluorobenzyl)-3-phenyl-7-trifluoromethyl-2H-indazole;
bq) 3-Phenyl-2-(3-pyrrol-1-yl-benzyl)-7-trifluoromethyl-2H-indazole;
br) 2-(2-Bromobenzyl)-3-phenyl-7-trifluoromethyl-2H-indazole;
bs) 2-(2-Methylbenzyl)-3-phenyl-7-trifluoromethyl-2H-indazole;
bt) 2-(2,5-Dichlorobenzyl)-7-trifluoromethyl-3-phenyl-2H-indazole;
bu) 2-(2-Methyl-5-fluorobenzyl)-3-phenyl-7-trifluoromethyl-2H-indazole;
bv) 2-(6-Chloro-2-fluoro-3-methylbenzyl)-3-phenyl-7-trifluoromethyl-2H-indazole;
bw) 2-Biphenyl-3-ylmethyl-3-phenyl-7-trifluoromethyl-2H-indazole;
ce) 2-(2-Chloro-benzyl)-3-phenyl-7-trifluoromethyl-2H-indazole;
cf) 2-Naphthalen-1-ylmethyl-3-phenyl-7-trifluoromethyl-2H-indazole;
dh) 3-Phenyl-2-(2-phenylethyl)-7-(trifluoromethyl)-2H-indazole;
di) 2-(4-Fluorobenzyl)-3-phenyl-7-(trifluoromethyl)-2H-indazole;
dj) 2-(2-Chloro-6-fluorobenzyl)-3-phenyl-7-(trifluoromethyl)-2H-indazole;
dk) 2-(4-Chloro-2-fluorobenzyl)-3-phenyl-7-(trifluoromethyl)-2H-indazole;

dn) 2-(2-chloro-4-fluoro-benzyl)-3-(4-fluoro-phenyl)-7-trifluoromethyl-2H-indazole;

do) 2-(2-fluorobenzyl)-3-(4-fluorophenyl)-7-(trifluoromethyl)-2H-indazole;

dp) 2-(2-chlorobenzyl)-3-(4-fluorophenyl)-7-(trifluoromethyl)-2H-indazole;

dq) 2-(3,4-difluorobenzyl)-3-(4-fluorophenyl)-7-(trifluoromethyl)-2H-indazole;

dr) 3-(4-fluorophenyl)-2-(2,4,6-trifluorobenzyl)-7-(trifluoromethyl)-2H-indazole;

ds) 2-(2,4-difluorobenzyl)-3-(4-fluorophenyl)-7-(trifluoromethyl)-2H-indazole;

dt) 2-(4-fluorobenzyl)-3-(4-fluorophenyl)-7-(trifluoromethyl)-2H-indazole;

du) 2-(4-chlorobenzyl)-3-(4-fluorophenyl)-7-(trifluoromethyl)-2H-indazole;

ee) 2-(2,4-dimethylbenzyl)-3-(4-fluorophenyl)-7-(trifluoromethyl)-2H-indazole;

ev) ethyl 1-{4-[2-(2,4-dimethylbenzyl)-7-(trifluoromethyl)-2H-indazol-3-yl]phenyl}piperidine-4-carboxylate;

fo) 3-(4-chlorophenyl)-2-(2,4-dirnethylbenzyl)-7-(trifluoromethyl)-2H-indazole;

fp) 2-(4-chloro-2-fluorobenzyl)-3-(4-fluorophenyl)-7-(trifluoromethyl)-2H-indazole;

fq) 2-(4-chloro-2-fluorobenzyl)-3-(4-chlorophenyl)-7-(trifluoromethyl)-2H-indazole;

fx) 3-(4-chlorophenyl)-2-(2,4,6-trifluorobenzyl)-7-(trifluoromethyl)-2H-indazole;

fy) 2-(2-chloro-4-fluorobenzyl)-3-(4-chlorophenyl)-7-.(trifluoromethyl)-2H-indazole;

fz) 2-(2-chloro-6-fluorobenzyl)-3-(4-chlorophenyl)-7-(trifluoromethyl)-2H-indazole;

ga) 2-(2-chloro-6-fluorobenzyl)-3-(4-fluorophenyl)-7-(trifluoromethyl)-2H-indazole;

gg) 3-(3,4-difluorophenyl)-2-(2,4,6-trifluorobenzyl)-7-(trifluoromethyl)-2H-indazole;

gh) 2-benzyl-3-(3,4-difluorophenyl)-7-(trifluoromethyl)-2H-indazole;

gi) 3-(3,4-difluorophenyl)-2-(2-fluorobenzyl)-7-(trifluoromethyl)-2H-indazole;

gj) 2-(2,4-difluorobenzyl)-3-(3,4-difluorophenyl)-7-(trifluoromethyl)-2H-indazole;

gk) 2-(3,4-dichlorobenzyl)-3-(3,4-difluorophenyl)-7-(trifluoromethyl)-2H-indazole;

gl) 3-(3,4-difluorophenyl)-2-(3-methylbenzyl)-7-(trifluoromethyl)-2H-indazole;

gn) 3-(2,4-difluorophenyl)-2-(2,4,6-trifluorobenzyl)-7-(trifluoromethyl)-2H-indazole;

gp) 2-(2-chlorobenzyl)-3-(4-chlorophenyl)-7-(trifluoromethyl)-2H-indazole;

gq) 2-(4-chlorobenzyl)-3-(4-chlorophenyl)-7-(trifluoromethyl)-2H-indazole;

gr) 3-(4-chlorophenyl)-2-(2-fluorobenzyl)-7-(trifluoromethyl)-2H-indazole;

gs) 3-(4-chlorophenyl)-2-(2,4-difluorobenzyl)-7-(trifluoromethyl)-2H-indazole;

gt) 3-(4-chlorophenyl)-.7-(trifluoromethyl)-2-[2-(trifluoromethyl)benzyl]-2H-indazole;

gu) 3-(4-chiorophenyl)-7-(trifluoromethyl)-2-[4-(trifluoromethyl)benzyl]-2H-indazole;

gv) 3-(4-chlorophenyl)-2-(3,4-dichlorobenzyl)-7-(trifluoromethyl)-2H-indazole;

hd) 3-(4-chlorophenyl)-2-(3-methoxybenzyl)-7-(trifluoromethyl)-2H-indazole;

he) 3-(4-chlorophenyl)-2-(3-methylbenzyl)-7-(trifluoromethyl)-2H-indazole;

hf) 3-(4-chlorophenyl)-2-(3-nitrobenzyl)-7-(trifluoromethyl)-2H-indazole;

hg) 3-(4-chlorophenyl)-2-(2-methylbenzyl)-7-(trifluoromethyl)-2H-indazole;

hh) 3-(4-chlorophenyl)-2-(2,6-dichlorobenzyl)-7-(trifluoromethyl)-2H-indazole;

hi) (1- {4-[2-(2,4,6-trifluorobenzyl)-7-(trifluoromethyl)-2H-indazol-3-yl]phenyl}piperidin-3-yl)methanol;

hj) (1- {4-[2-(2,4,6-trifluorobenzyl)-7-(trifluoromethyl)-2H-indazol-3-yl]phenyl}piperidin-4-yl)methanol;

hk) ethyl 1- {4-[2-(2,4,6-trifluorobenzyl)-7-(trifluoromethyl)-2H-indazol-3-yl]phenyl}piperidine-4-carboxylate;

hl) 3-(3-chlorophenyl)-2-(2,4,6-trifluorobenzyl)-7-(trifluoromethyl)-2H-indazole;

hm) 2-(4-chloro-2-fluorobenzyl)-3-(3-chlorophenyl)-7-(trifluoromethyl)-2H-indazole;

hn) 2-(2-chlorobenzyl)-3-(3-chlorophenyl)-7-(trifluoromethyl)-2H-indazole;

ho) 2-(4-chlorobenzyl)-3-(3-chlorophenyl)-7-(trifluoromethyl)-2H-indazole;

hu) 1- {4-[2-(2,4,6-trifluorobenzyl)-7-(trifluoromethyl)-2H-indazoi-3-yl]phenyl}pyrrolidin-3-ol;

hv) 1-benzyl-N- {4-[2-(2,4,6-trifluorobenzyl)-7-(trifluoromethyl)-2H-indazol-3-yl]phenyl}pyrrolidin-3-amine;

hw) 3-(3-chlorophenyl)-2-(2-fluorobenzyl)-7-(trifluoromethyl)-2H-indazole;

hx) 3-(3-chlorophenyl)-2-(2,4-difluorobenzyl)-7-(trifluoromethyl)-2H-indazoie;

hy) 3-(3-chlorophenyl)-2-(2,4-dimethylbenzyl)-7-(trifluoromethyl)-2H-indazole;

hz) 3-(3-chlorophenyl)-7-(trifluoromethyl)-2-[4-(trifluoromethyl)benzyl]-2H-indazole;

ia) 3-(3-chlorophenyl)-2-(3,4-dichlorobenzyl)-7-(trifluoromethyl)-2H-indazoie;

ib) 3-(3-chiorophenyl)-2-(3,4-difluorobenzyl)-7-(trifluoromethyl)-2H-indazoie;

ic) 3-(3-chiorphenyl)-2-(3-methoxybenzyl)-7-(trifluoromethyl)-2H-indazole;

id) 3-(3-chiorphenyl)-2-(3-methylbenzyl)-7-(trifluoromethyl)-2H-indazole;

ie) 3-(3-chiorphenyl)-2-(3-nitrobenzyl)-7-(trifluoromethyl)-2H-indazole;

if) 3-(3-chlorophenyl)-2-(2-methylbenzyl)-7-(trifluoromethyl)-2H-indazole;

ig) N-methyl-l- {4-[2-(2,4,6-trifluorobenzyl)-7-(trifluoromethyl)-2H-indazol-3-yl]phenyl}piperidin-4-amine;

ih) 3-[4-(2-methylpiperidin-1-yl)phenyl]-2-(2,4,6-trifluorobenzyl)-7-(trifluoromethyl)-2H-indazole;

ii) 3-[4-(3-methylpiperidin-1-yl)phenyl]-2-(2,4,6-trifluorobenzyl)-7-(trifluoromethyl)-2H-indazole;

ij) 3- [4-(4-methylpiperidin-1-yl)phenyl]-2-(2,4,6-trifluorobenzyl)-7-(trifluoromethyl)-2H-indazole;

ik) 1- {4- 2-(2,4,6-trifluorobenzyl)-7-(trifluoromethyl)-2H-indazol-3 -yl]phenyl}piperidin-3-ol;

il) (1- {4- [2-(2,4-dimethylbenzyl)-7-(trifluoromethyl)-2H-indazol-3 -yl]phenyl}piperidin-3-yl)methanol;

im) (1- {4-[2-(2,4-dimethylbenzyl)-7-(trifluoromethyl)-2H-indazol-3 -yl]phenyl}piperidin-4-yl)methanol;

in) 3-(4-bromophenyl)-2-(2,4,6-trifluorobenzyl)-7-(trifluoromethyl)-2H-indazole;

io) ethyl 1- {4- [2-(2,4-dimethylbenzyl)-7-(trifluoromethyl)-2H-indazol-3-yl]phenyl}piperidine-3-carboxylate;

ip) 2-(1- {4-[2-(2,4,6-trifluorobenzyl)-7-(trifluoromethyl)-2H-indazol-3-yl]phenyl}piperidin-4-yl)ethanol;

iq) 4-phenyl-1- {4-112-(2,4,6-trifluorobenzyl)-7-(trifluoromethyl)-2H-indazol-3-yl]phenyl}piperidin-4-ol;

ir) tert-butyl [(1- {4-112-(2,4,6-trifluorobenzyl)-7-(trifluoromethyl)-2H-indazol-3-yl]phenyl }piperidin-4-yl)methyl]carbamate;

is) ((3 R)-1- {4- [2-(2,4,6-trifluorobenzyl)-7-(trifluoromethyl)-2H-indazol-3-yl]phenyl }piperidin-3-yl)methanol;

it) ((3 S)-1- {4-[2-(2,4,6-trifluorobenzyl)-7-(trifluoromethyl)-2H-indazol-3-yl]phenyl}piperidin-3-yl)methanol;

iu) {4- [2-(2,4,6-trifluorobenzyl)-7-(trifluoromethyl)-2H-indazol-3-yl]phenyl }amine;

iv) 8- {4-[2-(2,4,6-trifluorobenzyl)-7-(trifluoromethyl)-2H-indazol-3-yl]phenyl 1-1 ,4-dioxa-8-azaspiro[4. 5]decane;

iw) (1- {3-[2-(2,4-difluorobenzyl)-7-(trifluoromethyl)-2H-indazol-3-yl]phenyl }piperidin-3-yl)methanol;

ix) (1- {3-2-(2,4-difluorobenzyl)-7-(trifluoromethyl)-2H-indazol-3-yl]phenyl}piperidin-4-yl)methanol;

iy) (1- {3-[2-(2,4,6-trifluorobenzyl)-.7-(trifluoromethyl)-2H-indazol-3-yl]phenyl }piperidin-3-yl)methanol;

iz) (1- {3-[2-(2,4,6-trifluorobenzyl)-7-(trifluoromethyl)-2H-indazol-3-yl]phenyl }piperidin-4-yl)methanol;

ja) (1- {3-[2-(3-methylbenzyl)-7-(trifluoromethyl)-2H-indazol-3-yl]phenyl }piperidin-3-yl)methanol;

jb) (1- {3-172-(3-methylbenzyl)-7-(trifluoromethyl)-2H-indazol-3 yl]phenyl }piperidin-4-yl)methanol;

jc) (1- {3-[2-(3,4-difluorobenzyl)-7-(trifluoromethyl)-2H-indazol-3-yl]phenyl }piperidin-3-yl)methanol;

jd) (1- {3-[2-(3 ,4-difluorobenzyl)-7-(trifluoromethyl)-2H-indazol-3-yl]phenyl }piperidin-4-yl)methanol;

je) (1- {4-[2-(2-methylbenzyl)-7-(trifluoromethyl)-2H-indazol-3-yl]phenyl }piperidin-3-yl)methanol;

jf) (1- {4-[2-(2-methylbenzyl)-7-(trifluoromethyl)-2H-indazol-3-yl]phenyl }piperidin-4-yl)methanol;

jg) (1- {4-[2-(2,4-difluorobenzyl)-7-(trifluoromethyl)-2H-indazol-3-yl]phenyl }piperidin-3-yl)methanol;

jh) N-(pyridin-4-ylmethyl)-N'- {4- [2-(2,4,6-trifluorobenzyl)-7-(trifluoromethyl)-2H-indazol-3-yl]phenyl}urea;

ji) N-(piperidin-4-ylmethyl)-N'- {4-[2-(2,4,6-trifluorobenzyl)-7-(trifluoromethyl)-2H-indazol-3-yl]phenyl }urea;

jj) N-(2-methoxybenzyl)-N'- {4-[2-(2,4,6-trifluorobenzyl)-7-(trifluoromethyl)-2H-indazol-3-yl]phenyl }urea;

jk) N-(4-bromophenyl)-N'- {4-[2-(2,4,6-trifluorobenzyl)-7-(trifluoromethyl)-2H-indazol-3-yl]phenyl }urea;

jl) N-(tetrahydrofuran-2-ylmethyl)-N'- {4-[2-(2,4,6-trifluorobenzyl)-7-(trifluoromethyl)-2H-indazol-3-yl]phenyl }urea;

jm) N-isobutyl-N'- {4- [2-(2,4,6-trifluorobenzyl)-7-(trifluoromethyl)-2H-indazol...3-yl]phenyl }urea;

jn) N,N-dipropyl-N'- {4- [2-(2 ,4,6-trifluorobenzyl)-7-(trifluoromethyl)-2H-indazol-3-yl]phenyl}urea;

jo) {3- [2-(2,4,6-trifluorobenzyl)-7-(trifluoromethyl)-2H-indazol-3-yl]phenyl }amine;

jp) 2-(2-fluorobenzyl)-3-[3-(4-methylpiperidin-1-yl)phenyl]-7-(trifluoromethyl)-2H-indazole;

jq) (3 S)-1-benzyl-N- {4- [2-(2,4,6-trifluorobenzyl)-7-(trifluoromethyl)-2H-indazol-3-yl]phenyl }pyrrolidin-3-amine;

jr) (3 R)-1-benzyl-N- {4-[2-(2,4,6-trifluorobenzyl)-7-(trifluoromethyl)-2H..indazoh3-yl]phenyl }pyrrolidin-3-amine;

js) 1- {4-[2-(2,4,6-trifluorobenzyl)-7-(trifluoromethyl)-2H-indazol3-yl]phenyl }piperidin-4-one;

jt) methyl ((3R)-1- {4-[2-(2,4,6-trifluorobenzyl)-7-(trifluoromethyl)-2H-indazol-3 -yl]phenyl }piperidin-3-yl)acetate;

jy) ((3R)-1- {4- [2-(2,4,6-trifluorobenzyl)-7-(trifluoromethyl)-2H-indazol-3-yl]phenyl }piperidin-3-yl)acetic acid;

jz) 1- {4-[2-(2,4,6-trifluorobenzyl)-7-(trifluoromethyl)-2H-indazol-3-yl]phenyl }-N-[4-(trifluoromethyl)benzyl]piperidin-4-amine;

ka) N-(2-fluorophenyl)-N'- {3-[2-(2,4,6-trifluorobenzyl)-7-(trifluoromethyl)-2H-indazol-3-yl]phenyl }urea;

kb) ethyl 1- {4-[2-(2,4,6-trifluorobenzyl)-7-(trifluoromethyl)-2H-indazol-3-yl]phenyl }piperidine-2-carboxylate;

kc) N-phenyl-N'- {3-[2-(2,4,6-trifluorobenzyl)-7-(trifluoromethyl)-2H-indazol-3-yl]phenyl}urea;

kd) N-(2-fluorophenyl)-Nt- {4-112-(2,4,6-trifluorobenzyl)-7-(trifluoromethyl)-2H-indazol-3-yl]phenyl }urea;

ke) N-(2-chlorophenyl)-N'- {4-[2-(2,4,6-trifluorobenzyl)-7-(trifluoromethyl)-2H-indazol-3-yllphenyl}urea;

kf) ethyl 1- {4-112-(2,4,6-trifluorobenzyl)-7-(trifluoromethyl)-2H-indazol-3-yl]phenyl }piperidine-3-carboxylate;

kg) N-(2-chlorophenyl)-N'- {3-[2-(2,4,6-trifluorobenzyl)-7-(trifluoromethyl)-2H-indazol-3-yl]phenyl }urea;

kh) N-phenyl-N'- {4- [2-(2,4,6-trifluorobenzyl)-7-(trifluoromethyl)-2H-indazol-3-yl]phenyl }urea;

ki) tert-butyl ((3 S)-1- {4-[2-(2,4,6-trifluorobenzyl)-7-(trifluoromethyl)-2H-indazol-3-yl]phenyl }pyrrolidin-3.-yl)carbamate;

kj) tert-butyl ((3 R)-1- {4-[2-(2,4,6-trifluorobenzyl)-7-(trifluoromethyl)-2H-indazol-3-yl]phenyl }pyrrolidin-3-yl)carbamate;

kk) N-(2-phenylethyl)-1- {4-[2-(2 ,4,6-trifluorobenzyl)-7-(trifluoromethyl)-2H-indazol-3-yl]phenyl }piperidin-4-amine;

kl) (3 S)-1-cyclohexyl-N- {4- [2-(2,4,6-trifluorobenzyl)-7-(trifluoromethyl)-2H-indazol-3-ylphenyl }pyrrolidin-3-amine;

kin) (3 S)-1- {4-112-(2,4,6-trifluorobenzyl)-7-(trifluoromethyl)-2H-indazol-3-yl]phenyl }pyrrolidin-3-amine;

kn) (3 R)-1- {4-[2-(2,4,6-trifluorobenzyl)-7-(trifluoromethyl)-2H-indazol-3-yl]phenyl }pyrrolidin-3-amine;

ko) N-butyl-1- {4-[2-(2,4,6-trifluorobenzyl)-7-(trifluoromethyl)-2H-indazol-3-yl]phenyl }piperidin-4-amine;

kp) 3-(4-piperazin-1-ylphenyl)-2-(2,4,6-trifluorobenzyl)-7-(trifluoromethyl)-2H-indazole;

kq) (3R)-1-(3-methylbut-2-enyl)-N- {4-[2-(2,4,6-trifluorobenzyl)-7-(trifluoromethyl)-2H-indazol-3-yl]phenyl }pyrrolidin-3-amine;

kr) (3 S)-1-(3-methylbut-2-enyl)-N- {4- [2-(2,4,6-trifluorobenzyl)-7-(trifluoromethyl)-2H-indazol-3-yl]phenyl }pyrrolidin-3-amine;

kt) (3R)-N- {4-[2-(2,4,6-trifluorobenzyl)-7-(trifluoromethyl)-2H-indazol-3-yl]phenyl }-1-(3,3,3-trifluoropropyl)pyrrolidin-3-amine;

ku) (3R)-1-(2-methylprop-2-enyl)-N- {4-[2-(2,4,6-trifluorobenzyl)-7-(trifluoromethyl)-2H-indazol-3-yl]phenyl }pyrrolidin-3-amine;

kv) (3R)-1-[(2E)-pent-2-enyl]-N- {4-[2-(2,4,6-trifluorobenzyl)-7-(trifluoromethyl)-2H-indazol-3-yl]phenyl }pyrrolidin-3-amine;

kw) (3R)-1-cyclopentyl-N- {4-[2-(2,4,6-trifluorobenzyl)-7-(trifluoromethyl)-2H-indazol-3-yl]phenyl }pyrrolidin-3-amine;

kx) 3- [4-(4-morpholin-4-ylpiperidin-1-yl)phenyl]-2-(2,4,6-trifluorobenzyl)-7-(trifluoromethyl)-2H-indazole;

ky) (3R)-1-hexyl-N- {4- [2-(2 ,4,6-trifluorobenzyl)-7-(trifluoromethyl)-2H-indazol-3-yl]phenyl }pyrrolidin-3-amine;

kz) (3 R)-1-isopropyl-N- {4-[2-(2,4,6-trifluorobenzyl)-7-(trifluoromethyl)-2H-indazol-3-yl]phenyl }pyrrolidin-3-amine;

la) (3 S)-1-cyclopentyl-N- {4- 2-(2,4,6-trifluorobenzyl)-7-(trifluoromethyl)-2H-indazol-3-yl jphenyl }pyrrolidin-3-amine;

lb) (3 S)-1-[(2E)-pent-2-enyl]-N- {4-[2-(2,4,6-trifluorobenzyl)-7-(trifluoromethyl)-2H-indazol-3-yl]phenyl }pyrrolidin-3-amine;

lc) (3 S)-1-(2-methylprop-2-enyl)-N- {4- [2-(2,4,6-trifluorobenzyl)-7-(trifluoromethyl)-2H-indazol-3-yl]phenyl }pyrrolidin-3-amine;

ld) (3 S)-N- {4-[2-(2,4,6-trifluorobenzyl)-7-(trifluoromethyl)-2H-indazol-3-yl]phenyl }-1-(3,3,3-trifluoropropyl)pyrrolidin-3-amine;

le) (3 S)-1-hexyl-N- {4- [2-(2,4,6-trifluorobenzyl)-7-(trifluoromethyl)-2H-indazol-3-yl]phenyl }pyrrolidin-3-amine;

lf) (3 S)-1-isobutyl-N- {4-[2-(2,4,6-trifluorobenzyl)-7-(trifluoromethyl)-2H-indazol-3-yl]phenyl }pyrrolidin-3-amine;

lg) 8- {3-[2-(2,4,6-trifluorobenzyl)-7-(trifluoromethyl)-2H-indazol-3-yl]phenyl }-1,4-dioxa-8-azaspiro[4.5]jdecane;

lh) 7- {3-[2-(2,4,6-trifluorobenzyl)-7-(trifluoromethyl)-2H-indazol-3-yl]phenyl }-1,4-dioxa-7-azaspiro [4.5]decane;

li) 7- {4-[2-(2,4,6-trifluorobenzyl)-7-(trifluoromethyl)-2H-indazol-3-yl]phenyl 1-1,4-dioxa-7-azaspiro[4.5]decane;

lj) methyl ((3 S)-1- {4- [2-(2,4,6-trifluorobenzyl)-7-(trifluoromethyl)-2H-indazol-3 -yl]phenyl }piperidin-3-yl)acetate;

lk) ((3 S)-1- {4-[2-(2,4,6-trifluorobenzyl)-7-(trifluoromethyl)-2H-indazol-3-yl]phenyl}piperidin-3-yl)acetic acid;

ll) 1- {3-[2-(2,4,6-trifluorobenzyl)-7-(trifluoromethyl)-2H-indazol-3-yl]phenyl }piperidin-4-one;

lm) 3-(4-bromophenyl)-2-(2-chloro-4-fluorobenzyl)-7-(trifluoromethyl)-2H-indazole;

ln) 3-[4-(4-benzoylpiperazin-1-yl)phenyl]-2-(2,4,6-trifluorobenzyl)-7-(trifluoromethyl)-2H-indazole;

lo) 3- {4-[4-(2-chlorobenzoyl)piperazin-1-yl]phenyl }-2-(2,4,6-trifluorobenzyl)-7-(trifluoromethyl)-2H-indazole;

lp) 3- {4-[4-(2-methoxybenzoyl)piperazin-1-yl]phenyl }-2-(2,4,6-trifluorobenzyl)-7-(trifluoromethyl)-2H-indazole;

lq) 3- {4-[4-(3-methoxybenzoyl)piperazin-1-yl]phenyl }-2-(2,4,6-trifluorobenzyl)-7-(trifluoromethyl)-2H-indazole;

lr) 3- {4-[4-(4-methylpiperazin-1-yl)piperidin-1-yl]phenyl }-2-(2,4,6-trifluorobenzyl)-7-(trifluoromethyl)-2H-indazole;

ls) methyl ((3 R)-1- {4-[2-(2-chloro-4-fluorobenzyl)-7-(trifluoromethyl)-2H-indazol-3-yl]phenyl }piperidin-3-yl)acetate;

lt) 3- {4- [4-(2-thienylcarbonyl)piperazin-1-yl]phenyl }-2-(2,4,6-trifluorobenzyl)-7-(trifluoromethyl)-2H-indazole;

lu) ((3R)-1- {4- [2-(2-chloro-4-fluorobenzyl)-7-(trifluoromethyl)-2H-indazol-3-yl]phenyl}piperidin-3-yl)acetic acid;

lv) 3- {4-[4-(4-methoxybenzoyl)piperazin-1-yl]phenyl }-2-(2,4,6-trifluorobenzyl)-7-(trifluoromethyl)-2H-indazole;

lw) 3-[3-(3-morpholin-4-ylpiperidin-1-yl)phenyl]-2-(2,4,6-trifluorobenzyl)-7-(trifluoromethyl)-2H-indazole;

lx) N,N-dipropyl-1- {4-[2-(2,4,6-trifluorobenzyl)-7-(trifluoromethyl)-2H-indazol-3-yl]phenyl }piperidin-4-amine;

ly) N-(cyclohexylmethyl)-1- {4- [2-(2,4,6-trifluorobenzyl)-7-(trifluoromethyl)-2H-indazol-3-yl]phenyl }piperidin-4-amine;

lz) N-phenyl-1- {4-[2-(2,4,6-trifluorobenzyl)-7-(trifluoromethyl)-2H-indazol-3-yl]phenyl }piperidin-4-amine;

ma) 3- [3-(4-morpholin-4-ylpiperidin-1-yl)phenyl]-2-(2,4,6-trifluorobenzyl)-7-(trifluoromethyl)-2H-indazole;

mb) N-ethyl-N-methyl-i- {3- [2-(2,4,6-trifluorobenzyl)-7-(trifluoromethyl)-2H-indazol-3-yl]phenyl }piperidin-4-amine;

mc) N-(2-phenylethyl)-1- {3-[2-(2,4,6-trifluorobenzyl)-7-(trifluoromethyl)-2H-indazol-3-yl]phenyl }piperidin-4-amine;

md) N-butyl-1- {3-[2-(2,4,6-trifluorobenzyl)-7-(trifluoromethyl)-2H-indazol-3 -yl]phenyl }piperidin-4-amine;

me) 3- {3-[4-(4-methylpiperazin-1-yl)piperidin-1-yl]phenyl }-2-(2,4,6-trifluorobenzyl)-7-(trifluoromethyl)-2H-indazole;

mf) N-(cyclohexylmethyl)-1- {3- [2-(2,4,6-trifluorobenzyl)-7-(trifluoromethyl)-2H-indazol-3-yl]phenyl }piperidin-4-amine;

mg) N-phenyl-1- {3-[2-(2,4,6-trifluorobenzyl)-7-(trifluoromethyl)-2H-indazol-3-yl]phenyl }piperidin-4-amine;

mh) 1- {3-[2-(2,4,6-trifluorobenzyl)-7-(trifluoromethyl)-2H-indazol-3-yl]phenyl }piperidin-4-ol;

ml) N-(1 H-indol-5-ylmethyl)-3-[2-(2,4,6-trifluorobenzyl)-7-(trifluoromethyl)-2H-indazol-3-yl]aniline;

mm) {3-[2-(2,4-difluorobenzyl)-7-(trifluoromethyl)-2H-indazol-3-yl]phenyl }amine; inn) N-[(1-methyl-i H-indol-5-yl)methyl]-3- [2-(2,4,6-trifluorobenzyl)-7-(trifluoromethyl)-2H-indazol-3-yl]aniline;

mo) 3-(4-bromophenyl)-2-(2,4-difluorobenzyl)-7-(trifluoromethyl)-2H-indazole;

mp) 3-(4-bromophenyl)-2-(2,6-dichlorobenzyl)-7-(trifluoromethyl)-2H-indazole;

mq) methyl ((3 R)-1- {4-[2-(2,4-difluorobenzyl)-7-(trifluoromethyl)-2H-indazol-3 -yl]phenyl }piperidin-3-yl)acetate;

mr) methyl ((3 R)-1- {4-[2-(2,6-dichlorobenzyl)-7-(trifluoromethyl)-2H-indazol-3 -yl]phenyl }piperidin-3-yl)acetate;

ms) ((3R)-1- {4-42-(2,4-difluorobenzyl)-7-(trifluoromethyl)-2H-indazol-3-yl]phenyl }piperidin-3-yl)acetic acid;

mt) ((3R)-1- {4-[2-(2,6-dichlorobenzyl)-7-(trifluoromethyl)-2H-indazol-3-yl]phenyl }piperidin-3-yl)acetic acid;

mu) 3-(3-bromophenyl)-2-(2,4,6-trifluorobenzyl)-7-(trifluoromethyl)-2H-indazole;

my) {3-[2-(2,4-difluorobenzyl)-7-(trifluoromethyl)-2H-indazol-3-yl]phenyl }[(1-methyl-i H-indol-2-yl)methyll amine;

mw) 3-(3-ethynylphenyl)-2-(2,4,6-trifluorobenzyl)-7-(trifluoromethyl)-2H-indazole;

my) N-(2-fluoro-4-methoxybenzyl)-3-[2-(2,4,6-trifluorobenzyl)-7-(trifluoromethyl)-2H-indazol-3-yl]aniline;

mz) N- [2-fluoro-5-(trifluoromethyl)benzyl]-3-[2-(2,4,6-trifluorobenzyl)-7-(trifluoromethyl)-2H-indazol-3-yl]aniline;

na) N-(2,5-dimethylbenzyl)-3- [2-(2,4,6-trifluorobenzyl)-7-(trifluoromethyl)-2H-indazol-3 -yl]aniline;

nb) N- [2-fluoro-3-(trifluoromethyl)benzyl]-3- [2-(2,4,6-trifluorobenzyl)-7-(trifluoromethyl)-2H-indazol-3-yl]aniline;

nc) N-(2,5-dimethylbenzyl)-4- [2-(2,4,6-trifluorobenzyl)-7-(trifluoromethyl)-2H-indazol-3 -yl]aniline;

nd) N-[2-fluoro-5-(trifluoromethyl)benzyl]-4-[2-(2,4,6-trifluorobenzyl)-7-(trifluoromethyl)-2H-indazol-3-yl]aniline;

ne) (3 R)-1-(2,4-dimethoxybenzoyl)-N- {4-[2-(2,4,6-trifluorobenzyl)-7-(trifluoromethyl)-2H-indazol-3-yl]phenyl }pyrrolidin-3-amine;

nf) N-(1 H-indol-4-ylmethyl)-3- [2-(2,4,6-trifluorobenzyl)-7-(trifluoromethyl)-2H-indazol-3-yl]aniline;

ng) N-[(3-methyl-1-benzothien-2-yl)methyl]-3-[2-(2,4,6-trifluorobenzyl)-7-(trifluoromethyl)-2H-indazol-3-yl]aniline;

nh) N-(pyridin-4-ylmethyl)-3-[2-(2,4,6-trifluorobenzyl)-7-(trifluoromethyl)-2H-indazol-3-yl7janiline;

ni) N-(pyridin-2-ylmethyl)-3-[2-(2,4,6-trifluorobenzyl)-7-(trifluoromethyl)-2H-indazol-3-yl]aniline;

nj) N-(pyridin-3-ylmethyl)-3-[2-(2,4,6-trifluorobenzyl)-7-(trifluoromethyl)-2H-indazol-3-yl]aniline;

nk) N-(1H-indol-7-ylmethyl)-3-[2-(2,4,6-trifluorobenzyl)-7-(trifluoromethyl)-2H-indazol-3-yl]aniline;

nl) N-[(3-methyl-2-thienyl)methyl]-3-[2-(2,4,6-trifluorobenzyl)-7-(trifluoromethyl)-2H-indazol-3-yl]aniline;

nm) N-[(5-methyl-2-thienyl)methyl]-3-[2-(2,4,6-trifluorobenzyl)-7-(trifluoromethyl)-2H-indazol-3-yl]aniline;

nn) N-[(4-bromo-2-thienyl)methyl]-3-[2-(2,4,6-trifluorobenzyl)-7-(trifluoromethyl)-2H-indazol-3-yl]aniline;

no) N-[(5-bromo-2-thienyl)methyl]-3-[2-(2,4,6-trifluorobenzyl)-7-(trifluoromethyl)-2H-indazol-3-yl]aniline;

np) N-[(5-chloro-2-thienyl)methyl]-3-[2-(2,4,6-trifluorobenzyl)-7-(trifluoromethyl)-2H-indazol-3-yl]aniline;

nq) ethyl 3-({3-[2-(2,4,6-trifluorobenzyl)-7-(trifluoromethyl)-2H-indazol-3-yl]phenyl}ethynyl)benzoate;

nv) ethyl 3-(2-{3-[2-(2,4,6-trifluorobenzyl)-7-(trifluoromethyl)-2H-indazol-3-yl]phenyl}ethyl)benzoate;

nw) 3-({3-[2-(2,4,6-trifluorobenzyl)-7-(trifluoromethyl)-2H-indazol-3-yl]phenyl}ethynyl)benzoic acid;

nz) 3-(2-{3-[2-(2,4,6-trifluorobenzyl)-7-(trifluoromethyl)-2H-indazol-3-yl]phenyl}ethyl)benzoic acid;

of) N-methyl-3-({3-L2-(2,4,6-trifluorobenzyl)-7-(trifluoromethyl)-2H-indazol-3-yl]phenyl}ethynyl)benzamide;

og) 3-(3-{[3-(morpholin-4-ylcarbonyl)phenyl]ethynyl}phenyl)-2-(2,4,6-trifluorobenzyl)-7-(trifluoromethyl)-2H-indazole;

oh) tert-butyl 4-[3-({3-[2-(2,4,6-trifluorobenzyl)-7-(trifluoromethyl)-2H-indazol-3-yl]phenyl}ethynyl)benzoyl]piperazine-1-carboxylate;

oi) N-methyl-3-(2-{3-[2-(2,4,6-trifluorobenzyl)-7-(trifluoromethyl)-2H-indazol-3-yl]phenyl}ethyl)benzamide;

oj) 3-(3-{2-[3-(morpholin-4-ylcarbonyl)phenyl]ethyl}phenyl)-2-(2,4,6-trifluorobenzyl)-7-(trifluoromethyl)-2H-indazole;

ok) tert-butyl 4-[3-(2-{3-[2-(2,4,6-trifluorobenzyl)-7-(trifluoromethyl)-2H-indazol-3-yl]phenyl}ethyl)benzoyl]piperazine-1-carboxylate;

ol) N-[(1-ethyl-1H-indol-5-yl)methyl]-3-[2-(2,4,6-trifluorobenzyl)-7-(trifluoromethyl)-2H-indazol-3-yl]aniline;

om) N-[(1-propyl-1H-indol-5-yl)methyl]-3-[2-(2,4,6-trifluorobenzyl)-7-(trifluoromethyl)-2H-indazol-3-yl]aniline;

on) N-[(1-butyl-1H-indol-5-yl)methyl]-3-[2-(2,4,6-trifluorobenzyl)-7-(trifluoromethyl)-2H-indazol-3-yl]aniline;

oo) N-[(1-isopropyl-1H-indol-5-yl)methyl]-3-[2-(2,4,6-trifluorobenzyl)-7-(trifluoromethyl)-2H-indazol-3-yl]aniline;

op) N-[(1-sec-butyl-1H-indol-5-yl)methyl]-3-[2-(2,4,6-trifluorobenzyl)-7-(trifluoromethyl)-2H-indazol-3-yl]aniline;

oq) N-[(2-methyl-1H-imidazol-5-yl)methyl]-3-[2-(2,4,6-trifluorobenzyl)-7-(trifluoromethyl)-2H-indazol-3-yl]aniline;

or) N-(2-naphthylmethyl)-3-[2-(2,4,6-trifluorobenzyl)-7-(trifluoromethyl)-2H-indazol-3-y17J aniline;

os) 3-{3-[(2,5-dichlorophenyl)ethynyl]phenyl}-2-(2,4,6-trifluorobenzyl)-7-(trifluoromethyl)-2H-indazole;

ot) 3-{3-[(2,4-dichlorophenyl)ethynyl]phenyl}-2-(2,4,6-trifluorobenzyl)-7-(trifluoromethyl)-2H-indazole;

ou) 3-{3-[2-(2,4-dichlorophenyl)ethyl]phenyl}-2-(2,4,6-trifluorobenzyl)-7-(trifluoromethyl)-2H-indazole;

ov) 2-(2,4,6-trifluorobenzyl)-7-(trifluoromethyl)-3-(3-{[2-(trifluoromethyl)phenyl]ethynyl}phenyl)-2H-indazole;

ow) 2-(2,4,6-trifluorobenzyl)-7-(trifluoromethyl)-3-(3-{2-[2-(trifluoromethyl)phenyl]ethyl}phenyl)-2H-indazole;

oz) 3-{3-[2-(2,5-dichlorophenyl)ethyl]phenyl}-2-(2,4,6-trifluorobenzyl)-7-(trifluoromethyl)-2H-indazole;

pa) 3-[3-(2-phenylethyl)phenyl]-2-(2,4,6-trifluorobenzyl)-7-(trifluoromethyl)-2H-indazole;

pd) 3-(3-{[2-chloro-5-(trifluoromethyl)phenyl]ethynyl}phenyl)-2-(2,4,6-trifluorobenzyl)-7-(trifluoromethyl)-2H-indazole;

pe) 3-{3-[(2-bromo-5-fluorophenyl)ethynyl]phenyl}-2-(2,4,6-trifluorobenzyl)-7-(trifluoromethyl)-2H-indazole;

pf) 3-(3-{2-[2-chloro-5-(trifluoromethyl)phenyl]ethyl}phenyl)-2-(2,4,6-trifluorobenzyl)-7-(trifluoromethyl)-2H-indazole;

pg) 3-{3-[2-(2-bromo-5-fluorophenyl)ethyl]phenyl}-2-(2,4,6-trifluorobenzyl)-7-(trifluoromethyl)-2H-indazole;

ph) 3-{3-[2-(3-fluorophenyl)ethyl]phenyl}-2-(2,4,6-trifluorobenzyl)-7-(trifluoromethyl)-2H-indazole;

pi) 4-amino-3-({3-[2-(2,4,6-trifluorobenzyl)-7-(trifluoromethyl)-2H-indazol-3-yl]phenyl}ethynyl)benzonitrile;

pj) 3-{3-[(3-chloro-2-fluorophenyl)ethynyl]phenyl}-2-(2,4,6-trifluorobenzyl)-7-(trifluoromethyl)-2H-indazole;

pk) [3-({3-[2-(2,4,6-trifluorobenzyl)-7-(trifluoromethyl)-2H-indazol-3-yl]phenyl}ethynyl)phenyl]methanol;

pl) 4-amino-3-(2-{3-[2-(2,4,6-trifluorobenzyl)-7-(trifluoromethyl)-2H-indazol-3-yl]phenyl}ethyl)benzonitrile;

pm) 3-{3-[(2,3-dichlorophenyl)ethynyl]phenyl}-2-(2,4,6-trifluorobenzyl)-7-(trifluoromethyl)-2H-indazole;

px) 3-{3-[2-(2,3-dichlorophenyl)ethyl]phenyl}-2-(2,4,6-trifluorobenzyl)-7-(trifluoromethyl)-2H-indazole;

py) 3-{3-[2-(3-chloro-2-fluorophenyl)ethyl]phenyl}-2-(2,4,6-trifluorobenzyl)-7-(trifluoromethyl)-2H-indazole;

pz) [3-(2-{3-[2-(2,4,6-trifluorobenzyl)-7-(trifluoromethyl)-2H-indazol-3-yl]phenyl}ethyl)phenyl]methanol;

qa) 3-(4-ethynylphenyl)-2-(2,4,6-trifluorobenzyl)-7-(trifluoromethyl)-2H-indazole; qb) ethyl 3-({4-[2-(2,4,6-trifluorobenzyl)-7-(trifluoromethyl)-2H-indazol-3-yl]phenyl}ethynyl)benzoate;

qc) 3-({4-[2-(2,4,6-trifluorobenzyl)-7-(trifluoromethyl)-2H-indazol-3-yl]phenyl}ethynyl)benzoic acid;

qd) N-[3-({3-[2-(2,4,6-trifluorobenzyl)-7-(trifluoromethyl)-2H-indazol-3-yl]phenyl}ethynyl)phenyl]morpholine-4-carboxamide;

qe) tert-butyl 4-({[3-({3-[2-(2,4,6-trifluorobenzyl)-7-(trifluoromethyl)-2H-indazol-3-yl]phenyl}ethynyl)phenyl]amino}carbonyl)piperazine-1-carboxylate;

qf) 2-methyl-N-[3-({3-[2-(2,4,6-trifluorobenzyl)-7-(trifluoromethyl)-2H-indazol-3-yl]phenyl}ethynyl)phenyl]piperidine-1-carboxamide;

qg) 3-methyl-N-[3-({3-[2-(2,4,6-trifluorobenzyl)-7-(trifluoromethyl)-2H-indazol-3-yl]phenyl}ethynyl)phenyl]piperidine-1-carboxamide;

qh) 4-methyl-N-[3-({3-[2-(2,4,6-trifluorobenzyl)-7-(trifluoromethyl)-2H-indazol-3-yl]phenyl}ethynyl)phenyl]piperidine-1-carboxamide;

qi) 3-(hydroxymethyl)-N-[3-({3-[2-(2,4,6-trifluorobenzyl)-7-(trifluoromethyl)-2H-indazol-3-yl]phenyl}ethynyl)phenyl]piperidine-1-carboxamide;

qj) N-isopropyl-N'-[3-({3-[2-(2,4,6-trifluorobenzyl)-7-(trifluoromethyl)-2H-indazol-3-yl]phenyl}ethynyl)phenyl]urea;

qk) N,N-dipropyl-Nt-[3-({3-[2-(2,4,6-trifluorobenzyl)-7-(trifluoromethyl)-2H-indazol-3-yl]phenyl}ethynyl)phenyl]urea;

ql) N-methyl-N'-[3-({3-[2-(2,4,6-trifluorobenzyl)-7-(trifluoromethyl)-2H-indazol-3-yl]phenyl}ethynyl)phenyl]urea;

qm) N,N-dimethyl-N'-[3-({3- [2-(2,4,6-trifluorobenzyl)-7-(trifluoromethyl)-2H-indazol-3-yl]phenyl}ethynyl)phenylurea;

qn) 3-(4- {[2-chloro-5-(trifluoromethyl)phenyl]ethynyl}phenyl)-2-(2,4,6-trifluorobenzyl)-7-(trifluoromethyl)-2H-indazole;

qo) 3- {4-[(2,4-difluorophenyl)ethynyl]phenyl}-2-(2,4,6-trifluorobenzyl)-7-(trifluoromethyl)-2H-indazole;

qp) 3- {4-[(3,5-dimethylphenyl)ethynyl]phenyl}-2-(2,4,6-trifluorobenzyl)-7-(trifluoromethyl)-2H-indazole;

qq) 3- {4- [(3-chloro-2-fluorophenyl)ethynyl]phenyl}-2-(2,4,6-trifluorobenzyl)-7-(trifluoromethyl)-2H-indazole;

qr) 3- {4- [(2,3-dichlorophenyl)ethynyl]phenyl}-2-(2,4,6-trifluorobenzyl)-7-(trifluoromethyl)-2H-indazole;

qs) 3- {4-[(2,3-dimethylphenyl)ethynyl]phenyl}-2-(2,4,6-trifluorobenzyl)-7-(trifluoromethyl)-2H-indazole;

qt) tert-butyl 4- [3-({4- [2-(2,4,6-trifluorobenzyl)-7-(trifluoromethyl)-2H-indazol-3-yl]phenyl}ethynyl)benzoyl]piperazine-1-carboxylate;

qu) 3-(3-bromophenyl)-2-(4-chloro-2-fluorobenzyl)-7-(trifluoromethyl)-2H-indazole;

qv) 1-methyl-3-[3-({3-[2-(2,4,6-trifluorobenzyl)-7-(trifluoromethyl)-2H-indazol-3-yl]phenyl}ethynyl)phenyl]imidazolidin-2-one;

qw) methyl [3-({3- [2-(2,4,6-trifluorobenzyl)-7-(trifluoromethyl)-2H-indazol-3 -yl]phenyl}ethynyl)phenyl]carbamate;

qx) N-(methylsulfonyl)-N-[3-({3- [2-(2,4,6-trifluorobenzyl)-7-(trifluoromethyl)-2H-indazol-3-yl]phenyl}ethynyl)phenyl]methanesulfonamide;

qy) 3-[3-(pyridin-3-ylethynyl)phenylll-2-(2,4,6-trifluorobenzyl)-7-(trifluoromethyl)-2H-indazole;

qz) 3- [3-(pyridin-4-ylethynyl)phenyl]-2-(2,4,6-trifluorobenzyl)-7-(trifluoromethyl)-2H-indazole;

ra) 6-methyl-2-({3-[2-(2,4,6-trifluorobenzyl)-7-(trifluoromethyl)-2H-indazol-3 -yl]phenyl}ethynyl)pyridin-3-ol;

rb) 3- [3-(pyridin-2-ylethynyl)phenyl]-2-(2,4,6-trifluorobenzyl)-7-(trifluoromethyl)-2H-indazole;

rc) 2-({3-[2-(2,4,6-trifluorobenzyl)-7-(trifluoromethyl)-2H-indazol-3-yl]phenyl}ethynyl)pyridin-3-ol;

rf) tert-butyl 6-methyl-5- {3- [2-(2,4,6-trifluorobenzyl)-7-(trifluoromethyl)-2H-indazol-3-yl]phenoxy}-1 H-indole-1-carboxylate;

rg) tert-butyl 6-fluoro-5- {3- [2-(2,4,6-trifluorobenzyl)-7-(trifluoromethyl)-2H-indazol-3-yl]phenoxy}-1 H-indole-1-carboxylate;

rh) 5- {3-[2-(4-chloro-2-fluorobenzyl)-7-(trifluoromethyl)-2H-indazol-3-yl]phenoxy}-3,4-dihydronaphthalen-1 (2H)-one;

ri) 3-(3-bromophenyl)-2-(2-chloro-4-fluorobenzyl)-7-(trifluoromethyl)-2H-indazole;

rj) 3- {3-[4-(morpholin-4-ylsulfonyl)phenoxy]phenyl}-2-(2,4,6-trifluorobenzyl)-7-(trifluoromethyl)-2H-indazole;

rk) 3- {3-[4-(pyrrolidin-1-ylsulfonyl)phenoxy]phenyl}-2-(2,4,6-trifluorobenzyl)-7-(trifluoromethyl)-2H-indazole;

rl) N-propyl-4- {3-[2-(2,4,6-trifluorobenzyl)-7-(trifluoromethyl)-2H-indazol-3-yl]phenoxy}benzenesulfonamide;

rm) N-ethyl-N-methyl-4- {3-[2-(2,4,6-trifluorobenzyl)-7-(trifluoromethyl)-2H-indazol-3 -yl]phenoxy}benzenesulfonamide;

rn) N,N-diethyl-4- {3- [2-(2,4,6-trifluorobenzyl)-7-(trifluoromethyl)-2H-indazol-3-yl]phenoxy}benzenesulfonamide;

ro) 3- {3- [4-(piperidin-1-ylsulfonyl)phenoxy]phenyl}-2-(2,4,6-trifluorobenzyl)-7-(trifluoromethyl)-2H-indazole;

rp) N,N-dimethyl-4- {3-[2-(2,4,6-trifluorobenzyl)-7-(trifluoromethyl)-2H-indazol-3-yl]phenoxy}benzenesulfonamide;

rq) 4-fluoro-2-({3- [2-(2,4,6-trifluorobenzyl)-7-(trifluoromethyl)-2H-indazol-3 -yl]phenyl}ethynyl)aniline;

rr) 4-chloro-2-fluoro-6-({3-[2-(2,4,6-trifluorobenzyl)-7-(trifluoromethyl)-2H-indazol-3-yl]phenyl}ethynyl)aniline;

rs) methyl [4-fluoro-2-({3-[2-(2,4,6-trifluorobenzyl)-7-(trifluoromethyl)-2H-indazol-3-yl]phenyl}ethynyl)phenyl]carbamate;

rt) 3- [3-(5-fluoro-1 H-indol-2-yl)phenyl]-2-(2,4,6-trifluorobenzyl)-7-(trifluoromethyl)-2H-indazole;

ru) 3- [3-(5-fluoro-1-methyl-i H-indol-2-yl)phenyl]-2-(2,4,6-trifluorobenzyl)-7-(trifluoromethyl)-2H-indazole;

tx) [3-({4-[2-(2,4,6-trifluorobenzyl)-7-(trifluoromethyl)-2H-indazol-3-yl]phenyl}amino)phenyl]acetic acid;

ue) [3-({4- [2-(4-chloro-2-fluorobenzyl)-7-(trifluoromethyl)-2H-indazol-3-yl]phenyl}amino)phenyl]acetic acid;

uf) [3-({4-[2-(2,4-dimethylbenzyl)-7-(trifluoromethyl)-2H-indazol-3-yl]phenyl}arnino)phenyllacetic acid;

ug) {3-[2-(4-chloro-2-fluorobenzyl)-7-(trifluoromethyl)-2H-indazol-3-yl]phenoxy}(phenyl)acetic acid;

ui) 2-(4-chloro-2-fluorobenzyl)-3-[3-(4-methoxybenzyl)phenyl]-7-(trifluoromethyl)-2H-indazole;

uj) 2-(4-chloro-2-fluorobenzyl)-3-[3-(3,5-dimethoxybenzyl)phenyl]-7-(trifluoromethyl)-2H-indazole;

uk) 2-(4-chloro-2-fluorobenzyl)-3-[3-(3,5-dimethylbenzyl)phenyl]-7-(trifluoromethyl)-2H-indazole;

ul) 2-(4-chloro-2-fluorobenzyl)-3- {3- [(2,3-dimethylphenoxy)methyl]phenyl}-7-(trifluoromethyl)-2H-indazole;

um) 2-(4-chloro-2-fluorobenzyl)-3-(3- {[2-chloro-5-(trifluoromethyl)phenoxy]methyl}phenyl)-7-(trifluoromethyl)-2H-indazole;

un) 2-(4-chloro-2-fluorobenzyl)-3-(3- {[2-chloro-3-(trifluoromethyl)phenoxy]rnethyl}phenyl)-7-(trifluoromethyl)-2H-indazole;

uo) 2-(4-chloro-2-fluorobenzyl)-3- {3- [(1-naphthyloxy)methyl]phenyl}-7-(trifluoromethyl)-2H-indazole;

up) 3- {3-[(2-tert-butyl-5-rnethylphenoxy)rnethyl]phenyl}-2-(4-chloro-2-fluorobenzyl)-7-(trifluorornethyl)-2H-indazole;

ur) 2-(4-chloro-2-fluorobenzyl)-3- {3-[(4-fluoro-2-methylphenoxy)rnethyl]phenyl}-7-(trifluorornethyl)-2H-indazole;

us) 2-(4-chloro-2-fluorobenzyl)-3- {3-[(2,6-dimethylphenoxy)methyl]phenyl}-7-(trifluoromethyl)-2H-indazole;

ut) 5-({3- [2-(4-chloro-2-fluorobenzyl)-7-(trifluoromethyl)-2H-indazol-3-yl]benzyl}oxy)-3,4-dihydronaphthalen-1 (2H)-one;

uu) 2-(4-chloro-2-fluorobenzyl)-3-[3-(2-methoxybenzyl)phenyl]-7-(trifluoromethyl)-2H-indazole;

uv) 2-(4-chloro-2-fluorobenzyl)-3-[3-(3-methoxybenzyl)phenyl]-7-(trifluoromethyl)-2H-indazole;

uw) 2-(4-chloro-2-fluorobenzyl)-3-[3-(2,3-dimethoxybenzyl)phenyl]-7-(trifluoromethyl)-2H-indazole;

ux) 2-(4-chloro-2-fluorobenzyl)-3-(3- {[(3,3-dimethyl-2,3-dihydro-1 -benzofuran-7-yl)oxy]methyl}phenyl)-7-(trifluoromethyl)-2H-indazole;

uy) 3- {3- [(2-tert-butylphenoxy)methyl]phenyl}-2-(4-chloro-2-fluorobenzyl)-7-(trifluoromethyl)-2H-indazole;

uz) 2-(4-chloro-2-fluorobenzyl)-3- {3- [(2,3-dimethoxyphenoxy)methyl]phenyl }-7-(trifluoromethyl)-2H-indazole;

va) 2-(4-chloro-2-fluorobenzyl)-3-[3-(3,4-dimethoxybenzyl)phenyl]-7-(trifluoromethyl)-2H-indazole;

vb) 2-(4-chloro-2-fluorobenzyl)-3-[3-(4-chloro-2-fluorobenzyl)phenyl]-7-(trifluoromethyl)-2H-indazole;

vc) 2-(4-chloro-2-fluorobenzyl)-3-[3-(2-chloro-4-fluorobenzyl)phenyl]-7-(trifluoromethyl)-2H-indazole;

vd) 2-(4-chloro-2-fluorobenzyl)-3- {3- [2-fluoro-4-(trifluoromethyl)benzyl]phenyl }-7-(trifluoromethyl)-2H-indazole;

ve) 3- {3-[2,4-bis(trifluoromethyl)benzyl]phenyl }-2-(4-chloro-2-fluorobenzyl)-7-(trifluoromethyl)-2H-indazole;

vf) 2-(4-chloro-2-fluorobenzyl)-3-[3-(2,4-difluorobenzyl)phenyl]-7-(trifluoromethyl)-2H-indazole;

vg) 3- {3-[2,5-bis(trifluoromethyl)benzyl]phenyl }-2-(4-chloro-2-fluorobenzyl)-7-(trifluoromethyl)-2H-indazole;

vh) 2-(4-chloro-2-fluorobenzyl)-3- {3-[(2,6-dichlorophenoxy)methyl]phenyl }-7-(trifluoromethyl)-2H-indazole;

vi) 2-(4-chloro-2-fluorobenzyl)-3- {3- [(2,6-dimethoxyphenoxy)methyl]phenyl }-7-(trifluoromethyl)-2H-indazole;

vj) 2-(4-chloro-2-fluorobenzyl)-3- {3-[(2,6-dibromophenoxy)methyl]phenyl }-7-(trifluoromethyl)-2H-indazole;

vk) 2-(4-chloro-2-fluorobenzyl)-3-[3-(2-fluoro-3-methylbenzyl)phenyl]-7-(trifluoromethyl)-2H-indazole;

vl) 2-(4-chloro-2-fluorobenzyl)-3-[3-(6-chloro-2-fluoro-3-methylbenzyl)phenyl]-7-(trifluoromethyl)-2H-indazole;

vm) 3- {3-[(2-allyl-6-methylphenoxy)methyl]phenyl }-2-(4-chloro-2-fluorobenzyl)-7-(trifluoromethyl)-2H-indazole;

vn) 2-(4-chloro-2-fluorobenzyl)-3- {3- [(2,6-diisopropylphenoxy)methyl]phenyl }-7-(trifluoromethyl)-2H-indazole;

vo) 3- {3-[(2-tert-butyl-6-methylphenoxy)methyl]phenyl }-2-(4-chloro-2-fluorobenzyl)-7-(trifluoromethyl)-2H-indazole;

vp) 3- {3-[(2-allyl-6-methoxyphenoxy)methyl]phenyl }-2-(4-chloro-2-fluorobenzyl)-7-(trifluoromethyl)-2H-indazole;

vq) 2-(4-chloro-2-fluorobenzyl)-3- {3-[(2,5-dichlorophenoxy)methyl]phenyl }-7-(trifluoromethyl)-2H-indazole;

vr) 2-(4-chloro-2-fluorobenzyl)-3- {3-[(2,6-difluorophenoxy)methyl]phenyl }-7-(trifluoromethyl)-2H-indazole;

vs) 2-(4-chloro-2-fluorobenzyl)-3- {3-[3-(difluoromethoxy)benzyl]phenyl }-7-(trifluoromethyl)-2H-indazole;

vt) 2-(4-chloro-2-fluorobenzyl)-3-[3-(2-phenylethyl)phenyl]-7-(trifluoromethyl)-2H-indazole;

vu) 3-({3-[2-(4-chloro-2-fluorobenzyl)-7-(trifluoromethyl)-2H-indazol-3-yl]phenoxy}methyl)-N-propylbenzamide;

vv) N-benzyl-3-({3-[2-(4-chloro-2-fluorobenzyl)-7-(trifluoromethyl)-2H-indazol-3 -yl]phenoxy}methyl)benzamide;

vw) 3-({3-[2-(4-chloro-2-fluorobenzyl)-7-(trifluoromethyl)-2H-indazol-3-yl]phenoxy}methyl)-N-cyclopropylbenzamide;

vx) 2-(4-chloro-2-fluorobenzyl)-3-(3- {[3-(morpholin-4-ylcarbonyl)benzyl]oxy}phenyl)-7-(trifluoromethyl)-2H-indazole;

vy) 3-({3-[2-(4-chloro-2-fluorobenzyl)-7-(trifluoromethyl)-2H-indazol-3 -yl]phenoxy}methyl)-N-isopropylbenzamide;

xs) 2-(2,4-dimethylbenzyl)-3- {3-[(2,6-dimethylbenzyl)oxy]phenyl }-7-(trifluoromethyl)-2H-indazole;

xt) 3- {3-[(2,6-dimethylbenzyl)oxy]phenyl }-2-(2,4,6-trifluorobenzyl)-7-(trifluoromethyl)-2H-indazole;

xu) 3- {3-[(2-fluoro-6-nitrobenzyl)oxy]phenyl }-2-(2,4,6-trifluorobenzyl)-7-(trifluoromethyl)-2H-indazole;

yo) 2-(2,4-difluorobenzyl)-3- {3- [(2,6-dimethylbenzyl)oxy]phenyl }-7-(trifluoromethyl)-2H-indazole;

yp) 2-(4-chloro-2-fluorobenzyl)-3- {3- [(2,6-dimethylbenzyl)oxy]phenyl }-7-(trifluoromethyl)-2H-indazole;

yq) 2-(2-chloro-4-fluorobenzyl)-3- {3-[(2,6-dimethylbenzyl)oxy]phenyl }-7-(trifluoromethyl)-2H-indazole;

yt) 2-(2,4-dichlorobenzyl)-3- {3-[(2,6-dimethylbenzyl)oxy]phenyl }-7-(trifluoromethyl)-2H-indazole;

za) 2-[4-({3-[2-(2,4-dimethylbenzyl)-7-(trifluoromethyl)-2H-indazol-3 -yl]phenoxy}methyl)phenyl]-2-methylpropanoic acid;

zb) 2-methyl-2-[4-({3-[2-(2,4,6-trifluorobenzyl)-7-(trifluoromethyl)-2H-indazol-3-yl]phenoxy}methyl)phenyl]propanoic acid;

zc) 2- [4-({3- [2-(2,4-dimethylbenzyl)-7-(trifluoromethyl)-2H-indazol-3 -yl]phenoxy}methyl)phenyl]propanoic acid;

zd) 2-[4-({3- [2-(2,4,6-trifluorobenzyl)-7-(trifluoromethyl)-2H-indazol-3 -yl]phenoxy}methyl)phenyl]propanoic acid;

ze) 2-(2,4-dimethylbenzyl)-3- {3-[(2-fluoro-6-nitrobenzyl)oxy]phenyl }-7-(trifluoromethyl)-2H-indazole;

zf) 3-({3-[2-(2,4-dimethylbenzyl)-7-(trifluoromethyl)-2H-indazol-3-yl]phenoxy}methyl)benzonitrile;

zg) 3-[3-(benzyloxy)phenyl]-2-(2,4-dimethylbenzyl)-7-(trifluoromethyl)-2H-indazole;

zh) 2-(4-chloro-2-fluorobenzyl)-3- {3- [(2-fluoro-6-nitrobenzyl)oxy]phenyl }-7-(trifluoromethyl)-2H-indazole;

zi) 3-({3- [2-(4-chloro-2-fluorobenzyl)-7-(trifluoromethyl)-2H-indazol-3-yl]phenoxy}methyl)benzonitrile;

zj) 2- {3-[2-(4-chloro-2-fluorobenzyl)-7-(trifluoromethyl)-2H-indazol-3-yl]phenoxy}-2-(4-methylphenyl)propanoic acid;

abk) 2-(4-chloro-2-fluorobenzyl)-3- {3- [2-chloro-5-(trifluoromethyl)benzyl]phenyl }-7-(trifluoromethyl)-2H-indazole;

abl) 2-(4-chloro-2-fluorobenzyl)-3- {3-[4-(methylsulfonyl)benzyl]phenyl }-7-(trifluoromethyl)-2H-indazole;

abm) 2-(4-chloro-2-fluorobenzyl)-3- {3-[2-methyl-5-(trifluoromethyl)benzyl]phenyl }-7-(trifluoromethyl)-2H-indazole;

abn) 2-(4-chloro-2-fluorobenzyl)-3-[3-(2-chloro-5-fluorobenzyl)phenyl]-7-(trifluoromethyl)-2H-indazole;

abo) 2-(4-chloro-2-fluorobenzyl)-3- {3- [5-fluoro-2-(trifluoromethyl)benzyl]phenyl }-7-(trifluoromethyl)-2H-indazole;

abp) 2-(4-chloro-2-fluorobenzyl)-3-[3-(2,5-dichlorobenzyl)phenyl]-7-(trifluoromethyl)-2H-indazole;

abq) 2-(4-chloro-2-fluorobenzyl)-3- {3- [5-chloro-2-(trifluoromethyl)benzyl]phenyl }-7-(trifluoromethyl)-2H-indazole;

abr) 2-(4-chloro-2-fluorobenzyl)-3- {3-[3-(morpholin-4-ylcarbonyl)benzyl]phenyl 1-7-(trifluoromethyl)-2H-indazole;

abs) N-benzyl-3- {3-[2-(4-chloro-2-fluorobenzyl)-7-(trifluoromethyl)-2H-indazol-3 -yl]benzyl }benzamide;

abt) 2-(4-chloro-2-fluorobenzyl)-3- {3-[3-(pyrrolidin-1-ylcarbonyl)benzyl]phenyl }-7-(trifluoromethyl)-2H-indazole;

abu) 2-(4-chloro-2-fluorobenzyl)-3- {3-[3-(piperidin-1-ylcarbonyl)benzyl]phenyl }-7-(trifluoromethyl)-2H-indazole;

abv) 2-(4-chloro-2-fluorobenzyl)-3-[3-(3-chlorophenoxy)phenyl]-7-(trifluoromethyl)-2H-indazole;

abw) 2-(4-chloro-2-fluorobenzyl)-3-[3-(2-fluorophenoxy)phenyl]-7-(trifluoromethyl)-2H-indazole;

abx) 6- {3-[2-(4-chloro-2-fluorobenzyl)-7-(trifluoromethyl)-2H-indazol-3-yl]phenoxy}-2-naphthonitrile;

aby) 2-(4-chloro-2-fluorobenzyl)-3-[3-(5,6,7,8-tetrahydronaphthalen-1-yloxy)phenyl]-7-(trifluoromethyl)-2H-indazole;

abz) 2-(4-chloro-2-fluorobenzyl)-3-[3-(2-ethoxyphenoxy)phenyl]-7-(trifluoromethyl)-2H-indazole;

aca) 1-(2- {3-[2-(4-chloro-2-fluorobenzyl)-7-(trifluoromethyl)-2H-indazol-3-yl]phenoxy}phenyl)propan-1-one;

acb) 3- {3- [2-(1 H-benzimidazol-2-yl)phenoxy]phenyl }-2-(4-chloro-2-fluorobenzyl)-7-(trifluoromethyl)-2H-indazole;

acc) 2-(4-chloro-2-fluorobenzyl)-3-[3-(2-pyrrolidin-1-ylphenoxy)phenyl]-7-(trifluoromethyl)-2H-indazole;

acd) 3- {3-[2-(4-chloro-2-fluorobenzyl)-7-(trifluoromethyl)-2H-indazol-3-yl]benzyl }-N,N-diethylbenzamide;

ace) 3- {3-[2-(4-chloro-2-fluorobenzyl)-7-(trifluoromethyl)-2H-indazol-3-yl]benzyl }-N-cyclopropylbenzamide;

acf) 3- {3-[2-(4-chloro-2-fluorobenzyl)-7-(trifluoromethyl)-2H-indazol-3-yl]benzyl }-N-isopropylbenzamide;

acg) 3- {3-[2-(4-chloro-2-fluorobenzyl)-7-(trifluoromethyl)-2H-indazol-3-yl]benzyl }-N-propylbenzamide;

ach) 3- {3-[2-(4-chloro-2-fluorobenzyl)-7-(trifluoromethyl)-2H-indazol-3-yl]benzyl }-N-ethylbenzamide;

aci) 3- {3-[2-(4-chloro-2-fluorobenzyl)-7-(trifluoromethyl)-2H-indazol-3-yl]benzyl }-N-methylbenzamide;

acm) 2- [4-({3-[2-(4-chloro-2-fluorobenzyl)-7-(trifluoromethyl)-2H-indazol-3-yl]phenoxy}methyl)phenyl]-2-methylpropanoic acid;

acn) 2-(2,4-difluorobenzyl)-3- {4-[(2,6-dimethylbenzyl)oxy]phenyl }-7-(trifluoromethyl)-2H-indazole;

aco) 2-(2,4-dichlorobenzyl)-3- {4-[(2,6-dimethylbenzyl)oxy]phenyl }-7-(trifluoromethyl)-2H-indazole;

acp) 2-(4-chloro-2-fluorobenzyl)-3- {4-[(2,6-dimethylbenzyl)oxy]phenyl }-7-(trifluoromethyl)-2H-indazole;

acq) 2-(2-chloro-4-fluorobenzyl)-3- {4- [(2,6-dimethylbenzyl)oxy]phenyl }-7-(trifluoromethyl)-2H-indazole;

acr) 2-(2,4-dimethylbenzyl)-3- {4-[(2,6-dimethylbenzyl)oxy]phenyl }-7-(trifluoromethyl)-2H-indazole;

acv) 2-(4-chloro-2-fluorobenzyl)-3- {3-{(2,5-dimethylbenzyl)oxy]phenyl }-7-(trifluoromethyl)-2H-indazole;

acw) 2-(2,4-dimethylbenzyl)-3- {3-[(2,5-dimethylbenzyl)oxy]phenyl }-7-(trifluoromethyl)-2H-indazole;

adb) 2-(2-chloro-4-fluorobenzyl)-3- {4-[(2,5-dimethylbenzyl)oxy]phenyl }-7-(trifluoromethyl)-2H-indazole;

adc) 2-(2,4-dichlorobenzyl)-3- {4-[(2,5-dimethylbenzyl)oxy]phenyl }-7-(trifluoromethyl)-2H-indazole;

add) 3- {3-[(2,5-dimethylbenzyl)oxy]phenyl }-2-(2,4,6-trifluorobenzyl)-7-(trifluoromethyl)-2H-indazole;

adq) 2-(4-chloro-2-fluorobenzyl)-3- {4-[(2,5-dimethylbenzyl)oxy]phenyl }-7-(trifluoromethyl)-2H-indazole;

adr) 2-(2,4-dimethylbenzyl)-3- {4-[(2,5-dimethylbenzyl)oxy]phenyl }-7-(trifluoromethyl)-2H-indazole;

ads) 3- {4-[(2,5-dimethylbenzyl)oxy]phenyl }-2-(2,4,6-trifluorobenzyl)-7-(trifluoromethyl)-2H-indazole;

adt) 2-(4-chloro-2-fluorobenzyl)-3- {3-[(2-methyl-3-nitrobenzyl)oxy]phenyl }-7-(trifluoromethyl)-2H-indazole;

adu) 2-(4-chloro-2-fluorobenzyl)-3- {3- [(5-methyl-2-nitrobenzyl)oxy]phenyl }-7-(trifluoromethyl)-2H-indazole;

adv) 2-(4-chloro-2-fluorobenzyl)-3- {3-[(2-chloro-5-nitrobenzyl)oxy]phenyl }-7-(trifluoromethyl)-2H-indazole;

adw) 2-(4-chloro-2-fluorobenzyl)-3- {3-[(2-fluoro-3-methylbenzyl)oxy]phenyl }-7-(trifluoromethyl)-2H-indazole;

adx) 2-(4-chloro-2-fluorobenzyl)-3-(3- {[5-fluoro-2-(trifluoromethyl)benzyl]oxy}phenyl)-7-(trifluoromethyl)-2H-indazole;

ady) 2-(4-chloro-2-fluorobenzyl)-3-(3- {[2-chloro-3-(trifluoromethyl)benzyl]oxy}phenyl)-7-(trifluoromethyl)-2H-indazole;

adz) 2-(4-chloro-2-fluorobenzyl)-3- {3-[(2-methoxy-5-nitrobenzyl)oxy]phenyl }-7-(trifluoromethyl)-2H-indazole;

aea) 2-(4-chloro-2-fluorobenzyl)-3-(3- {[2-methyl-5-(trifluoromethyl)benzyl]oxy}phenyl)-7-(trifluoromethyl)-2H-indazole;

aeb) 3- {3-[(2-bromo-5-methoxybenzyl)oxy]phenyl }-2-(4-chloro-2-fluorobenzyl)-7-(trifluoromethyl)-2H-indazole;

aec) 3-(3- {[2,5-bis(trifluoromethyl)benzyl]oxy}phenyl)-2-(4-chloro-2-fluorobenzyl)-7-(trifluoromethyl)-2H-indazole;

aed) 1- [3-({3-[2-(4-chloro-2-fluorobenzyl)-7-(trifluoromethyl)-2H-indazol-3 -yl]phenoxy}methyl)-4-methoxyphenyl]ethanone;

aee) 2-(4-chloro-2-fluorobenzyl)-3- {3-[(2,5-difluorobenzyl)oxy]phenyl}-7-(trifluoromethyl)-2H-indazole;

aef) 3- {3- [(2-bromo-5-fluorobenzyl)oxy]phenyl }-2-(4-chloro-2-fluorobenzyl)-7-(trifluoromethyl)-2H-indazole;

aeg) 2-(4-chloro-2-fluorobenzyl)-3- {3- [(3-chloro-2-fluorobenzyl)oxy]phenyl }-7-(trifluoromethyl)-2H-indazole;

aeh) 2-(4-chloro-2-fluorobenzyl)-3-(3- {[2-fluoro-5-(trifluoromethyl)benzyl]oxy}phenyl)-7-(trifluoromethyl)-2H-indazole;

aei) 2-(4-chloro-2-fluorobenzyl)-3- {3- [(2,3,6-trifluorobenzyl)oxy]phenyl }-7-(trifluoromethyl)-2H-indazole;

aej) 2-(4-chloro-2-fluorobenzyl)-3- {3-[(2,5-dichlorobenzyl)oxy]phenyl}-7-(trifluoromethyl)-2H-indazole;

aek) 2-(4-chloro-2-fluorobenzyl)-3-(3- {[2-chloro-5-(trifluoromethyl)benzyl]oxy}phenyl)-7-(trifluoromethyl)-2H-indazole;

ael) 2-(4-chloro-2-fluorobenzyl)-3-(3- {[5-chloro-2-(trifluoromethyl)benzyl]oxy) phenyl)-7-(trifluoromethyl)-2H-indazole;

aem) [4-({3-[2-(4-chloro-2-fluorobenzyl)-7-(trifluoromethyl)-2H-indazol-3-yl]phenoxy}methyl)phenyl]acetic acid;

aen) methyl [4-({3-[2-(4-chloro-2-fluorobenzyl)-7-(trifluoromethyl)-2H-indazol-3 -yl]phenoxy}methyl)phenyl]acetate;

aeo) 2-(4-chloro-2-fluorobenzyl)-3- {3-[(6-chloro-2-fluoro-3-methylbenzyl)oxy]phenyl}-7-(trifluoromethyl)-2H-indazole;

aep) 3- {3-[(2-chloro-3,6-difluorobenzyl)oxy]phenyl }-2-(4-chloro-2-fluorobenzyl)-7-(trifluoromethyl)-2H-indazole;

aeq) 3- {3-[(3-chloro-2,6-difluorobenzyl)oxy]phenyl }-2-(4-chloro-2-fluorobenzyl)-7-(trifluoromethyl)-2H-indazole;

aer) 2-(4-chloro-2-fluorobenzyl)-3- {3- [(5-chloro-2-fluorobenzyl)oxy]phenyl }-7-(trifluoromethyl)-2H-indazole;

aes) 2-(4-chloro-2-fluorobenzyl)-3- {3-[(2,5-dimethoxybenzyl)oxy]phenyl }-7-(trifluoromethyl)-2H-indazole;

aet) 2-(4-chloro-2-fluorobenzyl)-3- {3-[(5-fluoro-2-methylbenzyl)oxy]phenyl }-7-(trifluoromethyl)-2H-indazole;

aeu) 2-(4-chloro-2-fluorobenzyl)-3- {3- [(2,6-difluoro-3-methylbenzyl)oxy]phenyl }-7-(trifluoromethyl)-2H-indazole;

aev) 2-(4-chloro-2-fluorobenzyl)-3- {3-[(2,6-difluorobenzyl)oxy]phenyl }-7-(trifluoromethyl)-2H-indazole;

aew) 2-(4-chloro-2-fluorobenzyl)-3- {3- [(2-chloro-6-fluorobenzyl)oxy]phenyl }-7-(trifluoromethyl)-2H-indazole;

aex) 2-(4-chloro-2-fluorobenzyl)-3-(3- {[2-methoxy-5-(trifluoromethoxy)benzyl]oxy}phenyl)-7-(trifluoromethyl)-2H-indazole;

aey) 2-(4-chloro-2-fluorobenzyl)-3- {3-[(2,3-dimethoxybenzyl)oxy]phenyl}-7-(trifluoromethyl)-2H-indazole;

aez) 3-[3-(benzyloxy)phenyl]-2-(4-chloro-2-fluorobenzyl)-7-(trifluoromethyl)-2H-indazole;

afa) 2-(4-chloro-2-fluorobenzyl)-3- {3-[(4-methylbenzyl)oxy]phenyl}-7-(trifluoromethyl)-2H-indazole;

afb) 2-(4-chloro-2-fluorobenzyl)-3- {3- [(2-chloro-5-fluorobenzyl)oxy]phenyl}-7-(trifluoromethyl)-2H-indazole;

afc) 2-(2,4-dimethylbenzyl)-3-(3- {[5-fluoro-2-(trifluoromethyl)benzyl]oxy}phenyl)-7-(trifluoromethyl)-2H-indazole; afe)2-(4-chloro-2-fluorobenzyl)-3- {3-[(2-chloro-6-fluoro-3-methylbenzyl)oxy]phenyl }-7-(trifluoromethyl)-2H-indazole;

afg) {3-[2-(4-chloro-2-fluorobenzyl)-7-(trifluoromethyl)-2H-indazol-3-yl]phenoxy}(phenyl)acetic acid;

afh) 2- {3-[2-(4-chloro-2-fluorobenzyl)-7-(trifluoromethyl)-2H-indazol-3-yl]phenoxy}-2-phenylpropanoic acid;

afi) {3-[2-(4-chloro-2-fluorobenzyl)-7-(trifluoromethyl)-2H-indazol-3-yl]phenoxy}(3-methylphenyl)acetic acid;

afj) [4-({3-[2-(4-chloro-2-fluorobenzyl)-7-(trifluoromethyl)-2H-indazol-3-yl]phenoxy}methyl)-2,5-dimethylphenyl]acetic acid;

afk) [4-({3-[2-(2,4,6-trifluorobenzyl)-7-(trifluoromethyl)-2H-indazol-3-yl]phenoxy}methyl)phenyl]acetic acid;

afl) 1- [4-({3-[2-(4-chloro-2-fluorobenzyl)-7-(trifluoromethyl)-2H-indazol-3-yl]phenoxy}methyl)phenyl]cyclopropanecarboxylic acid;

afm) 3-(3- {[5-fluoro-2-(trifluoromethyl)benzyl]oxy}phcnyl)-2-(2,4,6-trifluorobenzyl)-7-(trifluoromethyl)-2H-indazole;

afn) [3-({3-[2-(4-chloro-2-fluorobenzyl)-7-(trifluoromethyl)-2H-indazol-3-yl]phenoxy}methyl)-2,4-dimethylphenyl]acetic acid;

afo) [4-({3-[2-(2,4-dimethylbenzyl)-7-(trifluoromethyl)-2H-indazol-3-yl]phenoxy}methyl)phcnyl]acetic acid;

afp) 3,3 '-[methylenebis(oxy-3,1-phenylcne)]bis[2-(4-chloro-2-fluorobenzyl)-7-(trifluoromethyl)-2H-indazole];

afq) 2-[3-({4-[2-(2,4-dimethylbenzyl)-7-(trifluoromethyl)-2H-indazol-3-yl]phenyl}amino)phenyl]-2-methylpropanoic acid;

afr) 3-(3- {[5-chloro-2-(trifluoromethyl)benzyl]oxy}phenyl)-2-(2,4,6-trifluorobenzyl)-7-(trifluoromethyl)-2H-indazole;

afs) 3-(3- {[2-chloro-5-(trifluoromethyl)benzyl]oxy}phenyl)-2-(2,4,6-trifluorobenzyl)-7-(trifluoromethyl)-2H-indazole;

aft) 2-(4-chloro-2-fluorobenzyl)-3-[3-(2-phenylethyl)phenyl]-7-(trifluoromethyl)-2H-indazole;

afu) 2-(4-chloro-2-fluorobenzyl)-3- {3-[2-(2,5-dimethylphenyl)ethyl]phenyl}-7-(trifluoromethyl)-2H-indazole;

afv) 2-(4-chloro-2-fluorobenzyl)-3- {3-[2-(2,5-dichlorophenyl)ethyl]phenyl}-7-(trifluoromethyl)-2H-indazole;

afw) 2-(4-chloro-2-fluorobenzyl)-3- {3-[2-(2,5-difluorophenyl)ethyl]phenyl}-7-(trifluoromethyl)-2H-indazole;

afx) 2-(4-chloro-2-fluorobenzyl)-3- {3-[2-(5-chloro-2-fluorophenyl)ethyl]phenyl}-7-(trifluoromethyl)-2H-indazole;

afy) 2-(4-chloro-2-fluorobenzyl)-3- {3- [2-(2-chloro-5-fluorophenyl)ethyl]phenyl}-7-(trifluoromethyl)-2H-indazole;

afz) 2-(4-chloro-2-fluorobenzyl)-3-(3- {2-[2-fluoro-5-(trifluoromethyl)phenyl]ethyl}phenyl)-7-(trifluoromethyl)-2H-indazole;

aga) 2-(4-chloro-2-fluorobenzyl)-3-(3- {2-[3 (trifluoromethoxy)phenyl]ethyl}phenyl)-7-(trifluoromethyl)-2H-indazole;

agb) 2-(4-chloro-2-fluorobenzyl)-3- {3-[2-(3-methoxyphenyl)ethyl]phenyl}-7-(trifluoromethyl)-2H-indazole;

agc) 2-(4-chloro-2-fluorobenzyl)-3-(3- {2- [3-(difluoromethoxy)phenyl]ethyl}phenyl)-7-(trifluoromethyl)-2H-indazole;

agd) 2-(4-chloro-2-fluorobenzyl)-3-(3- {2- [2-methyl-5-(trifluoromethyl)phenyl]ethyl}phenyl)-7-(trifluoromethyl)-2H-indazole;

age) 3-(3- {2-[2,5-bis(trifluoromethyl)phenyl]ethyl}phenyl)-2-(4-chloro-2-fluorobenzyl)-7-(trifluoromethyl)-2H-indazole;

agf) 2-(4-chloro-2-fluorobenzyl)-3- {3-[2-(2,3-dimethoxyphenyl)ethyl]phenyl 1-7-(trifluoromethyl)-2H-indazole;

agg) 2-(4-chloro-2-fluorobenzyl)-3-(3- {2-[2-chloro-5-(trifluoromethyl)phenyl]ethyl}phenyl)-7-(trifluoromethyl)-2H-indazole;

agh) 2-(4-chloro-2-fluorobenzyl)-3-(3- {2-[5-chloro-2-(trifluoromethyl)phenyl]ethyl}phenyl)-7-(trifluoromethyl)-2H-indazole;

agi) 2-(4-chloro-2-fluorobenzyl)-3-(3- {2-[5-fluoro-2-(trifluoromethyl)phenyl]ethyl) phenyl)-7-(trifluoromethyl)-2H-indazole;

agy) 2-(2,4-dimethylbenzyl)-3-[4-(2-methoxyphenoxy)phenyl]-7-(trifluoromethyl)-2H-indazole;

agz) 3-[4-(2-methoxyphenoxy)phenyl]-2-(2,4,6-trifluorobenzyl)-7-(trifluoromethyl)-2H-indazole;

aha) 2-(4-chloro-2-fluorobenzyl)-3- [4-(2-methoxyphenoxy)phenyl]-7-(trifluoromethyl)-2H-indazole;

ahb) (3- {4-112-(2,4-dimethylbenzyl)-7-(trifluoromethyl)-2H-indazol-3-yl]phenoxy}phenyl)dimethylamine;

ahd) N,N-dimethyl-3- {4-112-(2,4,6-trifluorobenzyl)-7-(trifluoromethyl)-2H-indazol-3-yl]phenoxy}aniline;

ahe) (3- {4- [2-(4-chloro-2-fluorobenzyl)-7-(trifluoromethyl)-2H-indazol-3-yl]phenoxy}phenyl)dimethylamine;

ahf) 3- {4-[2-(2,4-dimethylbenzyl)-7-(trifluoromethyl)-2H-indazol-3-yl]phenoxy}-N-methoxy-N-methylbenzamide;

ahg) N-methoxy-N-methyl-3- {4-[2-(2,4,6-trifluorobenzyl)-7-(trifluoromethyl)-2H-indazol-3 -yl]phenoxy}benzamide;

ahh) 3- {4- [2-(4-chloro-2-fluorobenzyl)-7-(trifluoromethyl)-2H-indazol-3-yl]phenoxy}-N-methoxy-N-methylbenzamide;

ahi) 5- {4-L2-(4-chloro-2-fluorobenzyl)-7-(trifluoromethyl)-2H-indazol-3-yl]phenoxy}-3,4-dihydronaphthalen-1 (2H)-one;

ahl) 3- {4-[2-(4-chloro-2-fluorobenzyl)-7-(trifluoromethyl)-2H-indazol-3-yl]phenoxy}benzaldehyde;

ahm) 2-(4-chloro-2-fluorobenzyl)-3-[4-(5,6,7,8-tetrahydronaphthalen-1-yloxy)phenyl]-7-(trifluoromethyl)-2H-indazole;

ahn) 5- {4- [2-(4-chloro-2-fluorobenzyl)-7-(trifluoromethyl)-2H-indazol-3-yl]phenoxy}-1,2,3,4-tetrahydronaphthalen-1-ol;

ahp) 3- {4-[2-(4-chloro-2-fluorobenzyl)-7-(trifluoromethyl)-2H-indazol-3-yl]phenoxy}-N,N-dimethylbenzamide;

ahq) 3- {4-[2-(4-chloro-2-fluorobenzyl)-7-(trifluoromethyl)-2H-indazol-3-yl]phenoxy}-N,N-diethylbenzamide;

ahr) 2-(4-chloro-2-fluorobenzyl)-3- {4-[3-{pyrrolidin-1-ylcarbonyl)phenoxy]phenyl}-7-(trifluoromethyl)-2H-indazole;

ahs) 2-(4-chloro-2-fluorobenzyl)-3- {4-[3-(piperidin-1-ylcarbonyl)phenoxy]phenyl}-7-(trifluoromethyl)-2H-indazole;

aht) 2-(4-chloro-2-fluorobenzyl)-3- {4-[3-(morpholin-4-ylcarbonyl)phenoxy]phenyl}-7-(trifluoromethyl)-2H-indazole;

ahv) 1-(3- {4-[2-(4-chloro-2-fluorobenzyl)-7-(trifluoromethyl)-2H-indazol-3 -yl]phenoxy}phenyl)ethanone;

ahw) N,N-dimethyl-3- {4-[2-(2 ,4,6-trifluorobenzyl)-7-(trifluoromethyl)-2H-indazol-3-yl]phenoxy}benzamide;

ahx) 3- {4-[2-(2,4-dimethylbenzyl)-7-(trifluoromethyl)-2H-indazol-3-yl]phenoxy}-N,N-dimethylbenzamide;

ahy) 2-(3- {4- [2-(4-chloro-2-fluorobenzyl)-7-(trifluoromethyl)-2H-indazol-3 -yl]phenoxy}phenyl)propan-2-ol;

aia) (1 S)-5- {4- [2-(4-chloro-2-fluorobenzyl)-7-(trifluoromethyl)-2H-indazol-3 -yl]phenoxy}-1,2,3 ,4-tetrahydronaphthalen-1-01;

aib) (1 R)-5- {4- [2-(4-chloro-2-fluorobenzyl)-7-(trifluoromethyl)-2H-indazol-3 -yl]phenoxy}-1 ,2,3 ,4-tetrahydronaphthalen-1-ol;

aid) 3- {4-[3-(piperidin-1-ylcarbonyl)phenoxy]phenyl }-2-(2,4,6-trifluorobenzyl)-7-(trifluoromethyl)-2H-indazole;

aie) 2-(3- {4-[2-(2,4,6-trifluorobenzyl)-7-(trifluoromethyl)-2H-indazol-3-yl]phenoxy}phenyl)propan-2-ol;

aif) 3- {4-[3-(morpholin-4-ylcarbonyl)phenoxy]phenyl }-2-(2,4,6-trifluorobenzyl)-7-(trifluoromethyl)-2H-indazole;

aig) 5- {3-[2-(2-chloro-4-fluorobenzyl)-7-(trifluoromethyl)-2H-indazol-3-yl]phenoxy}-3 ,4-dihydronaphthalen-1 (2H)-one;

aih) 2-(2-chloro-4-fluorobenzyl)-3-(4-methoxyphenyl)-7-(trifluoromethyl)-2H-indazole;

aii) 2-(4-chloro-2-fluorobenzyl)-3-(4-methoxyphenyl)-7-(trifluoromethyl)-2H-indazole;

aij) 3-(4-methoxyphenyl)-2-(2,4,6-trifluorobenzyl)-7-(trifluoromethyl)-2H-indazole;

aik) 5- {3-[2-(2-chloro-4-fluorobenzyl)-7-(trifluoromethyl)-2H-indazol-3-yl]phenoxy}quinoline;

ail) 5- {3-[2-(2-chloro-4-fluorobenzyl)-7-(trifluoromethyl)-2H-indazol-3-yl]phenoxy}isoquinoline;

aim) 4- {3-[2-(2-chloro-4-fluorobenzyl)-7-(trifluoromethyl)-2H-indazol-3-yl]phenoxy}quinazoline;

ain) 6- {3- [2-(2,4,6-trifluorobenzyl)-7-(trifluoromethyl)-2H-indazol-3-yl]phenoxy}-3 ,4-dihydronaphthalen-1 (2H)-one;

aio) 2-(2-chloro-4-fluorobenzyl)-3-[3-(5,6,7,8-tetrahydronaphthalen-2-yloxy)phenyl]-7-(trifluoromethyl)-2H-indazole;

aip) 2-(2-chloro-4-fluorobenzyl)-3-[3-(5 ,6,7,8-tetrahydronaphthalen-1-yloxy)phenyl]-7-(trifluoromethyl)-2H-indazole;

aiq) 2- {4-[2-(2,4,6-trifluorobenzyl)-7-(trifluoromethyl)-2H-indazol-3-yl]phenyl }-1 H-indole-5-carbonitrile;

air) 3- [4-(5-fluoro-1 H-indol-2-yl)phenyl]-2-(2,4,6-trifluorobenzyl)-7-(trifluoromethyl)-2H-indazole;

ais) 5- {3-112-(2,4,6-trifluorobenzyl)-7-(trifluoromethyl)-2H-indazol-3-yl]phenoxy}-3 ,4-dihydronaphthal en-i (2H)-one;

ait) 6- {3-[2-(2-chloro-4-fluorobenzyl)-7-(trifluoromethyl)-2H-indazol-3-yl]phenoxy}-3 ,4-dihydronaphthalen-1 (2H)-one;

aiu) 3- [3-(5-bromo-6-methyl-1 H-indol-2-yl)phenyl]-2-(2,4,6-trifluorobenzyl)-7-(trifluoromethyl)-2H-indazole;

aiv) 3- [4-(5-bromo-6-methyl-1 H-indol-2-yl)phenyl]-2-(2,4,6-trifluorobenzyl)-7-(trifluoromethyl)-2H-indazole;

aiw) 1-methyl-2- {4-2-(2,4,6-trifluorobenzy1)-7-(trifluoromethyl)-2H-indazo1-3-yl]phenyl}-1 H-indole-5-carbonitrile;

aix) 3-[4-(5-fluoro-1-methyl-i H-indol-2-yl)phenyl]-2-(2,4,6-trifluorobenzyl)-7-(trifluoromethyl)-2H-indazole;

aiy) 6- {3- [2-(2,4,6-trifluorobenzyl)-7-(trifluoromethyl)-2H-indazol-3-yl]phenoxy}-3 ,4-dihydronaphthalen-1 (2H)-one;

aiz) 2- {4- [2-(2,4,6-trifluorobenzyl)-7-(trifluoromethyl)-2H-indazol-3-yl]phenyl }-1 H-indole-5-carbonitrile;

aja) 3-[4-(5-fluoro-1 H-indol-2-yl)phenyl]-2-(2 ,4,6-trifluorobenzyl)-7-(trifluoromethyl)-2H-indazole;

ajb) 5- {3-[2-(2 ,4,6-trifluorobenzyl)-7-(trifluoromethyl)-2H-indazol-3-yl]phenoxy}-3 ,4-dihydronaphthal en-i (2H)-one;

ajc) 6- {3- [2-(2-chloro-4-fluorobenzyl)-7-(trifluoromethyl)-2H-indazol-3-yl]phenoxy}-3 ,4-dihydronaphthal en-i (2H)-one;

ajd) methyl (5- {3-{2-(2-chloro-4-fluorobenzyl)-7-(trifluoromethyl)-2H-indazol-3 -yl]phenoxy}-1-hydroxy-1,2,3 ,4-tetrahydronaphthalen-1-yl)acetate;

aje) ethyl [4-({3-[2-(2,4,6-trifluorobenzyl)-7-(trifluoromethyl)-2H-indazol-3-yl]phenoxy}methyl)phenyl]acetate;

ajf) (5- {3-[2-(2-chloro-4-fluorobenzyl)-7-(trifluoromethyl)-2H-indazol-3-yl]phenoxy}-3 ,4-dihydronaphthalen-1-yl)acetic acid;

ajg) ethyl [4-({4-[2-(4-chloro-2-fluorobenzyl)-7-(trifluoromethyl)-2H-indazol-3 -yl]phenoxy}methyl)phenyl]acetate; and ajh) 5- {3- [2-(4-chloro-2-fluorobenzyl)-7-(trifluoromethyl)-2H-indazol-3-yl]phenoxy}-1 ,2,3,4-tetrahydronaphthalen-l -ol; or a pharmaceutically acceptable salt thereof.

31. A pharmaceutical composition which comprises a compound of claim 1, or a pharmaceutically acceptable salt thereof and a pharmaceutical carrier.

32. The compound of claim 1, wherein the compound is selected from the group consisting of:

h) 2-Benzyl-3-phenyl-7-methyl-2H-indazole;

dv) 7-fluoro-2-(4-fluorobenzyl)-3-(4-fluorophenyl)-2H-indazole;

dw) 7-fluoro-2-(2-fluorobenzyl)-3-(4-fluorophenyl)-2H-indazole;

dx) 2-(4-chlorobenzyl)-7-fluoro-3-(4-fluorophenyl)-2H-indazole;

dy) 2-(2,4-difluorobenzyl)-7-fluoro-3-(4-fluorophenyl)-2H-indazole;

dz) 2-(3 ,4-difluorobenzyl)-7-fluoro-3-(4-fluorophenyl)-2H-indazole;

ea) 2-benzyl-3-(2,4-dimethoxyphenyl)-7-fluoro-2H-indazole;

eb) 3-(2,4-dimethoxyphenyl)-7-fluoro-2-(2-fluorobenzyl)-2H-indazole;

ec) 3-(2,4-dimethoxyphenyl)-7-fluoro-2-(4-fluorobenzyl)-2H-indazole;

ed) 2-(2-chloro-6-fluorobenzyl)-3-(2,4-dimethoxyphenyl)-7-fluoro-2H-indazole;

ef) methyl 2-(2,4-dimethylbenzyl).-3-(4-fluorophenyl)-2H-indazole-7-carboxylate;

eg) 2-benzyl-7-fluoro-3-(4-methoxy-2.-methylphenyl)-2H-indazole;

eh) 7-fluoro-2-(2-fluorobenzyl)-3-(4-methoxy-2-methylphenyl)-2H-indazole;

ei) 7-chloro-2-(2-fluorobenzyl)-3-(4-methoxy-2-methylphenyl)-2H-indazole;

ej) [2-(2,4-dimethylbenzyl)-3-(4-fluorophenyl)-2H-indazol-7-yl]methanol;

ek) 7-fluoro-2-(4-fluorobenzyl)-3-(4-methoxy-2-methylphenyl)-2H-indazole;

el) 2-(2-chloro-6-fluorobenzyl)-7-fluoro-3-(4-methoxy-2-methylphenyl)-2H-indazole;

em) 2-(2,4-dimethylbenzyl)-3-(4-fluorophenyl)-2H-indazole-7-carboxylic acid;

en) 2-(4-chlorobenzyl)-3-(2,4-dimethoxyphenyl)-7-fluoro-2H-indazole;
eo) 2-(3,4-difluorobenzyl)-3-(2,4-dimethoxyphenyl)-7-fluoro-2H-indazole;
ep) 2-benzyl-7.-chloro-3-(2,4-dimethoxyphenyl)-2H-indazole;
eq) 7-chloro-3-(2,4-dimethoxyphenyl)-2-(4-fluorobenzyl)-2H-indazole;
er) 7-chloro-3-(2,4-dimethoxyphenyl)-2-(2-fluorobenzyl)-2H-indazole;
es) 7-chloro-2-(4-fluorobenzyl)-3-(4-methoxy-2-methylphenyl)-2H-indazole;
et) 2-(2,4-difluorobenzyl)-7-fluoro-3-(4-methoxy-2-methylphenyl)-2H-indazole;
eu) 2-(2-chlorobenzyl)-3-(2,4-dimethoxyphenyl)-7-fluoro-2H-indazole;
ew) 2-(2,4-difluorobenzyl)-3-(2,4-dimethoxyphenyl)-7-fluoro-2H-indazole;
ex) 2-(2-chlorobenzyl)-7-fluoro-3-(4-methoxy-2-methylphenyl)-2H-indazole;
ey) 7-chloro-2-(4-fluorobenzyl)-3-(4-fluorophenyl)-2H-indazole;
ez) 7-chloro-2-(2-fluorobenzyl)-3-(4-fluorophenyl)-2H-indazole;
fa) 7-chloro-2-(4-chlorobenzyl)-3-(4-fluorophenyl)-2H-indazole;
fb) 7-chloro-2-(2,4-difluorobenzyl)-3.-(4-fluorophenyl)-2H-indazole;
fc) 7-chloro-2-(3,4-difluorobenzyl)-3-(4-fluorophenyl)-2H-indazole;
fe) 1-[2-(2,4-difluorobenzyl)-3-(4-fluorophenyl)-2H-indazol-7-yl]piperidine-4-carboxamide;
fg) 2-(2,4-difluorobenzyl)-3-(4-fluorophenyl)-7-morpholin-4-yl-2H-indazole;
fh) 2-(2,4-difluorobenzyl)-3-(4-fluorophenyl)-7-piperidin-1-yl-2H-indazole;
fi) 2-(2,4-difluorobenzyl)-3-(4-fluorophenyl)-N,N-dimethyl-2H-indazol-7-amine;
lj) 2-(2,4-difluorobenzyl)-N-ethyl-3-(4-fluorophenyl)-2H-indazol-7-amine;
fk) 2-(2,4-difluorobenzyl)-3-(4-fluorophenyl)-7-pyrrolidin-1-yl-2H-indazole;
fh) 2-(2,4-difluorobenzyl)-3-(4-fluorophenyl)-2H-indazole-7-carbonitrile;
fr) 7-chloro-2-(2-chloro-6-fluorobenzyl)-3-(4-fluorophenyl)-2H-indazole;
fs) 7-chloro-2-(2-chloro-4-fluorobenzyl)-3-(4-fluorophenyl)-2H-indazole;
ft) 7-chloro-2-(2,4-dichlorobenzyl)-3-(4-fluorophenyl)-2H-indazole;
fu) 7-chloro-2-.(2,6-difluorobenzyl)-3-(4-fluorophenyl)-2H-indazole;
fv) 7-chloro-3-(4-fluorophenyl)-2-(2,4,6-trifluorobenzyl)-2H-indazole; and
fw) 7-chloro-2-(2,4-dimethylbenzyl)-3-(4-fluorophenyl)-2H-indazole; or a pharmaceutically acceptable salt thereof.

33. The compound of claim 1, wherein the compound is selected from the group consisting of:
bx) 2-Benzyl-3-butyl-7-trifluoromethyl-2H-indazole;
by) 2-Benzyl-3-isobutyl-7-trifluoromethyl-2H-indazole;
bz) 2-Benzyl-3-cyclopentyl-7-trifluoromethyl-2H-indazole;
ca) 2-Benzyl-3-cyclohexanyl-7-trifluoromethyl-2H-indazole;
cg) 2-Benzyl-3-naphtalen-2-yl-7-trifluoromethyl-2H-indazole;

gx) 2-(2,4-difluorobenzyl)-3-(pyridin-2-ylmethyl)-7-(trifluoromethyl)-2H-indazole;
gy) 2-(2-chloro-4-fluorobenzyl)-3-(pyridin-2-ylmethyl)-7-(trifluoromethyl)-2H-indazole;
gz) 2-(2-chloro-6-fluorobenzyl)-3-(pyridin-2-ylmethyl)-7-(trifluoromethyl)-2H-indazole;
ha) 2-(2,6-difluorobenzyl)-3-(pyridin-2-ylmethyl)-7-(trifluoromethyl)-2H-indazole;
hb) 3-(pyridin-2.-ylmethyl)-2-(2,4,6-trifluorobenzyl)-7-(trifluoromethyl)-2H-indazole;
hc) 2-(2,6-dichlorobenzyl)-3-(pyridin-2-ylmethyl)-7-(trifluoromethyl)-2H-indazole;
hp) 2-(2,4-dichlorobenzyl)-3-pyridin-2-yl-7-(trifluoromethyl)-2H-indazole;
hq) 2-(2,6-difluorobenzyl)-3-pyridin-2-yl-7-(trifluoromethyl)-2H-indazole;
hr) 2-(2,4-difluorobenzyl)-3-pyridin-2-yl-7-(trifluoromethyl)-2H-indazole;
hs) 2-(2,4-dimethylbenzyl)-3-pyridin-2-yl-7-(trifluoromethyl)-2H-indazole;
ht) 3-pyridin-2-yl-2-(2,4,6-trifluorobenzyl)-7-(trifluoromethyl)-2H-indazole;
ju) 2-(4-chlorobenzyl)-3-pyridin-2-yl-7-(trifluoromethyl)-2H-indazole;
jv) 2-(2-chlorobenzyl)-3-pyridin-2-yl-7-(trifluoromethyl)-2H-indazole;
jw) 2-(2-chloro-4-fluorobenzyl)-3-pyridin-2-yl-7-(trifluoromethyl)-2H-indazole;
jx) 2-(2-chloro-6-fluorobenzyl)-3-pyridin-2-yl-7-(trifluoromethyl)-2H-indazole;
ks) 2-(2-methylphenyl)-3-pyridin-2-yl-7-(trifluoromethyl)-2H-indazole;
mi) N-(2,5-difluorobenzyl)-2-[2-(2,4-difluorobenzyl)-7-(trifluoromethyl)-2H-indazol-3-yl]pyridin-4-amine;
mj) 2-[2-(2,4-difluorobenzyl)-7-(trifluoromethyl)-2H-indazol-3-yl]-N-(2,5-dimethylbenzyl)pyridin-4-amine;
mk) N-(3,5-difluorobenzyl)-2-[2-(2,4-difluorobenzyl)-7-(trifluoromethyl)-2H-indazol-3-yl]pyridin-4-amine;
mx) 3-[2-(2-fluoro-4-methoxyphenyl)-1H-indol-6-yl]-2-(2,4,6-trifluorobenzyl)-7-(trifluoromethyl)-2H-indazole;
nr) 3-(1-benzothien-2-yl)-2-(2,4,6-trifluorobenzyl)-7-(trifluoromethyl)-2H-indazole;
ns) 3-(2-naphthyl)-2-(2,4,6-trifluorobenzyl)-7-(trifluoromethyl)-2H-indazole;
nt) 3-(1H-indol-5-yl)-2-(2,4,6-trifluorobenzyl)-7-(trifluoromethyl)-2H-indazole;
nu) 3-dibenzo[b,d]thien-4-yl-2-(2,4,6-trifluorobenzyl)-7-(trifluoromethyl)-2H-indazole;
nx) 3-[1-(4-chlorobenzyl)-1H-indol-5-yl]-2-(2,4,6-trifluorobenzyl)-7-(trifluoromethyl)-2H-indazole;
ny) 3-(1-benzyl-1H-indol-5-yl)-2-(2,4,6-trifluorobenzyl)-7-(trifluoromethyl)-2H-indazole;
oa) 3-{1-[5-chloro-2-(trifluoromethyl)benzyl]-1H-indol-5-yl}-2-(2,4,6-trifluorobenzyl)-7-(trifluoromethyl)-2H-indazole;
ob) 3-[1-(2,4-difluorobenzyl)-1H-indol-5-yl]-2-(2,4,6-trifluorobenzyl)-7-(trifluoromethyl)-2H-indazole;
oc) 3-[1-(2-fluorobenzyl)-1H-indol-5-yl]-2-{2,4,6-trifluorobenzyl)-7-(trifluoromethyl)-2H-indazole;
od) 3-[1-(2-chlorobenzyl)-1H-indol-5-yl]-2-(2,4,6-trifluorobenzyl)-7-(trifluoromethyl)-2H-indazole;
oe) 3-[1-(2,4-dichlorobenzyl)-1H-indol-5-yl]-2-(2,4,6-trifluorobenzyl)-7-(trifluoromethyl)-2H-indazole;
ox) 3-[1-(2-chloro-6-fluorobenzyl)-1H-indol-5-yl]-2-(2,4,6-trifluorobenzyl)-7-(trifluoromethyl)-2H-indazole;
oy) 3-[1-(2,6-difluorobenzyl)-1H-indol-5-yl]-2-(2,4,6-trifluorobenzyl)-7-(trifluoromethyl)-2H-indazole;

pb) 3-[1-(2,6-dichlorobenzyl)-1 H-indol-5-yl]-2-(2,4,6-trifluorobenzyl)-7-(trifluoromethyl)-2H-indazole;

pc) 3-[1-(2-chloro-4-fluorobenzyl)-1 H-indol-5-yl]-2-(2,4,6-trifluorobenzyl)-7-(trifluoromethyl)-2H-indazole;

pn) 3- {1-[5-chloro-2-(trifluoromethyl)benzyl]-1 H-indol-6-yl }-2-(2,4,6-trifluorobenzyl)-7-(trifluoromethyl)-2H-indazole;

po) 3-(1-benzyl-1 H-indol-6-yl)-2-(2,4,6-trifluorobenzyl)-7-(trifluoromethyl)-2H-indazole;

pp) 3-[1-(2,6-dichlorobenzyl)-1 H-indol-6-yl]-2-(2,4,6-trifluorobenzyl)-7-(trifluoromethyl)-2H-indazole;

pq) 3-[1-(2-chloro-4-fluorobenzyl)-1 H-indol-6-yl]-2-(2,4,6-trifluorobenzyl)-7-(trifluoromethyl)-2H-indazole;

pr) 3-[1-(2-chlorobenzyl)-1 H-indol-6-yl]-2-(2,4,6-trifluorobenzyl)-7-(trifluoromethyl)-2H-indazole;

ps) 3-[1-(2-chloro-6-fluorobenzyl)-1 H-indol-6-yl]-2-(2,4,6-trifluorobenzyl)-7-(trifluoromethyl)-2H-indazole;

pt) 3-[1-(2,6-difluorobenzyl)-1 H-indol-6-yl]-2-(2,4,6-trifluorobenzyl)-7-(trifluoromethyl)-2H-indazole;

pu) 3-[1-(2-fluorobenzyl)-1 H-indol-6-yl]-2-(2,4,6-trifluorobenzyl)-7-(trifluoromethyl)-2H-indazole;

pv) 3- [1-(2,4-difluorobenzyl)-1 H-indol-6-yl]-2-(2,4,6-trifluorobenzyl)-7-(trifluoromethyl)-2H-indazole;

pw) 3-[1-(4-chlorobenzyl)-1 H-indol-6-yl]-2-(2,4,6-trifluorobenzyl)-7-(trifluoromethyl)-2H-indazole;

rd) 2- {[3-[1-(2,6-dichlorobenzyl)-1 H-indol-6-yl]-7-(trifluoromethyl)-2H-indazol-2-yl]methyl}-3,5-difluorophenol;

re) 2- {[3-[1-(2-chloro-6-fluorobenzyl)-1 H-indol-6-yl]-7-(trifluoromethyl)-2H-indazol-2-yl]methyl}-3 ,5-difluorophenol;

rw) 2-benzyl-3-ethyl-7-(trifluoromethyl)-2H-indazole; or a pharmaceutically acceptable salt thereof.

34. The compound of claim 1, wherein the compound is selected from the group consisting of:

a) 2-Benzyl-3-(4-methoxyphenyl)-7-trifluoromethyl-2H-indazole;

b) 4- [4-(2-Benzyl-7-trifluoromethyl-2H-indazol-3-yl)-phenoxymethyl7j-benzoic acid;

c) 4-[4-(2-Benzyl-7-trifluoromethyl-2H-indazol-3-yl)-phenoxy]-benzoic acid;

d) [4-(2-Benzyl-7-trifluoromethyl-2H-indazol-3-yl)-phenyl]-phenyl-amine;

e) 3-[4-(2-Benzyl-7-trifluoromethyl-2H-indazol-.3-yl)-benzyl]-benzoic acid methyl ester;

f) 4t-(2-Benzyl-7-trifluoromethyl-2H-indazol-3-yl)-biphenyl-4-carboxylic acid;

g) 4-[3-(2-Benzyl-7-trifluoromethyl-2H-indazol-3-yl)-benzyloxymethyl]-benzoic acid;

i) 2-Benzyl-3-(4-phenoxyphenyl)-7-trifluoromethyl-2H-indazole;

j) 3-[4-(2-Benzyl-7-trifluoromethyl-2H-indazol-3-yl)-phenoxy]-benzoic acid;

k) {4-[4-(2-Benzyl-7-trifluoromethyl-2H-indazol-3-yl)-phenoxy]-phenoxy}-acetic acid;

l) {4-[4-(2-Benzyl-7-trifluoromethyl-2H-indazol-3-yl)-phenoxymethyl]-phenoxy}-acetic acid;

m) {3- [4-(2-Benzyl-7-trifluoromethyl-2H-indazol-3-yl)-phenoxyrnethyl]-phenoxy}-acetic acid;

n) {3-[4-(2-Benzyl-7-trifluoromethyl-2H-indazol-3-yl)-phenoxymethyl]-phenyl }-acetic acid;

o) 3-[4-(2-Benzyl-7-trifluoromethyl-2H-indazol-3-yl)-phenoxymethyl]-benzoic acid;

p) {4-[3-(2-Benzyl-7-trifluoromethyl-2H-indazol-3-yl)-benzyloxymethyl]-phenoxy}-acetic acid;

q) {3-[3-(2-Benzyl-7-trifluoromethyl-2H-indazol-3-yl)-benzyloxymethyl]-phenoxy}-acetic acid;

r) 3-[3-(2-Benzyl-7-trifluoromethyl-2H-indazol-3-yl)-benzyloxymethyl]-benzoic acid;

s) 2-Benzyl-3-(4-methoxy-2-methylphenyl)-7-trifluoromethyl-2H-indazole;

t) 2-Benzyl-3-(2-methoxyphenyl)-7-trifluoromethyl-2H-indazole;

u) 2-Benzyl-3-o-tolyl-7-trifluoromethyl-2H-indazole;

v) 2-Benzyl-3-(2 ,4-dimethylphenyl)-7-trifluoromethyl-2H-indazole;

w) 2-Benzyl-3-biphenyl-4-yl-7-trifluoromethyl-2H-indazole;

x) 2-Benzyl-7-trifluoromethyl-3-(2-vinylphenyl)-2H-indazole;

y) 2-Benzyl-7-trifluoromethyl-3-(3-trifluoromethylphenyl)-2H-indazole;

z) 2-Benzyl-3-(4-fluorophenyl)-7-trifluoromethyl-2H-indazole;

aa) 2-Benzyl-3-(3-chlorophenyl)-7-trifluoromethyl-2H-indazole;

ab) 2-Benzyl-3-(3-methoxyphenyl)-7-trifluoromethyl-2H-indazole;

ac) Benzyl-[4-(2-benzyl-7-trifluoromethyl-2H-indazol-3-yl)-phenyl]-methylamine;

ad) 2-(2-Benzyl-7-trifluoromethyl-2H-indazol-3-yl)-phenol;

ah) 2-Benzyl-3-(4-bromophenyl)-7-trifluoromethyl-2H-indazole;

ai) 2-Benzyl-3-(3-bromophenyl)-7-trifluoromethyl-2H-indazole;

aj) 4-[4-(2-Benzyl-7-trifluoromethyl-2H-indazol-3-yl)-benzyl]-benzoic acid;

ak) 4- [3-(2-Benzyl-7-trifluoromethyl-2H-indazol-3-yl)-benzyl]-benzoic acid;

al) 3- [4-(2-Benzyl-7-trifluoromethyl-2H-indazol-3-yl)-benzyl]-benzoic acid;

am) 3-[3-(2-Benzyl-7-trifluoromethyl-2H-indazol-3-yl)-benzyl]-benzoic acid;

an) {4-[4-(2-Benzyl-7-trifluoromethyl-2H-indazol-3-yl)-benzyl]-phenyl }-acetic acid;

ao) {4-[3-(2-Benzyl-7-trifluoromethyl-2H-indazol-3-yl)-benzyl]-phenyl }-acetic acid;

ap) N-Benzyl-N-[4-(2-benzyl-7-trifluoromethyl-2H-indazol-3-yl)-phenyl]-amine;

aq) Benzyl-[3-(2-benzyl-7-trifluoromethyl-2H-indazol-3-yl)-phenyl]-amine;

at) Methyl3-({3- [2-benzyl-7-(trifluoromethyl)-2H-indazol-3-yl]phenoxy}methyl)benzoate;

au) 2-Benzyl-3-[3-(benzyloxy)phenyl]-7-(trifluoromethyl)-2H-indazole;

av) [4-({3-[2-Benzyl-7-trifluoromethyl)-2H-indazol-3-yl]phenoxy}methyl)phenyl]acetic acid;

aw) 3-({3-[2-Benzyl-7-(trifluoromethyl)-2H-indazol-3-yl]phenoxy}methyl) benzoic acid;

ax) 4-({3-[2-Benzyl-7-(trifluoromethyl)-2H-indazol-3-yl]phenoxy}methyl) benzoic acid;

ay) [4-({3- [2-Benzyl-7-trifluoromethyl)-2H-indazol-3-yl]phenoxy}methyl)phenyl]propionic acid;

az) {3-[3-(2-Benzyl-7-trifluoromethyl-2H-indazol-3-yl)-phenoxymethyl])-phenoxy}-acetic acid;

ba) {4-[3-(2-Benzyl-7-trifluoromethyl-2H-indazol-3-yl)-phenoxymethyl])-phenoxy}-acetic acid;

bb) 2-Benzyl-3-phenyl-7-trifluoromethyl-2H-indazole;

cb) [3-(2-Benzyl-7-trifluoromethyl-2H-indazol-3-yl)-phenyl]-methanol;

cc) [3-(2-Benzyl-7-trifluoromethyl-2H-indazol-3-yl)-phenyl3-phenylamine;

cd) 3-(2-Benzyl-7-trifluoromethyl-2H-indazol-3-yl)-phenol;

ch) 2-Benzyl-3-(4-methoxy-3-methylphenyl)-7-trifluoromethyl-2H-indazole;

ci) 2-Benzyl-3-methylphenyl-7-trifluoromethyl-2H-indazole;

cj) 2-Benzyl-3-(2,3-dimethylphenyl)-7-trifluoromethyl-2H-indazole;

ck) 2-(2-Benzyl-7-trifluoromethyl-2H-indazol-3-yl)-benzaldehyde;

cl) 2-Benzyl-3-(2-isopropyl-phenyl)-7-trifluoromethyl-2H-indazole;

cm) 2-Benzyl-3-(2-cyclohexyl-phenyl)-7-trifluoromethyl-2H-indazole;

cn) 2-Benzyl-3-(2-benzylphenyl)-7-trifluoromethyl-2H-indazole;

co) 2-Benzyl-3-[2-(1,1,2,2-tetrafluoroethoxy)-phenyl]-7-trifluoromethyl-2H-indazole;

cp) 2-Benzyl-3-(2-chloro-5-fluoro-phenyl)-7-trifluoromethyl-2H-indazole;

cq) 2-Benzyl-3-(9H-flouren-2-yl)-7-trifluoromethyl-2H-indazole;

cr) 2-Benzyl-3-(4-benzylphenyl)-7-trifluoromethyl-2H-indazole;

cs) 3-(2-Benzyl-7-trifluoromethyl-2H-indazol-3-yl)-benzaldehyde;

ct) 2-Benzyl-3-(3-[i ,3-dioxolan-2-yl-phenyl)-7-trifluoromethyl indazole;

cu) 2-Benzyl-3-(4'-methoxy-biphenyl-4-yl)-7-trifluoromethyl indazole;

cv) 4'-(2-Benzyl-7-trifluoromethyl-2H-indazol-3-yl)-biphenyl-4-ol;

fd) 2-benzyl-3-(4-chlorophenyl)-7-(trifluoromethyl)-2H-indazole;

ff) 1- {4-[2-benzyl-7-(trifluoromethyl)-2H-indazol-3-yl]phenyl}piperidine-4-carboxamide;

fl) ethyl 1- {4- [2-benzyl-7-(trifluoromethyl)-2H-indazol-3-yl]phenyl}piperidine-4-carboxylate;

fm) (1- {4- [2-benzyl-7-(trifluoromethyl)-2H-indazol-3-yl]phenyl}piperidin-4-yl)methanol;

gb) (1- {4-[2-benzyl-7-{trifluoromethyl)-2H-indazol-3-yl]phenyl}piperidin-3 -yl)methanol;

gc) 2-(1- {442-benzyl-7-(trifluoromethyl)-2H-indazol-3-yl]phenyl}piperidin-4-yl) ethanol;

gd) 2-benzyl-3-(4-piperidin- I -ylphenyl)-7-(trifluoromethyl)-2H-indazole;

ge) 2-benzyl-3-(4-pyrrolidin-1-ylphenyl)-7-(trifluoromethyl)-2H-indazole;

gf) 1- {4-[2-benzyl-7-(trifluoromethyl)-2H-indazol-3-yl]phenyl}pyrrolidin-3-ol;

gm) 1-benzyl-N- {4- [2-benzyl-7-(trifluoromethyl)-2H-indazol-3-yl]phenyl}pyrrolidin-3-amine;

go) 2-benzyl-3-(2,4-difluorophenyl)-7-(trifluoromethyl)-2H-indazole;

gw) 1- {4-[2-benzyl-7-(trifluoromethyl)-2H-indazol-3-yl]phenyl}piperidine-4-carboxylic acid;

rv) 2-benzyl-3-(4-methoxyphenyl)-7-(trifluoromethyl)-2H-indazole;

rx) 4- [({3- [2-benzyl-7-(trifluoromethyl)-2H-indazol-3-yl]benzyl}oxy)methyl]benzoic acid;

ry) N- {4-[2-benzyl-7-(trifluoromethyl)-2H-indazol-3-yl]phenyl}-N-phenylamine;

rz) [4-({3-[2-benzyl-7-(trifluoromethyl)-2H-indazol-3-yl]phenyl}amino)phenyl]acetic acid;

sa) [4-({4-[2-benzyl-7-(trifluoromethyl)-2H-indazol-3-yl]phenyl}amino)phenyl]acetic acid;

sb) 2-benzyl-3-[4-(benzyloxy)phenyl]-7-(trifluoromethyl)-2H-indazole;

sc) 3-[4-({4-[2-benzyl-7-(trifluoromethyl)-2H-indazol-3-yl]phenyl}amino)phenyl]propanoic acid;

sd) 3-[4-({3-[2-benzyl-7-(trifluoromcthyl)-2H-indazol-3-yl]phenyl}amino)phenyl]propanoic acid;

se) 3- [3-({4-[2-benzyl-7-(trifluoromethyl)-2H-indazol-3-yl]phenyl}amino)phenyl]propanoic acid;

sf) 3-[3-({3-[2-benzyl-7-(trifluoromethyl)-2H-indazol-3-yl]phenyl}amino)phenyl]propanoic acid;

sg) 2-[4-({4-[2-benzyl-7-(trifluoromethyl)-2H-indazol-3-yl]phenyl}amino)phenoxy]-2-methylpropanoic acid;

sh) 2-[4-({3-[2-benzyl-7-(trifluoromethyl)-2H-indazol-3-yl]phenyl}amino)phenoxy]-2-methylpropanoic acid;

si) 2- {4-[({4- [2-benzyl-7-(trifluoromethyl)-2H-indazol-3-yl]phenyl}amino)methyl]phenyl}propanoic acid;

sj) ethyl [4-({4-[2-benzyl-7-(trifluoromethyl)-2H-indazol-3-yl]phenyl}amino)phenyl]acetate;

sk) methyl 3-[3-({4-[2-benzyl-7-(trifluoromethyl)-2H-indazol-3-yl]phenyl}amino)phenyl]propanoate;

sl) methyl 3-[3-({3-[2-benzyl-7-(trifluoromethyl)-2H-indazol-3-yl]phenyl}amino)phenyl]propanoate;

sm) methyl 2-[4-({4- [2-benzyl-7-(trifluoromethyl)-2H-indazol-3-yl]phenyl}amino)phenoxy]-2-methylpropanoate;

sn) methyl 2-[4-({3-[2-benzyl-7-(trifluoromethyl)-2H-indazol-3-yl]phenyl}amino)phenoxy]-2-methylpropanoate;

so) methyl 2- {4- [({4- [2-benzyl-7-(trifluoromethyl)-2H-indazol-3-yl]phenyl}amino)methyl]phenyl}propanoate;

sp) 2-[4-({4-[2-benzyl-7-(trifluoromethyl)-2H-indazol-3-yl]phenoxy}methyl)phenyl]propanoic acid;

sq) methyl 2- {4-[({3-[2-benzyl-7-(trifluoromethyl)-2H-indazol-3-yl]phenyl}amino)methyl]phenyl}propanoate;

sr) 2- {4-[({3-[2-benzyl-7-(trifluoromethyl)-2H-indazol-3-yl]phenyl}amino)methyl]phenyl}propanoic acid;

ss) methyl 3-[3-({3- [2-benzyl-7-(trifluoromethyl)-2H-indazol-3-yl]phenyl}amino)phenyl]butanoate;

st) methyl 3-[4-({3- [2-benzyl-7-(trifluoromethyl)-2H-indazol-3-yl]phenyl}amino)phenyl]butanoate;

su) methyl {4-[({3- [2-benzyl-7-(trifluoromethyl)-2H-indazol-3-yl]phenyl}amino)methyl]phenyl}acetate;

sv) methyl [3-({4-[2-benzyl-7-(trifluoromethyl)-2H-indazol-3-yl]phenyl}amino)phenyl]acetate;

sw) methyl [3-({3- [2-benzyl-7-(trifluoromethyl)-2H-indazol-3-yl]phenyl}amino)phenyl]acetate;

sx) 3-[3-({3-[2-benzyl-7-(trifluoromethyl)-2H-indazol-3-yl]phenyl}amino)phenyl]butanoic acid sy) 3-[4-({3-[2-benzyl-7-(trifluoromethyl)-2H-indazol-3-yl]phenyl}amino)phenyl]butanoic acid;

sz) [3-({3-[2-benzyl-7-(trifluoromethyl)-2H-indazol-3-yl]phenyl}amino)phenyl]acetic acid;

ta) [3-({4-[2-benzyl-7-(trifluoromethyl)-2H-indazol-3-yl]phenyl}amino)phenyl]acetic acid;

tb) {4- [({3-[2-benzyl-7-(trifluoromethyl)-2H-indazol-3-yl]phenyl}amino)methyl]phenyl}acetic acid;

tc) 1-[4-({3- [2-benzyl-7-(trifluoromethyl)-2H-indazol-3-yl]phenoxy}methyl)phenyl]cyclopentanecarboxylic acid;

td) 2-[4-({3-[2-benzyl-7-(trifluoromethyl)-2H-indazol-3-.yl]phenoxy}methyl)phenyl]-2-methylpropanoic acid;

te) {3-[2-benzyl-7-(trifluoromethyl)-2H-indazol-3-yl]phenyl}amine;

tf) {4-[2-benzyl-7-(trifluoromethyl)-2H-indazol-3-yl]phenyl}amine;

tg) methyl 2-[3-({4-[2-benzyl-7-(trifluoromethyl)-2H-indazol-3-yl]phenyl}amino)phenyl]propanoate;

th) methyl {4-[({4-[2-benzyl-7-(trifluoromethyl)-2H-indazol-3-yl]phenyl}amino)methyl]phenyl}acetate;

ti) 2-[3-({4-[2-benzyl-7-(trifluoromethyl)-2H-indazol-3-yl]phenyl}amino)phenyl]propanoic acid;

tj) {4-[({4-[2-benzyl-7-(trifluoromethyl)-2H-indazol-3-yl]phenyl}amino)methyl]phenyl}acetic acid;

tk) methyl 2-[3-({3-[2-benzyl-7-(trifluoromethyl)-2H-indazol-3-yl]phenyl}amino)phenyl]propanoate;

tl) 2-[3-({3-[2-benzyl-7-(trifluoromethyl)-2H-indazol-3-yl]phenyl}amino)phenyl]propanoic acid;

tm) 2-benzyl-3-(3-{[4-(1 H-tetrazol-5-yl)benzyl]oxy}phenyl)-7-(trifluoromethyl)-2H-indazole;

tn) ethyl hydrogen [4-({3-[2-benzyl-7-(trifluoromethyl)-2H-indazol-3-yl]phenoxy}methyl)benzyl]phosphonate;

to) ethyl {3-[({4-[2-benzyl-7-(trifluoromethyl)-2H-indazol-3-yl]phenyl}amino)methyl]phenyl}acetate;

tp) ethyl {3-[({3-[2-benzyl-7-(trifluoromethyl)-2H-indazol-3-yl]phenyl}amino)methyl]phenyl}acetate;

tq) methyl 1-{4-[({4-[2-benzyl-7-(trifluoromethyl)-2H-indazol-3-yl]phenyl}amino)methyl]phenyl}cyclopropanecarboxylate;

tr) methyl 1-{4-[({3-[2-benzyl-7-(trifluoromethyl)-2H-indazol-3-yl]phenyl}amino)methyl]phenyl}cyclopropanecarboxylate;

ts) 4-({3-[2-benzyl-7-(trifluoromethyl)-2H-indazol-3-yl]phenoxy}methyl)benzonitrile;

tt) {3-[({4-[2-benzyl-7-(trifluoromethyl)-2H-indazol-3-yl]phenyl}amino)methyl]phenyl}acetic acid;

tu) {3-[({3-[2-benzyl-7-(trifluoromethyl)-2H-indazol-3-yl]phenyl}amino)methyl]phenyl}acetic acid;

tv) 1-{4-[({3-[2-benzyl-7-(trifluoromethyl)-2H-indazol-3-yl]phenyl}amino)methyl]phenyl}cyclopropanecarboxylic acid;

tw) N-{3-[2-benzyl-7-(trifluoromethyl)-2H-indazol-3-yl]phenyl}-N-(2,6-dimethylbenzyl)amine;

ty) 2-[3-({4-[2-benzyl-7-(trifluoromethyl)-2H-indazol-3-yl]phenyl}amino)phenyl]-2-hydroxypropanoic acid;

tz) N-{4-[2-benzyl-7-(trifluoromethyl)-2H-indazol-3-yl]phenyl}-N-(2,6-dimethylbenzyl)amine;

uc) {4-[({4-[2-benzyl-7-(trifluoromethyl)-2H-indazol-3-yl]phenyl}amino)methyl]-3,5-dimethylphenyl}acetic acid;

ud) {4-[({3-[2-benzyl-7-(trifluoromethyl)-2H-indazol-3-yl]phenyl}amino)methyl]-3,5-dimethylphenyl}acetic acid;

uh) 2-benzyl-3-{3-[(2,5-difluorophenoxy)methyl]phenyl}-7-(trifluoromethyl)-2H-indazole;

vz) 2-benzyl-3-[4-(benzyloxy)phenyl]-7-(trifluoromethyl)-2H-indazole;

wa) 2-benzyl-3-{4-[(3-methoxybenzyl)oxy]phenyl}-7-(trifluoromethyl)-2H-indazole;

wb) 2-benzyl-3-{4-[(2-chlorobenzyl)oxy]phenyl}-7-(trifluoromethyl)-2H-indazole;

wc) 2-benzyl-7-(trifluoromethyl)-3-(4-{[2-(trifluoromethyl)benzyl]oxy}phenyl)-2H-indazole;

wd) 2-benzyl-3-{4-[(3-methylbenzyl)oxy]phenyl}-7-(trifluoromethyl)-2H-indazole;

we) 2-benzyl-3-{4-[(2-methylbenzyl)oxy]phenyl}-7-(trifluoromethyl)-2H-indazole;

wt) 2-benzyl-3-{4-[(3-chlorobenzyl)oxy3phenyl}-7-(trifluoromethyl)-2H-indazole;

wg) 2-benzyl-7-(trifluoromethyl)-3-(4-{[3-(trifluoromethyl)benzyl]oxy}phenyl)-2H-indazole;

wh) 2-benzyl-3-{4-[(3,5-dimethylbenzyl)oxy]phenyl}-7-(trifluoromethyl)-2H-indazole;

wi) 2-benzyl-3-{4-[(2,6-dichlorobenzyl)oxy]phenyl}-7-(trifluoromethyl)-2H-indazole;

wj) 2-benzyl-3-{4-[(3,5-dichlorobenzyl)oxy]phenyl}-7-(trifluoromethyl)-2H-indazole;

wk) 2-benzyl-3-{3-[(3-methoxybenzyl)oxy]phenyl}-7-(trifluoromethyl)-2H-indazole;

wl) 2-benzyl-3-{3-[(2-chlorobenzyl)oxy]phenyl}-7-(trifluoromethyl)-2H-indazole;

wm) 2-benzyl-7-(trifluoromethyl)-3-(3-{[2-(trifluoromethyl)benzyl]oxy}phenyl)-2H-indazole;

wn) 2-benzyl-3-{3-[(3-methylbenzyl)oxy3phenyl}-7-(trifluoromethyl)-2H-indazole;

wo) 2-benzyl-3-{3-[(2-methylbenzyl)oxy]phenyl}-7-(trifluoromethyl)-2H-indazole;

wp) 2-benzyl-7-(trifluoromethyl)-3-(3-{[3-(trifluoromethyl)benzyl]oxy}phenyl)-2H-indazole;

wq) 2-benzyl-3-(3-{[3,5-bis(trifluoromethyl)benzyl]oxy}phenyl)-7-(trifluoromethyl)-2H-indazole;

wr) 2-benzyl-3-{3-[(3,5-dimethylbenzyl)oxy]phenyl}-7-(trifluoromethyl)-2H-indazole;

ws) 2-benzyl-3-{3-[(2,6-dichlorobenzyl)oxy]phenyl}-7-(trifluoromethyl)-2H-indazole;

wt) 2-benzyl-3-{3-[(3,5-dichlorobenzyl)oxy]phenyl}-7-(trifluoromethyl)-2H-indazole;

wu) 1-[4-({3-[2-benzyl-7-(trifluoromethyl)-2H-indazol-3-yl]phenoxy}methyl)phenyl]cyclopentanecarboxylic acid;

wv) 1-[4-({3-[2-benzyl-7-(trifluoromethyl)-2H-indazol-3-yl]phenoxy}methyl)phenyl]cyclopropanecarboxylic acid;

ww) 2-benzyl-3-{3-[(2,6-dimethylbenzyl)oxy]phenyl}-7-(trifluoromethyl)-2H-indazole;

wx) 2-[4-({3-[2-benzyl-7-(trifluoromethyl)-2H-indazol-3-yl]phenoxy}methyl)phenyl]-2-methylpropanoic acid;

wy) 2-benzyl-3-{3-[(2-fluorobenzyl)oxy]phenyl}-7-(trifluoromethyl)-2H-indazole;

wz) 2-benzyl-3-{3-[(2-fluoro-6-nitrobenzyl)oxy]phenyl}-7-(trifluoromethyl)-2H-indazole;

xa) 2-benzyl-3-{3-[(2-chloro-6-fluorobenzyl)oxy]phenyl}-7-(trifluoromethyl)-2H-indazole;

xb) 2-benzyl-3-{3-[(2,6-difluorobenzyl)oxy]phenyl}-7-(trifluoromethyl)-2H-indazole;

xc) 2-benzyl-3-{4-[(2-fluorobenzyl)oxy]phenyl}-7-(trifluoromethyl)-2H-indazole;

xd) 2-benzyl-3-{4-[(2-chloro-6-fluorobenzyl)oxy]phenyl}-7-(trifluoromethyl)-2H-indazole;

xe) 2-benzyl-3-{4-[(2,6-difluorobenzyl)oxy]phenyl}-7-(trifluoromethyl)-2H-indazole;

xf) 2-benzyl-3-(3-{[3-(1 H-tetrazol-5-yl)benzyl]oxy}phenyl)-7-(trifluoromethyl)-2H-indazole;

xg) 2-benzyl-3-(4-{[4-(1 H-tetrazol-5-yl)benzyl]oxy}phenyl)-7-(trifluoromethyl)-2H-indazole;

xh) [4-({3-[2-benzyl-7-(trifluoromethyl)-2H-indazol-3-yl]phenoxy}methyl)benzyl]phosphonic acid;

xi) [3-({3-[2-benzyl-7-(trifluoromethyl)-2H-indazol-3-yl]phenoxy}methyl)phenyl]acetic acid;

xj) 3-[2-benzyl-7-(trifluoromethyl)-2H-indazol-3-yl]phenyl acetate;

xk) 2-benzyl-3-{4-[(2-fluoro-6-nitrobenzyl)oxy]phenyl}-7-(trifluoromethyl)-2H-indazole;

xl) 4-({3-[2-benzyl-7-(trifluoromethyl)-2H-indazol-3-yl]phenoxy}methyl)phenyl acetate;

xm) diethyl [4-({3-[2-benzyl-7-(trifluoromethyl)-2H-indazol-3-yl]phenoxy}methyl)benzyl]phosphonate;

xn) diethyl [4-({4-[2-benzyl-7-(trifluoromethyl)-2H-indazol-3-yl]phenoxy}methyl)benzyl]phosphonate;

xo) 3-({3-[2-benzyl-7-(trifluoromethyl)-2H-indazol-3-yl]phenoxy}methyl)benzonitrile;

xp) 4-({4-[2-benzyl-7-(trifluoromethyl)-2H-indazol-3-yl]phenoxy}methyl)benzonitrile;

xq) ethyl hydrogen [4-({4-[2-benzyl-7-(trifluoromethyl)-2H-indazol-3-yl]phenoxy}methyl)benzyl]phosphonate;

xr) [4-({4-[2-benzyl-7-(trifluoromethyl)-2H-indazol-3-yl]phenoxy}methyl)benzyl]phosphonic acid;

xv) 2-benzyl-3-[4-(3-methoxyphenoxy)phenyl]-7-(trifluoromethyl)-2H-indazole;

xw) 2-benzyl-3-[4-(2,3-difluorophenoxy)phenyl]-7-(trifluoromethyl)-2H-indazole;

xx) 2-benzyl-3-[4-(4-chlorophenoxy)phenyl]-7-(trifluoromethyl)-2H-indazole;

xy) 2-benzyl-3-[4-(2,3-dihydro-1H-inden-5-yloxy)phenyl]-7-(trifluoromethyl)-2H-indazole;

xz) 2-benzyl-3-[4-(2-fluorophenoxy)phenyl]-7-(trifluoromethyl)-2H-indazole;

ya) 2-benzyl-3- [4-(4-chloro-3.-methylphenoxy)phenyl]-7-(trifluoromethyl)-2H-. indazole;

yb) 2-benzyl-3- [4-(2-chlorophenoxy)phenyl]-7-(trifluoromethyl)-2H-indazole;

yc) N-(3- {4-[2-benzyl-7-(trifluoromethyl)-2H-indazol-3-yl]phenoxy}phenyl)-N,N-dimethylamine;

yd) 2-benzyl-3-[4-(3-nitrophenoxy)phenylll-7-(trifluoromethyl)-2H-indazole;

ye) 2-benzyl-3- {4- [(7-methoxy-2-naphthyl)oxy]phenyl}-7-(trifluoromethyl)-2H-indazole;

yf) 2-benzyl-3-[4-(4-fluorophenoxy)phenyl]-7-(trifluoromethyl)-2H-indazole;

yg) 4-(4- {4-[2-benzyl-7-(trifluoromethyl)-2H-indazol-3-y1phenoxy}benzy1)pheno1;

yh) 2-benzyl-3- [4-(5,6,7,8-tetrahydronaphthalen-2-yloxy)phenyl]-7-(trifluoromethyl)-2H-indazole;

yi) 7- {4- [2-benzyl-7-(trifluoromethyl)-2H-indazol-3-yl]phenoxy}quinoline;

yj) 2-benzyl-3-[4-(2,4-dichlorophenoxy)phenyl]-7-(trifluoromethyl)-2H-indazole;

yk) 2-benzyl-3- [4-(2-methoxyphenoxy)phenyl]-7-(trifluoromethyl)-2H-indazole;

yl) 2-benzyl-3-[4-(3,5-difluorophenoxy)phenyl]-7-(trifluoromethyl)-2H-indazole;

ym) 2-benzyl-3-[4-(2,3-dimethylphenoxy)phenyl]-7-(trifluoromethyl)-2H-indazole;

yn) 2-benzyl-3-[4-(3,5-dimethylphenoxy)phenyl]-7-(trifluoromethyl)-2H-indazole;

yr) 2-benzyl-3- {3-[(3,5-dimethoxybenzyl)oxy]phenyl}-7-(trifluoromethyl)-2H-indazole;

ys) 2-benzyl-3- {4-[(2,6-dimethylbenzyl)oxy]phenyl}-7-(trifluoromethyl)-2H-indazole;

yu) 2-benzyl-3-[4-(4-methylphenoxy)phenyl]-7-(trifluoromethyl)-2H-indazole;

yv) 2-benzyl-3-[4-(4-nitrophenoxy)phenyl]-7-(trifluoromethyl)-2H-indazole;

yw) 2-benzyl-3- {4-[(4'-nitro-1,1'-biphenyl-4-yl)oxy]phenyl}-7-(trifluoromethyl)-2H-indazole;

yx) 3- {4-[4-(4-acetylpiperazin-1-yl)phenoxy]phenyl}-2-benzyl-7-(trifluoromethyl)-2H-indazole;

yy) 2-benzyl-3- {3-[(2,5-dimethylbenzyl)oxy]phenyl}-7-(trifluoromethyl)-2H-indazole;

yz) 2-benzyl-3-(3- {[2-fluoro-6-(trifluoromethyl)benzyl]oxy) phenyl)-7-(trifluoromethyl)-2H-indazole;

zk) 2-benzyl-3-[4-(2,4-difluorophenoxy)phenyl]-7-(trifluoromethyl)-2H-indazole;

zl) 2-benzyl-3-[4-(3,4-dimethylphenoxy)phenyl]-7-(trifluoromethyl)-2H-indazole;

zm) 2-benzyl-3-[4-(2-isopropylphenoxy)phenyl]-7-(trifluoromethyl)-2H-indazole;

zn) 5- {4-[2-benzyl-7-(trifluoromethyl)-2H-indazol-3-yl]phenoxy}-3,4-dihydronaphthalen-1(2H)-one;

zo) 6- {4-[2-benzyl-7-(trifluoromethyl)-2H-indazol-3-yl]phenoxy}quinoline;

zp) 2-benzyl-3-[4-(2,6-dimethoxyphenoxy)phenyl]-7-(trifluoromethyl)-2H-indazole;

zq) 2-benzyl-3- [4-(2-methylphenoxy)phenyll-7-(trifluoromethyl)-2H4ndazole;

zr) 2- [4-({3-[2-(4-chloro-2-fluorobenzyl)-7-(trifluoromethyl)-2H-indazo[3-yl]phenoxy}methyl)phenyl]propanoic acid;

zs) 2-benzyl-3-[4-(3,4-dichlorophenoxy)phenyl]-7-(trifluoromethyl)-2H-indazole;

zt) 2-benzyl-3- [4-(3,4-difluorophenoxy)phenyl]-7-(trifluoromethyl)-2H-indazole;

zu) 2-benzyl-3- [4-(2,5-difluorophenoxy)phenyl]-7-(trifluoromethyl)-2H-indazole;

zv) 8- {4-[2-benzyl-7-(trifluoromethyl)-2H-indazol-3-yl]phenoxy}quinoline;

zw) 2-benzyl-3-[4-(4-ethylphenoxy)phenyl]-7-(trifluoromethyl)-2H-indazole;

zx) 2-benzyl-3- [4-(2,6-difluorophenoxy)phenyl]-7-(trifluoromethyl)-2H-indazole;

zy) 2-benzyl-3- {4-[4-(benzyloxy)phenoxy]phenyl}-7-(trifluoromethyl)-2H-indazole;

zz) 2-benzyl-3-[3-(3,4-dichlorophenoxy)phenyl]-7-(trifluoromethyl)-2H-indazole;

aaa) methyl 3-(4- {3-[2-benzyl-7-(trifluoromethyl)-2H-indazol-3-yl]phenoxy}phenyl)propanoate;

aab) 1-(2- {3-[2-benzyl-7-(trifluoromethyl)-2H-indazol-3-yl]phenoxy}phenyl)ethanone;

aac) 1-(3- {3-[2-benzyl-7-(trifluoromethyl)-2H-indazol-3-yl]phenoxy}phenyl)ethanone;

aad) 2-benzyl-3-[3-(3-methylphenoxy)phenyl]-7-(trifluoromethyl)-2H-indazole;

aae) 2-benzyl-3-[3-(2-chlorophenoxy)phenyl]-7-(trifluoromethyl)-2H-indazole;

aaf) (3- {3-[2-benzyl-7-(trifluoromethyl)-2H-indazol-3-yl]phenoxy}phenyl)dimethylamine;

aag) 2-benzyl-3-[3-(3-nitrophenoxy)phenyl]-7-(trifluoromethyl)-2H-indazole;

aah) 2-benzyl-3-[3-(2,3-dimethylphenoxy)phenyl]-7-(trifluoromethyl)-2H-indazole;

aai) 2-benzyl-3- {3-[2-(trifluoromethoxy)phenoxy]phenyl}-7-(trifluoromethyl)-2H-indazole;

aaj) 2-benzyl-3-[3-(3-methoxyphenoxy)phenyl]-7-(trifluoromethyl)-2H-indazole;

aak) methyl 3- {3- [2-benzyl-7-(trifluoromethyl)-2H-indazol-3-yl]phenoxy}benzoate;

aal) 5- {3-[2-benzyl-7-(trifluoromethyl)-2H-indazol-3-yl]phenoxy}-3,4-dihydronaphthalen-1(2H)-one;

aam) 7- {3- [2-benzyl-7-(trifluoromethyl)-2H-indazol-3-yl]phenoxy}quinoline;

aan) 2-benzyl-3-[3-(2-isopropylphenoxy)phenyl]-7-(trifluoromethyl)-2H-indazole;

aao) 8- {3-[2-benzyl-7-(trifluoromethyl)-2H-indazol-3-yl]phenoxy}quinoline;

aap) 2-benzyl-3- {3-[3,5-bis(trifluoromethyl)phenoxy]phenyl}-7-(trifluoromethyl)-2H-indazole;

aaq) 2-benzyl-3- {3- [(7-methyl-i-naphthyl)oxy]phenyl}-7-(trifluoromethyl)-2H-indazole;

aar) 4- {3- [2-benzyl-7-(trifluoromethyl)-2H-indazol-3-yl]phenoxy}acridine;

aas) 2-benzyl-3- {3-[2-(benzyloxy)phenoxy]phenyl}-7-(trifluoromethyl)-2H-indazole;

aat) (2- {3-[2-benzyl-7-(trifluoromethyl)-2H-indazol-3-yl]phenoxy}phenyl)(phenyl)methanone;

aau) 2-benzyl-3-[3-(biphenyl-2-yloxy)phenyl]-7-(trifluoromethyl)-2H-indazole;

aav) 2-(2- {3-[2-benzyl-7-(trifluoromethyl)-2H-indazol-3-yl7jphenoxy}phenyl)-1,3-benzothiazole;

aaw) 2-benzyl-3- {3-[2-(1H-pyrrol-1-yl)phenoxy]phenyl}-7-(trifluoromethyl)-2H-indazole;

aax) 2-benzyl-3-[3-(3,4-difluorophenoxy)phenyl]-7-(trifluoromethyl)-2H-indazole;
aay) 2-benzyl-3-[3-(2,3-difluorophenoxy)phenyl]-7-(trifluoromethyl)-2H-indazole;
aaz) 2-benzyl-3-[3-(2,5-difluorophenoxy)phenyl]-7-(trifluoromethyl)-2H-indazole;
aba) 2-benzyl-3-{3-[(7-methoxy-2-naphthyl)oxy]phenyl}-7-(trifluoromethyl)-2H-indazole;
abb) 1-(2-{3-[2-benzyl-7-(trifluoromethyl)-2H-indazol-3-yl]phenoxy}-4-methoxyphenyl)ethanone;
abc) 6-{3-[2-benzyl-7-(trifluoromethyl)-2H-indazol-3-yl]phenoxy}quinoline;
abd) 2-benzyl-3-[3-(3,5-dimethylphenoxy)phenyl]-7-(trifluoromethyl)-2H-indazole;
abe) 2-benzyl-3-[3-(2-methoxyphenoxy)phenyl]-7-(trifluoromethyl)-2H-indazole;
abf) 2-benzyl-3-[3-(1-naphthyloxy)phenyl]-7-(trifluoromethyl)-2H-indazole;
abg) 2-benzyl-3-(3-{2-[(1 E)-prop-1-en-i-yl]phenoxy}phenyl)-7-(trifluoromethyl)-2H-indazole;
abh) 2-benzyl-3-[3-(3,5-difluorophenoxy)phenyl]-7-(trifluoromethyl)-2H-indazole;
abi) 2-benzyl-3-[3-(3,5-dichlorophenoxy)phenyl]-7-(trifluoromethyl)-2H-indazole;
abj) 2-benzyl-3-[3-(3,5-dimethoxyphenoxy)phenyl]-7-(trifluoromethyl)-2H-indazole;
acj) 2-benzyl-3-[4-(bemzyloxy)phenyl]-7-(trifluoromethyl)-2H-indazole;
ack) 1-[4-({3-[2-benzyl-7-(trifluoromethyl)-2H-indazol-3-yl]phenoxy}methyl)phenyl]cyclopentanecarboxylic acid;
acl) 2-[4-({3-[2-benzyl-7-(trifluoromethyl)-2H-indazol-3-yl]phenoxy}methyl)phenyl]-2-methylpropanoic acid;
acs) 2-benzyl-3-(4-{[2-fluoro-6-(trifluoromethyl)benzyl]oxy}phenyl)-7-(trifluoromethyl)-2H-indazole;
act) [4-({3-[2-benzyl-7-(trifluoromethyl)-2H-indazol-3-yl]phenoxy}methyl)-3,5-dimethylphenyl]acetic acid;
acu) [4-({4-[2-benzyl-7-(trifluoromethyl)-2H-indazol-3-yl]phenoxy}methyl)-3,5-dimethylphenyl]acetic acid;
acx) 4-({3-[2-benzyl-7-(trifluoromethyl)-2H-indazol-3-yl]phenoxy}methyl)-3,5-dibromobenzoic acid;
acy) 4-({4-[2-benzyl-7-(trifluoromethyl)-2H-indazol-3-yl]phenoxy}methyl}-3,5-dibromobenzoic acid;
acz) 4-({3-[2-benzyl-7-(trifluoromethyl)-2H-indazol-3-yl]phenoxy}methyl)-3,5-dimethylbenzoic acid;
ada) 2-benzyl-3-{4-[(2,5-dimethylbenzyl)oxy]phenyl}-7-(trifluoromethyl)-2H-indazole;
ade) {4-[2-benzyl-7-(trifluoromethyl)-2H-indazol-3-yl]phenoxy}(3-methylphenyl)acetic acid;
adf) {3-[2-benzyl-7-(trifluoromethyl)-2H-indazol-3-yl]phenoxy}(3-methylphenyl)acetic acid;
adg) 2-benzyl-3-[4-(2-naphthylmethoxy)phenyl]-7-(trifluoromethyl)-2H-indazole;
adh) 2-benzyl-3-114-(1-naphthylmethoxy)phenyl]-7-(trifluoromethyl)-2H-indazole;
adi) 2-benzyl-3-{4-[(3-methyl-2-naphthyl)methoxy]phenyl}-7-(trifluoromethyl)-2H-indazole;
adj) 2-benzyl-3 43-(2-naphthylmethoxy)phenyl]-7-(trifluoromethyl)-2H-indazole;
adk) 2-benzyl-3-[3-(1-naphthylmethoxy)phenyl]-7-(trifluoromethyl)-2H-indazole;
adl) 2-benzyl-3-{3-[(3-methyl-2-naphthyl)methoxy]phenyl}-7-(trifluoromethyl)-2H-indazole;
adm) 2-benzyl-3-{4-[(2-methyl-1-naphthyl)methoxy]phenyl}-7-(trifluoromethyl)-2H-indazole;
adn) 3-[4-(9-anthrylmethoxy)phenyl]-2-benzyl-7-(trifluoromethyl)-2H-indazole;
ado) 2-benzyl-3-{3-[(2-methyl-i-naphthyl)methoxy]phenyl}-7-(trifluoromethyl)-2H-indazole;
adp) 3-[3-(9-anthrylmethoxy)phenyl]-2-benzyl-7-(trifluoromethyl)-2H-indazole;
agj) 2-benzyl-3-(3-phenoxyphenyl)-7-(trifluoromethyl)-2H-indazole;
agk) 2-benzyl-3-[3-(4-methoxyphenoxy)phenyl]-7-(trifluoromethyl)-2H-indazole;
agl) 3-{4-[2-benzyl-7-(trifluoromethyl)-2H-indazol-3-yl]phenoxy}benzaldehyde;
agm) 2-benzyl-3-{3-[3-(1,3-dioxolan-2-ylmethyl)phenoxy]phenyl}-7-(trifluoromethyl)-2H-indazole;
agn) (3-{3-[2-benzyl-7-(trifluoromethyl)-2H-indazol-3-yl]phenoxy}phenyl)acetic acid;
ago) (3-{4-[2-benzyl-7-(trifluoromethyl)-2H-indazol-3-yl]phenoxy}phenyl)acetic acid;
agp) 2-benzyl-3-{4-[3-(1,3-dioxolan-2-ylmethyl)phenoxy]phenyl}-7-(trifluoromethyl)-2H-indazole;
agq) 2-benzyl-3-[4-(3,5-dimethylphenoxy)phenyl]-7-(trifluoromethyl)-2H-indazole;
agr) methyl 2-(4-{3-[2-benzyl-7-(trifluoromethyl)-2H-indazol-3-yl]phenoxy}phenyl)-2-methylpropanoate;
ags) methyl 3-{4-[2-benzyl-7-(trifluoromethyl)-2H-indazol-3-yl]phenoxy}benzoate;
agt) (3-{4-[2-benzyl-7-(trifluoromethyl)-2H-indazol-3-yl]phenoxy}phenyl)methanol;
agu) 3-{4-[2-benzyl-7-(trifluoromethyl)-2H-indazol-3-yl]phenoxy}-N-methoxy-N-methylbenzamide;
agv) 3-{4-[2-benzyl-7-(trifluoromethyl)-2H-indazol-3-yl]phenoxy}-N,N-dimethylbenzamide;
agw) 3-{4-[2-benzyl-7-(trifluoromethyl)-2H-indazol-3-yl]phenoxy}-N-methylbenzamide;
agx) 3-{4-[2-benzyl-7-(trifluoromethyl)-2H-indazol-3-yl]phenoxy}benzamide;
ahj) 2-benzyl-3-{4-[2-(trifluoromethoxy)phenoxy]phenyl}-7-(trifluoromethyl)-2H-indazole;
ahk) 2-benzyl-3-[4-(1-naphthyloxy)phenyl]-7-(trifluoromethyl)-2H-indazole;
aho) 2-{3-[2-benzyl-7-(trifluoromethyl)-2H-indazol-3-yl]phenoxy}benzaldehyde;
ahu) 2-(3-{4-[2-benzyl-7-(trifluoromethyl)-2H-indazol-3-yl]phenoxy}phenyl)propan-2-ol;
ahz) 3-{3-[2-benzyl-7-(trifluoromethyl)-2H-indazol-3-yl]phenoxy}-N,N-dimethylbenzamide; and
aic) 2-(3-{3-[2-benzyl-7-(trifluoromethyl)-2H-indazol-3-yl]phenoxy}phenyl)-2-methylpropanoic acid; or a pharmaceutically acceptable salt thereof.

35. The compound of claim 1, wherein the compound is 2-(2-chloro-4-fluoro-benzyl)-3-(4-fluoro-phenyl)-7-trifluoromethyl-2H-indazole or a pharmaceutically acceptable salt thereof.

36. The compound of claim 1, wherein the compound is 2-(2-fluorobenzyl)-3-(4-fluorophenyl)-7-(trifluoromethyl)-2H-indazole or a pharmaceutically acceptable salt thereof.

37. The compound of claim 1, wherein the compound is 2-(2-chlorobenzyl)-3-(4-fluorophenyl)-7-(trifluoromethyl)-2H-indazole or a pharmaceutically acceptable salt thereof.

38. The compound of claim 1, wherein the compound is 2-(3,4-difluorobenzyl)-3-(4-fluorophenyl)-7-(trifluoromethyl)-2H-indazole or a pharmaceutically acceptable salt thereof.

39. The compound of claim 1, wherein the compound is 2-(2,4-difluorobenzyl)-3-(4-fluorophenyl)-7-(trifluoromethyl)-2H-indazole or a pharmaceutically acceptable salt thereof.

40. The compound of claim 1, wherein the compound is 2-(4-fluorobenzyl)-3-(4-fluorophenyl)-7-(trifluoromethyl)-2H-indazole or a pharmaceutically acceptable salt thereof.

41. The compound of claim 1, wherein the compound is 2-(4-chlorobenzyl)-3-(4-fluorophenyl)-7-(trifluoromethyl)-2H-indazole or a pharmaceutically acceptable salt thereof.

42. The compound of claim 1, wherein the compound is 2-(4-chloro-2-fluorobenzyl)-3-(4-fluorophenyl)-7-(trifluoromethyl)-2H-indazole or a pharmaceutically acceptable salt thereof.

43. The compound of claim 1, wherein the compound is 2-(2-chloro-6-fluorobenzyl)-3 .-(4-fluorophenyl)-7-(trifluoromethyl)-2H-indazole or a pharmaceutically acceptable salt thereof.

* * * * *